US011458206B2

(12) United States Patent
Alargova et al.

(10) Patent No.: US 11,458,206 B2
(45) Date of Patent: *Oct. 4, 2022

(54) TARGETED CONJUGATES AND PARTICLES AND FORMULATIONS THEREOF

(71) Applicant: TVA (ABC), LLC, Wilmington, DE (US)

(72) Inventors: Rossitza G. Alargova, Brighton, MA (US); Mark T. Bilodeau, Waltham, MA (US); Craig A. Dunbar, Needham, MA (US); Sudhakar Kadiyala, Newton, MA (US); Rajesh R. Shinde, Lexington, MA (US); Patrick Lim Soo, Andover, MA (US); Beata Sweryda-Krawiec, Marlborough, MA (US); Brian H. White, Malden, MA (US); Patrick Rosaire Bazinet, Somerville, MA (US); Richard Wooster, Natick, MA (US)

(73) Assignee: TVA (ABC), LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 16/793,094

(22) Filed: Feb. 18, 2020

(65) Prior Publication Data
US 2020/0206356 A1 Jul. 2, 2020

Related U.S. Application Data

(60) Division of application No. 15/652,947, filed on Jul. 18, 2017, now Pat. No. 10,624,967, which is a continuation of application No. 15/382,487, filed on Dec. 16, 2016, now Pat. No. 9,750,818, which is a continuation of application No. PCT/US2015/038569, filed on Jun. 30, 2015.

(60) Provisional application No. 62/150,413, filed on Apr. 21, 2015, provisional application No. 62/077,487, filed on Nov. 10, 2014, provisional application No. 62/019,001, filed on Jun. 30, 2014.

(51) Int. Cl.
| A61K 51/00 | (2006.01) |
| A61K 47/64 | (2017.01) |
| A61K 47/65 | (2017.01) |
| A61K 31/337 | (2006.01) |
| A61K 47/55 | (2017.01) |
| A61K 31/5383 | (2006.01) |

(52) U.S. Cl.
CPC ............ *A61K 47/64* (2017.08); *A61K 31/337* (2013.01); *A61K 31/5383* (2013.01); *A61K 47/55* (2017.08); *A61K 47/65* (2017.08)

(58) Field of Classification Search
CPC combination set(s) only.
See application file for complete search history.

(56) References Cited

U.S. PATENT DOCUMENTS

| 5,416,064 A | 5/1995 | Chari |
| 5,702,717 A | 12/1997 | Cha |
| 6,358,491 B1 | 3/2002 | Lister-James |
| 6,552,007 B2 | 4/2003 | Chen |
| 7,270,808 B2 | 9/2007 | Cheng |
| 7,276,497 B2 | 10/2007 | Chari |
| 7,771,727 B2 | 8/2010 | Fuselier |
| 8,685,920 B2 | 4/2014 | Chari |
| 2001/0029035 A1 | 10/2001 | Eisenhut |
| 2004/0219205 A1 | 11/2004 | Kan |
| 2004/0247527 A1 | 12/2004 | Spangler |
| 2005/0169933 A1 | 8/2005 | Steeves |
| 2006/0193865 A1 | 8/2006 | Govindan |
| 2008/0112953 A1 | 5/2008 | McAuley |
| 2010/0129314 A1 | 5/2010 | Singh |
| 2011/0021744 A1 | 1/2011 | Dai |
| 2013/0029900 A1 | 1/2013 | Widdison |
| 2013/0039848 A1 | 2/2013 | Bradbury |

(Continued)

FOREIGN PATENT DOCUMENTS

| CA | 2597407 | 8/2006 |
| CA | 2597407 A1 | 8/2006 |

(Continued)

OTHER PUBLICATIONS

National Institute of Cancer—understanding and related topics, accessed Aug. 21, 2014 at URL: cancer.gov/cancertopics/understandingcancer, 63 pages (Year: 2014).*
Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*
Merck Manuals Neuroblastoma accessed Mar. 12, 2017 at URL merckmanuals.com/professional/ pediatrics/pediatric-cancers/neuroblastoma, 4 pages (Year: 2017).*
Merck Manual Colorectal Cancer accessed Aug. 21, 2014 at URL merckmanuals.com/home/digestive_disorders/tumors_of_the_digestive_system/colorectal_cancer.htm, 5 pages (Year: 2014).*

(Continued)

*Primary Examiner* — Julie Ha
*Assistant Examiner* — Kristina M Hellman
(74) *Attorney, Agent, or Firm* — DT Ward, PC; Donna T. Ward; Heng Zhu

(57) ABSTRACT

Nanoparticles and microparticles, and pharmaceutical formulations thereof, containing conjugates of an active agent such as a therapeutic, prophylactic, or diagnostic agent attached to a targeting moiety, such as a somatostatin receptor binding moiety, via a linker have been designed. Such nanoparticles and microparticles can provide improved temporospatial delivery of the active agent and/or improved biodistribution. Methods of making the conjugates, the particles, and the formulations thereof are provided. Methods of administering the formulations to a subject in need thereof are provided, for example, to treat or prevent cancer or infectious diseases.

6 Claims, 5 Drawing Sheets

(56) References Cited

U.S. PATENT DOCUMENTS

| | | | |
|---|---|---|---|
| 2013/0287681 | A1 | 10/2013 | Kundra |
| 2014/0023665 | A1 | 1/2014 | Fishkin |
| 2014/0140993 | A1 | 5/2014 | Ross |

FOREIGN PATENT DOCUMENTS

| | | | |
|---|---|---|---|
| EA | 200800952 | | 2/2009 |
| EA | 200870615 | | 4/2009 |
| EA | 201001774 | | 6/2011 |
| EA | 201171360 | | 5/2012 |
| EP | 1118336 | | 7/2001 |
| EP | 2518086 | | 10/2012 |
| JP | 2000502055 | | 2/2000 |
| JP | 2001515494 | | 9/2001 |
| JP | 2004520450 | | 7/2004 |
| JP | 200568046 | | 3/2005 |
| JP | 2011519894 | | 7/2011 |
| JP | 2012502990 | | 2/2012 |
| JP | 6602834 | B2 | 10/2019 |
| RU | 2009111350 | | 11/2010 |
| WO | 9719954 | | 6/1997 |
| WO | 9841540 | | 9/1998 |
| WO | 2001032218 | | 5/2001 |
| WO | 2002098883 | | 12/2002 |
| WO | 2003004559 | | 1/2003 |
| WO | 2003072754 | | 9/2003 |
| WO | 2004093807 | | 11/2004 |
| WO | 2004103272 | | 12/2004 |
| WO | 2004103272 | A2 | 12/2004 |
| WO | 2005037992 | | 4/2005 |
| WO | 2005037992 | A2 | 4/2005 |
| WO | 2007038658 | | 4/2007 |
| WO | 2007144709 | | 12/2007 |
| WO | 2008045604 | | 4/2008 |
| WO | 2009135855 | | 11/2009 |
| WO | 2009140128 | | 11/2009 |
| WO | 2010033207 | | 3/2010 |
| WO | 2010128258 | | 11/2010 |
| WO | 2011078250 | | 6/2011 |
| WO | 2012031198 | | 3/2012 |
| WO | 2012118909 | | 9/2012 |
| WO | 2012138911 | | 10/2012 |
| WO | 2012156918 | | 11/2012 |
| WO | 2013130683 | | 9/2013 |
| WO | 2014043625 | | 3/2014 |
| WO | 2014134483 | | 9/2014 |
| WO | 2015057852 | | 4/2015 |
| WO | 2016004048 | | 1/2016 |

OTHER PUBLICATIONS

Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages (Year: 2014).*

Cholangiocarcinoma accessed Mar. 12, 2017 at URL surgery.usc.edu/divisions/tumor/pancreasdiseases/web%20pages/BILIARY%20SYSTEM/cholangiocarcinoma, 2 pages (Year: 2017).*

Thyroid cancer accessed Mar. 12, 2017 at URL www.merckmanuals.com/professional/endocrine-and-metabolic-disorders/thyroid-disorders/thyroid-cancers, 4 pages (Year: 2017).*

Renal cell carcinoma, accessed Mar. 12, 2017 at URL merckmanuals.com/professional/genitourinary-disorders/genitourinary-cancer/renal-cell-carcinoma, 6 pages (Year: 2017).*

Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*

Dumontet et al., "Microtubule-binding agents: a dynamic field of cancer therapeutics," nature reviews drug Discovery 9:790-803 (2010) (Year: 2010).*

Office Action dated Sep. 1, 2020 in corresponding Japanese application No. 2019-185670 entitled Targeted Conjugates and Particles and Formulations Thereof.

Butler, J.S. and P.J. Sadler, "Targeted delivery of platinum-based anticancer complexes" (2013) Current Opinion in Chemical Biology 17:175-188.

Erickson, H.K. et al., "Antibody-Maytansinoid Conjugates are Activated in Targeted Cancer Cells by Lysosmal Degradation and Linker-Dependent Intracellular Processing" (2006) Cancer Res. 66(8):4426-4433.

Murty, S.B. et al., "Identification of Chemically Modified Peptide from Poly(D,L-lactide-co-glycolide) Micrspheres Under In Vitro Release Conditions" (2003) AAPS Pharm Sci Tech 4(4) 392-405.

Nagy et al. , "Synthesis and biologival evaluation of cytotoxic analogs of somatostatin containing doxorubicin or its intensely potent derivative, 2-pyrrolinodoxorubicin" (1998) PNAS vol. 95, pp. 1794-1799.

Nightingale et al. "Cabazilaxel (Jevtana) A Naval Agent for Metastatic Castration-Resistant Prostate Cancer" (2012) P & T vol. 37 (8):440-448.

Pohl, E. et al. "Structure of Octreotide, a Somatostatin Analogue" (1995) Acta Cryst. D51:48-59.

Sun et al., "Design of Antibody—Maytansinoid Conjugates Allows for Efficient Detoxification via Liver Metabolism" (2011) Bioconjugate Chemistry 22:728-735.

Sun, L.-C. et al., "Targeted Chemotherapy Using a Cytotoxic Somatostatin Conjugate to Inhibit Tumor Growth and Matastasis in Nude Mice" (2008) Clin. Med. Oncol. 2:491-499.

Sun, L.-C., and D.H. Coy, "Somatostatin Receptor-Targeted Anti-Cancer Therapy" (2011) Current Drug Delivery 8(1):2-10.

Sun, L. et al., "Effects of Camptothecin Conjugated to a Somatostatin Analog Vector Growth of Tumors in Rodents" (2004) Drug Delivery 11:231-238.

Tassone, P. et al., "Cytotoxic activity of the maytansinoid immunoconjugate B-B4-DM1 against CD138+ multiple myeloma cells" (2004) Blood 104(12):3688-3696.

Watanabe, N. et al., "Expressions of Somatostatin Receptor Subtypes (SSTR-1, 2, 3,4 and 5) in Neuroblastic Tumors; Special Reference to Clinicopathological Correlations with International Neuroblastoma Pathology Classification and Outcomes" (2014) Acta Histochem. Cytochem. 47(5):219-229.

Xiao et al., "Co-delivery of doxorubicin and siRNA using octreotide-conjugated gold nanorods for targeted neuroendocrine cancer therapy" (2012) Nanoscale vol. 4(22):1-21.

Zhang, Y. et al., "The eradication of breast cancer and cancer stem cells using octreotide modified paclitaxel active targeting micelles and salinomycin passive targeting micelles" (2012) Biomaterials 33:679-691.

Office Action (with translation) dated Sep. 12, 2017, in co-pending Japanese application No. 2017-500064, entitled: Targeted Conjugates and Particles and Formulations Thereof.

Examination Report No. 1 for standard patent application dated Sep. 13, 2017, in co-pending Australia application No. 2015284236, entitled: Targeted Conjugates and Particles and Formulations Thereof.

Examination Report No. 2 for Standard Patent Application dated Dec. 21, 2017, in co-pending Australia application No. 2015284236 entitled, Targeted Conjugates and Particles and Formulations Thereof.

Canadian Examination Report dated Feb. 8, 2018, in co-pending Canada application No. 2,953,371, entitled Targeted Conjugates and Particles and Formulations Thereof.

Partial Supplementary European Search Report dated Jan. 18, 2018, in co-pending Europe application No. 15815040.9, entitled Targeted Conjugates and Particles and Formulations Thereof.

Office Action dated Mar. 20, 2018, in co-pending Japanese application No. 2017-500064 entitled, Targeted Conjugates and Particles and Formulations Thereof.

Tóth, I. et al., "Novel Lipoamino Acid- and Liposaccharide-Based System for Peptide Delivery: Application for Oral Administration of Tumor-Selective Somatostatin Analogues" (1999) J. Med. Chem. 42(19) 4010-4013.

Extended European Search Report dated Apr. 19, 2018 in co-pending Europe application No. 15815040.9, entitled Targeted Conjugates and Particles and Formulations Thereof.

(56) References Cited

OTHER PUBLICATIONS

Office Action dated May 29, 2018, from co-pending Russia Patent Application No. 2016151859, entitled, "Targeted Conjugates and Particles and Formulations Thereof".
Office Action dated Jul. 31, 2018, from co-pending Canada Patent Application No. 2,953,371, entitled,"Targeted Conjugates and Particles and Formulations Thereof".
Office Action dated Sep. 5, 2018, from co-pending Russia Patent Application No. 2016151859, entitled, "Targeted Conjugates and Particles and Formulations Thereof".
Office Action dated Dec. 4, 2017 in co-pending Japanese application No. 2017-500064 entitled "Targeted Conjugates and Particles and Formulations Thereof".
Office Action dated Dec. 11, 2018 in co-pending Israeli application No. 249647 entitled "Targeted Conjugates and Particles and Formulations Thereof".
Office Action dated Dec. 11, 2018 in co-pending Russian application No. 2016151859 entitled, Targeted Conjugates and Particles and Formulations Thereof.
Office Action dated Jan. 4, 2019 in co-pending Chinese application No. 2015800448364 entitled "Targeted Conjugates and Particles and Formulations Thereof".
Office Action dated Jan. 30, 2019 in co-pending Korean application No. 10-2017-7002414 entitled "Targeted Conjugates and Particles and Formulations Thereof".
First Examination Report dated Feb. 14, 2019 in co-pending Indian application No. 201617043274, entitled "Targeted Conjugates and Particles and Formulations Thereof".
Examiner's Report dated Mar. 19, 2019 in co-pending Canadian application No. 2,953,371, entitled "Targeted Conjugates and Particles and Formulations Thereof".
Examination Report No. 1 for standard patent application dated Apr. 9, 2019 in co-pending Australia application No. 2018204037, entitled "Targeted Conjugates and Particles and Formulations Thereof".
Office Action dated Jun. 11, 2019 in co-pending Japanese application No. 2017500064, entitled "Targeted Conjugates and Particles and Formulations Thereof".
Examination Report Stage 1 dated Jul. 25, 2019 in corresponding Indonesia patent application No. P00201700600, entitled, "Targeted Conjugates and Particles and Formulations Thereof".
Final Rejection dated Aug. 21, 2019 in corresponding Korea patent application No. 10-2017-7002414, entitled "Targeted Conjugates and Particles and Formulations Thereof".
Examination Report No. 2 for Standard Patent Application dated Oct. 23, 2019, in co-pending Australia application No. 2018204037 entitled, Targeted Conjugates and Particles and Formulations Thereof.
Office Action dated Dec. 3, 2019, in co-pending Israel application No. 249647 entitled, Targeted Conjugates and Particles and Formulations Thereof.
Substantive Examination Report (Restriction) dated Jan. 10, 2020, in co-pending Philippines application No. 1/2017/500023 entitled, Targeted Conjugates and Particles and Formulations Thereof.
Zhang, Y. et al., "The eradication of breast cancer and cancer stem cells using octreotide modified paclitaxel active targeting micelles and salinomycin passive targeting micelles" (2012) Biomaterials 33:679-691 Previously cited.
Murty, S.B. et al., "Identification of Chemically Modified Peptide from Poly(D,L-lactide-co-glycolide) Microspheres Under In Vitro Release Conditions" (2003) AAPS Pharm Sci Tech 4(4) 392-405. Previously cited.
Erickson, H.K. et al., "Antibody-Maytansinoid Conjugates are Activated in Targeted Cancer Cells by Lysosmal Degradation and Linker-Dependent Intracellular Processing" (2006) Cancer Res 66(8):4426-4433. Previously cited.
Tassone, P. et al., "Cytotoxic activity of the maytansinoid immunoconjugate B-B4-DM1 against CD138+ multiple myeloma cells" (2004) Blood 104(12):3688-3696. Previously cited.
Communication pursuant to Article 94(3) EPC dated Oct. 6, 2020 in corresponding application No. 15 815 040.9 entitled Targeted Conjugates and Particles and Formulations Thereof.
Examination Report dated Jul. 2, 2020 in corresponding Canadian application No. 2,953,371 entitled Targeted Conjugates and Particles and Formulations Thereof.
Tóth, I. et al., "Novel Lipoamino Acid- and Liposaccharide-Based System for Peptide Delivery: Application for Oral Administration of Tumor-Selective Somatostatin Analogues" (1999) J. Med. Chem. 42(19) 4010-4013. Previously cited.
Sun, L-C. et al., "Targeted Chemotherapy Using a Cytotoxic Somatostatin Conjugate to Inhibit Tumor Growth and Matastasis in Nude Mice" (2008) Clin. Med. Oncol. 2:491-499. Previously cited.
Substantive Examination Adverse Report dated Jun. 30, 2021 in corresponding Malaysia application No. PI 2016002299, entitled Targeted Conjugates and Particles and Formulations Thereof.

\* cited by examiner

Dose given

TARGETED CONJUGATES AND PARTICLES AND FORMULATIONS THEREOF

REFERENCE TO RELATED APPLICATIONS

The present application is a divisional application of U.S. application Ser. No. 15/652,947 filed Jul. 18, 2017, entitled TARGETED CONJUGATES AND PARTICLES AND FORMULATIONS THEREOF, which is a continuation application of U.S. application Ser. No. 15/382,487 filed Dec. 16, 2016, entitled TARGETED CONJUGATES AND PARTICLES AND FORMULATIONS THEREOF, which is a continuation application of PCT application No. PCT/US2015/038569 filed Jun. 30, 2015, entitled TARGETED CONJUGATES AND PARTICLES AND FORMULATIONS THEREOF, which claims priority to U.S. Provisional Patent Application No. 62/019,001 filed Jun. 30, 2014, entitled TARGETED CONJUGATES ENCAPSULATED IN PARTICLES AND FORMULATIONS THEREOF, U.S. Provisional Patent Application No. 62/077,487 filed Nov. 10, 2014, entitled TARGETED CONJUGATES ENCAPSULATED IN PARTICLES AND FORMULATIONS THEREOF and U.S. Provisional Patent Application No. 62/150,413 filed Apr. 21, 2015, entitled TARGETED CONJUGATES AND PARTICLES AND FORMULATIONS THEREOF, the contents of each of which are herein incorporated by reference in their entirety.

FIELD OF THE INVENTION

The invention generally relates to the field of targeting ligands, conjugates thereof, and particles for drug delivery. More particularly, the invention relates to the use of molecules targeting somatostatin receptors, e.g., for treating cancer.

BACKGROUND OF THE INVENTION

Developments in nanomedicine are generally directed towards improving the pharmaceutical properties of the drugs and, in some cases, enhancing the targeted delivery in a more cell-specific manner. Several cell-specific drugs have been described, and include monoclonal antibodies, aptamers, peptides, and small molecules. Despite some of the potential advantages of such drugs, a number of problems have limited their clinical application, including size, stability, manufacturing cost, immunogenicity, poor pharmacokinetics and other factors.

Nanoparticulate drug delivery systems are attractive for systemic drug delivery because they may be able to prolong the half-life of a drug in circulation, reduce non-specific uptake of a drug, and improve accumulation of a drug at tumors, e.g., through an enhanced permeation and retention (EPR) effect. There are limited examples of therapeutics formulated for delivery as nanoparticles, which include DOXIL® (liposomal encapsulated doxorubicin) and ABRAXANE® (albumin bound paclitaxel nanoparticles).

The development of nanotechnologies for effective delivery of drugs or drug candidates to specific diseased cells and tissues, e.g., to cancer cells, in specific organs or tissues, in a temporospatially regulated manner potentially can overcome or ameliorate therapeutic challenges, such as systemic toxicity. However, while targeting of the delivery system may preferentially deliver drug to a site where therapy is needed, the drug released from the nanoparticle may not for example, remain in the region of the targeted cells in efficacious amounts or may not remain in the circulation in a relatively non-toxic state for a sufficient amount of time to decrease the frequency of treatment or permit a lower amount of drug to be administered while still achieving a therapeutic effect. Accordingly, there is a need in the art for improved drug targeting and delivery, including identification of targeting molecules that can be incorporated into particles and whose presence does not substantially interfere with efficacy of the drug.

SUMMARY OF THE INVENTION

Applicants have created molecules that are conjugates of a somatostatin receptor binding moiety and an active agent, e.g., a cancer therapeutic agent such as a platinum-containing agent. Furthermore, such conjugates can be encapsulated into particles. The conjugates and particles are useful for delivering active agents such as tumor cytotoxic agents to cells expressing somatostatin receptors (SSTRs).

Applicants have developed novel conjugates and particles, including polymeric nanoparticles, and pharmaceutical formulations thereof. The conjugates of an active agent such as a therapeutic, prophylactic, or diagnostic agent are attached via a linker to a targeting moiety that can bind a somatostatin receptor. The conjugates and particles can provide improved temporospatial delivery of the active agent and/or improved biodistribution compared to delivery of the active agent alone. In some cases, the targeting moiety can also act as a therapeutic agent. In some embodiments, the targeting agent does not substantially interfere with efficacy of the therapeutic agent in vivo. Methods of making conjugates, particles, and formulations comprising such particles are described herein. Such particles are useful for treating or preventing diseases that are susceptible to the active agent, for example, treating or preventing cancer or infectious diseases.

The conjugates include a targeting ligand and an active agent connected by a linker, wherein the conjugate in some embodiments has the formula:

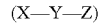

wherein X is a somatostatin receptor targeting moiety; Y is a linker; and Z is an active agent.

One ligand can be conjugated to two or more active agents where the conjugate has the formula: X—(Y—Z)$_n$. In other embodiments, one active agent molecule can be linked to two or more ligands wherein the conjugate has the formula: (X—Y)$_n$—Z. n is an integer equal to or greater than 1.

The targeting moiety, X, can be any somatostatin receptor binding moiety such as, but not limited to, somatostatin, octreotide, octreotate, vapreotide, pasireotide, lanreotide, seglitide, or any other example of somatostatin receptor binding ligands. In some embodiments, the targeting moiety is a somatostatin receptor binding moiety that binds to somatostatin receptors 2 and/or 5.

The linker, Y, is bound to one or more active agents and one or more targeting ligands to form a conjugate. The linker Y is attached to the targeting moiety X and the active agent Z by functional groups independently selected from an ester bond, disulfide, amide, acylhydrazone, ether, carbamate, carbonate, and urea. Alternatively the linker can be attached to either the targeting ligand or the active drug by a non-cleavable group such as provided by the conjugation between a thiol and a maleimide, an azide and an alkyne. The linker is independently selected from the group consisting alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

In some embodiments, the linker comprises a cleavable functionality. The cleavable functionality may be hydrolyzed in vivo or may be designed to be hydrolyzed enzymatically, for example by Cathepsin B.

The active agent, Z, also referred as a payload, can be a therapeutic, prophylactic, diagnostic, or nutritional agent. In some embodiments, the active agent, Z, may be an anti-cancer agent, chemotherapeutic agent, antimicrobial, anti-inflammatory agent, or combination thereof.

In some embodiments, the conjugate can be a compound according to Formula Ia:

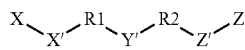

Ia wherein X is a somatostatin receptor targeting moiety defined above; Z is an active agent; X', R$^1$, Y', R$^2$ and Z' are as defined herein.

X' is either absent or independently selected from carbonyl, amide, urea, amino, ester, aryl, arylcarbonyl, aryloxy, arylamino, one or more natural or unnatural amino acids, thio or succinimido; R$^1$ and R$^2$ are either absent or comprised of alkyl, substituted alkyl, aryl, substituted aryl, polyethylene glycol (2-30 units); Y' is absent, substituted or unsubstituted 1,2-diaminoethane, polyethylene glycol (2-30 units) or an amide; Z' is either absent or independently selected from carbonyl, amide, urea, amino, ester, aryl, arylcarbonyl, aryloxy, arylamino, thio or succinimido. In some embodiments, the linker can allow one active agent molecule to be linked to two or more targeting ligands, or one targeting ligand to be linked to two or more active agents.

In some embodiments, the conjugate can be a compound where linker Y is A$_m$ according to Formula Ib:

Ib wherein A is defined herein, m=0-20.

A in Formula Ia is a spacer unit, either absent or independently selected from the following substituents. For each substituent, the dashed lines represent substitution sites with X, Z or another independently selected unit of A wherein the X, Z, or A can be attached on either side of the substituent:

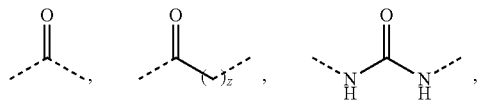

-continued

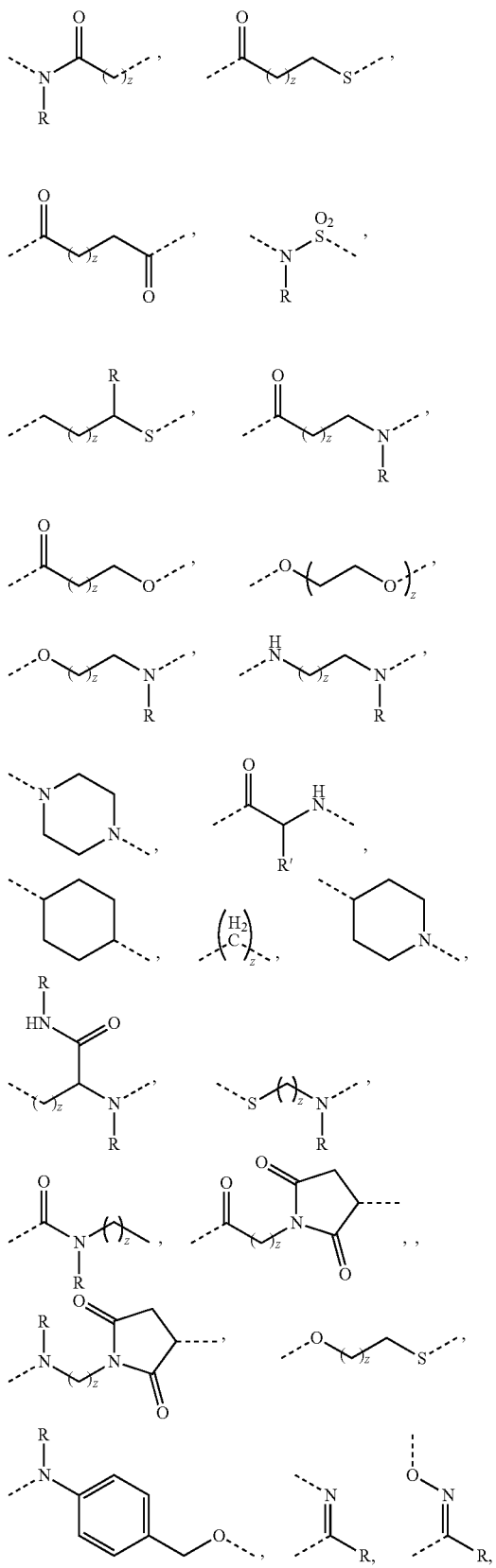

-continued

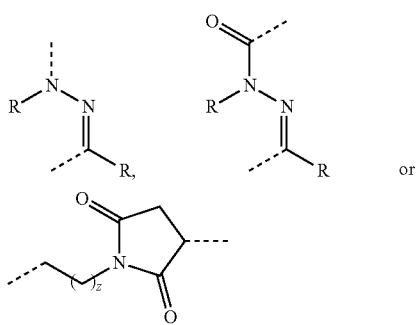

wherein z=0-40, R is H or an optionally substituted alkyl group, and R' is any side chain found in either natural or unnatural amino acids.

In some embodiments, the linker can be a compound according to Formula Ic:

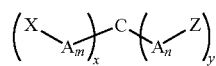

Ic wherein A is defined above, m=0-40, n=0-40, x=1-5, y=1-5, and C is a branching element defined herein.

C in Formula Ic is a branched unit containing three to six functionalities for covalently attaching spacer units, ligands, or active drugs, selected from amines, carboxylic acids, thiols, or succinimides, including amino acids such as lysine, 2,3-diaminopropanoic acid, 2,4-diaminobutyric acid, glutamic acid, aspartic acid, and cysteine.

A non-limiting example of a conjugate of the invention is a compound selected from the group consisting of the following compounds:

1

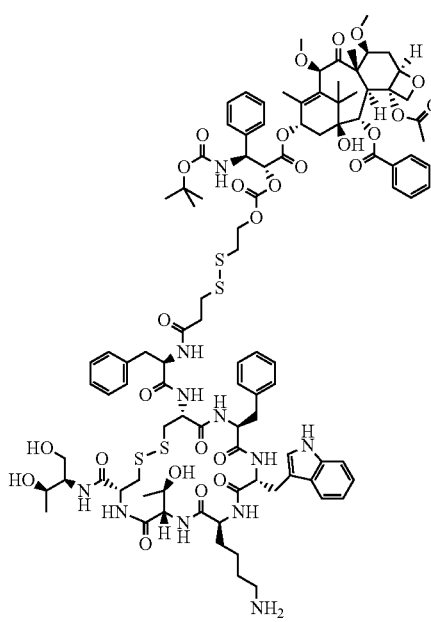

2

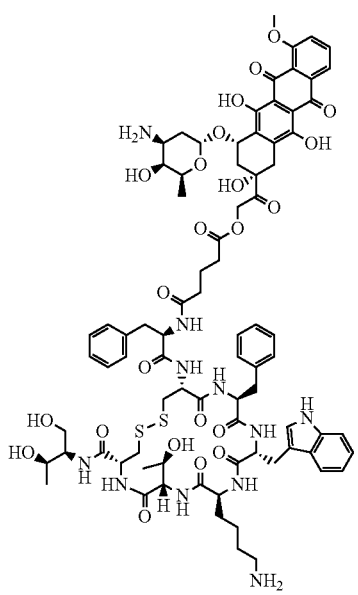

3

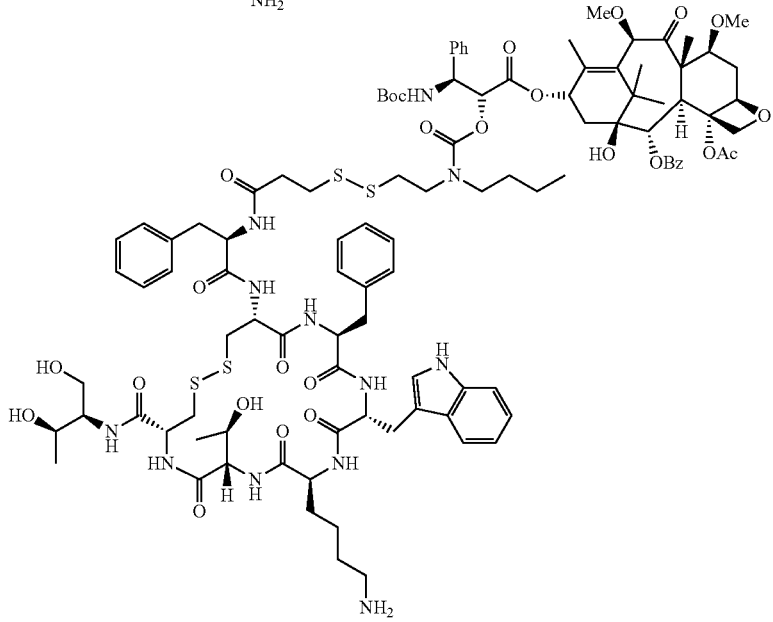

4
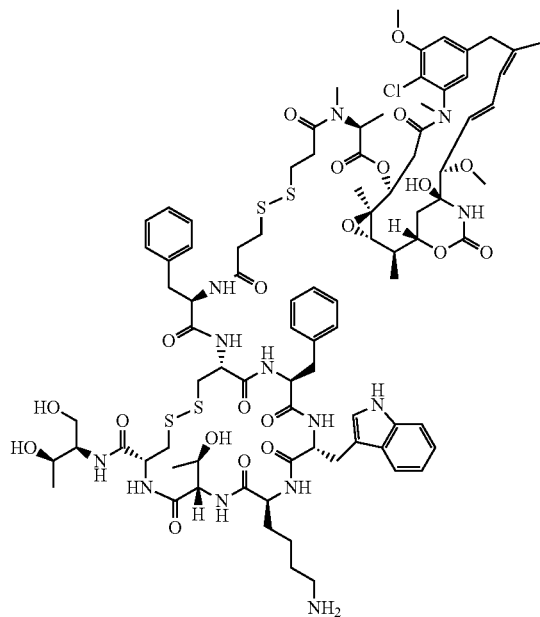
5
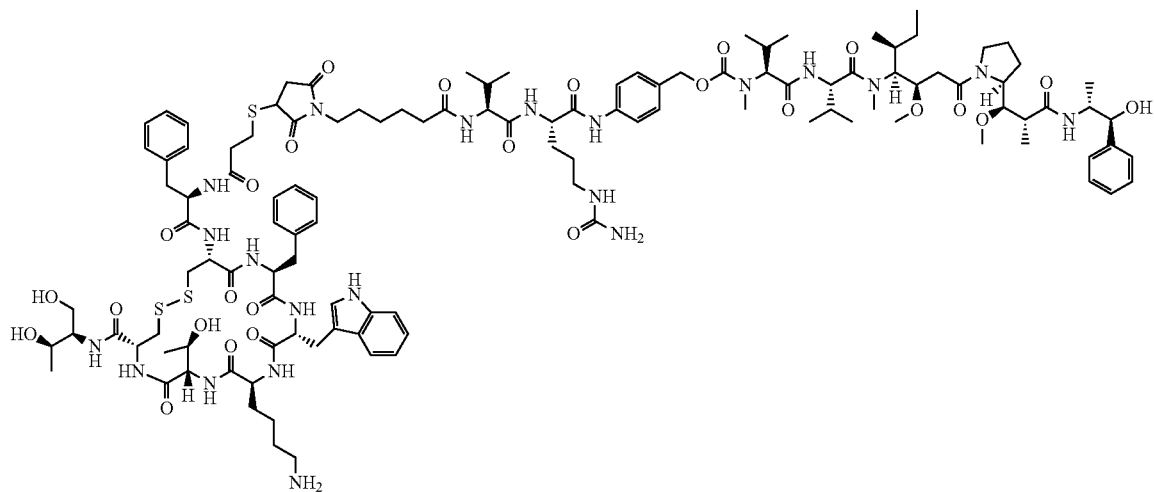
6
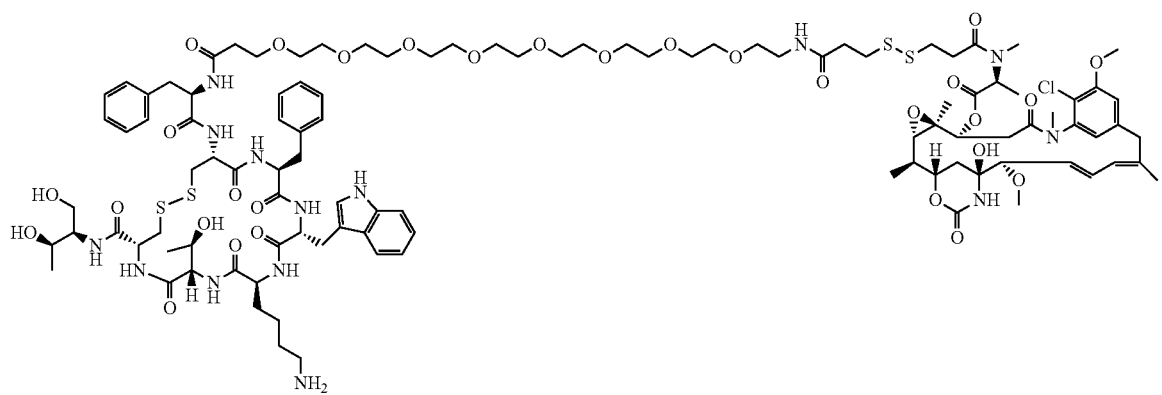

-continued

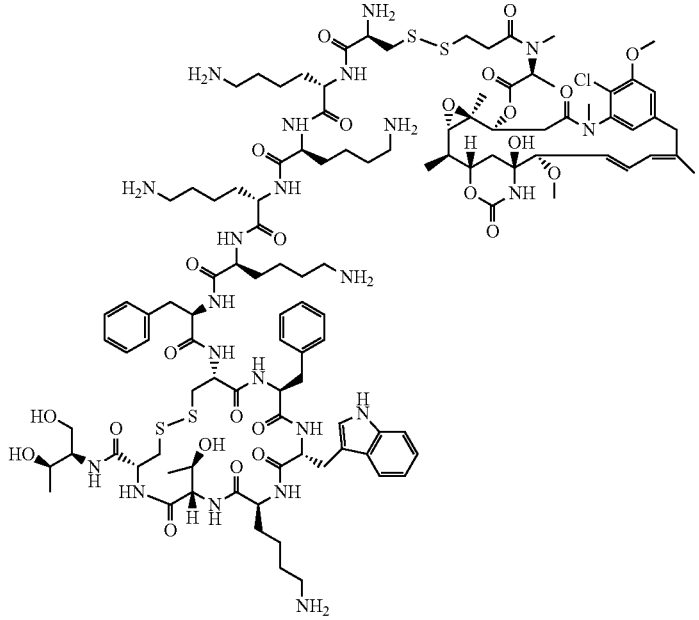

In some embodiments, the active agent Z is DM1. In some embodiments, the somatostatin receptor targeting moiety X is selected from somatostatin, seglitide, Tyr$^3$-octreotate (TATE), cyclo(AA-Tyr-DTrp-Lys-Thr-Phe), or analogs or derivatives thereof. X may covalently bind to linker Y at its C-terminus or N-terminus. In some embodiments, the targeting moiety X comprises at least one D-Phe residue and the phenyl ring of the D-Phe residue of the targeting moiety X has been replaced by a linker-containing moiety.

In one aspect, hydrophobic ion-pairing complexes containing the conjugate of the invention and counterions are provided. In some embodiments, the counterions are negatively charged. In another aspect, particles containing the conjugate of the invention or the hydrophobic ion-pairing complexes of the conjugate of the invention are provided. In another aspect, pharmaceutical formulations are provided containing the conjugates or particles containing the conjugates described herein, or pharmaceutically acceptable salts thereof, in a pharmaceutically acceptable vehicle.

In one aspect, particles containing the conjugate of the invention are provided. In some embodiments, the particle has a diameter between 10 nm and 5000 nm. In some embodiments, the particle has a diameter between 30 nm and 70 nm, 120 nm and 200 nm, 200 nm and 5000 nm, or 500 nm-1000 nm.

Methods of making the conjugates and particles containing the conjugates are provided. Methods are also provided for treating a disease or condition, the method comprising administering a therapeutically effective amount of the particles containing a conjugate to a subject in need thereof. In an embodiment, the conjugates are targeted to a cancer or hyperproliferative disease, for example, lymphoma, renal cell carcinoma, leukemia, prostate cancer, lung cancer (e.g., small cell lung cancer (SCLC) and non-SCLC), pancreatic cancer (e.g., ductal), melanoma, colorectal cancer, ovarian cancer (e.g., epithelial ovarian cancer), breast cancer, glioblastoma (e.g., astrocytoma and glioblastoma multiforme), stomach cancer, liver cancer, sarcoma, bladder cancer, testicular cancer, esophageal cancer, head and neck cancer, endometrial cancer and leptomeningeal carcinomatosis.

DETAILED DESCRIPTION OF THE INVENTION

Figure 1:
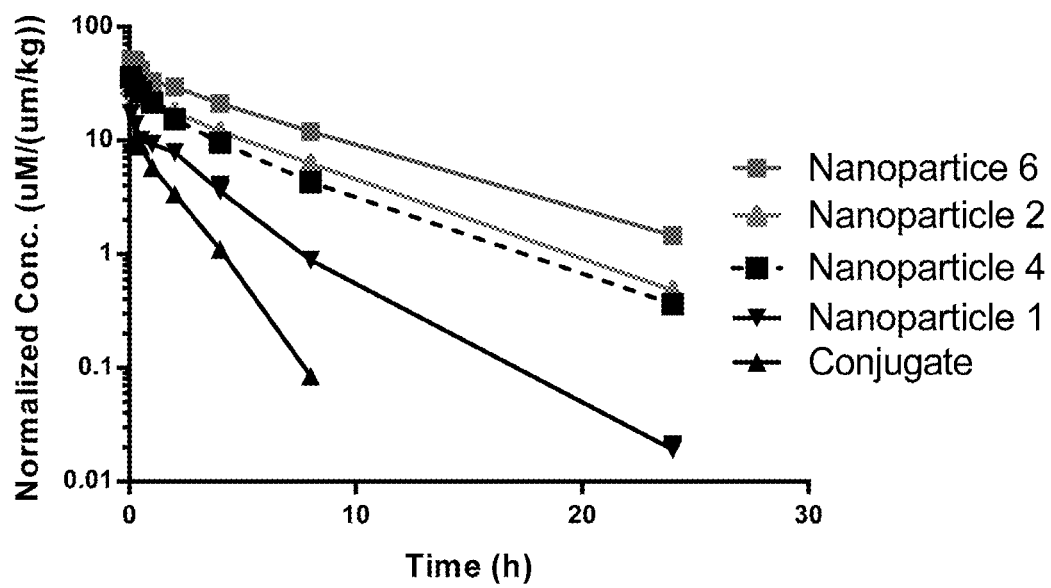
FIG. 1 is a graph of the blood plasma concentration (μM) of the octreotide-cabazitaxel conjugate of Example 1 as a function of time (hours) after tail vein injection in rats. The formulations injected contained either the free octreotide-cabazitaxel conjugate or octreotide-cabazitaxel nanoparticles of Example 11.

At least five somatostatin receptors subtypes have been characterized, and tumors can express various receptor subtypes. (e.g., see Shaer et al., Int. 3. Cancer 70:530-537, 1997). Naturally occurring somatostatin and its analogs exhibit differential binding to receptor subtypes. Applicants have exploited this feature to create novel particles to improve targeting of a conjugate comprising an active agent to a disease tissue target. Such targeting can, for example, improve the amount of active agent at a site and decrease active agent toxicity to the subject. As used herein, "toxicity" refers to the capacity of a substance or composition to be harmful or poisonous to a cell, tissue organism or cellular environment. Low toxicity refers to a reduced capacity of a substance or composition to be harmful or poisonous to a cell, tissue organism or cellular environment. Such reduced or low toxicity may be relative to a standard measure, relative to a treatment or relative to the absence of a treatment.

Toxicity may further be measured relative to a subject's weight loss. where weight loss over 15%, over 20% or over 30% of the body weight is indicative of toxicity. Other metrics of toxicity may also be measured such as patient presentation metrics including lethargy and general malaise. Neutropenia or thrombopenia may also be metrics of toxicity.

Pharmacologic indicators of toxicity include elevated AST/ALT levels, neurotoxicity, kidney damage, GI damage and the like.

The conjugates are released after administration of the particles. The targeted drug conjugates utilize active molecular targeting in combination with enhanced permeability and retention effect (EPR) and improved overall biodistribution of the particles to provide greater efficacy and tolerability as compared to administration of targeted particles or encapsulated untargeted drug.

In addition, the toxicity of a conjugate containing a somatostatin targeting moiety linked to an active agent for cells that do not express SSTRs is predicted to be decreased compared to the toxicity of the active agent alone. Without committing to any particular theory, applicants believe that this feature is because the ability of the conjugated active agent to enter a cell is decreased compared the ability to enter a cell of the active agent alone. Accordingly, the conjugates comprising an active agent and particles containing the conjugates as described herein generally have decreased toxicity for non-SSTR expressing cells and at least the same or increased toxicity for SSTR expressing cells compared to the active agent alone.

It is an object of the invention to provide improved compounds, compositions, and formulations for temporospatial drug delivery.

It is further an object of the invention to provide methods of making improved compounds, compositions, and formulations for temporospatial drug delivery.

It is also an object of the invention to provide methods of administering the improved compounds, compositions, and formulations to individuals in need thereof.

I. Definitions

The term "compound", as used herein, is meant to include all stereoisomers, geometric isomers, tautomers, and isotopes of the structures depicted. In the present application, compound is used interchangeably with conjugate. Therefore, conjugate, as used herein, is also meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

The terms "subject" or "patient", as used herein, refer to any organism to which the particles may be administered, e.g., for experimental, therapeutic, diagnostic, and/or prophylactic purposes. Typical subjects include animals (e.g., mammals such as mice, rats, rabbits, guinea pigs, cattle, pigs, sheep, horses, dogs, cats, hamsters, lamas, non-human primates, and humans).

The terms "treating" or "preventing", as used herein, can include preventing a disease, disorder or condition from occurring in an animal that may be predisposed to the disease, disorder and/or condition but has not yet been diagnosed as having the disease, disorder or condition; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

A "target", as used herein, shall mean a site to which targeted constructs bind. A target may be either in vivo or in vitro. In certain embodiments, a target may be cancer cells found in leukemias or tumors (e.g., tumors of the brain, lung (small cell and non-small cell), ovary, prostate, breast and colon as well as other carcinomas and sarcomas). In still other embodiments, a target may refer to a molecular structure to which a targeting moiety or ligand binds, such as a hapten, epitope, receptor, dsDNA fragment, carbohydrate or enzyme. A target may be a type of tissue, e.g., neuronal tissue, intestinal tissue, pancreatic tissue, liver, kidney, prostate, ovary, lung, bone marrow, or breast tissue.

The "target cells" that may serve as the target for the method or conjugates or particles, are generally animal cells, e.g., mammalian cells. The present method may be used to modify cellular function of living cells in vitro, i.e., in cell culture, or in vivo, in which the cells form part of or otherwise exist in animal tissue. Thus, the target cells may include, for example, the blood, lymph tissue, cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject invention), dermal/epidermal cells, cells of the vagina and rectum, cells of internal organs including cells of the placenta and the so-called blood/brain barrier, etc. In general, a target cell expresses at least one type of SSTR. In some embodiments, a target cell can be a cell that expresses an SSTR and is targeted by a conjugate described herein, and is near a cell that is affected by release of the active agent of the conjugate. For example, a blood vessel expressing an SSTR that is in proximity to a tumor may be the target, while the active agent released at the site will affect the tumor.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease, disorder or condition in the enhancement of desirable physical or mental development and conditions in an animal, e.g., a human.

The term "modulation" is art-recognized and refers to up regulation (i.e., activation or stimulation), down regulation (i.e., inhibition or suppression) of a response, or the two in combination or apart. The modulation is generally compared to a baseline or reference that can be internal or external to the treated entity.

"Parenteral administration", as used herein, means administration by any method other than through the digestive tract (enteral) or non-invasive topical routes. For example, parenteral administration may include administration to a patient intravenously, intradermally, intraperitoneally, intrapleurally, intratracheally, intraossiously, intracerebrally, intrathecally, intramuscularly, subcutaneously, subjunctivally, by injection, and by infusion.

"Topical administration", as used herein, means the non-invasive administration to the skin, orifices, or mucosa. Topical administration can be delivered locally, i.e., the therapeutic can provide a local effect in the region of delivery without systemic exposure or with minimal systemic exposure. Some topical formulations can provide a systemic effect, e.g., via adsorption into the blood stream of the individual. Topical administration can include, but is not limited to, cutaneous and transdermal administration, buccal administration, intranasal administration, intravaginal administration, intravesical administration, ophthalmic administration, and rectal administration.

"Enteral administration", as used herein, means administration via absorption through the gastrointestinal tract. Enteral administration can include oral and sublingual administration, gastric administration, or rectal administration.

"Pulmonary administration", as used herein, means administration into the lungs by inhalation or endotracheal administration. As used herein, the term "inhalation" refers to intake of air to the alveoli. The intake of air can occur through the mouth or nose.

The terms "sufficient" and "effective", as used interchangeably herein, refer to an amount (e.g., mass, volume, dosage, concentration, and/or time period) needed to achieve one or more desired result(s). A "therapeutically effective amount" is at least the minimum concentration required to affect a measurable improvement or prevention of at least one symptom or a particular condition or disorder, to affect a measurable enhancement of life expectancy, or to generally improve patient quality of life. The therapeutically effective amount is thus dependent upon the specific biologically active molecule and the specific condition or disorder to be treated. Therapeutically effective amounts of many active agents, such as antibodies, are known in the art. The therapeutically effective amounts of compounds and compositions described herein, e.g., for treating specific disorders may be determined by techniques that are well within the craft of a skilled artisan, such as a physician.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The term "prodrug" refers to an agent, including a small organic molecule, peptide, nucleic acid or protein, that is converted into a biologically active form in vitro and/or in vivo. Prodrugs can be useful because, in some situations, they may be easier to administer than the parent compound (the active compound). For example, a prodrug may be bioavailable by oral administration whereas the parent compound is not. The prodrug may also have improved solubility in pharmaceutical compositions compared to the parent drug. A prodrug may also be less toxic than the parent. A prodrug may be converted into the parent drug by various mechanisms, including enzymatic processes and metabolic hydrolysis. Harper, N.J. (1962) Drug Latentiation in Jucker, ed. *Progress in Drug Research,* 4:221-294; Morozowich et al. (1977) Application of Physical Organic Principles to Prodrug Design in E. B. Roche ed. *Design of Biopharmaceutical Properties through Prodrugs and Analogs,* APhA; Acad. Pharm. Sci.; E. B. Roche, ed. (1977) *Bioreversible Carriers in Drug in Drug Design, Theory and Application,* APhA; H. Bundgaard, ed. (1985) *Design of Prodrugs,* Elsevier; Wang et al. (1999) Prodrug approaches to the improved delivery of peptide drug, Curr. Pharm. Design. 5(4):265-287; Pauletti et al. (1997) Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996) Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., *Transport Processes in Pharmaceutical Systems*, Marcell Dekker, p. 185-218; Balant et al. (1990) Prodrugs for the improvement of drug absorption via different routes of administration, *Eur. J. Drug Metab. Pharmacokinet.*, 15(2): 143-53; Balimane and Sinko (1999). Involvement of multiple transporters in the oral absorption of nucleoside analogues, *Adv. Drug Delivery Rev.*, 39(1-3): 183-209; Browne (1997). Fosphenytoin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) *Design of Prodrugs*, New York: Elsevier; Fleisher et al. (1996) Improved oral drug delivery: solubility limitations overcome by the use of prodrugs, *Adv. Drug Delivery Rev.* 19(2): 115-130; Fleisher et al. (1985) Design of prodrugs for improved gastrointestinal absorption by intestinal enzyme targeting, *Methods Enzymol.* 112: 360-81; Farquhar D, et al. (1983) Biologically Reversible Phosphate-Protective Groups, *J. Pharm. Sci.*, 72(3): 324-325; Han, H. K. et al. (2000) Targeted prodrug design to optimize drug delivery, *AAPS PharmSci.*, 2(1): E6; Sadzuka Y. (2000) Effective prodrug liposome and conversion to active metabolite, *Curr. Drug Metab.*, 1(1):31-48; D. M. Lambert (2000) Rationale and applications of lipids as prodrug carriers, *Eur. J. Pharm. Sci.*, 11 Suppl. 2:S15-27; Wang, W. et al. (1999) Prodrug approaches to the improved delivery of peptide drugs. *Curr. Pharm. Des.*, 5(4):265-87.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the U.S. Food and Drug Administration. A "pharmaceutically acceptable carrier", as used herein, refers to all components of a pharmaceutical formulation that facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Me). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than 2000 g/mol in molecular weight, less than 1500 g/mol, less than 1000 g/mol, less than 800 g/mol, or less than 500 g/mol. Small molecules are non-polymeric and/or non-oligomeric.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties. "Amphiphilic material" as used herein refers to a material containing a hydrophobic or more hydrophobic oligomer or polymer (e.g., biodegradable oligomer or polymer) and a hydrophilic or more hydrophilic oligomer or polymer.

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. In some embodiments, a targeting moiety can specifically bind to a selected molecule.

The term "reactive coupling group", as used herein, refers to any chemical functional group capable of reacting with a second functional group to form a covalent bond. The selection of reactive coupling groups is within the ability of those in the art. Examples of reactive coupling groups can include primary amines (—NH$_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene and Wuts, Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyryl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2.2-trifluoroethyl, 2,6-dichlorobenzyl, 2-(3,5-dimethoxyphenyl)-2-propyl oxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

The term "activated ester", as used herein, refers to alkyl esters of carboxylic acids where the alkyl is a good leaving group rendering the carbonyl susceptible to nucleophilic attack by molecules bearing amino groups. Activated esters are therefore susceptible to aminolysis and react with amines to form amides. Activated esters contain a carboxylic acid ester group —CO$_2$R where R is the leaving group.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., C$_1$-C$_{30}$ for straight chains, C$_3$-C$_{30}$ for branched chains), 20 or fewer, 12 or fewer, or 7 or fewer. Likewise, in some embodiments cycloalkyls have from 3-10 carbon atoms in their ring structure, e.g., have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. In some embodiments, alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

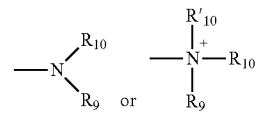

wherein R$_9$, R$_{10}$, and R'$_{10}$ each independently represent a hydrogen, an alkyl, an alkenyl, —(CH$_2$)$_m$—R$_8$ or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In some embodiments, only one of R$_9$ or R$_{10}$ can be a carbonyl, e.g., R$_9$, R$_{10}$ and the nitrogen together do not form an imide. In still other embodiments, the term "amine" does not encompass amides, e.g., wherein one of R$_9$ and R$_{10}$ represents a carbonyl. In additional embodiments, R$_9$ and R$_{10}$ (and optionally R'$_{10}$) each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R$_9$ and R$_{10}$ is an alkyl group.

The term "amido" is art-recognized as an amino-substituted carbonyl and includes a moiety that can be represented by the general formula:

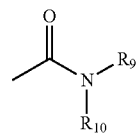

wherein R$_9$ and R$_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, for example, from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, and —CN.

The term "carbonyl" is art-recognized and includes such moieties as can be represented by the general formula:

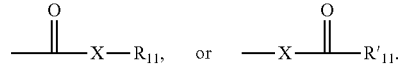

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone"

group. Where X is a bond, and $R_{11}$ is hydrogen, the above formula represents an "aldehyde" group.

The term "monoester" as used herein refers to an analog of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other useful heteroatoms include silicon and arsenic.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, for example, 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation, for example, by rearrangement, cyclization, or elimination.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, $-CN$, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

The term "copolymer" as used herein, generally refers to a single polymeric material that is comprised of two or more different monomers. The copolymer can be of any form, for example, random, block, or graft. The copolymers can have any end-group, including capped or acid end groups.

The term "mean particle size", as used herein, generally refers to the statistical mean particle size (diameter) of the particles in the composition. The diameter of an essentially spherical particle may be referred to as the physical or hydrodynamic diameter. The diameter of a non-spherical particle may refer to the hydrodynamic diameter. As used herein, the diameter of a non-spherical particle may refer to the largest linear distance between two points on the surface of the particle. Mean particle size can be measured using methods known in the art such as dynamic light scattering. Two populations can be said to have a "substantially equivalent mean particle size" when the statistical mean particle size of the first population of particles is within 20% of the statistical mean particle size of the second population of particles; for example, within 15%, or within 10%.

The terms "monodisperse" and "homogeneous size distribution", as used interchangeably herein, describe a population of particles, microparticles, or nanoparticles all having the same or nearly the same size. As used herein, a monodisperse distribution refers to particle distributions in which 90% of the distribution lies within 5% of the mean particle size.

The terms "polypeptide," "peptide" and "protein" generally refer to a polymer of amino acid residues. As used herein, the term also applies to amino acid polymers in which one or more amino acids are chemical analogs or modified derivatives of corresponding naturally-occurring amino acids or are unnatural amino acids. The term "protein", as generally used herein, refers to a polymer of amino acids linked to each other by peptide bonds to form a polypeptide for which the chain length is sufficient to produce tertiary and/or quaternary structure. The term "protein" excludes small peptides by definition, the small peptides lacking the requisite higher-order structure necessary to be considered a protein.

The terms "nucleic acid," "polynucleotide," and "oligonucleotide" are used interchangeably to refer to a deoxyribonucleotide or ribonucleotide polymer, in linear or circular conformation, and in either single- or double-stranded form. These terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general and unless otherwise specified, an analog of a particular nucleotide has the same base-pairing specificity; i.e., an analog of A will base-pair with T. The term "nucleic acid" is a term of art that refers to a string of at least two base-sugar-phosphate monomeric units. Nucleotides are the monomeric units of nucleic acid polymers. The term includes deoxyribonucleic acid (DNA) and ribonucleic acid (RNA) in the form of a messenger RNA, antisense, plasmid DNA, parts of a plasmid DNA or genetic material derived from a virus. An antisense nucleic acid is a polynucleotide that interferes with the expression of a DNA and/or RNA sequence. The term nucleic acids refers to a string of at least two base-sugar-phosphate combinations. Natural nucleic acids have a phosphate backbone. Artificial nucleic acids may contain other types of backbones, but contain the same bases as natural nucleic acids. The term also includes PNAs (peptide nucleic acids), phosphorothioates, and other variants of the phosphate backbone of native nucleic acids.

A "functional fragment" of a protein, polypeptide or nucleic acid is a protein, polypeptide or nucleic acid whose sequence is not identical to the full-length protein, polypeptide or nucleic acid, yet retains at least one function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA binding function of a polypeptide can be determined, for example, by filter-binding, electrophoretic mobility shift, or immunoprecipitation assays. DNA cleavage can be assayed by gel electrophoresis. The ability of a protein to interact with another protein can be determined, for example, by co-immunoprecipitation, two-hybrid assays or complementation, e.g., genetic or biochemical. See, for example, Fields et al. (1989) Nature 340:245-246; U.S. Pat. No. 5,585,245 and PCT WO 98/44350.

As used herein, the term "linker" refers to a carbon chain that can contain heteroatoms (e.g., nitrogen, oxygen, sulfur, etc.) and which may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 atoms long. Linkers may be substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. Those of skill in the art will recognize that each of these groups may in turn be substituted. Examples of linkers include, but are not limited to, pH-sensitive linkers, protease cleavable peptide linkers, nuclease sensitive nucleic acid linkers, lipase sensitive lipid linkers, glycosidase sensitive carbohydrate linkers, hypoxia sensitive linkers, photo-cleavable linkers, heat-labile linkers, enzyme cleavable linkers (e.g., esterase cleavable linker), ultrasound-sensitive linkers, and x-ray cleavable linkers.

The term "pharmaceutically acceptable counter ion" refers to a pharmaceutically acceptable anion or cation. In various embodiments, the pharmaceutically acceptable counter ion is a pharmaceutically acceptable ion. For example, the pharmaceutically acceptable counter ion is selected from citrate, malate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate; ethanesulfonate, benzenesulfonate, p-toluenesulfonate and pamoate (i.e., 1,1'-methylene-bis-(2-hydroxy-3-naphthoate)). In some embodiments, the pharmaceutically acceptable counter ion is selected from chloride, bromide, iodide, nitrate, sulfate, bisulfate, phosphate, acid phosphate, citrate, malate, acetate, oxalate, acetate, and lactate. In particular embodiments, the pharmaceutically acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present compositions. Compounds included in the present compositions that are basic in nature are capable of forming a variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, malate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

If the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

The term "bioavailable" is art-recognized and refers to a form of the subject invention that allows for it, or a portion of the amount administered, to be absorbed by, incorporated to, or otherwise physiologically available to a subject or patient to whom it is administered.

II. Conjugates

Conjugates include an active agent or prodrug thereof attached to a targeting moiety, e.g., a molecule that can bind to an SSTR, by a linker. The conjugates can be a conjugate between a single active agent and a single targeting moiety, e.g., a conjugate having the structure X—Y—Z where X is the targeting moiety, Y is the linker, and Z is the active agent.

In some embodiments the conjugate contains more than one targeting moiety, more than one linker, more than one active agent, or any combination thereof. The conjugate can have any number of targeting moieties, linkers, and active agents. The conjugate can have the structure X—Y—Z—Y—X, $(X-Y)_n$—Z, X—$(Y-Z)_n$, X—Y—$Z_n$, $(X-Y-Z)_n$, $(X-Y-Z-Y)_n$—Z where X is a targeting moiety, Y is a linker, Z is an active agent, and n is an integer between 1 and 50, between 2 and 20, for example, between 1 and 5. Each occurrence of X, Y, and Z can be the same or different, e.g., the conjugate can contain more than one type of targeting moiety, more than one type of linker, and/or more than one type of active agent.

The conjugate can contain more than one targeting moiety attached to a single active agent. For example, the conjugate can include an active agent with multiple targeting moieties each attached via a different linker. The conjugate can have the structure X—Y—Z—Y—X where each X is a targeting moiety that may be the same or different, each Y is a linker that may be the same or different, and Z is the active agent.

The conjugate can contain more than one active agent attached to a single targeting moiety. For example the conjugate can include a targeting moiety with multiple active agents each attached via a different linker. The conjugate can have the structure Z—Y—X-Y—Z where X is the targeting moiety, each Y is a linker that may be the same or different, and each Z is an active agent that may be the same or different.

A. Active Agents

A conjugate as described herein contains at least one active agent (a first active agent). The conjugate can contain more than one active agent, that can be the same or different from the first active agent. The active agent can be a therapeutic, prophylactic, diagnostic, or nutritional agent. A variety of active agents are known in the art and may be used in the conjugates described herein. The active agent can be a protein or peptide, small molecule, nucleic acid or nucleic acid molecule, lipid, sugar, glycolipid, glycoprotein, lipoprotein, or combination thereof. In some embodiments, the active agent is an antigen, an adjuvant, radioactive, an imaging agent (e.g., a fluorescent moiety) or a polynucleotide. In some embodiments the active agent is an organometallic compound.

Anti-Cancer-Agents

The active agent can be a cancer therapeutic. Cancer therapeutics include, for example, death receptor agonists such as the TNF-related apoptosis-inducing ligand (TRAIL) or Fas ligand or any ligand or antibody that binds or activates a death receptor or otherwise induces apoptosis. Suitable death receptors include, but are not limited to, TNFR1, Fas, DR3, DR4, DR5, DR6, LTβR and combinations thereof.

Cancer therapeutics such as chemotherapeutic agents, cytokines, chemokines, and radiation therapy agents can be used as active agents. Chemotherapeutic agents include, for example, alkylating agents, antimetabolites, anthracyclines, plant alkaloids, topoisomerase inhibitors, and other antitumor agents. Such agents typically affect cell division or DNA synthesis and function. Additional examples of therapeutics that can be used as active agents include monoclonal antibodies and the tyrosine kinase inhibitors e.g. imatinib mesylate, which directly targets a molecular abnormality in certain types of cancer (e.g., chronic myelogenous leukemia, gastrointestinal stromal tumors).

Chemotherapeutic agents include, but are not limited to cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab, cetuximab, and rituximab, bevacizumab, and combinations thereof. Any of these may be used as an active agent in a conjugate.

In some embodiments, the active agent can be 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, anti estrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cabazitaxel, cactinomycin, calcipotriol, calphostin C, calusterone, camptothecin, camptothecin derivatives, canarypox IL-2, capecitabine, caracemide, carbetimer, carboplatin, carboxamide-amino-tri azole, carboxyamidotriazole, carest M3, carmustine, earn 700, cartilage derived inhibitor, carubicin hydrochloride, carzelesin, casein kinase inhibitors, castano spermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, larotaxel, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, maytansinoid, mertansine (DM1), mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/mycobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum(IV) complexes, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxy ethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, siRNA, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

In some embodiments the active agent is cabazitaxel, or an analog, derivative, prodrug, or pharmaceutically acceptable salt thereof.

The active agent can be an inorganic or organometallic compound containing one or more metal centers. In some examples, the compound contains one metal center. The active agent can be, for example, a platinum compound, a ruthenium compound (e.g., trans-[RuCl$_2$ (DMSO)$_4$], or trans-[RuCl$_4$(imidazole)]$_2$, etc.), cobalt compound, copper compound, or iron compounds.

In certain embodiments, the active agent of the conjugate comprises a predetermined molar weight percentage from about 1% to about 10%, or about 10% to about 20%, or about 20% to about 30%, or about 30% to about 40%, or about 40% to about 50%, or about 50% to about 60%, or about 60% to about 70%, or about 70% to about 80%, or about 80% to about 90%, or about 90% to about 99% such that the sum of the molar weight percentages of the components of the conjugate is 100%. The amount of active agent(s) of the conjugate may also be expressed in terms of proportion to the targeting ligand(s). For example, the present teachings provide a ratio of active agent to ligand of about 10:1, 9:1, 8:1, 7:1, 6:1, 5:1, 4:1, 3:1, 2:1, 1:1, 1:2, 1:3, 1:4; 1:5, 1:6, 1:7, 1:8, 1:9, or 1:10.

B. Targeting Moieties

Targeting ligands (also referred to as targeting moieties) as described herein include any molecule that can bind one or more SSTRs, e.g., human SSTR1, SSTR2, SSTR3, SSTR4, or SSTR5. Such targeting ligands can be peptides, antibody mimetics, nucleic acids (e.g., aptamers), polypeptides (e.g., antibodies), glycoproteins, small molecules, carbohydrates, or lipids. In some embodiments, the targeting moiety is somatostatin or a somatostatin analog.

The cytotoxic or therapeutic conjugates of the invention can employ any somatostatin analog that binds somatostatin receptor. In some embodiments, the somatostatin analog portion of the conjugate contains between 8 and 18 amino acids, and includes the core sequence: cyclo[Cys-Phe-D-Trp-Lys-Thr-Cys] (SEQ ID NO:1) or cyclo[Cys-Tyr-D-Trp-Lys-Thr-Cys] (SEQ ID NO. 2). For example, the C-terminus of the analog is Thr-NH2.

In some embodiments, the targeting moiety, X, may be selected from somatostatin, octreotide, Tyr$^3$-octreotate (TATE), vapreotide, cyclo(AA-Tyr-DTrp-Lys-Thr-Phe) where AA is α-N-Me lysine or N-Me glutamic acid, pasireotide, lanreotide, seglitide, or any other example of somatostatin receptor binding ligands. In some embodiments, the targeting moiety is a somatostatin receptor binding moiety that binds to somatostatin receptors 2 and/or 5. In some embodiments, X binds to the linker moiety Y at the C-terminal. In some embodiments, X binds to the linker moiety Y at the N-terminal. In some embodiments, the targeting moiety X comprises at least one D-Phe residue and the phenyl ring of the D-Phe residue of the targeting moiety X has been replaced by a linker-containing moiety.

Examples of somatostatin analogs that are peptides useful in the present invention are described herein. Further examples useful somatostatin analogs are disclosed in publications set forth below, each of which is hereby incorporated by reference in its entirety:

PCT Application No. WO 03/057214 (2003)
U.S. Application No. 20030191134 (2003)
U.S. Application No. 20030083241 (2003)
U.S. Pat. No. 6,316,414 (2001)
PCT Application No. WO 02/10215 (2002)
PCT Application No. WO 99/22735 (1999)
PCT Application No. WO 98/08100 (1998)
PCT Application No. WO 98/44921 (1998)
PCT Application No. WO 98/45285 (1998)
PCT Application No. WO 98/44922 (1998)
EP Application No. P5164 EU (Inventor: G. Keri);
Van Binst, G. et al., Peptide Research, 1992, 5:8;
Horvath, A. et al., Abstract, "Conformations of Somatostatin Analogs Having Antitumor Activity", 22nd European peptide Symposium, Sep. 13-19, 1992, Interlaken, Switzerland;
PCT Application No. WO 91/09056 (1991);
EP Application No. 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application No. 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,199 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);

PCT Application No. WO 90/12811 (1990);
PCT Application No. WO 97/01579 (1997);
PCT Application No. WO 91/18016 (1991);
U.K. Application No. GB 2,095,261 (1981);
French Application No. FR 2,522,655 (1983); and
PCT Application No. WO 04/093807 (2004).
U.S. Pat. No. 5,620,955 (1997)
U.S. Pat. No. 5,723,578 (1998)
U.S. Pat. No. 5,843,903 (1998)
U.S. Pat. No. 5,877,277 (1999)
U.S. Pat. No. 6,156,725 (2000)
U.S. Pat. No. 6,307,017 (2001)
PCT Application No. WO 90/03980 (1990)
PCT Application No. WO 91/06563 (1991)
PCT Application No. WO 91/17181 (1991)
PCT Application No. WO 94/02018 (1994)
PCT Application No. WO 94/21674 (1994)
PCT Application No. WO 04/093807 (2004);

Methods for synthesizing somatostatin peptides and analogs are well documented and are within the ability of a person of ordinary skill in the art as exemplified in the references listed supra. Further synthetic procedures are provided in the following examples. The following examples also illustrate methods for synthesizing the targeted cytotoxic compounds of the present invention. Specific targeting of therapeutic or cytotoxic agents allows selective destruction of a tumor expressing a receptor specific for a biologically active peptide. For example, a tumor expressing a somatostatin receptor includes a neoplasm of the lung, breast, prostate, colon, brain, gastrointestinal tract, neuroendocrine axis, liver, or kidney (see Schaer et al., Int. J. Cancer, 70:530-537, 1997; Chave et al., Br. J. Cancer 82(1):124-130, 2000; Evans et al., Br. J. Cancer 75(6):798-803, 1997).

In some embodiments, the targeting moiety has therapeutic features, e.g., the targeting moiety is cytotoxic or anti-angiogenic. In some embodiments, a targeting moiety has some increased affinity for tumor vasculature, or angiogenic blood vessels, e.g., those that over-express somatostatin receptors (see Denzler and Reubi, Cancer 85:188-198, 1999; Gulec et al., J. Surg. Res. 97(2):131-137, 2001; Woltering et al., J. Surg. Res. 50:245, 1991).

In some embodiments, the targeting moiety, e.g., somatostatin analog, used in the invention is hydrophilic, and is therefore water soluble. In some embodiments, such conjugates and particles containing such conjugates are used in treatment paradigms in which this feature is useful, e.g., compared to conjugates comprising hydrophobic analogs. Hydrophilic analogs described herein can be soluble in blood, cerebrospinal fluid, and other bodily fluids, as well as in urine, which may facilitate excretion by the kidneys. This feature can be useful, e.g., in the case of a composition that would otherwise exhibit undesirable liver toxicity. The invention also discloses specific hydrophilic elements (e.g., incorporation of a PEG linker, and other examples in the art) for incorporation into peptide analogs, allowing modulation of the analog's hydrophilicity to adjust for the chemical and structural nature of the various conjugated cytotoxic agents, e.g., conjugate 6 infra.

In some embodiments, the targeting moiety is an antibody mimetic such as a monobody, e.g., an ADNECTIN™ (Bristol-Myers Squibb, New York, N.Y.), an Affibody® (Affibody AB, Stockholm, Sweden), Affilin, nanofitin (affitin, such as those described in WO 2012/085861, an Anticalin™, an avimers (avidity multimers), a DARPin™, a Fynomer™, Centyrin™ and a Kunitz domain peptide. In certain cases, such mimetics are artificial peptides or proteins with a molar mass of about 3 to 20 kDa. Nucleic acids and small molecules may be antibody mimetic.

In another example, a targeting moiety can be an aptamer, which is generally an oligonucleotide (e.g., DNA, RNA, or an analog or derivative thereof) that binds to a particular target, such as a polypeptide. In some embodiments, the targeting moiety is a polypeptide (e.g., an antibody that can specifically bind a tumor marker). In certain embodiments, the targeting moiety is an antibody or a fragment thereof. In certain embodiments, the targeting moiety is an Fc fragment of an antibody.

In certain embodiments, the targeting moiety or moieties of the conjugate are present at a predetermined molar weight percentage from about 0.1% to about 10%, or about 1% to about 10%, or about 10% to about 20%, or about 20% to about 30%, or about 30% to about 40%, or about 40% to about 50%, or about 50% to about 60%, or about 60% to about 70%, or about 70% to about 80%, or about 80% to about 90%, or about 90% to about 99% such that the sum of the molar weight percentages of the components of the conjugate is 100%. The amount of targeting moieties of the conjugate may also be expressed in terms of proportion to the active agent(s), for example, in a ratio of ligand to active agent of about 10:1, 9:1, 8:1, 7:1, 6:1, 5:1, 4:1, 3:1, 2:1, 1:1, 1:2, 1:3, 1:4; 1:5, 1:6, 1:7, 1:8, 1:9, or 1:10.

C. Linkers

The conjugates contain one or more linkers attaching the active agents and targeting moieties. The linker, Y, is bound to one or more active agents and one or more targeting ligands to form a conjugate. The linker Y is attached to the targeting moiety X and the active agent Z by functional groups independently selected from an ester bond, disulfide, amide, acylhydrazone, ether, carbamate, carbonate, and urea. Alternatively the linker can be attached to either the targeting ligand or the active drug by a non-cleavable group such as provided by the conjugation between a thiol and a maleimide, an azide and an alkyne. The linker is independently selected from the group consisting alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heterocyclyl, heteroaryl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

In some embodiments, the linker comprises a cleavable functionality that is cleavable. The cleavable functionality may be hydrolyzed in vivo or may be designed to be hydrolyzed enzymatically, for example by Cathepsin B. A "cleavable" linker, as used herein, refers to any linker which can be cleaved physically or chemically. Examples for physical cleavage may be cleavage by light, radioactive emission or heat, while examples for chemical cleavage include cleavage by re-dox-reactions, hydrolysis, pH-dependent cleavage or cleavage by enzymes.

In some embodiments the alkyl chain of the linker may optionally be interrupted by one or more atoms or groups selected from —O—, —C(=O)—, —NR, —O—C(=O)—NR—, —S—, —S—S—. The linker may be selected from dicarboxylate derivatives of succinic acid, glutaric acid or diglycolic acid. In some embodiments, the linker Y may be X'—R¹—Y'—R²—Z' and the conjugate can be a compound according to Formula Ia:

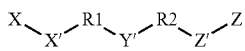

wherein X is a targeting moiety defined above; Z is an active agent; X', R¹, Y', R² and Z' are as defined herein.

X' is either absent or independently selected from carbonyl, amide, urea, amino, ester, aryl, arylcarbonyl, aryloxy, arylamino, one or more natural or unnatural amino acids, thio or succinimido; R¹ and R² are either absent or comprised of alkyl, substituted alkyl, aryl, substituted aryl, polyethylene glycol (2-30 units); Y' is absent, substituted or unsubstituted 1,2-diaminoethane, polyethylene glycol (2-30 units) or an amide; Z' is either absent or independently selected from carbonyl, amide, urea, amino, ester, aryl, arylcarbonyl, aryloxy, arylamino, thio or succinimido. In some embodiments, the linker can allow one active agent molecule to be linked to two or more ligands, or one ligand to be linked to two or more active agent molecules.

In some embodiments, the linker Y may be $A_m$ and the conjugate can be a compound according to Formula Ib:

wherein A is defined herein, m=0-20.

A in Formula Ia is a spacer unit, either absent or independently selected from the following substituents. For each substituent, the dashed lines represent substitution sites with X, Z or another independently selected unit of A wherein the X, Z, or A can be attached on either side of the substituent:

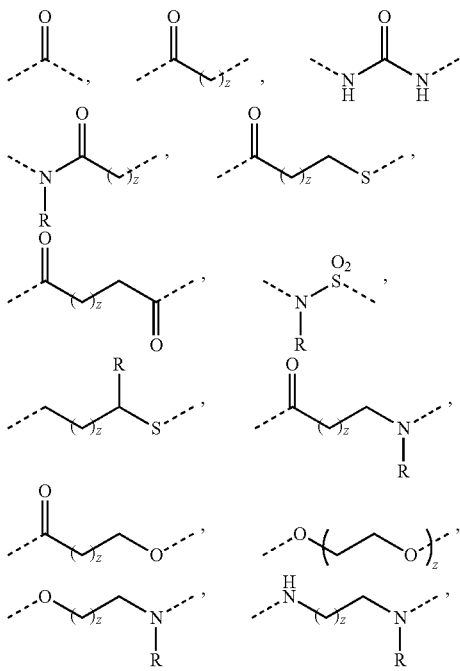

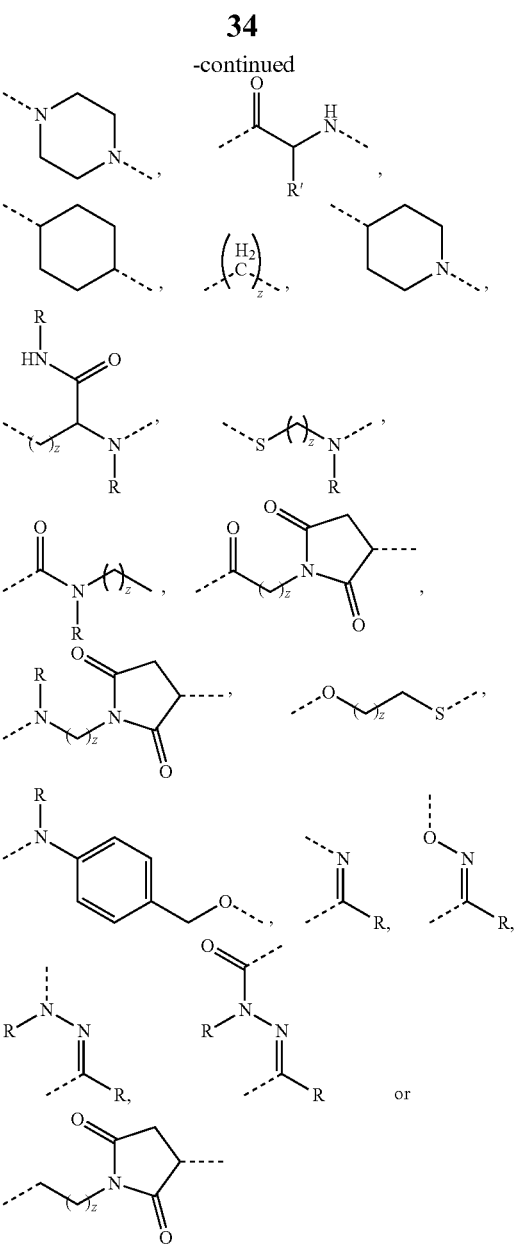

wherein z=0-40, R is H or an optionally substituted alkyl group, and R' is any side chain found in either natural or unnatural amino acids.

In some embodiments, the conjugate may be a compound according to Formula Ic:

$$\left( X \diagdown_{A_m} \right)_x - C - \left( _{A_n} \diagup^Z \right)_y \qquad \text{Ic}$$

wherein A is defined above, m=0-40, n=0-40, x=1-5, y=1-5, and C is a branching element defined herein.

C in Formula Ic is a branched unit containing three to six functionalities for covalently attaching spacer units, ligands, or active drugs, selected from amines, carboxylic acids, thiols, or succinimides, including amino acids such as lysine, 2,3-diaminopropanoic acid, 2,4-diaminobutyric acid, glutamic acid, aspartic acid, and cysteine.

Non-limiting examples of conjugates of the present invention include the following compounds:
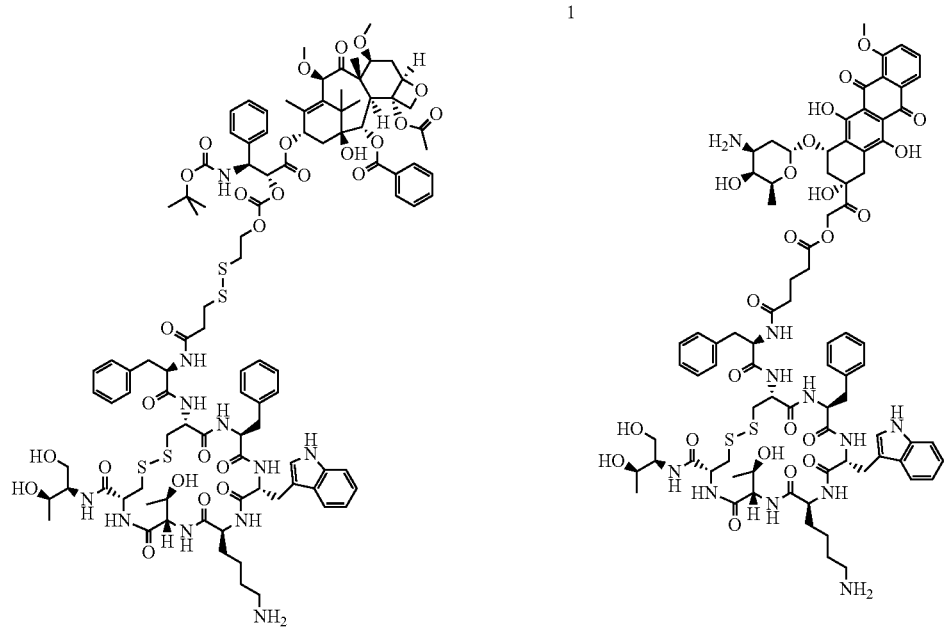
1
2
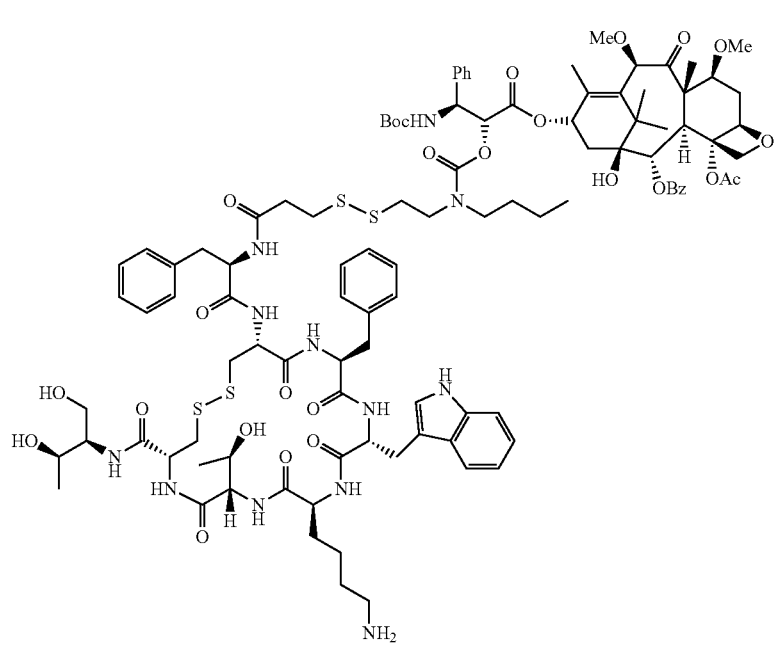
3

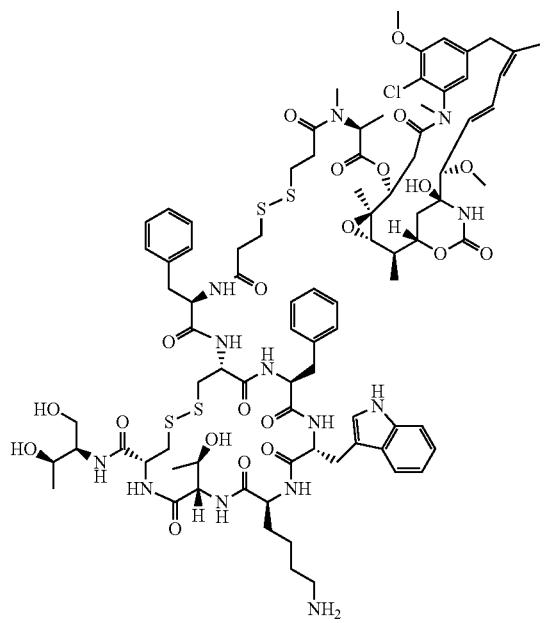
4
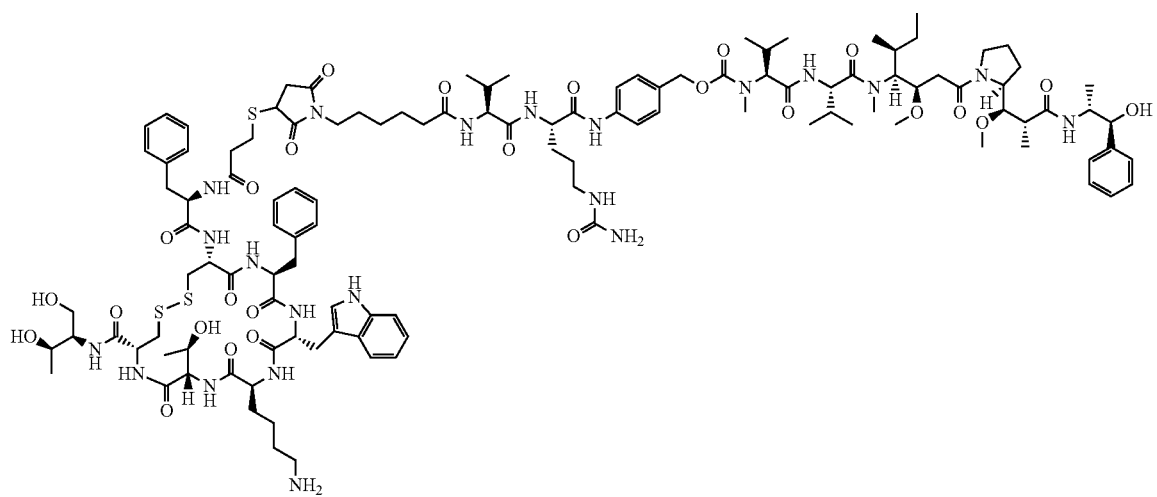
5

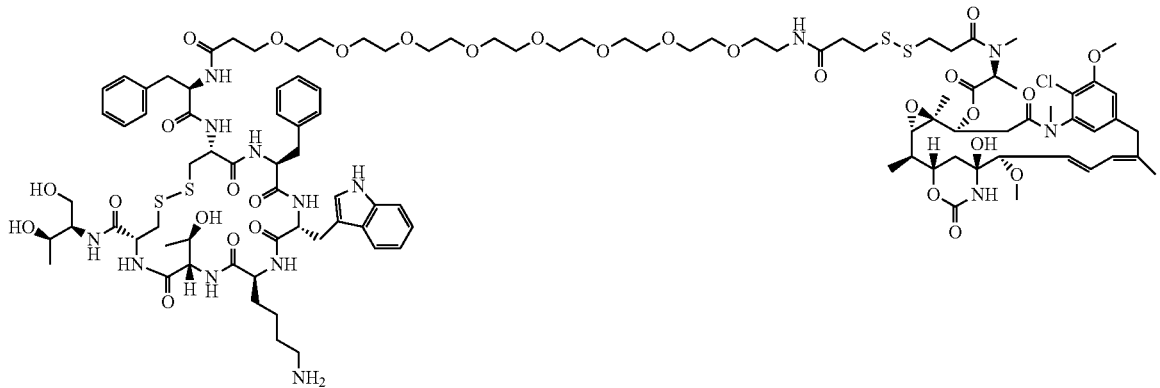

6

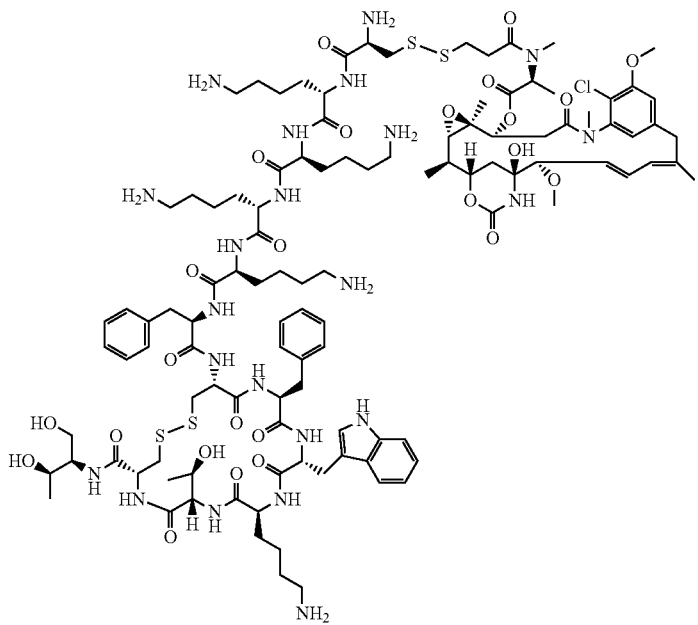

7

In some embodiments, the active agent Z is DM1 and the somatostatin receptor binding agent X is selected from somatostatin, cyclo(AA-Tyr-DTrp-Lys-Thr-Phe), vapreotide or TATE. In some embodiments, DM1 is connected to the C-terminus of X with the linker Y. In some embodiments, DM1 is connected to the N-terminus of X with the linker Y. In some embodiments, DM1 is connected to X with the linker Y, wherein the targeting moiety X comprises at least one D-Phe residue and the phenyl ring of the D-Phe residue has been replaced by a group containing linker Y.

Non-limiting examples of conjugates comprising DM1, referred to as DM1 conjugates of the invention, include the following compounds:

1) Cyclo(AA-Tyr-DTrp-Lys-Thr-Phe)-Based DM1 Conjugates

In some embodiments, cyclo(AA-Tyr-DTrp-Lys-Thr-Phe) is used as a somatostatin receptor targeting moiety and the conjugates have a general structure of:

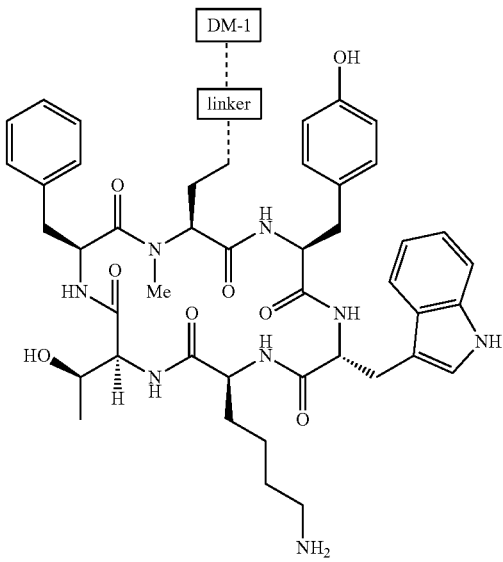

8

In some embodiments, the targeting moiety contains an amino acid capable of making an amide bond. In some embodiments, the linker is bound to the targeting moiety via an amide bond, i.e., —NH—CO—, or —CO—NH— (the hydrogen on the nitrogen may be substituted). In some embodiments, the linker is not bound to the targeting moiety via an amide bond. In some embodiments, the linker includes an amide bond, i.e., —NH—CO—, or —CO—NH— (the hydrogen on the nitrogen may be substituted).

Non-limiting examples of conjugates comprising cyclo (AA-Tyr-DTrp-Lys Thr-Phe) and DM1 are shown in Table 1:

TABLE 1 cyclo(AA-Tyr-DTrp-Lys-Thr-Phe)-based Conjugates

| Linker* | Full structure |
| --- | --- |
| 9 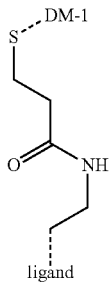 | 10 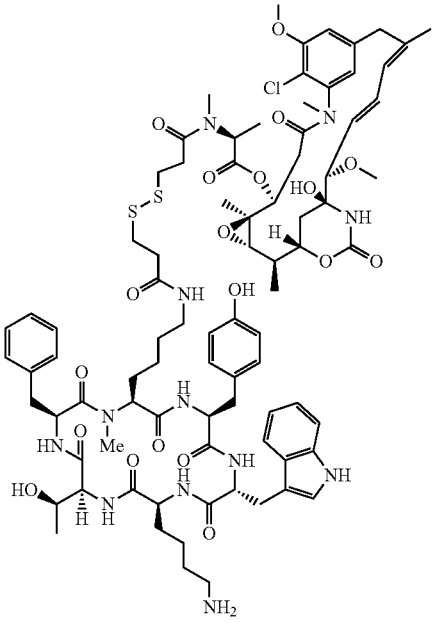 [SMILES: COc1cc2cc(c1Cl)N(C)C(=O)C[C@H](OC(=O)[C@H](C)N(C)C(=O)CCSSCCC(=O)NCCCC[C@H]1C(=O)N[C@@H](Cc3ccc(O)cc3)C(=O)N[C@H](Cc3c[nH]c4ccccc34)C(=O)N[C@@H](CCCCN)C(=O)N[C@@H]([C@@H](C)O)C(=O)N[C@@H](Cc3ccccc3)C(=O)N1C)[C@]1(C)O[C@H]1[C@H](C)[C@@H]1C[C@@](O)(NC(=O)O1)[C@H](OC)/C=C/C=C(\C)C2] |
| 11 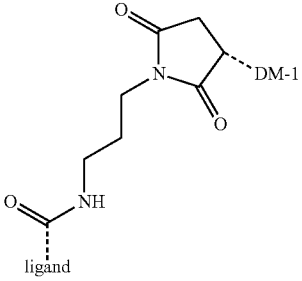 | 12 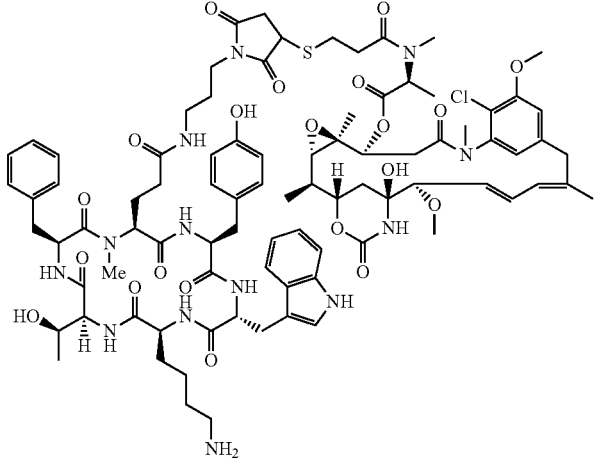 [SMILES: COc1cc2cc(c1Cl)N(C)C(=O)C[C@H](OC(=O)[C@H](C)N(C)C(=O)CCSC1CC(=O)N(CCCNC(=O)CC[C@H]3C(=O)N[C@@H](Cc4ccc(O)cc4)C(=O)N[C@H](Cc4c[nH]c5ccccc45)C(=O)N[C@@H](CCCCN)C(=O)N[C@@H]([C@@H](C)O)C(=O)N[C@@H](Cc4ccccc4)C(=O)N3C)C1=O)[C@]1(C)O[C@H]1[C@H](C)[C@@H]1C[C@@](O)(NC(=O)O1)[C@H](OC)/C=C/C=C(\C)C2] |

TABLE 1-continued
cyclo(AA-Tyr-DTrp-Lys-Thr-Phe)-based Conjugates
| Linker* | Full structure |
|---|---|
| 13 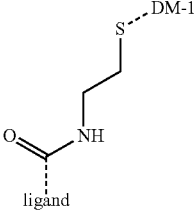 | 14 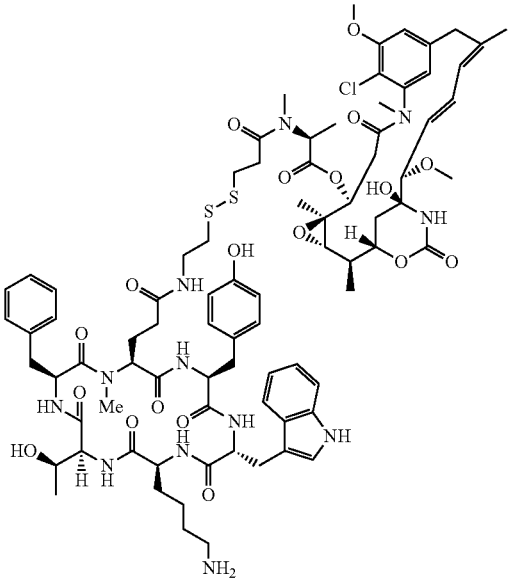 [SMILES: COc1cc2cc(c1Cl)N(C)C(=O)C[C@H](OC(=O)[C@H](C)N(C)C(=O)CCSSCCNC(=O)CC[C@H]1C(=O)N[C@@H](Cc3ccc(O)cc3)C(=O)N[C@H](Cc3c[nH]c4ccccc34)C(=O)N[C@@H](CCCCN)C(=O)N[C@@H]([C@@H](C)O)C(=O)N[C@@H](Cc3ccccc3)C(=O)N1C)[C@]1(C)O[C@H]1[C@H](C)[C@@H]1C[C@@](O)(NC(=O)O1)[C@H](OC)/C=C/C=C(\C)C2] |
| 15 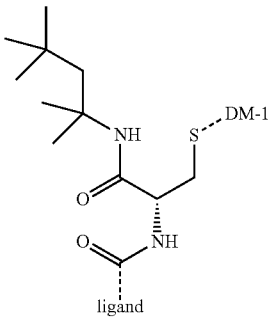 | 16 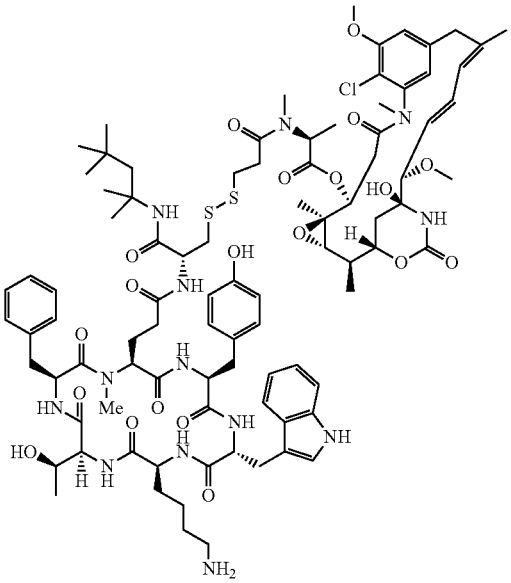 [SMILES: COc1cc2cc(c1Cl)N(C)C(=O)C[C@H](OC(=O)[C@H](C)N(C)C(=O)CCSSC[C@H](NC(=O)CC[C@H]1C(=O)N[C@@H](Cc3ccc(O)cc3)C(=O)N[C@H](Cc3c[nH]c4ccccc34)C(=O)N[C@@H](CCCCN)C(=O)N[C@@H]([C@@H](C)O)C(=O)N[C@@H](Cc3ccccc3)C(=O)N1C)C(=O)NC(C)(C)CC(C)(C)C)[C@]1(C)O[C@H]1[C@H](C)[C@@H]1C[C@@](O)(NC(=O)O1)[C@H](OC)/C=C/C=C(\C)C2] |

TABLE 1-continued
cyclo(AA-Tyr-DTrp-Lys-Thr-Phe)-based Conjugates
| Linker* | Full structure |
|---|---|
| 17 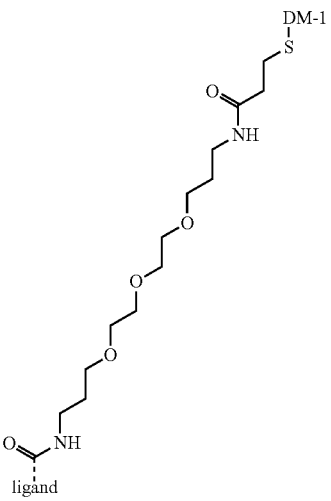 | 18 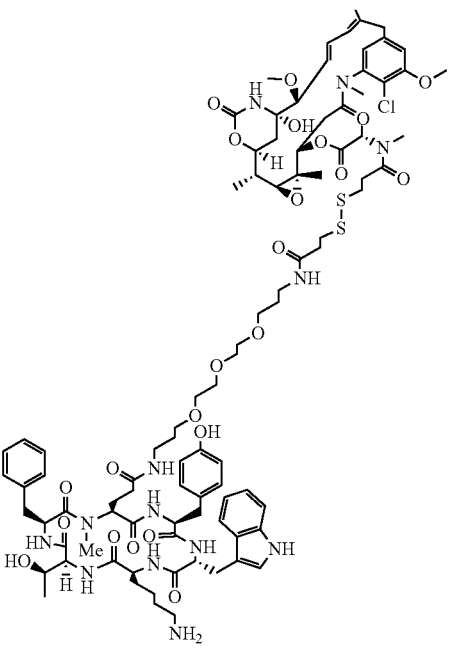 [SMILES: COc1cc2cc(c1Cl)N(C)C(=O)C[C@H](OC(=O)[C@H](C)N(C)C(=O)CCSSCCC(=O)NCCCOCCOCCOCCCNC(=O)CC[C@H]1C(=O)N[C@@H](Cc3ccc(O)cc3)C(=O)N[C@H](Cc3c[nH]c4ccccc34)C(=O)N[C@@H](CCCCN)C(=O)N[C@@H]([C@@H](C)O)C(=O)N[C@@H](Cc3ccccc3)C(=O)N1C)[C@]1(C)O[C@H]1[C@H](C)[C@@H]1C[C@@](O)(NC(=O)O1)[C@H](OC)/C=C/C=C(\C)C2] |
| 19 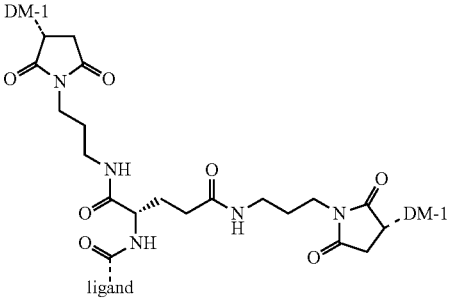 | 20 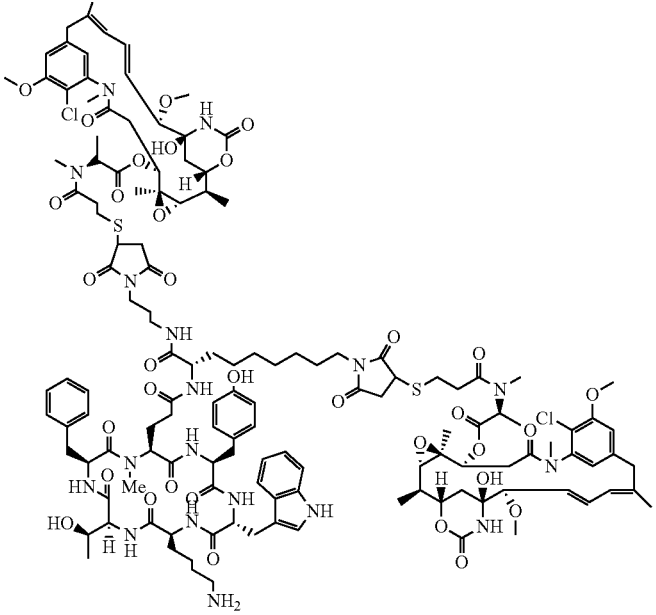 |

TABLE 1-continued
cyclo(AA-Tyr-DTrp-Lys-Thr-Phe)-based Conjugates
| Linker* | Full structure |
| --- | --- |
| 21 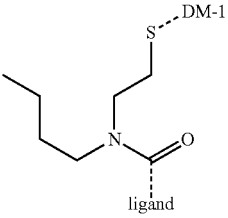 | 22 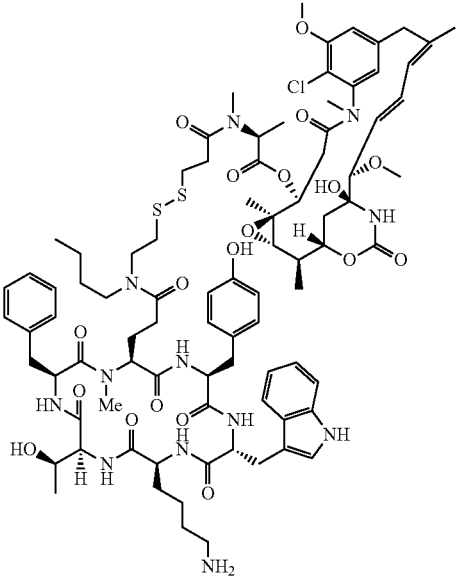 [SMILES: CCCCN(CCSSCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C)C(=O)CC[C@H]1C(=O)N[C@@H](Cc2ccc(O)cc2)C(=O)N[C@H](Cc2c[nH]c3ccccc23)C(=O)N[C@@H](CCCCN)C(=O)N[C@@H]([C@@H](C)O)C(=O)N[C@@H](Cc2ccccc2)C(=O)N1C] |
| 23 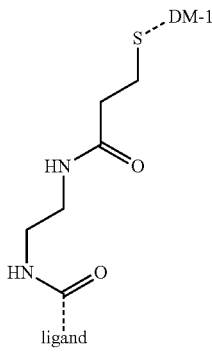 | 24 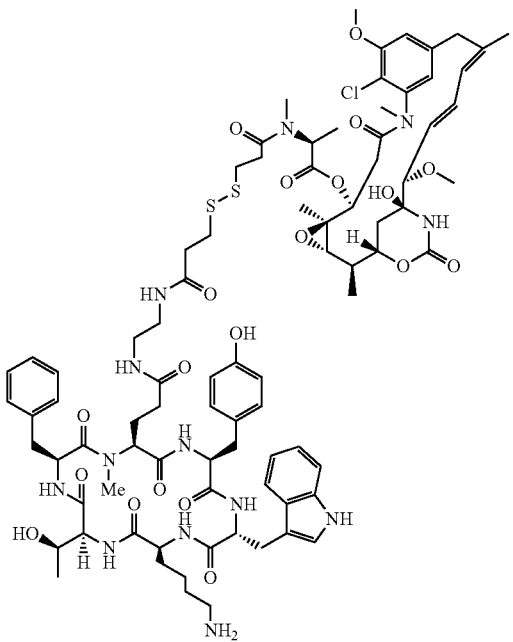 [SMILES: COc1cc2cc(c1Cl)N(C)C(=O)C[C@H](OC(=O)[C@H](C)N(C)C(=O)CCSSCCC(=O)NCCNC(=O)CC[C@H]1C(=O)N[C@@H](Cc3ccc(O)cc3)C(=O)N[C@H](Cc3c[nH]c4ccccc34)C(=O)N[C@@H](CCCCN)C(=O)N[C@@H]([C@@H](C)O)C(=O)N[C@@H](Cc3ccccc3)C(=O)N1C)[C@]1(C)O[C@H]1[C@H](C)[C@@H]1C[C@@](O)(NC(=O)O1)[C@H](OC)/C=C/C=C(\C)C2] |

TABLE 1-continued
cyclo(AA-Tyr-DTrp-Lys-Thr-Phe)-based Conjugates
| Linker* | Full structure |
| --- | --- |
| 25 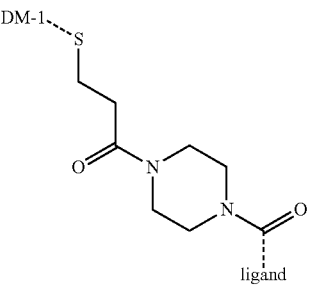 | 26 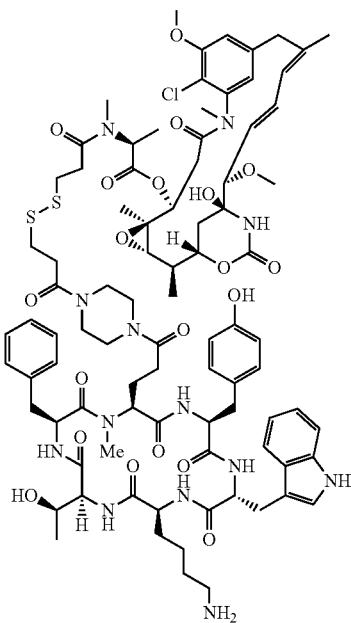 [SMILES: COc1cc2cc(c1Cl)N(C)C(=O)C[C@H](OC(=O)[C@H](C)N(C)C(=O)CCSSCCC(=O)N1CCN(C(=O)CC[C@H]3C(=O)N[C@@H](Cc4ccc(O)cc4)C(=O)N[C@H](Cc4c[nH]c5ccccc45)C(=O)N[C@@H](CCCCN)C(=O)N[C@@H]([C@@H](C)O)C(=O)N[C@@H](Cc4ccccc4)C(=O)N3C)CC1)[C@]1(C)O[C@H]1[C@H](C)[C@@H]1C[C@@](O)(NC(=O)O1)[C@H](OC)/C=C/C=C(\C)C2] |
| 27 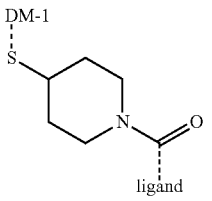 | 28 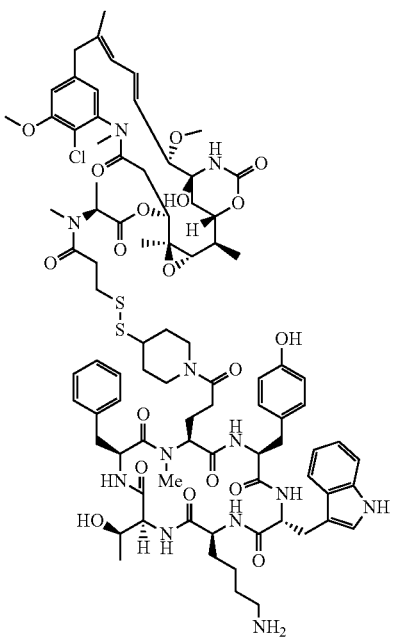 [SMILES: COc1cc2cc(c1Cl)N(C)C(=O)C[C@H](OC(=O)[C@H](C)N(C)C(=O)CCSSC1CCN(C(=O)CC[C@H]3C(=O)N[C@@H](Cc4ccc(O)cc4)C(=O)N[C@H](Cc4c[nH]c5ccccc45)C(=O)N[C@@H](CCCCN)C(=O)N[C@@H]([C@@H](C)O)C(=O)N[C@@H](Cc4ccccc4)C(=O)N3C)CC1)[C@]1(C)O[C@H]1[C@H](C)[C@@H]1C[C@@](O)(NC(=O)O1)[C@H](OC)/C=C/C=C(\C)C2] |

TABLE 1-continued cyclo(AA-Tyr-DTrp-Lys-Thr-Phe)-based Conjugates

| Linker* | Full structure |
|---|---|
| 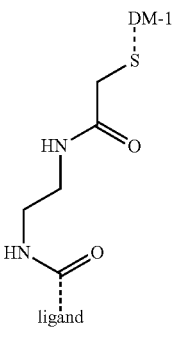 29 | 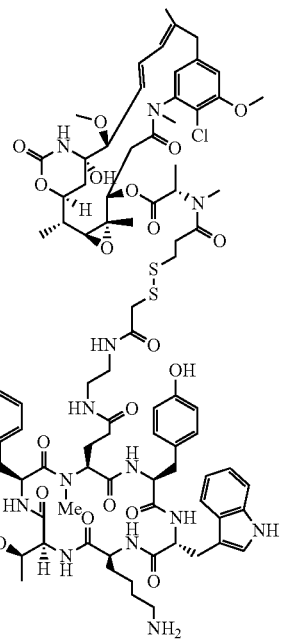 30 |
| 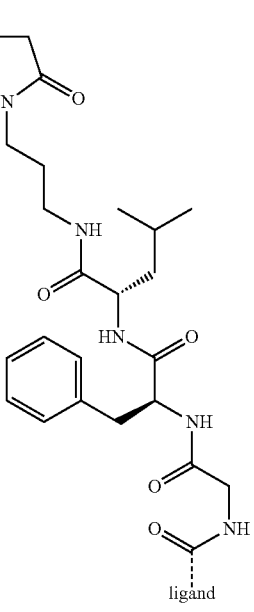 31 | 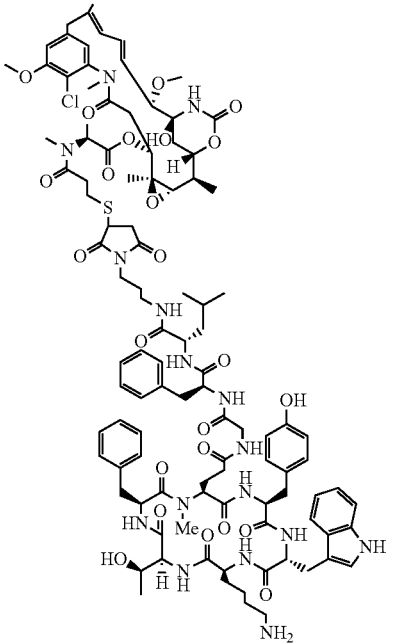 [SMILES: COc1cc2cc(c1Cl)N(C)C(=O)C[C@H](OC(=O)[C@H](C)N(C)C(=O)CCSC1CC(=O)N(CCCNC(=O)[C@H](CC(C)C)NC(=O)[C@H](Cc3ccccc3)NC(=O)CNC(=O)CC[C@H]3C(=O)N[C@@H](Cc4ccc(O)cc4)C(=O)N[C@H](Cc4c[nH]c5ccccc45)C(=O)N[C@@H](CCCCN)C(=O)N[C@@H]([C@@H](C)O)C(=O)N[C@@H](Cc4ccccc4)C(=O)N3C)C1=O)[C@]1(C)O[C@H]1[C@H](C)[C@@H]1C[C@@](O)(NC(=O)O1)[C@H](OC)/C=C/C=C(\C)C2] 32 |

*In order to show linker structures, the somatostatin receptor targeting moiety is referred to as ligand in the structures.

2) C-Terminal DM1 Conjugates:

In some embodiments, the somatostatin receptor targeting moiety is a peptide and the linker binds to the C-terminus of the somatostatin receptor targeting moiety. In some embodiments, the somatostatin receptor targeting moiety is TATE or a TATE derivative, wherein the linker binds to the C-terminus of TATE or the TATE derivative. The C-terminal DM1 conjugates have a general structure of:

wherein R is selected from H, alkyl, aryl, carbonyl, amide, alcohol, or amine, optionally substituted with one or more groups; and Ar$_1$ and Ar$_2$ are independently selected from heterocyclyl, aryl, and heteroaryl groups optionally substituted with one or more groups.

In some embodiments, the covalent bond connecting the linker and the C-terminus of the somatostatin receptor targeting moiety is an amide bond.

Non-limiting examples of DM1 conjugates wherein the linker binds to the C-terminus of the somatostatin receptor targeting moiety, wherein the somatostatin receptor targeting moiety is TATE, are shown in Table 2:

TABLE 2
C-terminal DM1-TATE conjugates
| R | Ar1 | Ar2 | Linker* | Full Structure |
|---|---|---|---|---|
| H | 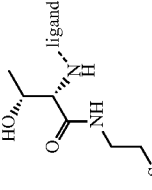 | 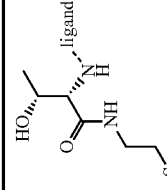 | 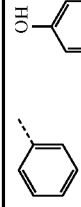 34 |  35 |
| H | 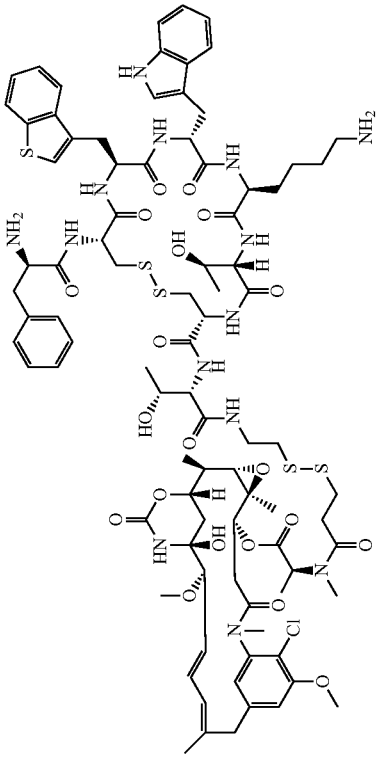 | 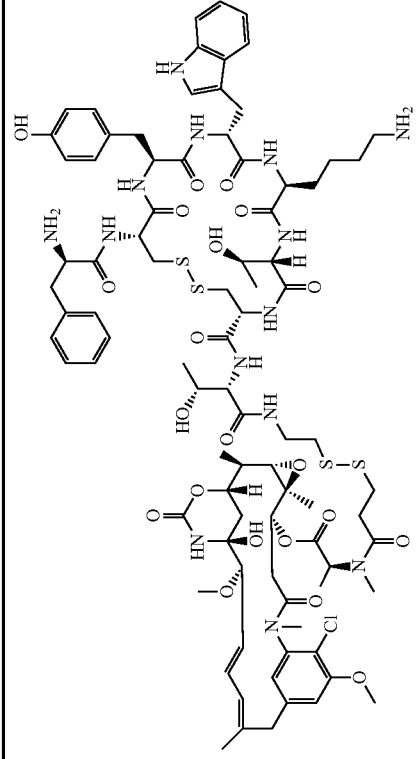 | 36 | 37 |

TABLE 2-continued
C-terminal DM1-TATE conjugates
| R | Ar1 | Ar2 | Linker* | Full Structure |
|---|---|---|---|---|
| H | 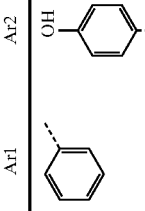 |  | 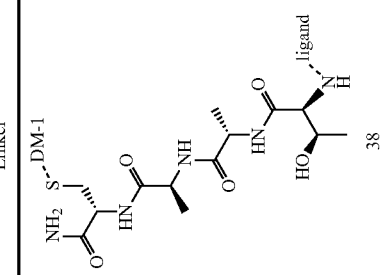 38 | 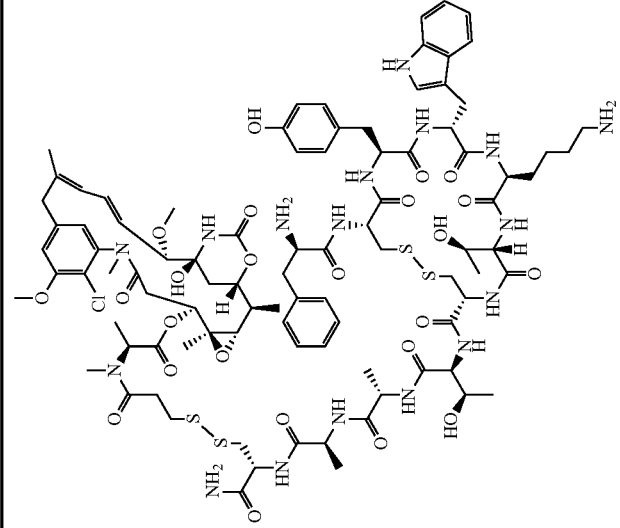 39 |

TABLE 2-continued
C-terminal DM1-TATE conjugates
| R | Ar1 | Ar2 | Linker* | Full Structure |
|---|---|---|---|---|
| H |  | 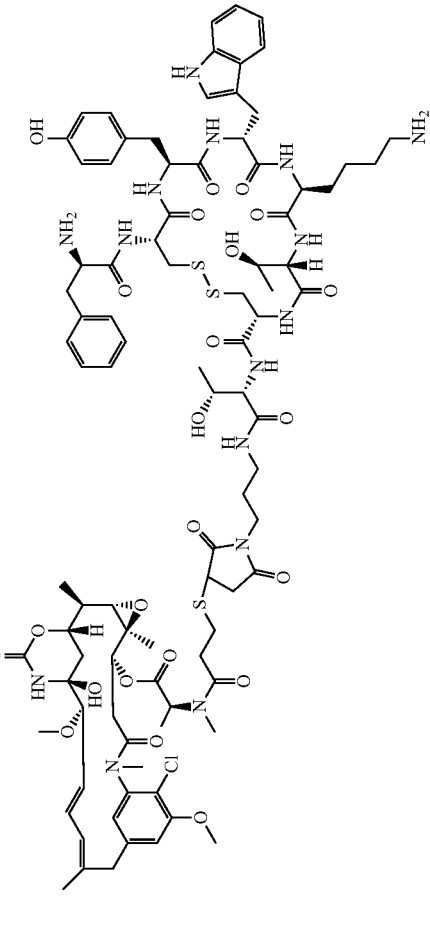 |  40 | 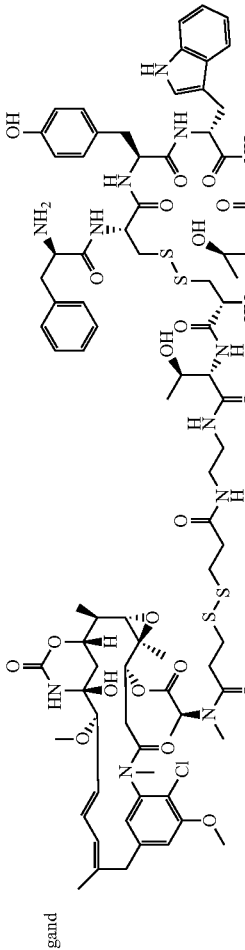 41 |
| H |  | 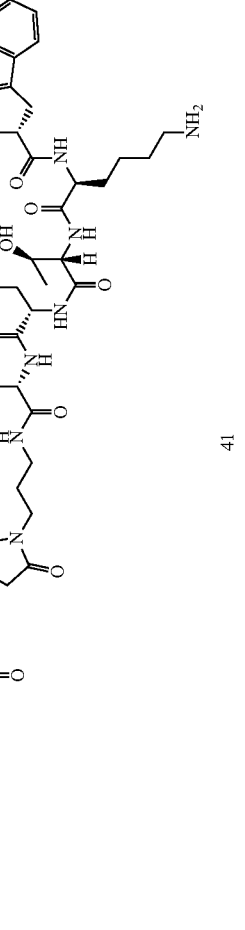 |  42 |  43 |

TABLE 2-continued
C-terminal DM1-TATE conjugates
| R | Ar1 | Ar2 | Linker* | Full Structure |
|---|-----|-----|---------|----------------|
| H |  |  | 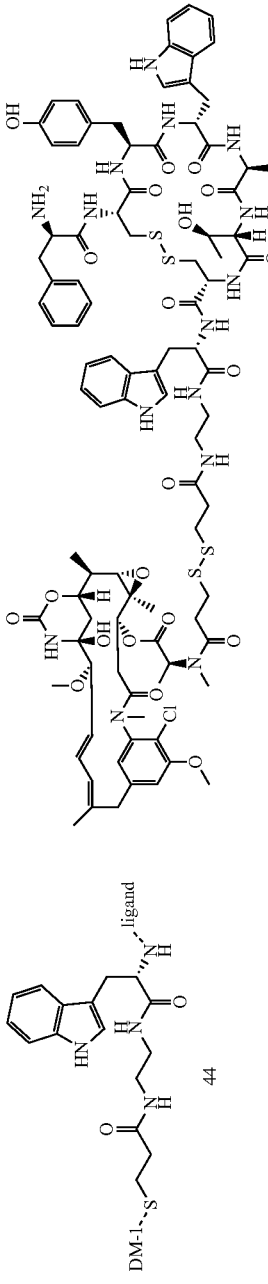 44 | 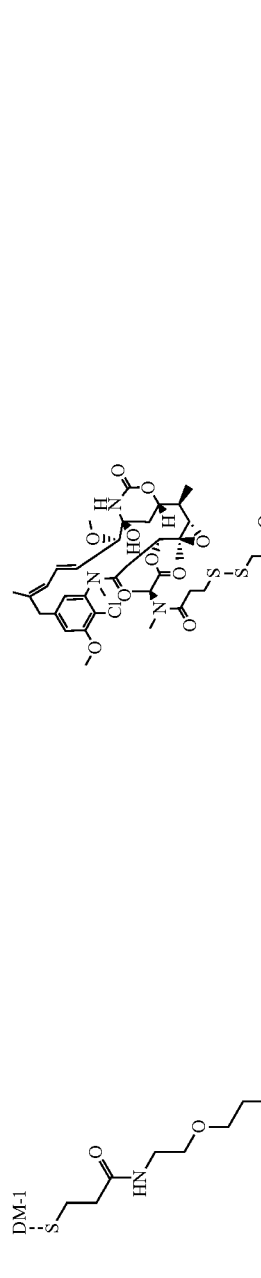 45 |
| H | 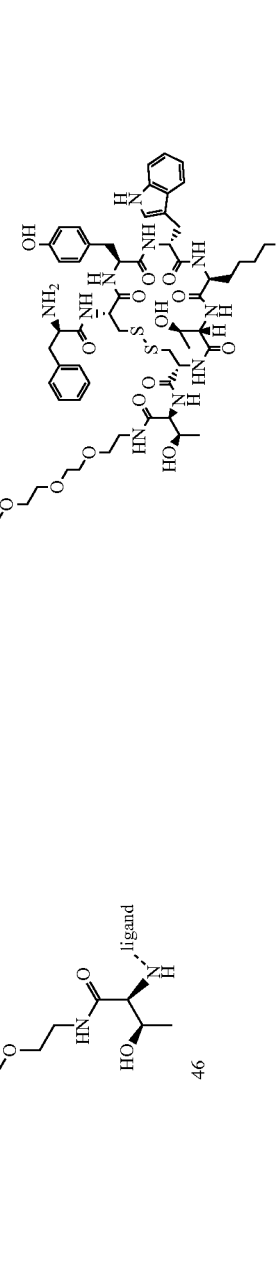 |  | 46 | 47 |

TABLE 2-continued

C-terminal DM1-TATE conjugates

| R | Ar1 | Ar2 | Linker* | Full Structure |
|---|---|---|---|---|
| H | (phenyl) | (4-hydroxyphenyl) | 48 | 49 |

TABLE 2-continued
C-terminal DM1-TATE conjugates
| R | Ar1 | Ar2 | Linker* | Full Structure |
|---|---|---|---|---|
| H | 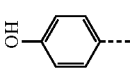 |  | 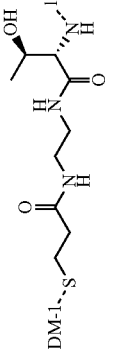 50 |  51 |

TABLE 2-continued
C-terminal DM1-TATE conjugates
| R | Ar1 | Ar2 | Linker* | Full Structure |
|---|---|---|---|---|
| H | 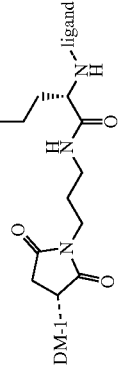 |  | 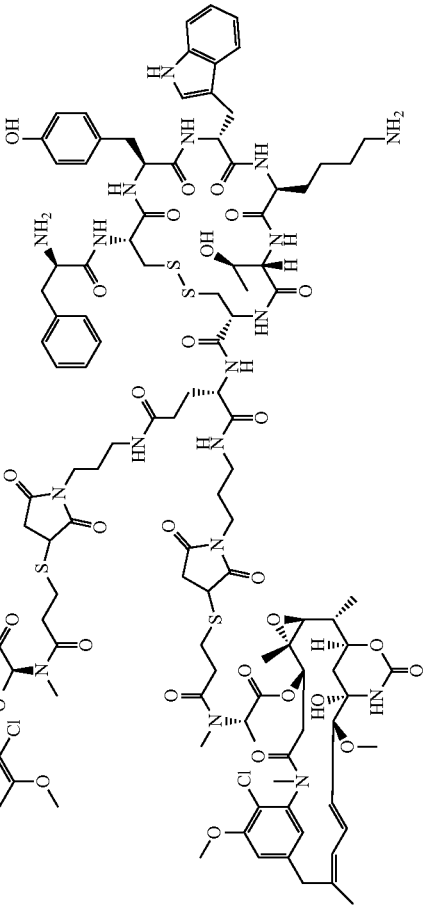 52 | 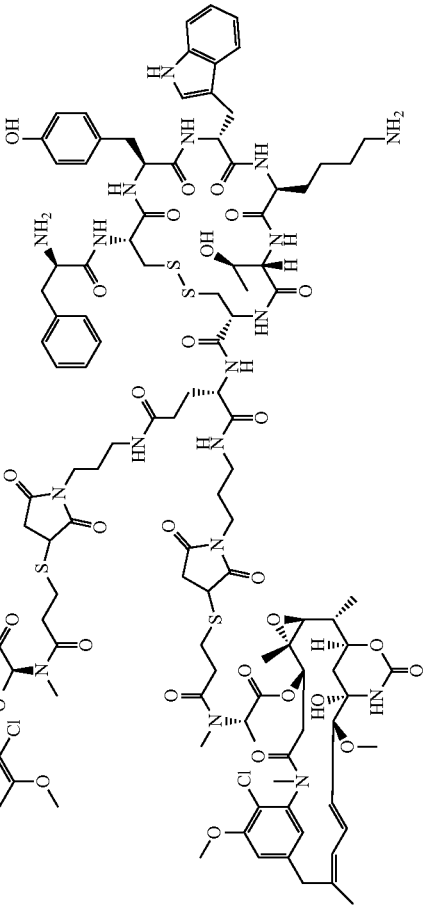 53 |

TABLE 2-continued

C-terminal DM1-TATE conjugates

| R | Ar1 | Ar2 | Linker* | Full Structure |
|---|---|---|---|---|
| (nonyl chain) | (phenyl) | (4-hydroxyphenyl) | 54 | 55 |

TABLE 2-continued
C-terminal DM1-TATE conjugates
| R | Ar1 | Ar2 | Linker* | Full Structure |
|---|-----|-----|---------|----------------|
| H | 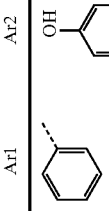 |  | 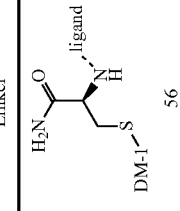 56 | 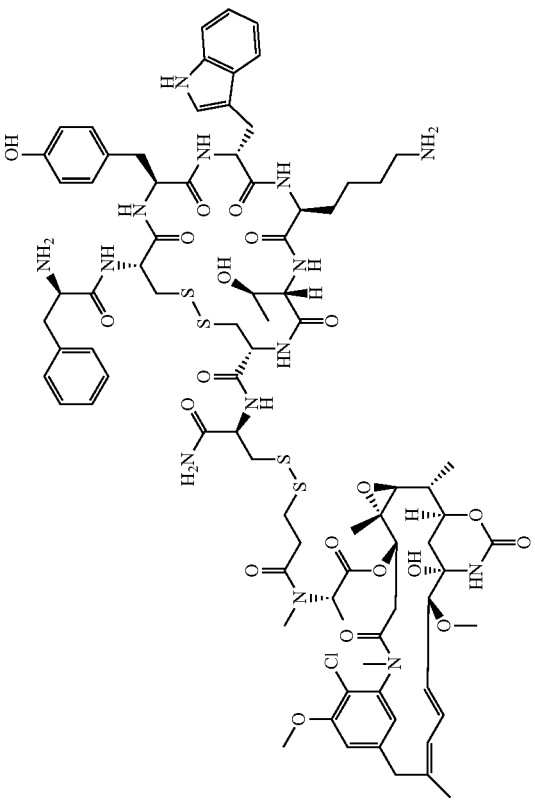 57 |

TABLE 2-continued
C-terminal DM1-TATE conjugates
| R | Ar1 | Ar2 | Linker* | Full Structure |
|---|---|---|---|---|
| H |  |  | 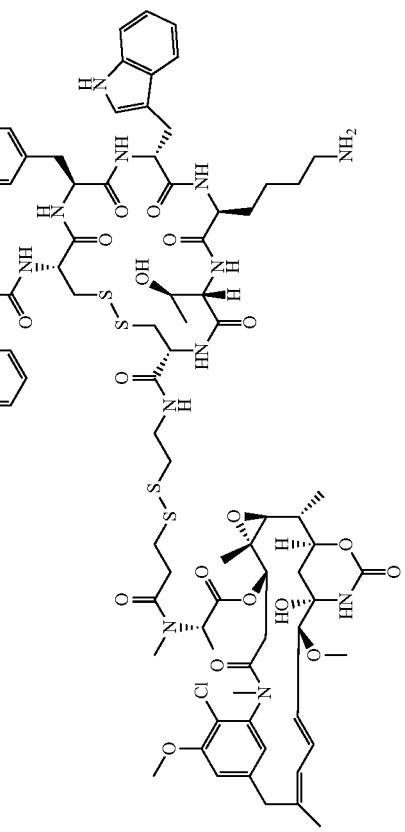  58 | 59 |

TABLE 2-continued
C-terminal DM1-TATE conjugates
| R | Ar1 | Ar2 | Linker* | Full Structure |
|---|-----|-----|---------|----------------|
| H |  | 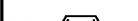 | 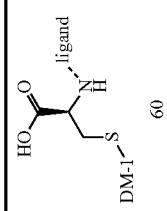  60 | 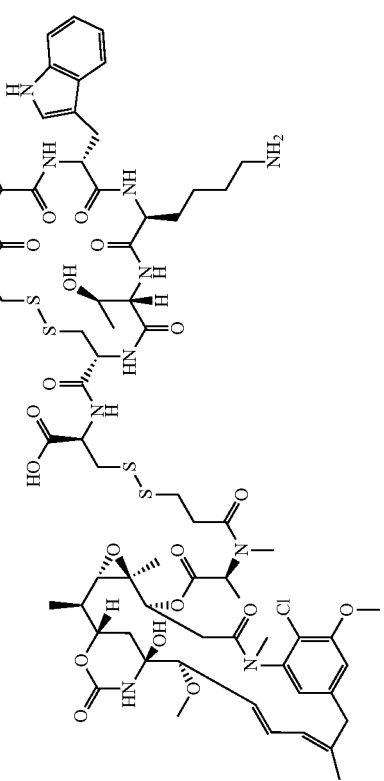  61 |

TABLE 2-continued
C-terminal DM1-TATE conjugates
| R | Ar1 | Ar2 | Linker* | Full Structure |
|---|---|---|---|---|
| H |  | 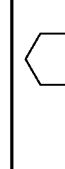 | 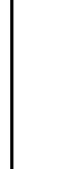  62 | 63 |

TABLE 2-continued

C-terminal DM1-TATE conjugates

| R | Ar1 | Ar2 | Linker* | Full Structure |
|---|---|---|---|---|

*In order to show linker structures, the somatostatin receptor targeting moiety is referred to as ligand in the structures.

3) N-Terminal DM1 Conjugates

In some embodiments, the somatostatin receptor targeting moiety is a peptide and the linker binds to the N-terminus of the somatostatin receptor targeting moiety. In some embodiments, the target moiety is selected from octreotide, vapreotide, and TATE. In some embodiments, the covalent bond connecting the linker and the N-terminal of the somatostatin receptor targeting moiety is an amide bond, i.e., —NH—CO—. In some embodiments, the linker binds to the N-terminus of the somatostatin receptor targeting moiety via an amine bond, i.e., —NH—CH2-(hydrogen on the carbon may be substituted). In some embodiments, the linker binds to the N-terminus of the somatostatin receptor targeting moiety via a urea bond, i.e. —NH—CO—NH—. The N-terminal DM1 conjugate has a general structure of:

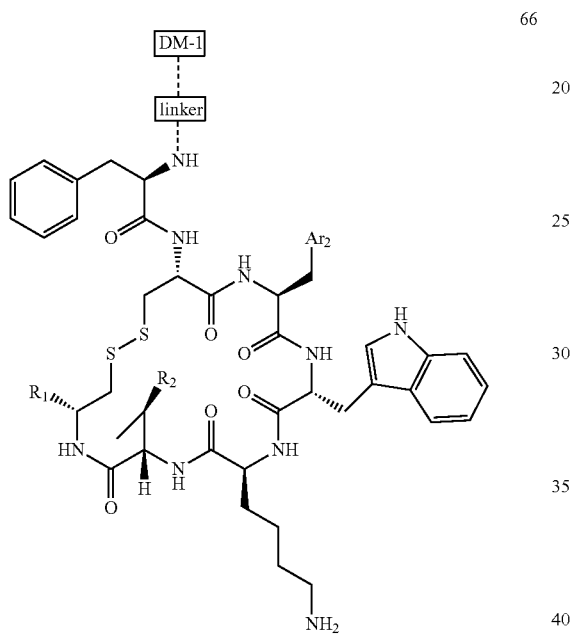

66 wherein $R_1$ and $R_2$ are independently selected from H, OH, alkyl, aryl, carbonyl, ester, amide, ether, alcohol, or amine, optionally substituted with one or more groups; and $Ar_1$ is selected from heterocyclyl, aryl, and heteroaryl groups optionally substituted with one or more groups. In some embodiments, at least one of R1 or R2 comprises DM1.

Non-limiting examples of DM1 conjugates wherein the linker binds to the N-terminus of the somatostatin receptor targeting moiety are shown in Table 3:

TABLE 3

N-terminal DM1 conjugates

| $R_1$ | $R_2$ | $Ar_1$ | Linker* | Full structure |
|---|---|---|---|---|

TABLE 3-continued

N-terminal DM1 conjugates

| $R_1$ | $R_2$ | $Ar_1$ | Linker* | Full structure |
|---|---|---|---|---|
| (Trp-NH$_2$ with acetyl, structure shown) | —Me | (4-OH-phenyl, structure shown) | DM-1–S–(CH$_2$)$_2$–C(O)–ligand (69) | (structure shown) 70 |

TABLE 3-continued

N-terminal DM1 conjugates

| $R_1$ | $R_2$ | $Ar_1$ | Linker* | Full structure |
|---|---|---|---|---|

TABLE 3-continued

N-terminal DM1 conjugates

| $R_1$ | $R_2$ | $Ar_1$ | Linker* | Full structure |
|---|---|---|---|---|
| (structure) | —OH | (4-hydroxyphenyl) | (DM-1 linker structure) 73 | (full conjugate structure) 74 |

TABLE 3-continued
N-terminal DM1 conjugates
| $R_1$ | $R_2$ | $Ar_1$ | Linker* | Full structure |
|---|---|---|---|---|
| 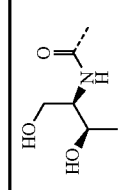 | —OH | 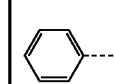 |  75 | 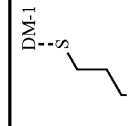 76 |

TABLE 3-continued
N-terminal DM1 conjugates
| $R_1$ | $R_2$ | $Ar_1$ | Linker* | Full structure |
|---|---|---|---|---|
| 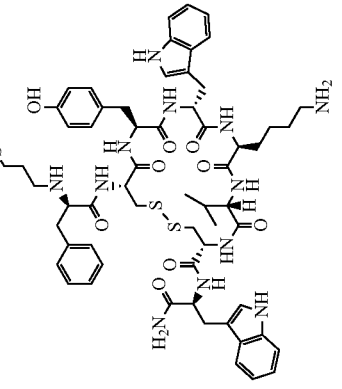 | —Me | 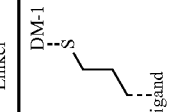 |  77 | 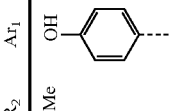 78 |

TABLE 3-continued
N-terminal DM1 conjugates
| $R_1$ | $R_2$ | $Ar_1$ | Linker* | Full structure |
|---|---|---|---|---|
| 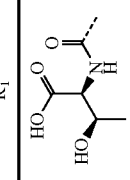 | —OH | 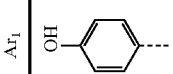 |  79 |  80 |

TABLE 3-continued
N-terminal DM1 conjugates
| $R_1$ | $R_2$ | $Ar_1$ | Linker* | Full structure |
|---|---|---|---|---|
| 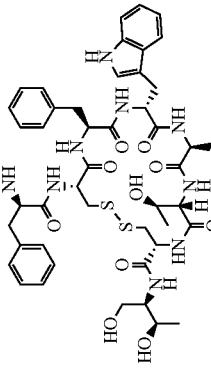 | —OH | 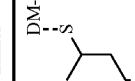 | 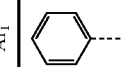 81 | 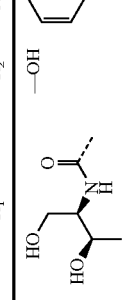 82 |

TABLE 3-continued
N-terminal DM1 conjugates
| R₁ | R₂ | Ar₁ | Linker* | Full structure |
|---|---|---|---|---|
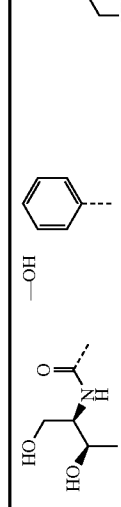

TABLE 3-continued
N-terminal DM1 conjugates
| $R_1$ | $R_2$ | $Ar_1$ | Linker* | Full structure |
|---|---|---|---|---|
| 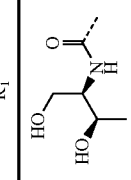 | —OH | 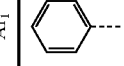 | 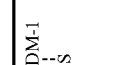 85 | 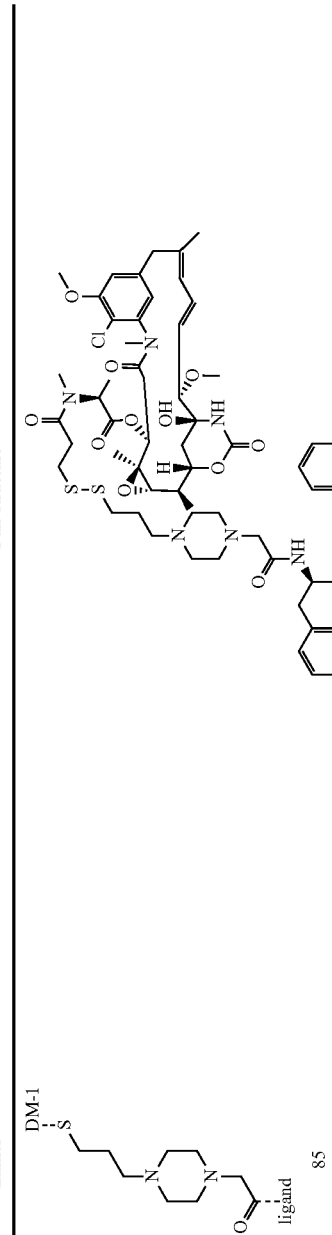 86 |

TABLE 3-continued
N-terminal DM1 conjugates
| $R_1$ | $R_2$ | $Ar_1$ | Linker* | Full structure |
|---|---|---|---|---|
| 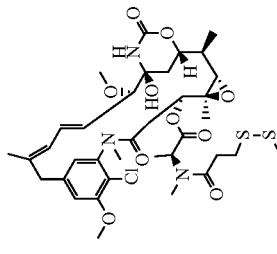 | —OH | 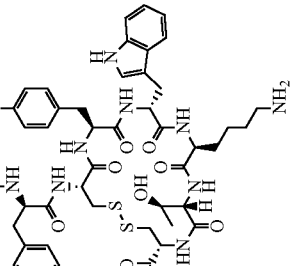 | 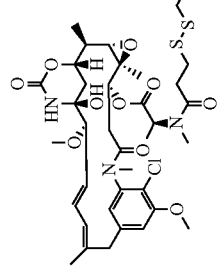 | |

TABLE 3-continued
N-terminal DM1 conjugates
| R1 | R2 | Ar1 | Linker* | Full structure |
|---|---|---|---|---|
| 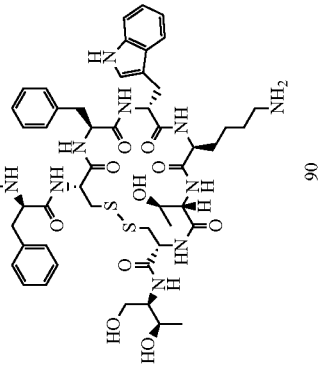 | —OH |  | 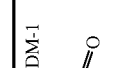 89 | 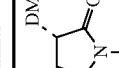 90 |

TABLE 3-continued
N-terminal DM1 conjugates
| $R_1$ | $R_2$ | $Ar_1$ | Linker* | Full structure |
|---|---|---|---|---|
| 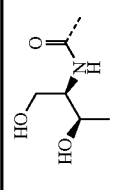 | —OH | 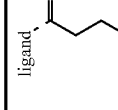 |  91 |  |

TABLE 3-continued

N-terminal DM1 conjugates

| $R_1$ | $R_2$ | $Ar_1$ | Linker* | Full structure |
|---|---|---|---|---|
| | | | | 92 |

TABLE 3-continued

N-terminal DM1 conjugates

| R₁ | R₂ | Ar₁ | Linker* | Full structure |
|---|---|---|---|---|

TABLE 3-continued

N-terminal DM1 conjugates

| $R_1$ | $R_2$ | $Ar_1$ | Linker* | Full structure |
|---|---|---|---|---|

TABLE 3-continued

N-terminal DM1 conjugates

| R₁ | R₂ | Ar₁ | Linker* | Full structure |
|---|---|---|---|---|
| (serinol-threonine amide group) | —OH | (phenyl) | PEG4-propanoyl linker with disulfide to DM-1 (97) | Full conjugate structure (98) |

TABLE 3-continued
N-terminal DM1 conjugates
| $R_1$ | $R_2$ | $Ar_1$ | Linker* | Full structure |
|---|---|---|---|---|
| 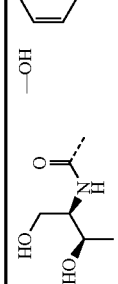 | —OH |  |  99 |  100 |

TABLE 3-continued
N-terminal DM1 conjugates
| $R_1$ | $R_2$ | $Ar_1$ | Linker* | Full structure |
|---|---|---|---|---|
| 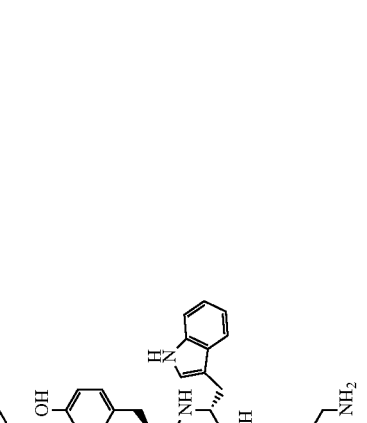 | —Me |  | 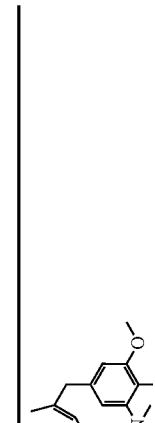 101 | 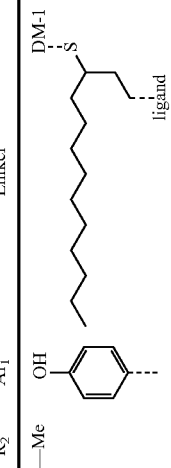 102 |

TABLE 3-continued
N-terminal DM1 conjugates
| R₁ | R₂ | Ar₁ | Linker* | Full structure |
|---|---|---|---|---|
| 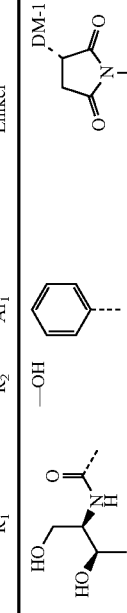 | —OH | 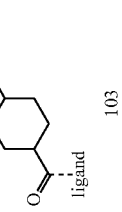 | 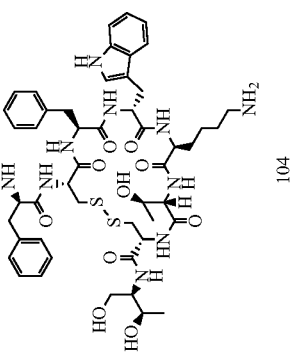 103 | 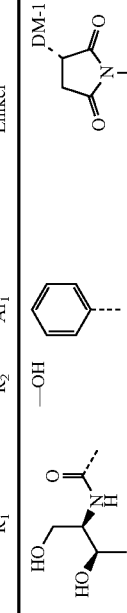 104 |

TABLE 3-continued

N-terminal DM1 conjugates

| $R_1$ | $R_2$ | $Ar_1$ | Linker* | Full structure |
|---|---|---|---|---|
| (structure) | —OH | (phenyl) | 105 | 106 |

TABLE 3-continued
N-terminal DM1 conjugates
| R₁ | R₂ | Ar₁ | Linker* | Full structure |
|---|---|---|---|---|
| 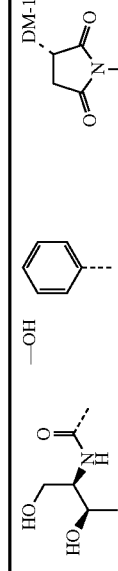 | —OH |  |  107 |  108 |
*In order to show linker structures, the somatostatin receptor targeting moiety is referred to as ligand in the structures.

4) D-Phe Replacement DM1 Conjugates

In some embodiments, the somatostatin receptor targeting moiety is a targeting ligand such as octreotide or TATE, wherein the phenyl ring of the D-Phe residue of the targeting ligand has been replaced by a linker-containing moiety. The D-Phe replacement DM1 conjugate has a general structure of:

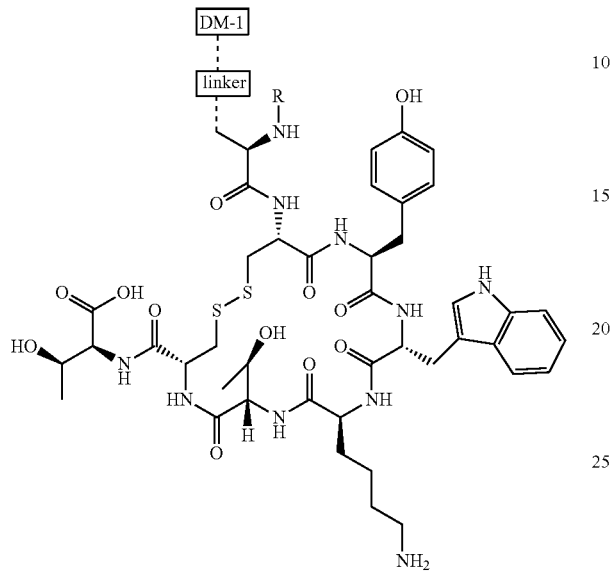

109

Wherein R is selected from H, OH, alkyl, aryl, carbonyl, ester, amide, ether, alcohol, or amine, optionally substituted with one or more groups. In some embodiments, R comprises DM1.

Non-limiting examples of DM1 conjugates wherein the phenyl ring of the D-Phe residue of the targeting ligand has been replaced by a linker-containing moiety are shown in Table 4:

TABLE 4

D-Phe replacement conjugates

| R | Linker* | Full structure |
|---|---------|----------------|
| H | 110 | 111 |

TABLE 4-continued
D-Phe replacement conjugates
| R | Linker* | Full structure |
|---|---------|----------------|
| H |  112 | 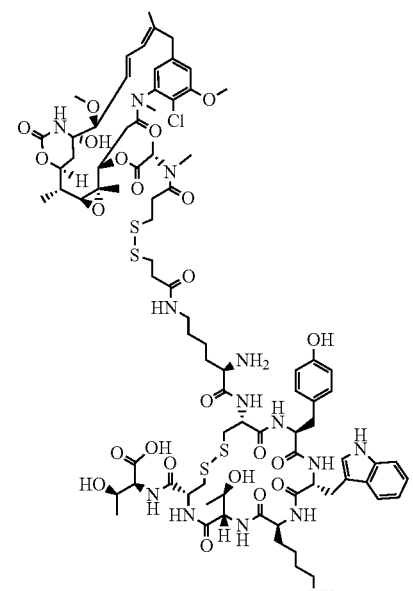 113 |
| H |  114 | 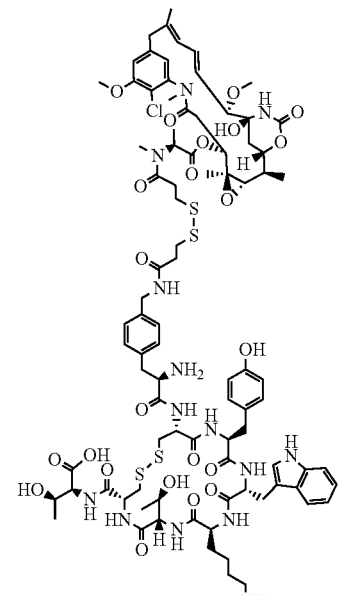 115 |

TABLE 4-continued

D-Phe replacement conjugates

| R | Linker* | Full structure |
|---|---------|----------------|
| 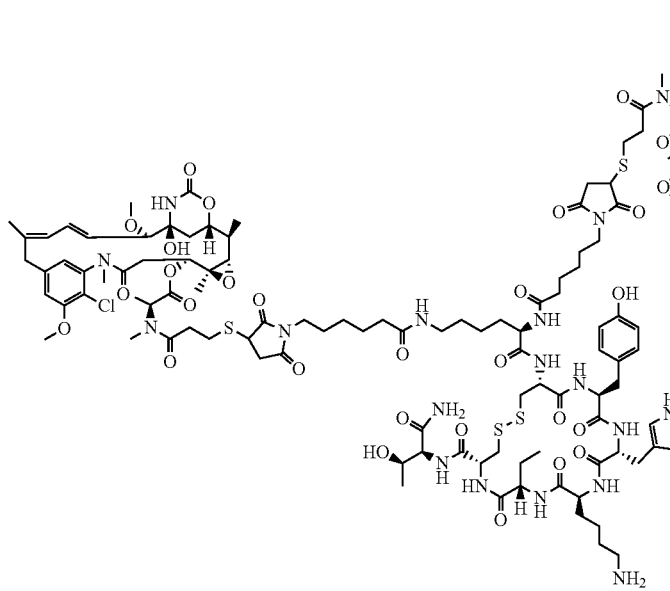 | | |
| H | | |

*In order to show linker structures, the somatostatin receptor targeting moiety is referred to as ligand in the structures.

III. Particles

Particles containing one or more conjugates can be polymeric particles, lipid particles, solid lipid particles, inorganic particles, or combinations thereof (e.g., lipid stabilized polymeric particles). In some embodiments, the particles are polymeric particles or contain a polymeric matrix. The particles can contain any of the polymers described herein or derivatives or copolymers thereof. The particles generally contain one or more biocompatible polymers. The polymers can be biodegradable polymers. The polymers can be hydrophobic polymers, hydrophilic polymers, or amphiphilic polymers. In some embodiments, the particles contain one or more polymers having an additional targeting moiety attached thereto.

The size of the particles can be adjusted for the intended application. The particles can be nanoparticles or microparticles. The particle can have a diameter of about 10 nm to about 10 microns, about 10 nm to about 1 micron, about 10 nm to about 500 nm, about 20 nm to about 500 nm, or about 25 nm to about 250 nm. In some embodiments the particle is a nanoparticle having a diameter from about 25 nm to about 250 nm. It is understood by those in the art that a plurality of particles will have a range of sizes and the diameter is understood to be the median diameter of the particle size distribution.

In various embodiments, a particle may be a nanoparticle, i.e., the particle has a characteristic dimension of less than about 1 micrometer, where the characteristic dimension of a particle is the diameter of a perfect sphere having the same volume as the particle. The plurality of particles can be characterized by an average diameter (e.g., the average diameter for the plurality of particles). In some embodiments, the diameter of the particles may have a Gaussian-type distribution. In some embodiments, the plurality of particles have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm. In some embodiments, the particles have an average diameter of at least about 5 nm, at least about 10 nm, at least about 30 nm, at least about 50 nm, at least about 100 nm, at least about 150 nm, or greater. In certain embodiments, the plurality of the particles has an average diameter of about 10 nm, about 25 nm, about 50 nm, about 100 nm, about 150 nm, about 200 nm, about 250 nm, about 300 nm, about 500 nm, or the like. In some embodiments, the plurality of particles has an average diameter between about 10 nm and about 500 nm, between about 50 nm and about 400 nm, between about 100 nm and about 300 nm, between about 150 nm and about 250 nm, between about 175 nm and about 225 nm, or the like. In some embodiments, the plurality of particles has an average diameter between about 10 nm and about 500 nm, between about 20 nm and about 400 nm, between about 30 nm and about 300 nm, between about 40 nm and about 200 nm, between about 50 nm and about 175 nm, between about 60 nm and about 150 nm, between about 70 nm and about 130 nm, or the like. For example, the average diameter can be between about 70 nm and 130 nm. In some embodiments, the plurality of particles has an average diameter between about 20 nm and about 220 nm, between about 30 nm and about 200 nm, between about 40 nm and about 180 nm, between about 50 nm and about 170 nm, between about 60 nm and about 150 nm, or between about 70 nm and about 130 nm. In one embodiment, the particles have a size of 40 to 120 nm with a zeta potential close to 0 mV at low to zero ionic strengths (1 to 10 mM), with zeta potential values between +5 to −5 mV, and a zero/neutral or a small −ve surface charge.

A. Conjugates

The particles contain one or more conjugates as described above. The conjugates can be present on the interior of the particle, on the exterior of the particle, or both. The particles may comprise hydrophobic ion-pairing complexes or hydrophobic ion-pairs formed by one or more conjugates described above and counterions.

Hydrophobic ion-pairing (HIP) is the interaction between a pair of oppositely charged ions held together by Coulombic attraction. HIP, as used here in, refers to the interaction between the conjugate of the present invention and its counterions, wherein the counterion is not H$^+$ or HO$^-$ ions. Hydrophobic ion-pairing complex or hydrophobic ion-pair, as used herein, refers to the complex formed by the conjugate of the present invention and its counterions. In some embodiments, the counterions are hydrophobic. In some embodiments, the counterions are provided by a hydrophobic acid or a salt of a hydrophobic acid. In some embodiments, the counterions are provided by bile acids or salts, fatty acids or salts, lipids, or amino acids. In some embodiments, the counterions are negatively charged (anionic). Non-limited examples of negative charged counterions include the counterions sodium sulfosuccinate (AOT), sodium oleate, sodium dodecyl sulfate (SDS), human serum albumin (HSA), dextran sulphate, sodium deoxycholate, sodium cholate, anionic lipids, amino acids, or any combination thereof. Without wishing to be bound by any theory, in some embodiments, HIP may increase the hydrophobicity and/or lipophilicity of the conjugate of the present invention. In some embodiments, increasing the hydrophobicity and/or lipophilicity of the conjugate of the present invention may be beneficial for particle formulations and may provide higher solubility of the conjugate of the present invention in organic solvents. Without wishing to be bound by any theory, it is believed that particle formulations that include HIP pairs have improved formulation properties, such as drug loading and/or release profile. Without wishing to be bound by any theory, in some embodiments, slow release of the conjugate of the invention from the particles may occur, due to a decrease in the conjugate's solubility in aqueous solution. In addition, without wishing to be bound by any theory, complexing the conjugate with large hydrophobic counterions may slow diffusion of the conjugate within a polymeric matrix. In some embodiments, HIP occurs without covalent confutation of the counterion to the conjugate of the present invention.

Without wishing to be bound by any theory, the strength of HIP may impact the drug load and release rate of the particles of the invention. In some embodiments, the strength of the HIP may be increased by increasing the magnitude of the difference between the pKa of the conjugate of the present invention and the pKa of the agent providing the counterion. Also without wishing to be bound by any theory, the conditions for ion pair formation may impact the drug load and release rate of the particles of the invention.

In some embodiments, any suitable hydrophobic acid or a combination thereof may form a HIP pair with the conjugate of the present invention. In some embodiments, the hydrophobic acid may be a carboxylic acid (such as but not limited to a monocarboxylic acid, dicarboxylic acid, tricarboxylic acid), a sulfinic acid, a sulfenic acid, or a sulfonic acid. In some embodiments, a salt of a suitable hydrophobic acid or a combination thereof may be used to form a HIP pair with the conjugate of the present invention. Examples of hydrophobic acids, saturated fatty acids, unsaturated fatty acids, aromatic acids, bile acid, polyelectrolyte, their dissociation constant in water (pKa) and log P values were disclosed in WO2014/043,625, the contents of which are incorporated herein by reference in their entirety. The strength of the hydrophobic acid, the difference between the pKa of the hydrophobic acid and the pKa of the conjugate of the present invention, log P of the hydrophobic acid, the phase transition temperature of the hydrophobic acid, the molar ratio of the hydrophobic acid to the conjugate of the present invention, and the concentration of the hydrophobic acid were also disclosed in WO2014/043,625, the contents of which are incorporated herein by reference in their entirety.

In some embodiments, particles of the present invention comprising a HIP complex and/or prepared by a process that provides a counterion to form HIP complex with the conjugate may have a higher drug loading than particles without a HIP complex or prepared by a process that does not provide any counterion to form HIP complex with the conjugate. In some embodiments, drug loading may increase 50%, 100%, 2 times, 3 times, 4 times, 5 times, 6 times, 7 times, 8 times, 9 times, or 10 times.

In some embodiments, the particles of the invention may retain the conjugate for at least about 1 minute, at least about 15 minutes, at least about 1 hour, when placed in a phosphate buffer solution at 37° C.

In some embodiments, the weight percentage of the conjugate in the particles is at least about 0.05%, 0.1%, 0.5%, 1%, 5%, 10%, 15%, 20%, 25%, 30%, 35%; 40%, 45%, or 50% such that the sum of the weight percentages of the components of the particles is 100%. In some embodiments, the weight percentage of the conjugate in the particles is from about 0.5% to about 10%, or about 10% to about 20%, or about 20% to about 30%, or about 30% to about 40%, or about 40% to about 50%, or about 50% to about 60%, or about 60% to about 70%, or about 70% to about 80%, or about 80% to about 90%, or about 90% to about 99% such that the sum of the weight percentages of the components of the particles is 100%.

In some instances, a conjugate may have a molecular weight of less than about 50,000 Da, less than about 40,000 Da, less than about 30,000 Da, less than about 20,000 Da, less than about 15,000 Da, less than about 10,000 Da, less than about 8,000 Da, less than about 5,000 Da, or less than about 3,000 Da. In some cases, the conjugate may have a molecular weight of between about 1,000 Da and about 50,000 Da, between about 1,000 Da and about 40,000 Da, in some embodiments between about 1,000 Da and about 30,000 Da, in some embodiments bout 1,000 Da and about 50,000 Da, between about 1,000 Da and about 20,000 Da, in some embodiments between about 1,000 Da and about 15,000 Da, in some embodiments between about 1,000 Da and about 10,000 Da, in some embodiments between about 1,000 Da and about 8,000 Da, in some embodiments between about 1,000 Da and about 5,000 Da, and in some embodiments between about 1,000 Da and about 3,000 Da. The molecular weight of the conjugate may be calculated as the sum of the atomic weight of each atom in the formula of the conjugate multiplied by the number of each atom. It may also be measured by mass spectrometry, NMR, chromatography, light scattering, viscosity, and/or any other methods known in the art. It is known in the art that the unit of molecular weight may be g/mol, Dalton (Da), or atomic mass unit (amu), wherein 1 g/mol=1 Da=1 amu.

B. Polymers

The particles may contain one or more polymers. Polymers may contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(ε-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker.

The particles may contain one or more hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol); polyoxazoline; and copolymers thereof.

The particles may contain one or more hydrophobic polymers. Examples of suitable hydrophobic polymers include polyhydroxyacids such as poly(lactic acid), poly (glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetal s; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In certain embodiments, the hydrophobic polymer is an aliphatic polyester. In some embodiments, the hydrophobic polymer is poly(lactic acid), poly(glycolic acid), or poly (lactic acid-co-glycolic acid).

The particles can contain one or more biodegradable polymers. Biodegradable polymers can include polymers that are insoluble or sparingly soluble in water that are converted chemically or enzymatically in the body into water-soluble materials. Biodegradable polymers can include soluble polymers crosslinked by hydrolyzable crosslinking groups to render the crosslinked polymer insoluble or sparingly soluble in water.

Biodegradable polymers in the particle can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose such as methyl cellulose and ethyl cellulose, hydroxyalkyl celluloses such as hydroxypropyl cellulose, hydroxypropyl methyl cellulose, and hydroxybutyl methyl cellulose, cellulose ethers, cellulose esters, nitro celluloses, cellulose acetate, cellulose propionate, cellulose acetate butyrate, cellulose acetate phthalate, carboxylethyl cellulose, cellulose triacetate, cellulose sulphate sodium salt, polymers of acrylic and methacrylic esters such as poly (methyl methacrylate), poly(ethylmethacrylate), poly(butylmethacrylate), poly(isobutylmethacrylate), poly(hexylmethacrylate), poly (isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxyalkanoates), poly (hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In some embodiments the particle contains biodegradable polyesters or polyanhydrides such as poly(lactic acid), poly(glycolic acid), and poly(lactic-co-glycolic acid).

The particles can contain one or more amphiphilic polymers. Amphiphilic polymers can be polymers containing a hydrophobic polymer block and a hydrophilic polymer block. The hydrophobic polymer, block can contain one or more of the hydrophobic polymers above or a derivative or copolymer thereof. The hydrophilic polymer block can contain one or more of the hydrophilic polymers above or a derivative or copolymer thereof. In some embodiments the amphiphilic polymer is a di-block polymer containing a hydrophobic end formed from a hydrophobic polymer and a hydrophilic end formed of a hydrophilic polymer. In some embodiments, a moiety can be attached to the hydrophobic end, to the hydrophilic end, or both. The particle can contain two or more amphiphilic polymers.

C. Lipids

The particles may contain one or more lipids or amphiphilic compounds. For example, the particles can be liposomes, lipid micelles, solid lipid particles, or lipid-stabilized polymeric particles. The lipid particle can be made from one or a mixture of different lipids. Lipid particles are formed from one or more lipids, which can be neutral, anionic, or cationic at physiologic pH. The lipid particle, in some embodiments, incorporates one or more biocompatible lipids. The lipid particles may be formed using a combination of more than one lipid. For example, a charged lipid may be combined with a lipid that is non-ionic or uncharged at physiological pH.

The particle can be a lipid micelle. Lipid micelles for drug delivery are known in the art. Lipid micelles can be formed, for instance, as a water-in-oil emulsion with a lipid surfactant. An emulsion is a blend of two immiscible phases wherein a surfactant is added to stabilize the dispersed droplets. In some embodiments the lipid micelle is a microemulsion. A microemulsion is a thermodynamically stable system composed of at least water, oil and a lipid surfactant producing a transparent and thermodynamically stable system whose droplet size is less than 1 micron, from about 10 nm to about 500 nm, or from about 10 nm to about 250 nm. Lipid micelles are generally useful for encapsulating hydrophobic active agents, including hydrophobic therapeutic agents, hydrophobic prophylactic agents, or hydrophobic diagnostic agents.

The particle can be a liposome. Liposomes are small vesicles composed of an aqueous medium surrounded by lipids arranged in spherical bilayers. Liposomes can be classified as small unilamellar vesicles, large unilamellar vesicles, or multi-lamellar vesicles. Multi-lamellar liposomes contain multiple concentric lipid bilayers. Liposomes can be used to encapsulate agents, by trapping hydrophilic agents in the aqueous interior or between bilayers, or by trapping hydrophobic agents within the bilayer.

The lipid micelles and liposomes typically have an aqueous center. The aqueous center can contain water or a mixture of water and alcohol. Suitable alcohols include, but are not limited to, methanol, ethanol, propanol, (such as isopropanol), butanol (such as n-butanol, isobutanol, sec-butanol, tert-butanol, pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

The particle can be a solid lipid particle. Solid lipid particles present an alternative to the colloidal micelles and liposomes. Solid lipid particles are typically submicron in size, i.e from about 10 nm to about 1 micron, from 10 nm to about 500 nm, or from 10 nm to about 250 nm. Solid lipid particles are formed of lipids that are solids at room temperature. They are derived from oil-in-water emulsions, by replacing the liquid oil by a solid lipid.

Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy) propyl]-N,N-dimethyl amine (DODAP), 1,2-diacyloxy-3-dimethylammonium propanes, N-[1-(2,3-dioleyloxy) propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), $diC_{14}$-amidine, N-tert-butyl-N'-tetradecyl-3-tetradecylamino-propionamidine, N-(alpha-trimethylammonio-acetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N, N, N', N'-tetramethyl-, N-bis(2-hydroxyethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl) imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxy ethyl ammonium bromide (DSRIE).

Suitable solid lipids include, but are not limited to, higher saturated alcohols, higher fatty acids, sphingolipids, synthetic esters, and mono-, di-, and triglycerides of higher saturated fatty acids. Solid lipids can include aliphatic alcohols having 10-40, for example, 12-30 carbon atoms, such as cetostearyl alcohol. Solid lipids can include higher fatty acids of 10-40, for example, 12-30 carbon atoms, such as stearic acid, palmitic acid, decanoic acid, and behenic acid. Solid lipids can include glycerides, including monoglycerides, diglycerides, and triglycerides, of higher saturated fatty acids having 10-40, for example, 12-30 carbon atoms, such as glyceryl monostearate, glycerol behenate, glycerol palmitostearate, glycerol trilaurate, tricaprin, trilaurin, trimyristin, tripalmitin, tristearin, and hydrogenated castor oil. Suitable solid lipids can include cetyl palmitate, beeswax, or cyclodextrin.

Amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), for example, between 0.1-30 (weight lipid/w polymer). Phospholipids that may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

D. Additional Active Agents

The particles can contain one or more additional active agents in addition to those in the conjugates. The additional active agents can be therapeutic, prophylactic, diagnostic, or nutritional agents as listed above. The additional active agents can be present in any amount, e.g. from about 0.5% to about 90%, from about 0.5% to about 50%, from about 0.5% to about 25%, from about 0.5% to about 20%, from about 0.5% to about 10%, or from about 5% to about 10% (w/w) based upon the weight of the particle. In one embodiment, the agents are incorporated in an about 0.5% to about 10% loading w/w.

E. Additional Targeting Moieties

The particles can contain one or more targeting moieties targeting the particle to a specific organ, tissue, cell type, or subcellular compartment in addition to the targeting moieties of the conjugate. The additional targeting moieties can be present on the surface of the particle, on the interior of the particle, or both. The additional targeting moieties can be immobilized on the surface of the particle, e.g., can be covalently attached to polymer or lipid in the particle. In some embodiments, the additional targeting moieties are covalently attached to an amphiphilic polymer or a lipid such that the targeting moieties are oriented on the surface of the particle.

IV. Formulations

In some embodiments, compositions are administered to humans, human patients or subjects. For the purposes of the present disclosure, the phrase "active ingredient" generally refers to the conjugate or particles comprising the conjugates to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

The conjugates or particles of the present invention can be formulated using one or more excipients to: (1) increase stability; (2) permit the sustained or delayed release (e.g., from a depot formulation of the monomaleimide); (3) alter the biodistribution (e.g., target the monomaleimide compounds to specific tissues or cell types); (4) alter the release profile of the monomaleimide compounds in vivo. Non-limiting examples of the excipients include any and all solvents, dispersion media, diluents, or other liquid vehicles, dispersion or suspension aids, surface active agents, isotonic agents, thickening or emulsifying agents, and preservatives. Excipients of the present invention may also include, without limitation, lipidoids, liposomes, lipid nanoparticles, polymers, lipoplexes, core-shell nanoparticles, peptides, proteins, hyaluronidase, nanoparticle mimics and combinations thereof. Accordingly, the formulations of the invention may include one or more excipients, each in an amount that together increases the stability of the monomaleimide compounds.

Excipients

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006; incorporated herein by reference in its entirety) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN® 20], polyoxyethylene sorbitan [TWEENn® 60], polyoxyethylene sorbitan monooleate [TWEEN® 80], sorbitan monopalmitate [SPAN® 40], sorbitan monostearate [SPAN® 60], sorbitan tristearate [SPAN® 65], glyceryl monooleate, sorbitan monooleate [SPAN® 80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F 68, POLOXAMER® 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Administration

The conjugates or particles of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them to cross the blood-brain barrier, vascular barrier, or other epithelial barrier.

The formulations described herein contain an effective amount of conjugates or particles in a pharmaceutical carrier appropriate for administration to an individual in need thereof. The formulations may be administered parenterally (e.g., by injection or infusion). The formulations or variations thereof may be administered in any manner including enterally, topically (e.g., to the eye), or via pulmonary administration. In some embodiments the formulations are administered topically.

A. Parenteral Formulations

The particles can be formulated for parenteral delivery, such as injection or infusion, in the form of a solution, suspension or emulsion. The formulation can be administered systemically, regionally or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In some cases, an isotonic agent is included, for example, one or more sugars, sodium chloride, or other suitable agent known in the art.

Solutions and dispersions of the particles can be prepared in water or another solvent or dispersing medium suitably mixed with one or more pharmaceutically acceptable excipients including, but not limited to, surfactants, dispersants, emulsifiers, pH modifying agents, and combinations thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s) or particles.

The formulation is typically buffered to a pH of 3-8 for parenteral administration upon reconstitution. Suitable buffers include, but are not limited to, phosphate buffers, acetate buffers, and citrate buffers. If using 10% sucrose or 5% dextrose, a buffer may not be required.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the particles in the required amount in the appropriate solvent or dispersion medium with one or more of the excipients listed above, as required, followed by filtered sterilization. Generally, dispersions are prepared by incorporating the various sterilized particles into a sterile vehicle which contains the basic dispersion medium and the required other ingredients from those listed above. In the case of sterile powders for the preparation of sterile injectable solutions, examples of methods of preparation include vacuum-drying and freeze-drying techniques that yield a powder of the particle plus any additional desired ingredient from a previously sterile-filtered solution thereof. The powders can be prepared in such a manner that the particles are porous in nature, which can increase dissolution of the particles. Methods for making porous particles are known in the art.

Pharmaceutical formulations for parenteral administration can be in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral administration may also contain one or more tonicity agents to adjust the isotonic range of the formulation. Suitable tonicity agents are well known in the art and some examples include glycerin, sucrose, dextrose, mannitol, sorbitol, sodium chloride, and other electrolytes.

Solutions, suspensions, or emulsions for parenteral administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration may also contain one or more excipients known art, such as dispersing agents, wetting agents, and suspending agents.

B. Mucosal Topical Formulations

The particles can be formulated for topical administration to a mucosal surface Suitable dosage forms for topical administration include creams, ointments, salves, sprays, gels, lotions, emulsions, liquids, and transdermal patches. The formulation may be formulated for transmucosal transepithelial, or transendothelial administration. The compositions contain one or more chemical penetration enhancers, membrane permeability agents, membrane transport agents, emollients, surfactants, stabilizers, and combination thereof. In some embodiments, the particles can be administered as a liquid formulation, such as a solution or suspension, a semi-solid formulation, such as a lotion or ointment, or a solid formulation. In some embodiments, the particles are formulated as liquids, including solutions and suspensions, such as eye drops or as a semi-solid formulation, to the mucosa, such as the eye or vaginally or rectally.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

Dosing

The present invention provides methods comprising administering conjugates or particles containing the conjugate as described herein to a subject in need thereof. Conjugates or particles containing the conjugates as described herein may be administered to a subject using any amount and any route of administration effective for preventing or treating or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like.

Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

As used herein, a "split dose" is the division of single unit dose or total daily dose into two or more doses, e.g, two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the monomaleimide compounds of the present invention are administered to a subject in split doses. The monomaleimide compounds may be formulated in buffer only or in a formulation described herein.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous).

Liquid Dosage Forms

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions may be mixed with solubilizing agents such as CREMOPHOR®, alcohols, oils, modified oils, glycols, polysorbates, cyclodextrins, polymers, and/or combinations thereof.

Injectable

Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it may be desirable to slow the absorption of the active ingredient from subcutaneous or intramuscular injection. This may be accomplished by the use of a liquid suspension of crystalline or amorphous material with poor water solubility. The rate of absorption of the monomaleimide compounds then depends upon its rate of dissolution which, in turn, may depend upon crystal size and crystalline form. Alternatively, delayed absorption of a parenterally administered monomaleimide compound may be accomplished by dissolving or suspending the monomalimide in an oil vehicle. Injectable depot forms are made by forming microencapsule matrices of the monomaleimide compounds in biodegradable polymers such as polylactide-polyglycolide. Depending upon the ratio of monomaleimide compounds to polymer and the nature of the particular polymer employed, the rate of monomaleimide compound release can be controlled. Examples of other biodegradable polymers include, but are not limited to, poly(orthoesters) and poly(anhydrides). Depot injectable formulations may be prepared by entrapping the monomaleimide compounds in liposomes or microemulsions which are compatible with body tissues.

Pulmonary

Formulations described herein as being useful for pulmonary delivery may also be used for intranasal delivery of a pharmaceutical composition. Another formulation suitable for intranasal administration may be a coarse powder comprising the active ingredient and having an average particle from about 0.2 um to 500 um. Such a formulation may be administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, contain about 0.1% to 20% (w/w) active ingredient, where the balance may comprise an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

V. Methods of Making Particles

In various embodiments, a method of making the particles includes providing a conjugate; providing a base component such as PLA-PEG or PLGA-PEG for forming a particle; combining the conjugate and the base component in an organic solution to form a first organic phase; and combining the first organic phase with a first aqueous solution to form a second phase; emulsifying the second phase to form an emulsion phase; and recovering particles. In various embodiments, the emulsion phase is further homogenized. In some embodiments, the first phase includes about 5 to about 50% weight, e.g. about 1 to about 40% solids, or about 5 to about 30% solids, e.g. about 5%, 10%, 15%, and 20%, of the conjugate and the base component. In certain embodiments, the first phase includes about 5% weight of the conjugate and the base component. In various embodiments, the organic phase comprises acetonitrile, tetrahydrofuran, ethyl acetate, isopropyl alcohol, isopropyl acetate, dimethylformamide, methylene chloride, dichloromethane, chloroform, acetone, benzyl alcohol, TWEEN® 80, SPAN® 80, or a combination thereof. In some embodiments, the organic phase includes benzyl alcohol, ethyl acetate, or a combination thereof.

In various embodiments, the aqueous solution includes water, sodium cholate, ethyl acetate, or benzyl alcohol. In various embodiments, a surfactant is added into the first phase, the second phase, or both. A surfactant, in some instances, can act as an emulsifier or a stabilizer for a composition disclosed herein. A suitable surfactant can be a cationic surfactant, an anionic surfactant, or a nonionic surfactant. In some embodiments, a surfactant suitable for making a composition described herein includes sorbitan fatty acid esters, polyoxyethylene sorbitan fatty acid esters and polyoxyethylene stearates. Examples of such fatty acid ester nonionic surfactants are the TWEEN® 80, SPAN® 80, and MYJ® surfactants from ICI. SPAN® surfactants include $C_{12}$-$C_{18}$ sorbitan monoesters. TWEEN® surfactants include poly(ethylene oxide) $C_{12}$-$C_{18}$ sorbitan monoesters. MYJ® surfactants include poly(ethylene oxide) stearates. In certain embodiments, the aqueous solution also comprises a surfactant (e.g., an emulsifier), including a polysorbate. For example, the aqueous solution can include polysorbate 80. In some embodiments, a suitable surfactant includes a lipid-based surfactant. For example, the composition can include 1,2-dihexanoyl-sn-glycero-3-phosphocholine, 1,2-diheptanoyl-sn-glycero-3-phosphocholine, PEGlyated 1,2-distearoyl-sn-glycero-3-phosphoethanolamine (including PEG5000-DSPE), PEGlyated 1,2-dioleoyl-sn-glycero-3-phosphoethanolamine (including 1,2-dioleoyl-sn-glycero-3-phosphoethanolamine-N-[methoxy(polyethylene glycol)-5000] (ammonium salt)).

Emulsifying the second phase to form an emulsion phase may be performed in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g. a probe sonicator or a high pressure homogenizer, e.g. by pass(es) through a homogenizer. For example, when a high pressure homogenizer is used, the pressure used may be about 4000 to about 8000 psi, about 4000 to about 5000 psi, or 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. Quenching may be performed at least partially at a temperature of about 5° C. or less. For example, water used in the quenching may be at a temperature that is less that room temperature (e.g. about 0 to about 10° C., or about 0 to about 5° C.).

In various embodiments, the particles are recovered by filtration. For example, ultrafiltration membranes can be used. Exemplary filtration may be performed using a tangential flow filtration system. For example, by using a membrane with a pore size suitable to retain particles while allowing solutes, micelles, and organic solvent to pass, particles can be selectively separated. Exemplary membranes with molecular weight cut-offs of about 300-500 kDa (~5-25 nm) may be, used.

In various embodiments, the particles are freeze-dried or lyophilized, in some instances, to extend their shelf life. In some embodiments, the composition also includes a lyoprotectant. In certain embodiments, a lyoprotectant is selected from a sugar, a polyalcohol, or a derivative thereof. In some embodiments, a lyoprotectant is selected from a monosaccharide, a disaccharide, or a mixture thereof. For example, a lyoprotectant can be sucrose, lactulose, trehalose, lactose, glucose, maltose, mannitol, cellobiose, or a mixture thereof.

Methods of making particles containing one or more conjugates are provided. The particles can be polymeric particles, lipid particles, or combinations thereof. The various methods described herein can be adjusted to control the size and composition of the particles, e.g. some methods are best suited for preparing microparticles while others are better suited for preparing particles. The selection of a method for preparing particles having the descried characteristics can be performed by the skilled artisan without undue experimentation.

i. Polymeric Particles

Methods of making polymeric particles are known in the art. Polymeric particles can be prepared using any suitable method known in the art. Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

1. Spray Drying

Methods for forming polymeric particles using spray drying techniques are described in U.S. Pat. No. 6,620,617. In this method, the polymer is dissolved in an organic solvent such as methylene chloride or in water. A known amount of one or more conjugates or additional active agents to be incorporated in the particles is suspended (in the case of an insoluble active agent) or co-dissolved (in the case of a soluble active agent) in the polymer solution. The solution or dispersion is pumped through a micronizing nozzle driven by a flow of compressed gas, and the resulting aerosol is suspended in a heated cyclone of air, allowing the solvent to evaporate from the microdroplets, forming particles. Microspheres/nanospheres ranging between 0.1 10 microns can be obtained using this method.

2. Interfacial Polymerization

Interfacial polymerization can also be used to encapsulate one or more conjugates and/or active agents. Using this method, a monomer and the conjugates or active agent(s) are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Hot Melt Microencapsulation

Microspheres can be formed from polymers such as polyesters and polyanhydrides using hot melt microencapsulation methods as described in Mathiowitz et al., Reactive Polymers, 6:275 (1987). In some embodiments employing this method, polymers with molecular weights between 3,000-75,000 daltons are used. In this method, the polymer first is melted and then mixed with the solid particles of one or more active agents to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decanting with petroleum ether to produce a free flowing powder.

4. Phase Separation Microencapsulation

In phase separation microencapsulation techniques, a polymer solution is stirred, optionally in the presence of one or more active agents to be encapsulated. While continuing to uniformly suspend the material through stirring, a non-solvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

a. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

b. Solvent Evaporation Microencapsulation

Methods for forming microspheres using solvent evaporation techniques are described in Mathiowitz et al., J. Scanning Microscopy, 4:329 (1990); Beck et al., Fertil. Steril., 31:545 (1979); Beck et al., Am. J. Obstet. Gynecol. 135(3) (1979); Benita et al., J. Pharm. Sci., 73:1721 (1984); and U.S. Pat. No. 3,960,757. The polymer is dissolved in a volatile organic solvent, such as methylene chloride. One or more active agents to be incorporated are optionally added to the solution, and the mixture is suspended in an aqueous solution that contains a surface active agent such as poly (vinyl alcohol). The resulting emulsion is stirred until most of the organic solvent evaporated, leaving solid microparticles/nanoparticles. This method is useful for relatively stable polymers like polyesters and polystyrene.

c. Solvent Removal Microencapsulation

The solvent removal microencapsulation technique is primarily designed for polyanhydrides and is described, for example, in WO 93/21906. In this method, the substance to be incorporated is dispersed or dissolved in a solution of the selected polymer in a volatile organic solvent, such as methylene chloride. This mixture is suspended by stirring in an organic oil, such as silicon oil, to form an emulsion. Microspheres that range between 1-300 microns can be obtained by this procedure. Substances which can be incorporated in the microspheres include pharmaceuticals, pesticides, nutrients, imaging agents, and metal compounds.

5. Coacervation

Encapsulation procedures for various substances using coacervation techniques are known in the art, for example, in GB-B-929 406; GB-B-929 40 1; and U.S. Pat. Nos. 3,266,987, 4,794,000, and 4,460,563. Coacervation involves the separation of a macromolecular solution into two immiscible liquid phases. One phase is a dense coacervate phase, which contains a high concentration of the polymer encapsulant (and optionally one or more active agents), while the second phase contains a low concentration of the polymer. Within the dense coacervate phase, the polymer encapsulant forms nanoscale or microscale droplets. Coacervation may be induced by a temperature change, addition of a non-solvent or addition of a micro-salt (simple coacervation), or by the addition of another polymer thereby forming an interpolymer complex (complex coacervation).

6. Low Temperature Casting of Microspheres

Methods for very low temperature casting of controlled release particles are described in U.S. Pat. No. 5,019,400. In this method, a polymer is dissolved in a solvent optionally with one or more dissolved or dispersed active agents. The mixture is then atomized into a vessel containing a liquid non-solvent at a temperature below the freezing point of the polymer substance solution which freezes the polymer droplets. As the droplets and non-solvent for the polymer are warmed, the solvent in the droplets thaws and is extracted into the non-solvent, resulting in the hardening of the microspheres.

7. Phase Inversion Nanoencapsulation (PIN)

Particles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer. See, e.g., U.S. Pat. No. 6,143,211. The method can be used to produce monodisperse populations of nanoparticles and microparticles in a wide range of sizes, including, for example, about 100 nanometers to about 10 microns.

Advantageously, an emulsion need not be formed prior to precipitation. The process can be used to form microspheres from thermoplastic polymers.

8. Emulsion Methods

In some embodiments, a particle is prepared using an emulsion solvent evaporation method. For example, a polymeric material is dissolved in a water immiscible organic solvent and mixed with a drug solution or a combination of drug solutions. In some embodiments a solution of a therapeutic, prophylactic, or diagnostic agent to be encapsulated is mixed with the polymer solution. The polymer can be, but is not limited to, one or more of the following: PLA, PGA, PCL, their copolymers, polyacrylates, the aforementioned PEGylated polymers. The drug molecules can include one or more conjugates as described above and one or more additional active agents. The water immiscible organic solvent, can be, but is not limited to, one or more of the following: chloroform, dichloromethane, and acyl acetate. The drug can be dissolved in, but is not limited to, one or more of the following: acetone, ethanol, methanol, isopropyl alcohol, acetonitrile and Dimethyl sulfoxide (DMSO).

An aqueous solution is added into the resulting polymer solution to yield emulsion solution by emulsification. The emulsification technique can be, but not limited to, probe sonication or homogenization through a homogenizer.

9. Nanoprecipitation

In another embodiment, a conjugate containing nanoparticle is prepared using nanoprecipitation methods or microfluidic devices. The conjugate containing polymeric material is mixed with a drug or drug combinations in a water miscible organic solvent, optionally containing additional polymers. The additional polymer can be, but is not limited to, one or more of the following: PLA, PGA, PCL, their copolymers, polyacrylates, the aforementioned PEGylated polymers. The water miscible organic solvent, can be, but is not limited to, one or more of the following: acetone, ethanol, methanol, isopropyl alcohol, acetonitrile and dimethyl sulfoxide (DMSO). The resulting mixture solution is then added to a polymer non-solvent, such as an aqueous solution, to yield nanoparticle solution.

10. Microfluidics

Methods of making particles using microfluidics are known in the art. Suitable methods include those described in U.S. Patent Application Publication No. 2010/0022680 A1. In general, the microfluidic device comprises at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymer, targeting moieties, lipids, drug, payload, etc. converge and mix, and the resulting mixture is combined with a polymer non-solvent solution to form the particles having the desired size and density of moieties on the surface. By varying the pressure and flow rate in the inlet channels and the nature and composition of the fluid sources particles can be produced having reproducible size and structure.

ii. Lipid Particles

Methods of making lipid particles are known in the art. Lipid particles can be lipid micelles, liposomes, or solid lipid particles prepared using any suitable method known in the art. Common techniques for created lipid particles encapsulating an active agent include, but are not limited to high pressure homogenization techniques, supercritical fluid methods, emulsion methods, solvent diffusion methods, and spray drying. A brief summary of these methods is presented below.

1. High Pressure Homogenization (HPH) Methods

High pressure homogenization is a reliable and powerful technique, which is used for the production of smaller lipid particles with narrow size distributions, including lipid micelles, liposomes, and solid lipid particles. High pressure homogenizers push a liquid with high pressure (100-2000 bar) through a narrow gap (in the range of a few microns). The fluid can contain lipids that are liquid at room temperature or a melt of lipids that are solid at room temperature. The fluid accelerates on a very short distance to very high velocity (over 1000 Km/h). This creates high shear stress and cavitation forces that disrupt the particles, generally down to the submicron range. Generally, 5-10% lipid content is used but up to 40% lipid content has also been investigated.

Two approaches of HPH are hot homogenization and cold homogenization, work on the same concept of mixing the drug in bulk of lipid solution or melt.

a. Hot homogenization:

Hot homogenization is carried out at temperatures above the melting point of the lipid and can therefore be regarded as the homogenization of an emulsion. A pre-emulsion of the drug loaded lipid melt and the aqueous emulsifier phase is obtained by a high-shear mixing. HPH of the pre-emulsion is carried out at temperatures above the melting point of the lipid. A number of parameters, including the temperature, pressure, and number of cycles, can be adjusted to produce lipid particles with the desired size. In general, higher temperatures result in lower particle sizes due to the decreased viscosity of the inner phase. However, high temperatures increase the degradation rate of the drug and the carrier. Increasing the homogenization pressure or the number of cycles often results in an increase of the particle size due to high kinetic energy of the particles.

b. Cold Homogenization

Cold homogenization has been developed as an alternative to hot homogenization. Cold homogenization does not suffer from problems such as temperature-induced drug degradation or drug distribution into the aqueous phase during homogenization. The cold homogenization is particularly useful for solid lipid particles, but can be applied with slight modifications to produce liposomes and lipid micelles. In this technique the drug containing lipid melt is cooled, the solid lipid ground to lipid microparticles and these lipid microparticles are dispersed in a cold surfactant solution yielding a pre-suspension. The pre-suspension is homogenized at or below room temperature, where the gravitation force is strong enough to break the lipid microparticles directly to solid lipid nanoparticles.

2. Ultrasonication/High Speed Homogenization Methods

Lipid particles, including lipid micelles, liposomes, and solid lipid particles, can be prepared by ultrasonication/high speed homogenization. The combination of both ultrasonication and high-speed homogenization is particularly useful for the production of smaller lipid particles. Liposomes are formed in the size range from 10 nm to 200 nm, for example, 50 nm to 100 nm, by this process.

3. Solvent Evaporation Methods

Lipid particles can be prepared by solvent evaporation approaches. The lipophilic material is dissolved in a water-immiscible organic solvent (e.g. cyclohexane) that is emulsified in an aqueous phase. Upon evaporation of the solvent, particles dispersion is formed by precipitation of the lipid in the aqueous medium. Parameters such as temperature, pressure, choices of solvents can be used to control particle size and distribution. Solvent evaporation rate can be adjusted through increased/reduced pressure or increased/reduced temperature.

4. Solvent Emulsification-Diffusion Methods

Lipid particles can be prepared by solvent emulsification-diffusion methods. The lipid is first dissolved in an organic phase, such as ethanol and acetone. An acidic aqueous phase is used to adjust the zeta potential to induce lipid coacervation. The continuous flow mode allows the continuous diffusion of water and alcohol, reducing lipid solubility, which causes thermodynamic instability and generates liposomes 5. Supercritical Fluid Methods Lipid particles, including liposomes and solid lipid particles, can be prepared from supercritical fluid methods. Supercritical fluid approaches have the advantage of replacing or reducing the amount of the organic solvents used in other preparation methods. The lipids, active agents to be encapsulated, and excipients can be solvated at high pressure in a supercritical solvent. The supercritical solvent is most commonly $CO_2$, although other supercritical solvents are known in the art. To increase solubility of the lipid, a small amount of co-solvent can be used. Ethanol is a common co-solvent, although other small organic solvents that are generally regarded as safe for formulations can be used. The lipid particles, lipid micelles, liposomes, or solid lipid particles can be obtained by expansion of the supercritical solution or by injection into a non-solvent aqueous phase. The particle formation and size distribution can be controlled by adjusting the supercritical solvent, co-solvent, non-solvent, temperatures, pressures, etc.

6. Microemulsion Based Methods

Microemulsion based methods for making lipid particles are known in the art. These methods are based upon the dilution of a multiphase, usually two-phase, system. Emulsion methods for the production of lipid particles generally involve the formation of a water-in-oil emulsion through the addition of a small amount of aqueous media to a larger volume of immiscible organic solution containing the lipid. The mixture is agitated to disperse the aqueous media as tiny droplets throughout the organic solvent and the lipid aligns itself into a monolayer at the boundary between the organic and aqueous phases. The size of the droplets is controlled by pressure, temperature, the agitation applied and the amount of lipid present.

The water-in-oil emulsion can be transformed into a liposomal suspension through the formation of a double emulsion. In a double emulsion, the organic solution containing the water droplets is added to a large volume of aqueous media and agitated, producing a water-in-oil-in-water emulsion. The size and type of lipid particle formed can be controlled by the choice of and amount of lipid, temperature, pressure, co-surfactants, solvents, etc.

7. Spray Drying Methods

Spray drying methods similar to those described above for making polymeric particle can be employed to create solid lipid particles. Typically, this method is used with lipids with a melting point above 70° C.

In some embodiments, conjugates of the present invention may be encapsulated in polymeric particles using a single oil in water emulsion method. As a non-limiting example, the conjugate and a suitable polymer or block copolymer or a mixture of polymers/block copolymers, are dissolved in organic solvents such as, but not limited to, dichloromethane (DCM), ethyl acetate (EtAc) or chroloform to form the oil phase. Co-solvents such as, but not limited to, dimethyl formamide (DMF), acetonitrile (CAN) or benzyl alcohol (BA) may be used to control the size of the particles and/or to solubilize the conjugate. Polymers used in the formulation may include, but not limited to, PLA97-b-PEG5, PLA35-b-PEG5 and PLA16-b-PEG5 copolymers.

In some embodiments, particle formulations may be prepared by varying the lipophilicity of conjugates of the present invention. The lipophilicity may be varied by using hydrophobic ion-pairs or hydrophobic ion-paring (HIP) of the conjugates with different counterions. HIP alters the solubility of the conjugates of the present invention. The aqueous solubility may drop and the solubility in organic phases may increase.

Any suitable agent may be used to provide counterions to form HIP complex with the conjugate of the present invention. In some embodiments, the HIP complex may be formed prior to formulation of the particles.

VI. Methods of Using the Conjugates and Particles

The conjugates or particles as described herein can be administered to treat any hyperproliferative disease, metabolic disease, infectious disease, or cancer, as appropriate. The formulations can be used for immunization. Formulations may be administered by injection, orally, or topically, typically to a mucosal surface (lung, nasal, oral, buccal, sublingual, vaginally, rectally) or to the eye (intraocularly or transocularly).

In various embodiments, methods for treating a subject having a cancer are provided, wherein the method comprises administering a therapeutically-effective amount of the conjugates or particles, as described herein, to a subject having a cancer, suspected of having cancer, or having a predisposition to a cancer. According to the present invention, cancer embraces any disease or malady characterized by uncontrolled cell proliferation, e.g., hyperproliferation. Cancers may be characterized by tumors, e.g., solid tumors or any neoplasm.

In some embodiments, the subject may be otherwise free of indications for treatment with the conjugates or particles. In some embodiments, methods include use of cancer cells, including but not limited to mammalian cancer cells. In some instances, the mammalian cancer cells are human cancer cells.

In some embodiments, the conjugates or particles of the present teachings have been found to inhibit cancer and/or tumor growth. They may also reduce, including cell proliferation, invasiveness, and/or metastasis, thereby rendering them useful for the treatment of a cancer.

In some embodiments, the conjugates or particles of the present teachings may be used to prevent the growth of a tumor or cancer, and/or to prevent the metastasis of a tumor or cancer. In some embodiments, compositions of the present teachings may be used to shrink or destroy a cancer.

In some embodiments, the conjugates or particles provided herein are useful for inhibiting proliferation of a cancer cell. In some embodiments, the conjugates or particles provided herein are useful for inhibiting cellular proliferation, e.g., inhibiting the rate of cellular proliferation, preventing cellular proliferation, and/or inducing cell death. In general, the conjugates or particles as described herein can inhibit cellular proliferation of a cancer cell or both inhibiting proliferation and/or inducing cell death of a cancer cell.

The cancers treatable by methods of the present teachings generally occur in mammals. Mammals include, for example, humans, non-human primates, dogs, cats, rats, mice, rabbits, ferrets, guinea pigs, horses, pigs, sheep, goats, and cattle. In various embodiments, the cancer is lung cancer, breast cancer, e.g., mutant BRCA1 and/or mutant BRCA2 breast cancer, non-BRCA-associated breast cancer, colorectal cancer, ovarian cancer, pancreatic cancer, colorectal cancer, bladder cancer, prostate cancer, cervical cancer, renal cancer, leukemia, central nervous system cancers, myeloma, and melanoma. In some embodiments, the cancer is lung cancer. In certain embodiments, the cancer is human lung carcinoma, ovarian cancer, pancreatic cancer or colorectal cancer.

The conjugates or particles as described herein or formulations containing the conjugates or particles as described herein can be used for the selective tissue delivery of a therapeutic, prophylactic, or diagnostic agent to an individual or patient in need thereof. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. Dosage unit form as used herein refers to physically discrete units suited as unitary dosages for the mammalian subjects to be treated; each unit containing a predetermined quantity of active compound calculated to produce the desired therapeutic.

In various embodiments, a conjugate contained within a particle is released in a controlled manner. The release can be in vitro or in vivo. For example, particles can be subject to a release test under certain conditions, including those specified in the U.S. Pharmacopeia and variations thereof.

In various embodiments, less than about 90%, less than about 80%, less than about 70%, less than about 60%, less than about 50%, less than about 40%, less than about 30%, less than about 20% of the conjugate contained within particles is released in the first hour after the particles are exposed to the conditions of a release test. In some embodiments, less that about 90%, less than about 80%, less about 70%, less than about 60%, or less than about 50% of the conjugate contained within particles is released in the first hour after the particles are exposed to the conditions of a release test. In certain embodiments, less than about 50% of the conjugate contained within particles is released in the first hour after the particles are exposed to the conditions of a release test.

With respect to a conjugate being released in vivo, for instance, the conjugate contained within a particle administered to a subject may be protected from a subject's body, and the body may also be isolated from the conjugate until the conjugate is released from the particle.

Thus, in some embodiments, the conjugate may be substantially contained within the particle until the particle is delivered into the body of a subject. For example, less than about 90%, less than about 80%, less than about 70%, less than about 60%, less than about 50%, less than about 40%, less than about 30%, less than about 20%, less than about 15%, less than about 10%, less than about 5%, or less than about 1% of the total conjugate is released from the particle prior to the particle being delivered into the body, for example, a treatment site, of a subject. In some embodiments, the conjugate may be released over an extended period of time or by bursts (e.g., amounts of the conjugate are released in a short period of time, followed by a period of time where substantially no conjugate is released). For example, the conjugate can be released over 6 hours, 12 hours, 24 hours, or 48 hours. In certain embodiments, the conjugate is released over one week or one month.

VII. Kits and Devices

The invention provides a variety of kits and devices for conveniently and/or effectively carrying out methods of the present invention. Typically, kits will comprise sufficient amounts and/or numbers of components to allow a user to perform multiple treatments of a subject(s) and/or to perform multiple experiments.

In one embodiment, the present invention provides kits for inhibiting tumor cell growth in vitro or in vivo, comprising a conjugate and/or particle of the present invention or a combination of conjugates and/or particles of the present invention, optionally in combination with any other active agents.

The kit may further comprise packaging and instructions and/or a delivery agent to form a formulation composition. The delivery agent may comprise a saline, a buffered solution, or any delivery agent disclosed herein. The amount of each component may be varied to enable consistent, reproducible higher concentration saline or simple buffer formulations. The components may also be varied in order to increase the stability of the conjugates and/or particles in the buffer solution over a period of time and/or under a variety of conditions.

The present invention provides for devices which may incorporate conjugates and/or particles of the present invention. These devices contain in a stable formulation available to be immediately delivered to a subject in need thereof, such as a human patient. In some embodiments, the subject has cancer.

Non-limiting examples of the devices include a pump, a catheter, a needle, a transdermal patch, a pressurized olfactory delivery device, iontophoresis devices, multi-layered microfluidic devices. The devices may be employed to deliver conjugates and/or particles of the present invention according to single, multi- or split-dosing regiments. The devices may be employed to deliver conjugates and/or particles of the present invention across biological tissue, intradermal, subcutaneously, or intramuscularly.

It will be appreciated that the following examples are intended to illustrate but not to limit the present invention. Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

EXAMPLES

Example A: HPLC Analytical Methods: Analysis of the Product by C18 Reverse Phase HPLC (Method 1)

HPLC analysis of the compounds described herein was carried out on Zorbax Eclipse XDB-C18 reverse phase column (4.6×100 mm, 3.5 µm, Agilent PN: 961967-902) with a mobile phase consisting of water+0.1% TFA (solvent A) and acetonitrile+0.1% TFA (solvent B at a flow rate of the 1.5 mL/min and column temperature of 35° C. The injection volume was 10 µL and the analyte was detected using UV at 220 and 254 nm. The gradient is shown in Table 5.

TABLE 5

| | Gradient | |
|---|---|---|
| Time (mins) | % A | % B |
| 0 | 95 | 5 |
| 6 | 5 | 95 |
| 8 | 5 | 95 |
| 8.01 | 95 | 5 |
| 10 | 95 | 5 |

Example 1: Synthesis of Conjugate 1

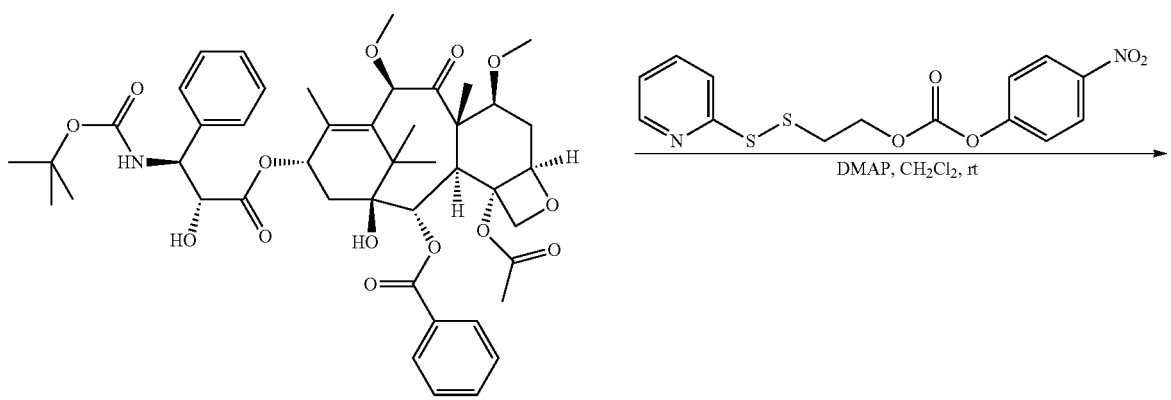

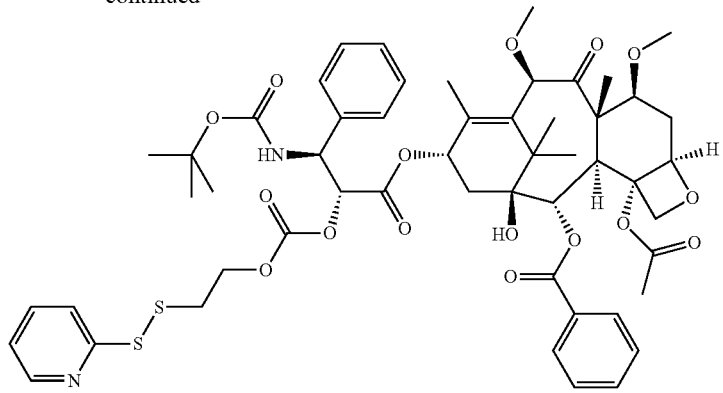

To a solution of cabazitaxel (2.00 g, 2.40 mmol) and 2-(2-pyridinyldithio)ethanol p-nitrophenyl carbonate (915 mg, 2.60 mmol) in dichloromethane (48 mL) was added DMAP (439 mg, 3.60 mmol). The solution was stirred at room temperature overnight, then washed with 0.1N HCl (3×20 mL), saturated aqueous NaCl (50 mL), and dried with sodium sulfate. The solvent was removed in vacuo, the remaining residue purified by silica gel chromatography (2:1 petroleum ether:ethyl acetate) to give cabazitaxel 2-(2-pyridyldithio)ethylcarbonate (2.50 g, 2.38 mmol, 99% yield). LCMS m/z: 1049 (M+H).

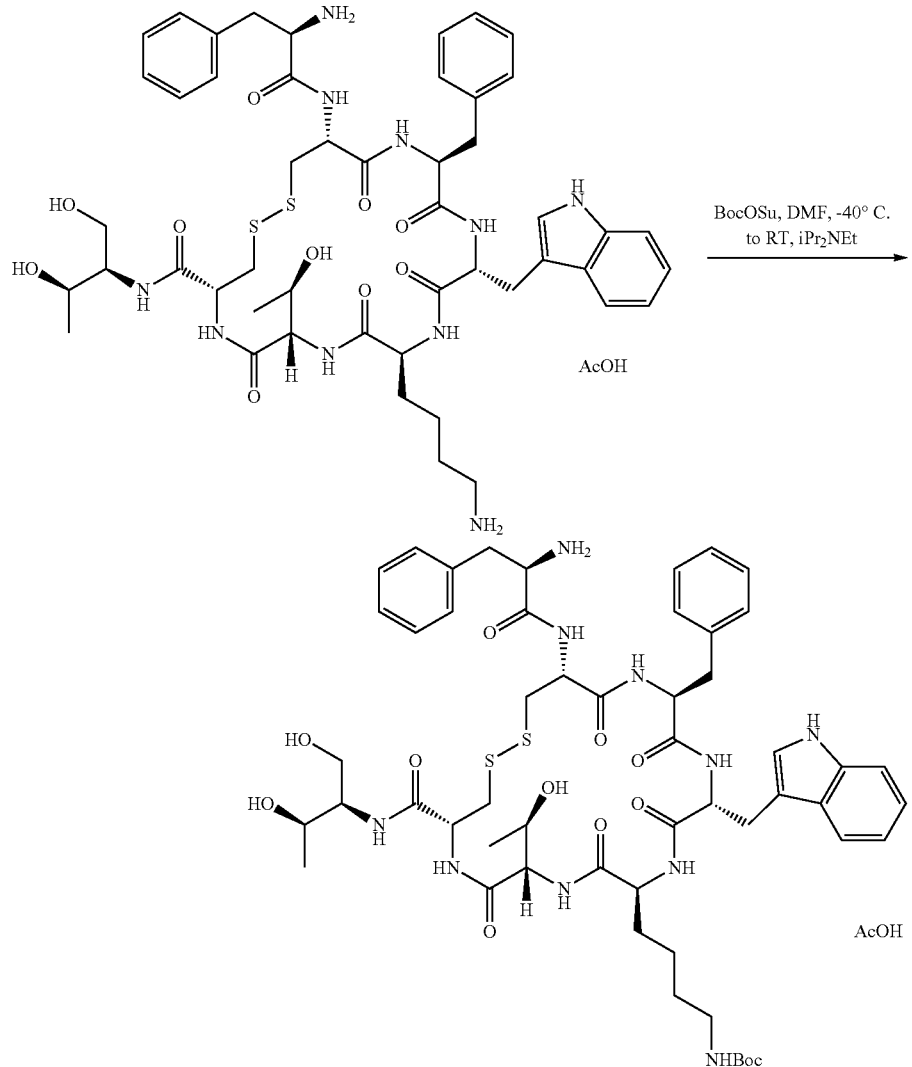

To a solution of octreotide acetate. (2.08 g, 1.93 mmol) in DMF (20 mL) and diisopropylethylamine (2.0 mL), cooled to −40° C., was added a solution of BocOSu (419 mg, 1.95 mmol) in DMF (5 mL) dropwise. The reaction was gradually warmed to room temperature, over 3 hours. Most of the DMF was removed, and the reaction mixture loaded onto a C18 column, eluting with 15% to 60% acetonitrile in water with 0.1% AcOH, to give the product as the acetate salt (1.53 g, 1.30 mmol, 67% yield). LCMS m/z: 510.3 (M-Boc+2H)/2.

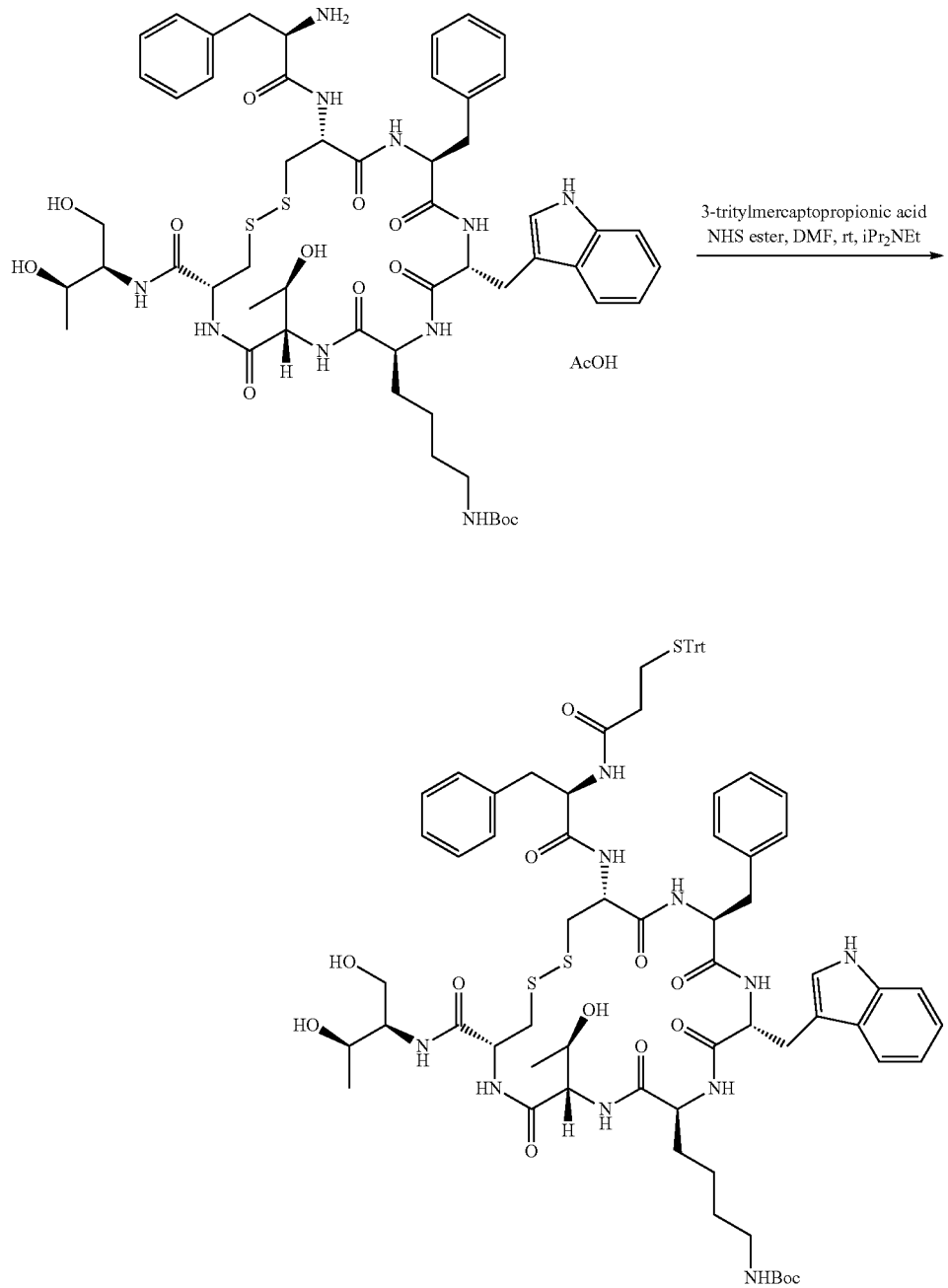

To a solution of Lys-Boc octreotide acetate (545 mg, 0.462 mmol) in DMF (10 mL) and diisopropylethylamine (1 mL) was added a solution of 3-tritylmercaptopropionic acid NHS ester (308 mg, 0.676 mmol) in DMF (4 mL). The reaction was stirred at 50° C. for 2 hours, after which HPLC shows complete consumption of starting material. All solvent was removed in vacuo, and the remaining material purified by reverse phase chromatography to give the product (623 mg, 0.430 mmol, 93% yield).

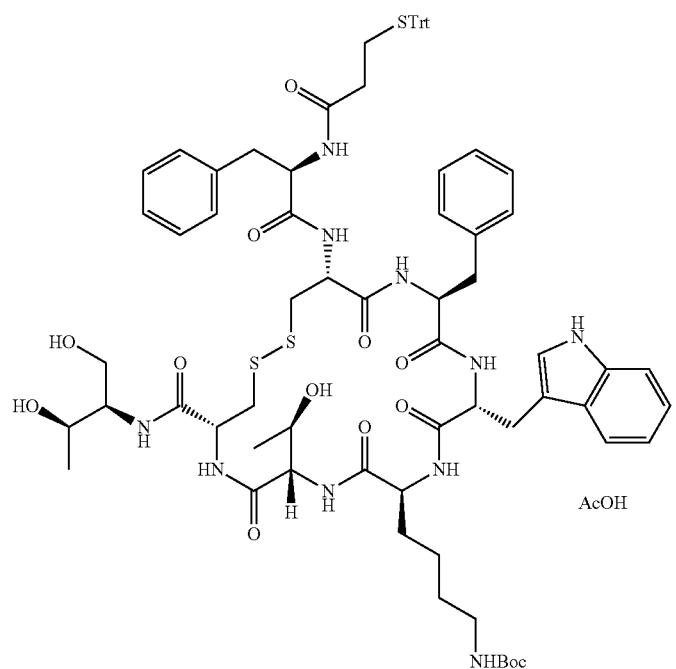
1) TFA, H₂O, iPr₃SiH
2) Cabazitaxel
2-(2-pyridyldithio)ethylcarbonate,
DMF, iPr₂NEt
AcOH
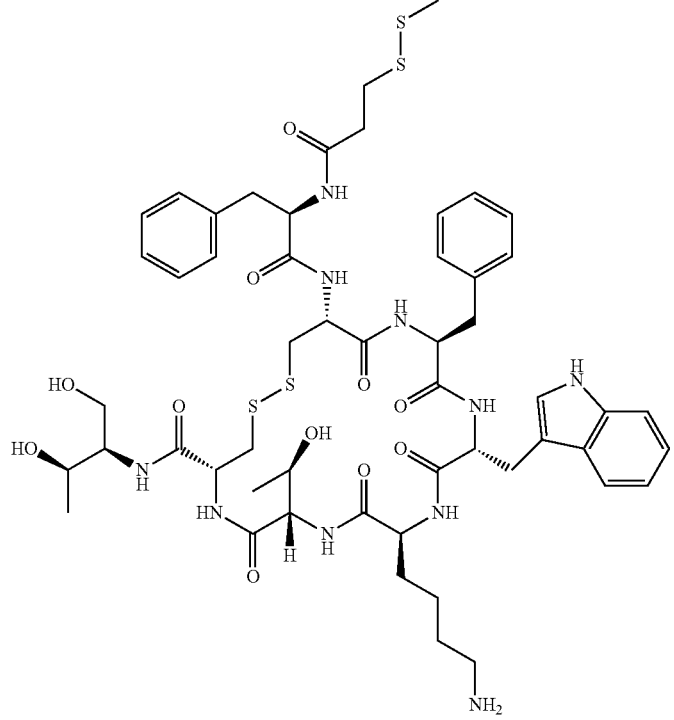

A vial was charged with Lys-Boc octreotide 3-tritylmercaptopropionamide (443 mg, 0.306 mmol), and water (0.25 mL), trifluoroacetic acid (10 mL) and triisopropylsilane (0.25 mL) were added. The reaction was stirred at room temperature for 10 min, and all solvents were removed in vacuo. The remaining residue was dissolved in DMF (7 mL) and diisopropylethylamine (0.50 mL). A solution of cabazitaxel 2-(2-pyridyldithio)ethylcarbonate (407 mg, 0.388 mmol) in DMF (3 mL) was added to the solution, and the reaction stirred at room temperature for 1 hour. The reaction was loaded onto a C18 column, eluting with 30% to 70% acetonitrile in water with 0.1% AcOH to give the desired product, conjugate 1, as the acetate salt (288 mg, 0.137 mmol, 45% yield). LCMS m/z: 1023.0 (M+2H)/2.

Example 2: Synthesis of Conjugate 2

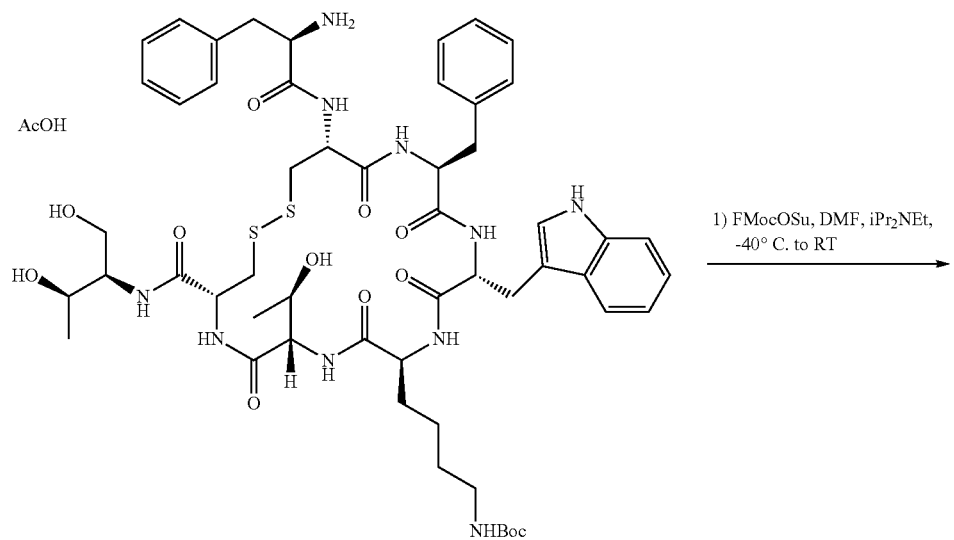

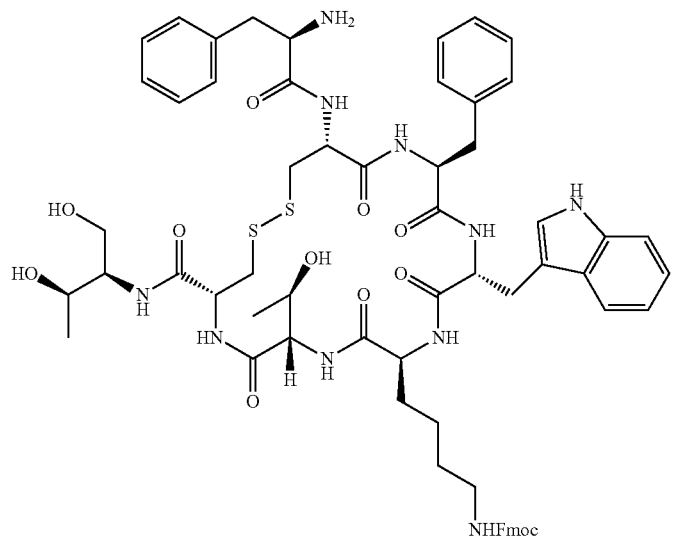

Octreotide acetate (515 mg, 0.477 mmol) was dissolved in DMF (6 mL) and diisopropylethylamine (1.0 mL). The solution was cooled to −40° C., and a solution of FMocOSu (182 mg, 0.539 mmol) in DMF (4 mL) was added dropwise. The reaction was gradually warmed to room temperature over 2 hours. pH 8.0 phosphate buffer (1 mL) was added, and the reaction mixture loaded onto a 50 g C18 column. Eluting with 15% to 85% acetonitrile in water gave Lys-Fmoc octreotide (419 mg, 0.337 mmol, 71% yield). LCMS m/z: 621.3 (M+2H)/2.

(1.84 g, 2.40 mmol, 100% yield). LCMS m/z: 397.1 (FMoc daunosamine), 352.2 (M-daunosamine).

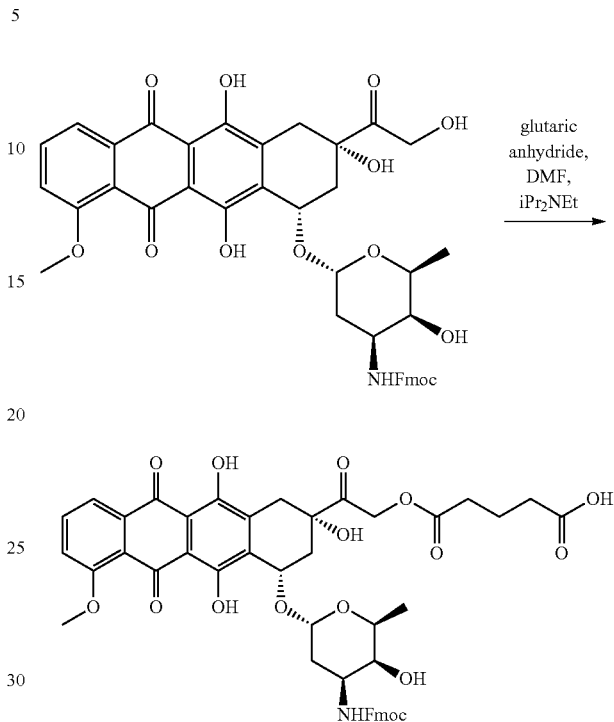

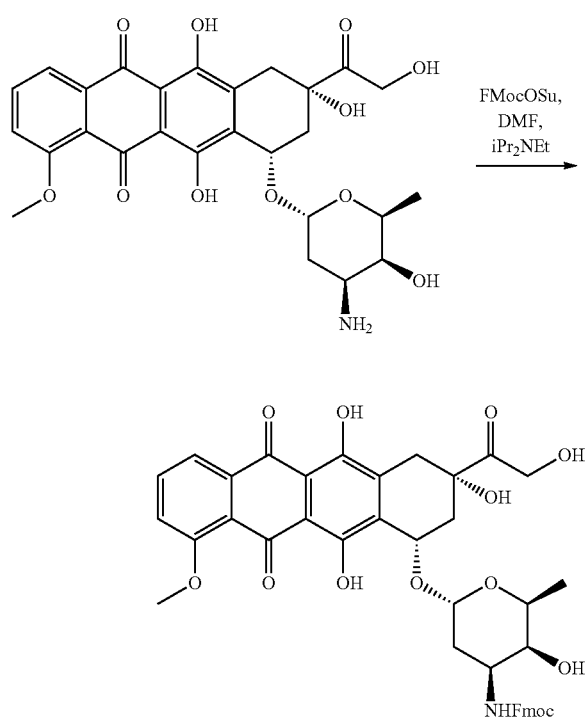

A flask was charged with doxorubicin (1.39 g, 2.40 mmol) and FMocOSu (1.69 g, 5.00 mmol). DMF (10 mL) and diisopropylethylamine (875 µL, 5.00 mmol) were added, and the reaction stirred at room temperature for 3 hours. All solvent was removed in vacuo, and the remaining residue loaded on an 80 g silica gel column, eluting with 0% to 8% methanol in dichloromethane to give FMoc doxorubicin A flask was charged with Fmoc doxorubicin (1.84 g, 2.40 mmol) and glutaric anhydride (1.09 g, 9.60 mmol). DMF (10 mL) and diisopropylethylamine (875 µL, 5.00 mmol) were added, and the reaction stirred at room temperature for 3 hours. Most of the solvent was removed in vacuo, until the total volume was ~5 mL. This solution was added dropwise into rapidly stirring 0.1% aqueous trifluoroacetic acid (100 mL), cooled to 0° C. The remaining suspension was filtered, the remaining solid washed with water (20 mL), and the solid dried in vacuo. The solid was taken up in 2% methanol in dichloromethane, and loaded onto an 80 g silica gel column. Eluting with 0% to 15% methanol in 99.5/0.5 dichloromethane/diisopropylethylamine gave Fmoc doxorubicin hemiglutarate (1.10 g, 1.25 mmol, 52% yield). LCMS m/z: 493.1 (M-daunosamine), 397.1 (FMoc daunosamine).

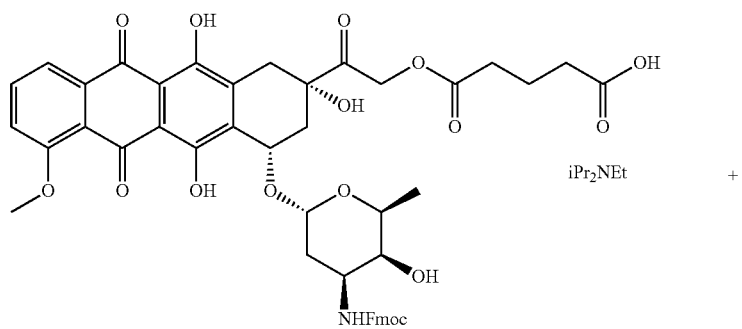

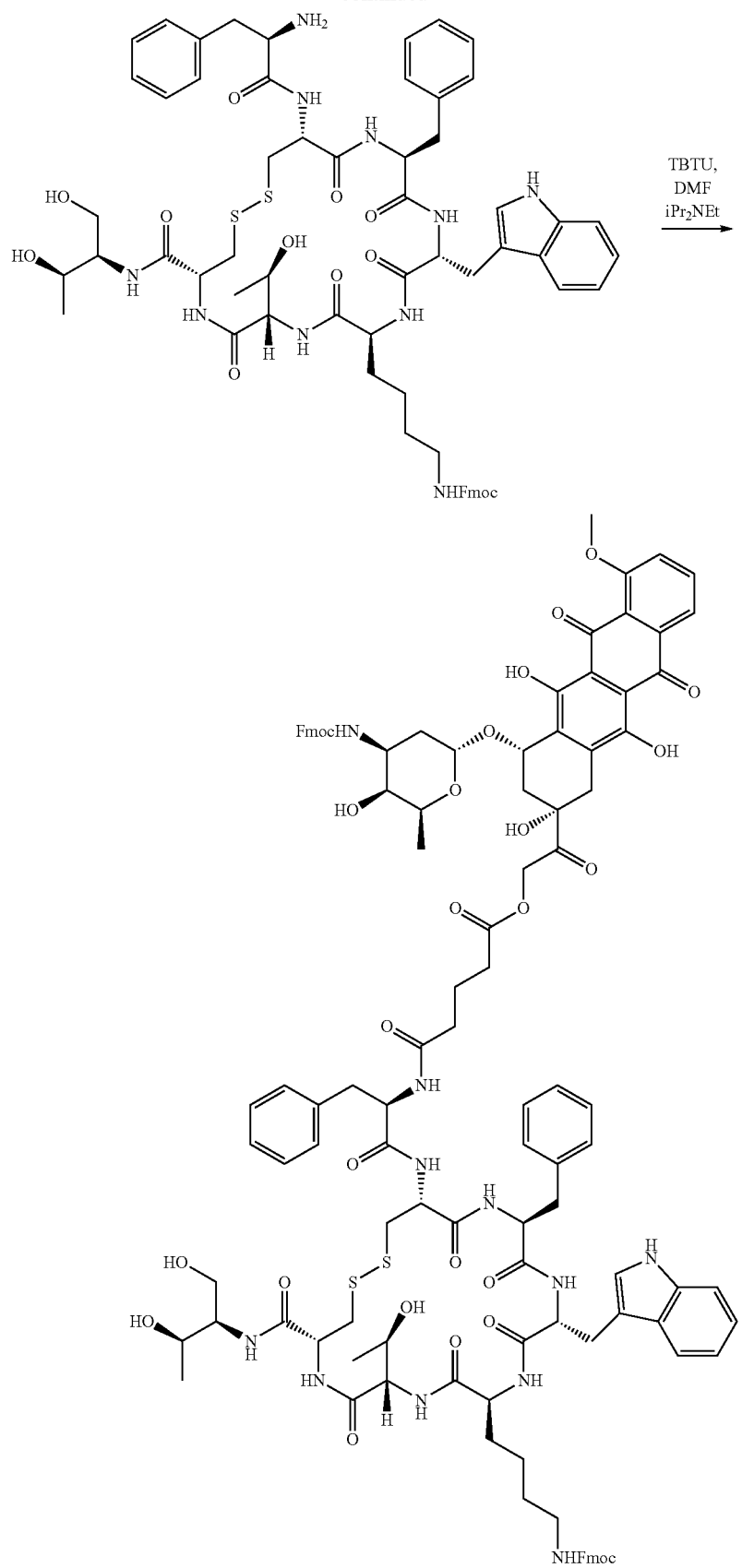

A vial was charged with Fmoc doxorubicin hemiglutarate (104 mg, 0.103 mmol), and to this was added a solution of Lys-FMoc octreotide (134 mmol, 0.107 mmol) in DMF (3 mL), followed by a solution of TBTU (66.1 mg, 0.206 mmol) in DMF (3 mL). Diisopropylethylamine (50 µL, 0.287 mmol) was added, and the reaction stirred at room temperature for 2 h. All solvent was removed in vacuo, and the remaining material loaded on a 24 g silica gel column. Eluting with 0% to 15% methanol in dichloromethane gave Lys-Fmoc octreotide hemiglutarate FMoc doxorubicin (208 mg, 0.0989 mmol, 96% yield).

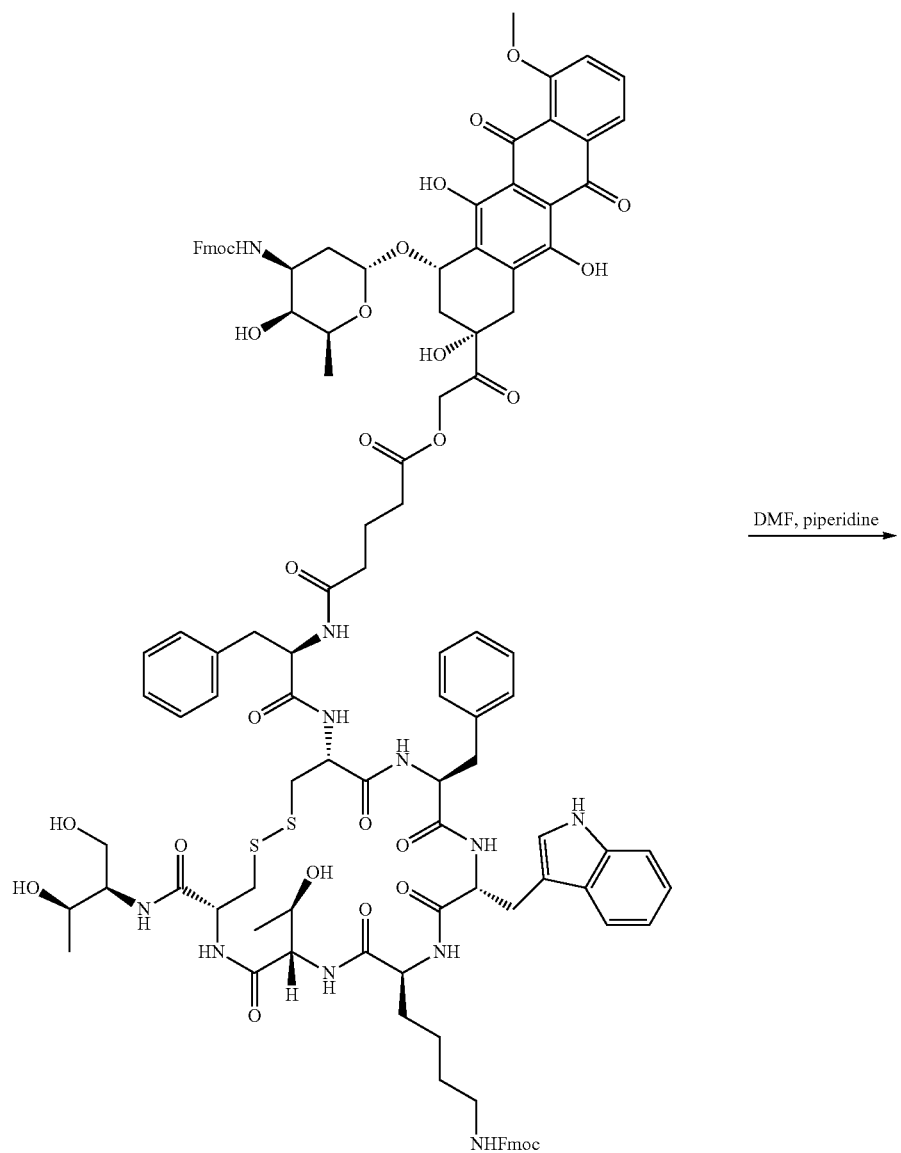

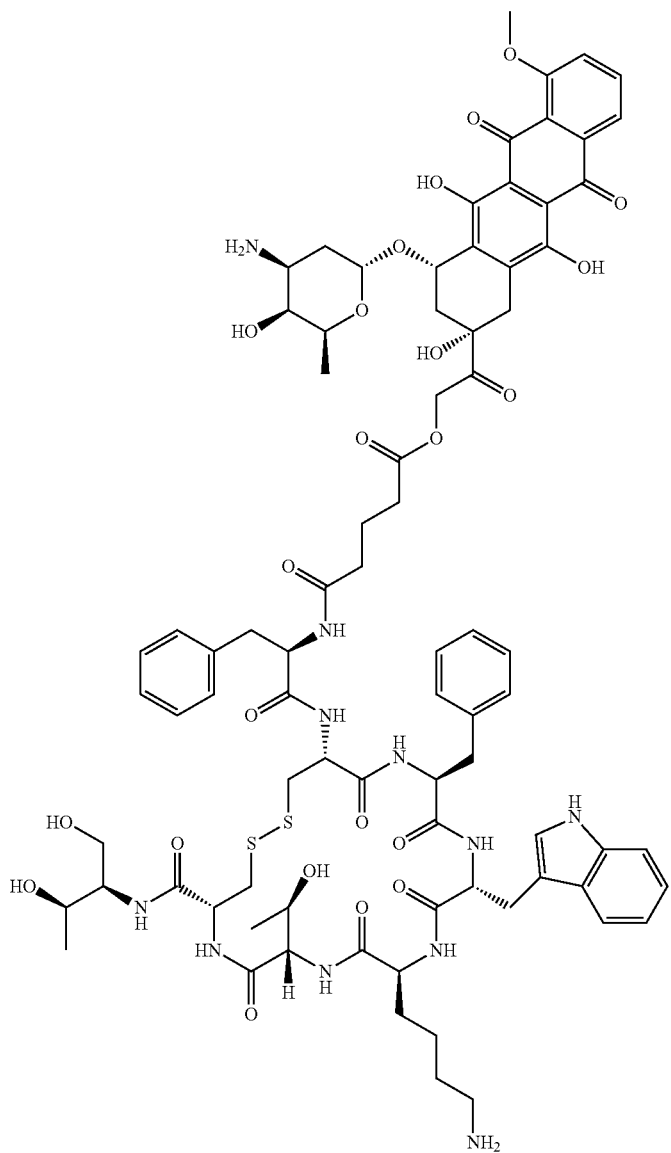

2

Lys-Fmoc octreotide hemiglutarate Fmoc doxorubicin (208 mg, 0.0989 mmol) was dissolved in 5 mL DMF, and 1 mL piperidine. After stirring for 30 minutes, all solvent was removed in vacuo, and the remaining residue was dissolved in DMF (1 mL), and this solution added dropwise into rapidly stirring ethyl acetate (100 mL). This suspension was stirred at room temperature for 5 min, filtered, the remaining solid washed with ethyl acetate (20 mL), and dried in vacuo. The remaining solid was purified by reverse phase chromatography (5% to 50% acetonitrile in water, with 0.1% TFA) to give the desired product as the bis-TFA salt (55.8 mg, 0.0296 mmol, 28% yield). LCMS m/z: 829.9 (M+2H)/2.

Example 3: Synthesis of Conjugate 3

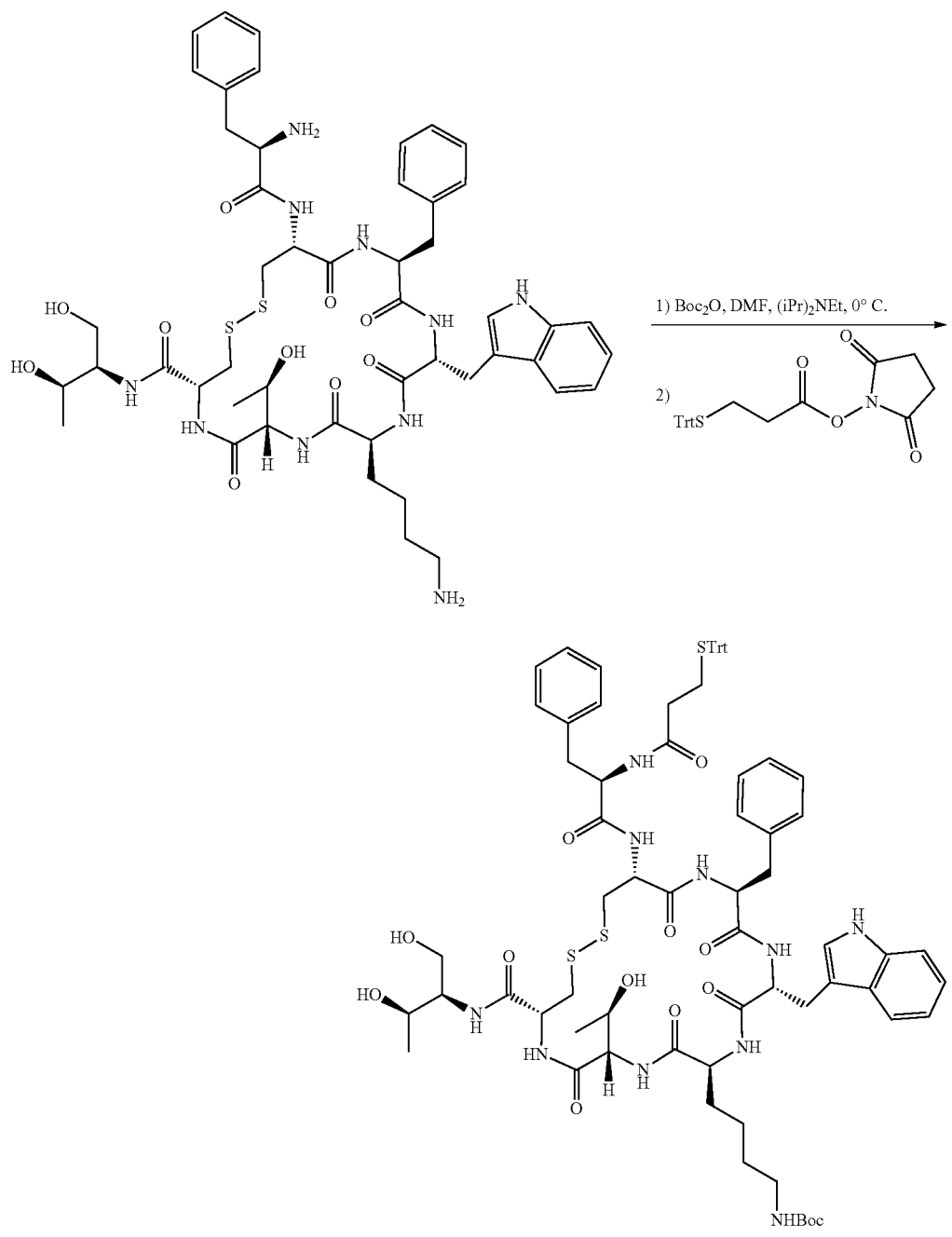

To a solution of octreotide acetate (540 mg, 0.501 mmol) in DMF (8 mL) and N,N-diisopropylethylamine (175 µL, 1.00 mmol), cooled to 0° C., was added a solution of di-tert-butyl dicarbonate (109 mg, 0.499 mmol) in DMF (7 mL). The reaction was stirred at 0° C. for 1 hour, then at room temperature for 1 hour. S-trityl-3-mercaptopropionic acid N-hydroxysuccinimide ester (668 mg, 1.50 mmol) was then added as a solid, and the reaction stirred at room temperature for 16 hours. The solvents were removed in vacuo, and the remaining material purified by silica gel chromatography (0% to 8% methanol in dichloromethane) to give A (560 mg, 0.386 mmol, 77% yield).

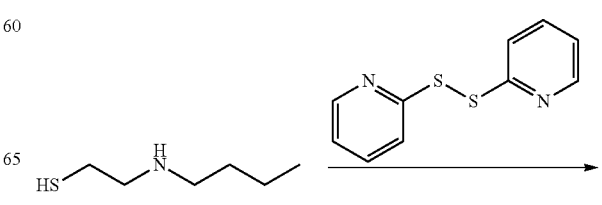

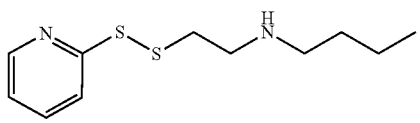

B

To a solution of 2,2'-dipyridyl disulfide (1.51 g, 6.85 mmol) in methanol (20 mL) was added 2-(butylamino)ethanethiol (500 µL, 3.38 mmol). The reaction was stirred at room temperature for 18 hours, then the solvents removed in vacuo. The remaining material was purified by silica gel chromatography to give disulfide B (189 mg, 0.780 mmol, 23% yield) which was stored at −18° C. until use.

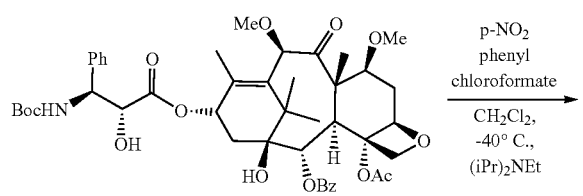

$\xrightarrow{\substack{\text{p-NO}_2\\\text{phenyl}\\\text{chloroformate}\\\text{CH}_2\text{Cl}_2,\\-40°\text{ C.,}\\(\text{iPr})_2\text{NEt}}}$

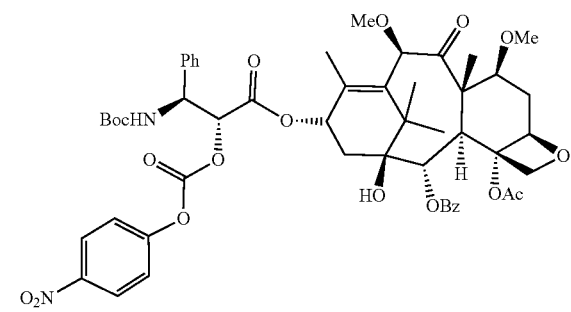

To a solution of cabazitaxel (410 mg, 0.490 mmol) in dichloromethane (10 mL) and pyridine (0.50 mL), cooled to −40° C., was added a solution of p-nitrophenyl chloroformate (600 mg, 2.98 mmol) in dichloromethane (10 mL). The reaction was stirred at −40° C. for 2 hours, and the reaction warmed to room temperature and washed with 0.1N HCl (20 mL). The aqueous layer was extracted with dichloromethane (2×20 mL), and the combined organic layers dried with MgSO$_4$, and the solvent removed in vacuo. The remaining material was purified by silica gel chromatography to give cabazitaxel-2'-p-nitrophenylcarbonate (390 mg, 0.390 mmol, 80% yield.)

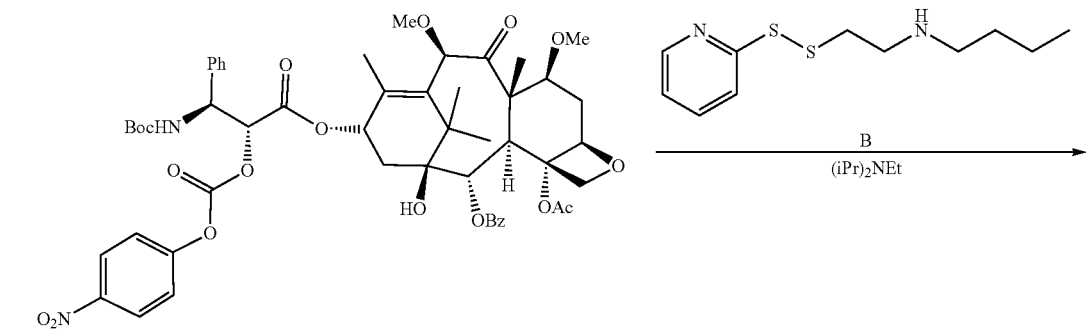

$\xrightarrow[(\text{iPr})_2\text{NEt}]{B}$

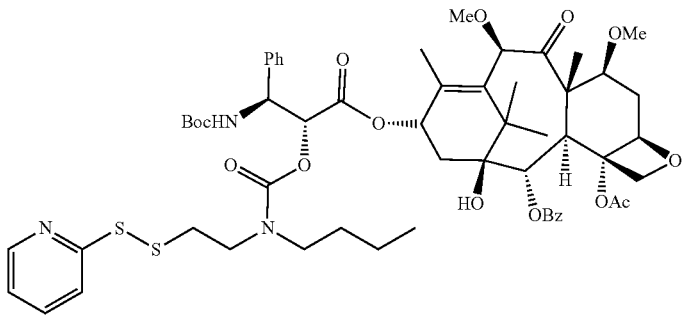

A solution of cabazitaxel-2'-p-nitrophenylcarbonate (390 mg, 0.390 mmol) in dichloromethane (15 mL) was added to B (190 mg, 0.784 mmol). N,N-diisopropylethylamine (1.0 mL, 5.74 mmol) was added, and the reaction stirred at 30° C. for 18 hours, then the solvents removed in vacuo and the remaining material purified by silica gel chromatography to give the cabazitaxel disulfide (326 mg, 0.295 mmol, 78% yield). ESI MS: calc'd 1103.4. found 1103.9 [M+1].

room temperature for 5 min until it turned colorless, then all solvents were removed in vacuo. To this residue was added the cabazitaxel disulfide (10.4 mg, 0.00942 mmol), pH 8.0 phosphate buffer (1.0 mL) and THF (1.0 mL). The reaction was stirred at room temperature for 2 hours. DMSO (1.0 mL) was added to solubilize any remaining solid residue, and the resulting solution purified by preparative HPLC (30% to 85% acetonitrile in water with 0.2% acetic acid) to

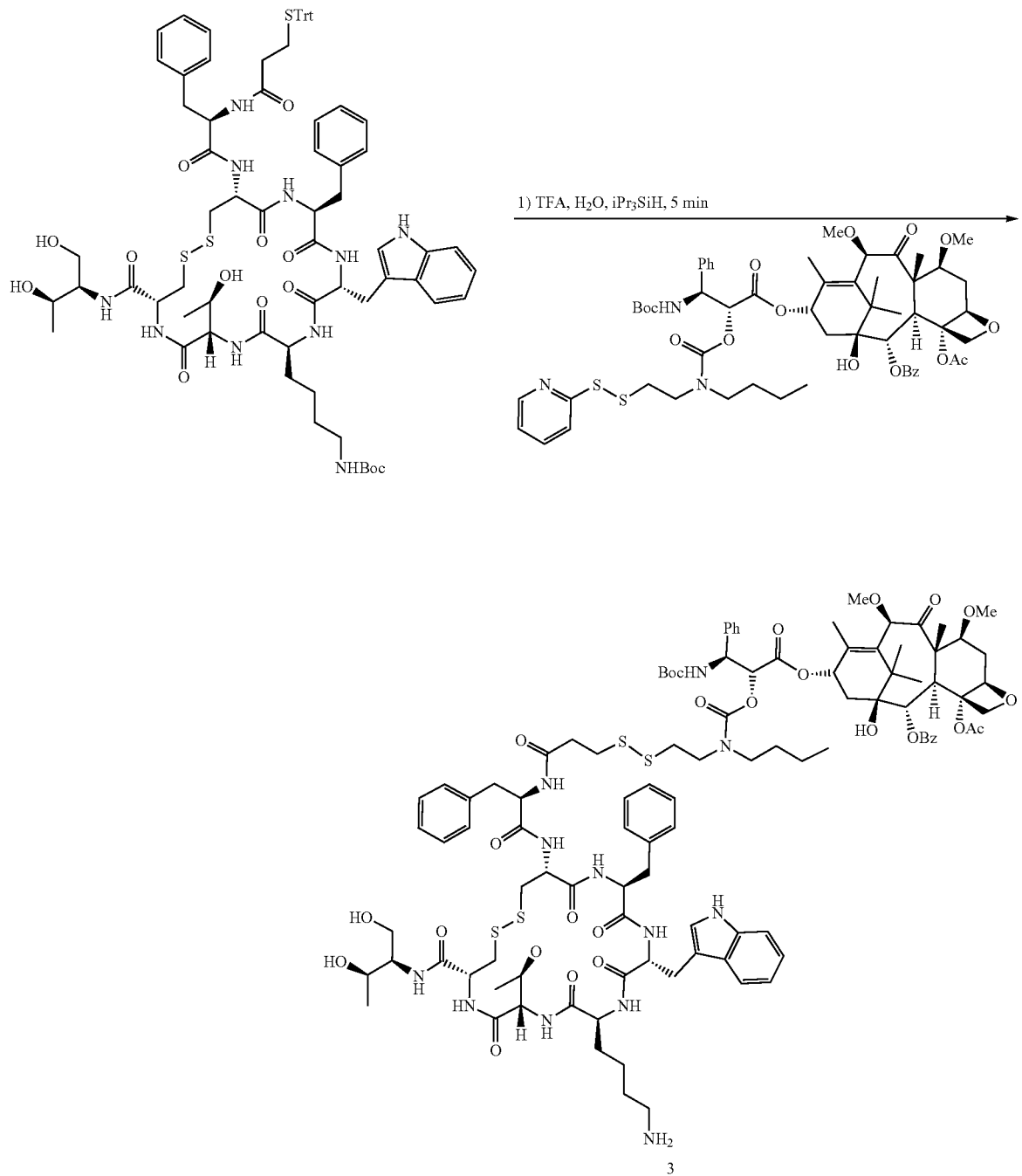

A vial was charged with A (10.0 mg, 0.00690 mmol), and water (25 μL), trifluoroacetic acid (500 μL) and triisopropylsilane (10 μL) were added. The reaction was stirred at give the product as the acetate salt (10.3 mg, 0.00477 mmol, 69% yield). ESI MS: calc'd 2098.9. found 1050.6 [(M+2)/2].

Example 4: Synthesis of Conjugate 4

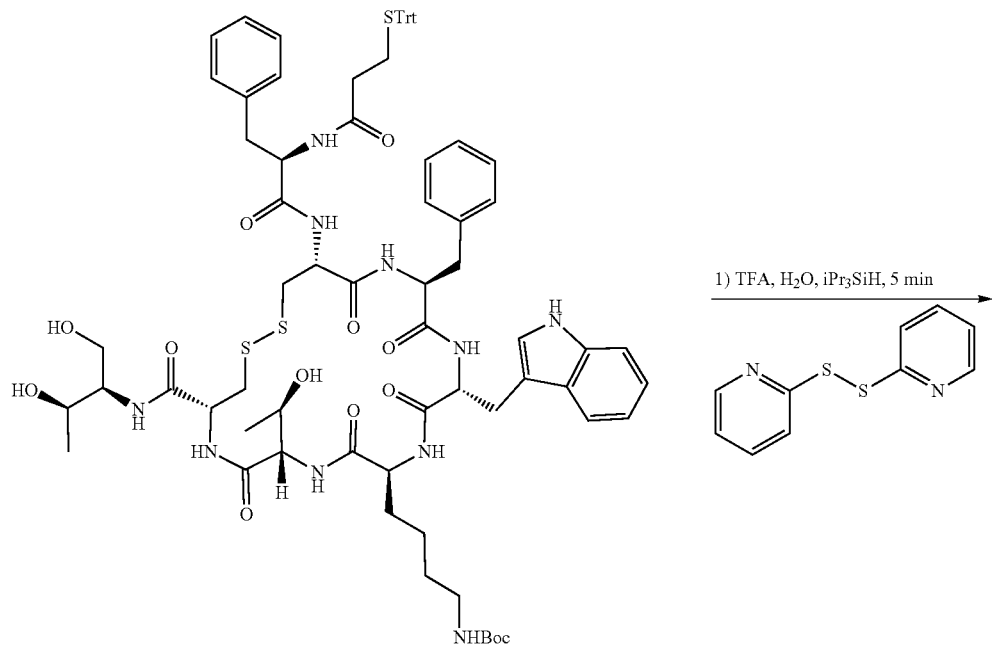

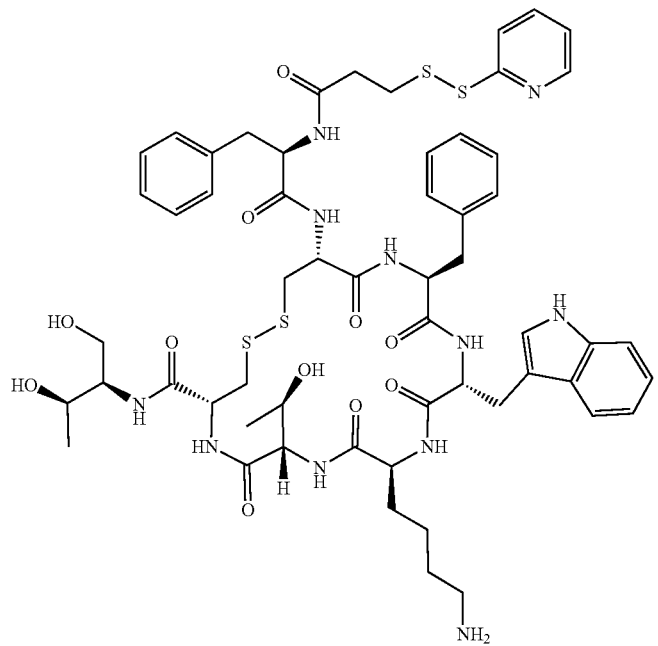

A vial was charged with trityl thio octreotide derivative (20.9 mg, 0.0144 mmol), and water (25 μL), trifluoroacetic acid (1.0 mL), and triisopropylsilane (10 μL) were added. The reaction was stirred at room temperature until it turned colorless (5 min), then all solvents were removed in vacuo. To this residue was added 2,2'-dipyridyl disulfide (10.5 mg, 0.0477 mmol), water (1.0 mL) and methanol (1.0 mL). The reaction was stirred at room temperature for 2 hours, then DMSO (1.0 mL) was added to solubilize any remaining solids. The reaction was purified by preparative HPLC (5% to 50% acetonitrile in water with 0.2% acetic acid) to give the disulfide as the acetate salt (12.6 mg, 0.00987 mmol, 69% yield). ESI MS: calc'd 1215.4. found 608.8 [(M+2)/2].

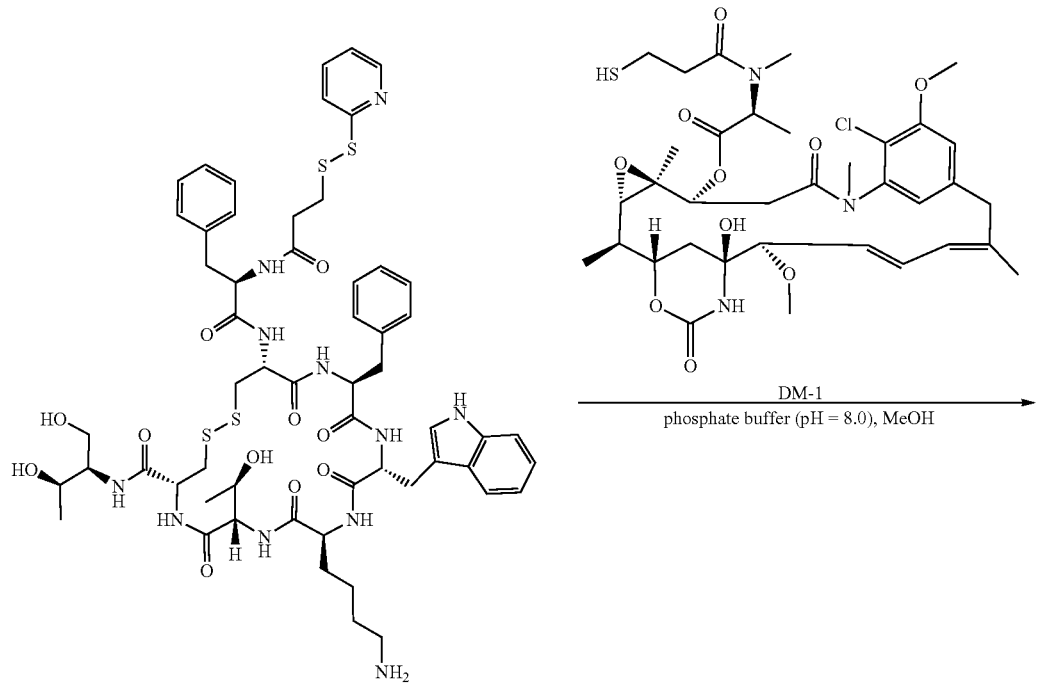

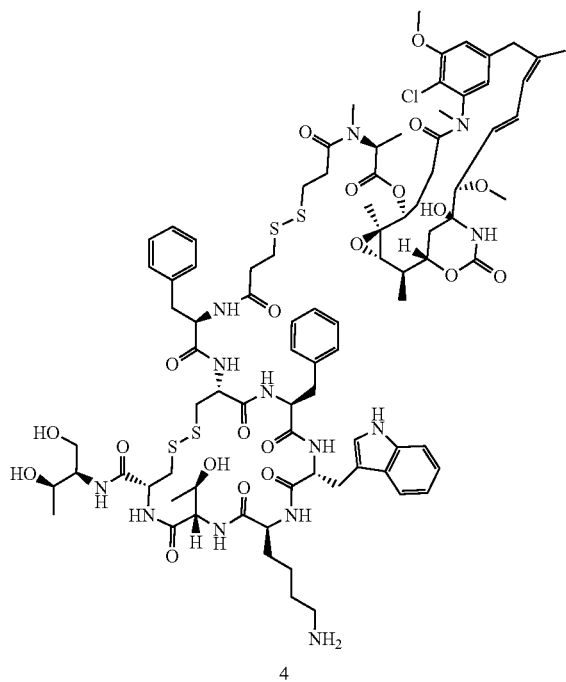

4

A vial was charged with the disulfide (10.0 mg, 0.00783 mmol) and DM-1 (6.00 mg, 0.00813). Phosphate buffer (pH 8, 2.0 mL) and methanol (3.0 mL) were added, and the reaction stirred for 2 hours at room temperature. DMSO (3.0 mL) was added to solubilize any remaining solids in the reaction mixture, and the reaction solution purified by preparative HPLC (25% to 75% acetonitrile in water with 0.2% acetic acid) to give the product as the acetate salt (9.32 mg, 0.00490 mmol, 63% yield). ESI MS: calc'd 1841.7, found 912.9 [(M+2-$H_2O$)/2].

Example 5: Synthesis of Conjugate 5

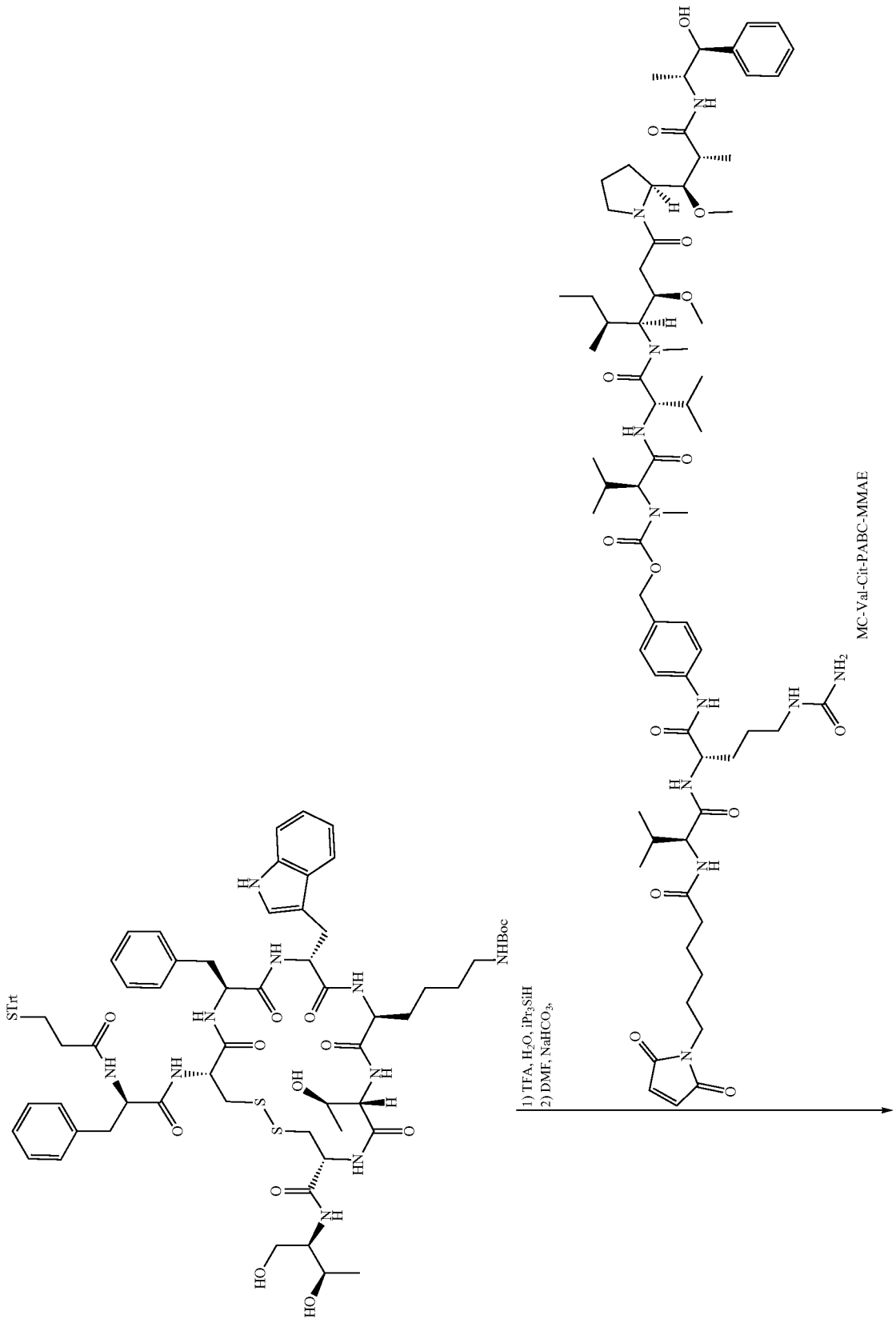

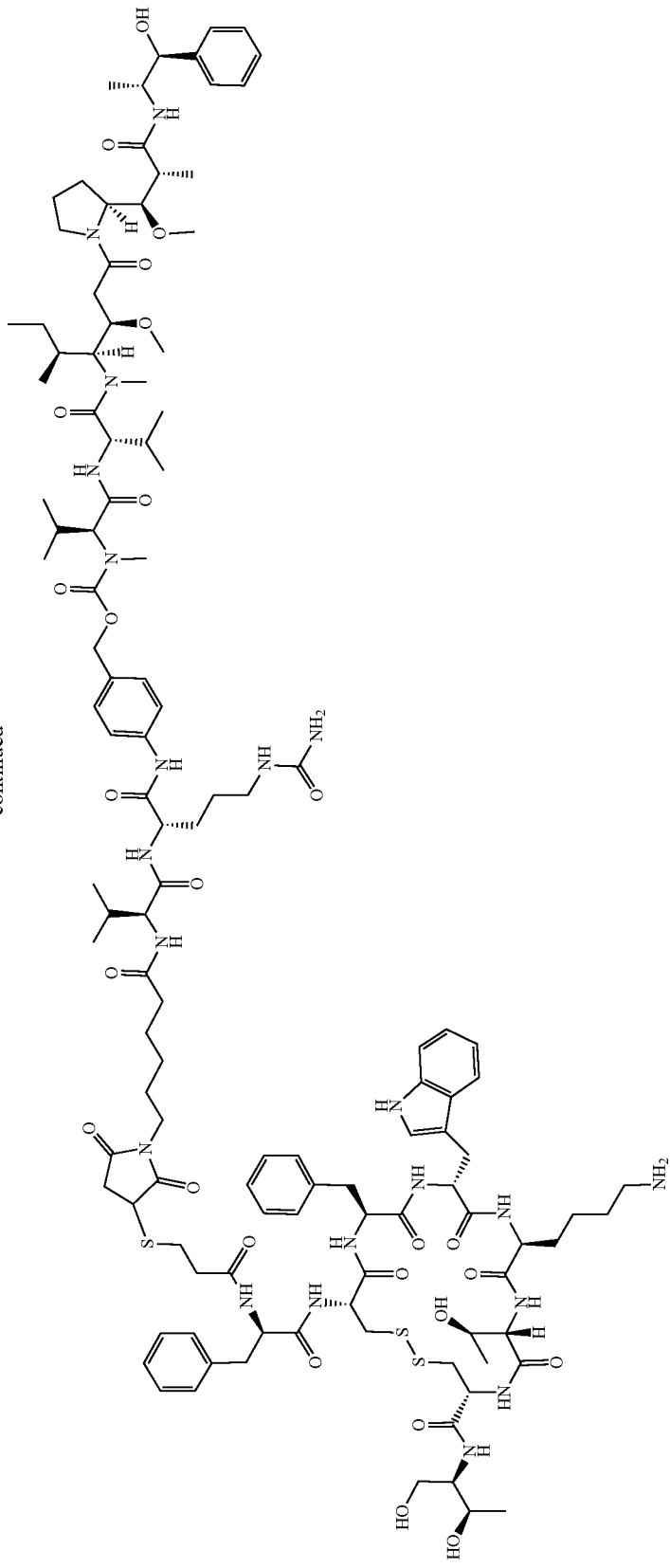

A vial was charged with trityl thio octreotide derivative (5.2 mg, 0.0036 mmol), and water (25 μL), trifluoroacetic acid (500 μL), and triisopropylsilane (10 μL) were added. The reaction was stirred until it turned colorless (5 minutes), then all solvents were removed in vacuo. To this was added a solution of MC-Val-Cit-PABC-MMAE (4.8 mg, 0.0036 mmol) in DMF (1.0 mL). Saturated sodium bicarbonate (100 μL) was added, and the reaction stirred at room temperature for 2 hours. Additional water (1 mL) was added, and the resulting solution was purified by preparative HPLC (30% to 75% acetonitrile in water with 0.2% acetic acid) to yield the product as the acetate salt (4.9 mg, 0.0020 mmol, 56% yield). ESI MS: calc'd 2422.2. found 1212.9 [(M+2)/2].

Example 6: Synthesis of Conjugate 6

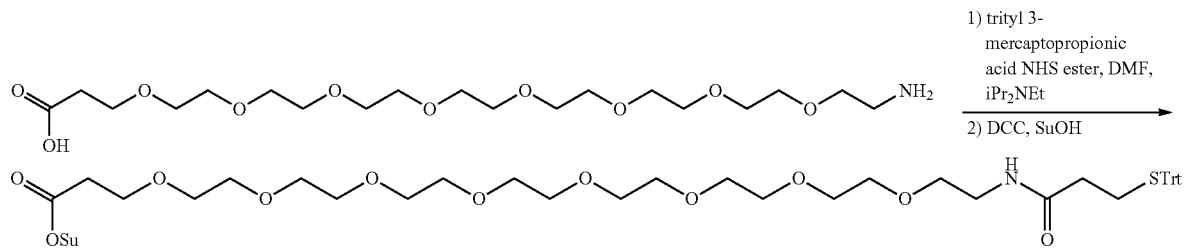

A vial was charged with amino-PEG8-acid (221 mg, 0.501 mmol) and trityl 3-mercaptopropionic acid NHS ester (223 mg, 0.501 mmol). DMF (5 mL) and diisopropylethylamine (500 μL) were added, and the reaction stirred at room temperature for 24 hours. After 24 hours, DCC (206 mg, 1.00 mmol) and N-hydroxysuccinimide (115 mg, 1.00 mmol) were added, and the reaction stirred for another 24 hours. The reaction mixture was filtered, washing the solid with 3 mL DMF, and the collected filtrate was concentrated in vacuo. The remaining material was purified by silica gel chromatography to give the product (406 mg, 0.467 mmol, 93% yield).

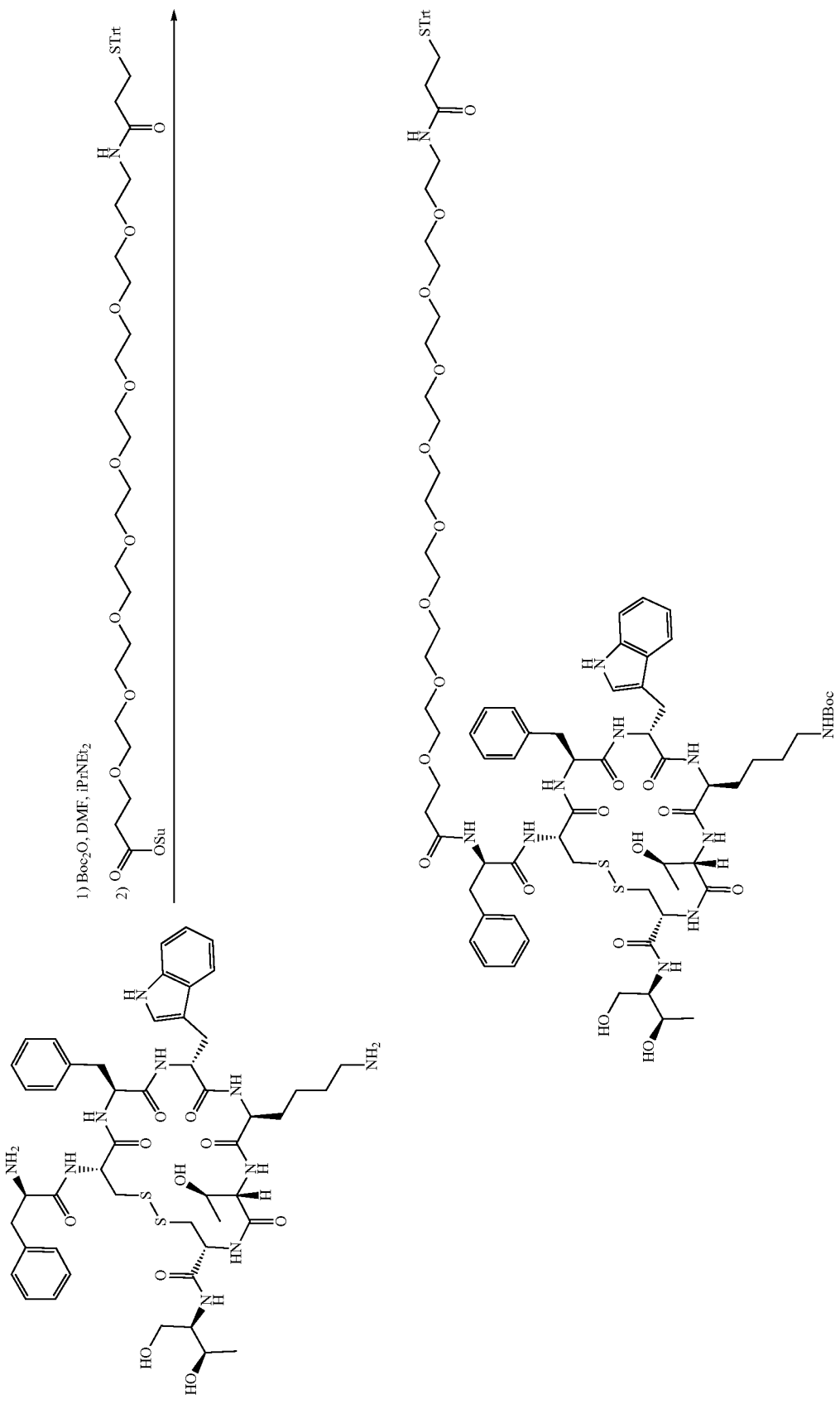

Octreotide acetate (335 mg, 0.311 mmol) was dissolved in DMF (5 mL), the solution cooled to 0° C., diisopropylethylamine (150 μL) was added, and a solution of $Boc_2O$ (67.9 mg, 0.311 mmol) in DMF (3 mL) was added dropwise. The reaction was stirred at 0° C. for 30 minutes, then warmed to room temperature for 30 minutes. A solution of the NHS ester in 5 mL DMF was then added, and the reaction stirred at room temperature for 3 days. All solvent was removed in vacuo, and the remaining residue purified by silica gel chromatography to give the product (249 mg, 0.133 mmol, 43% yield).

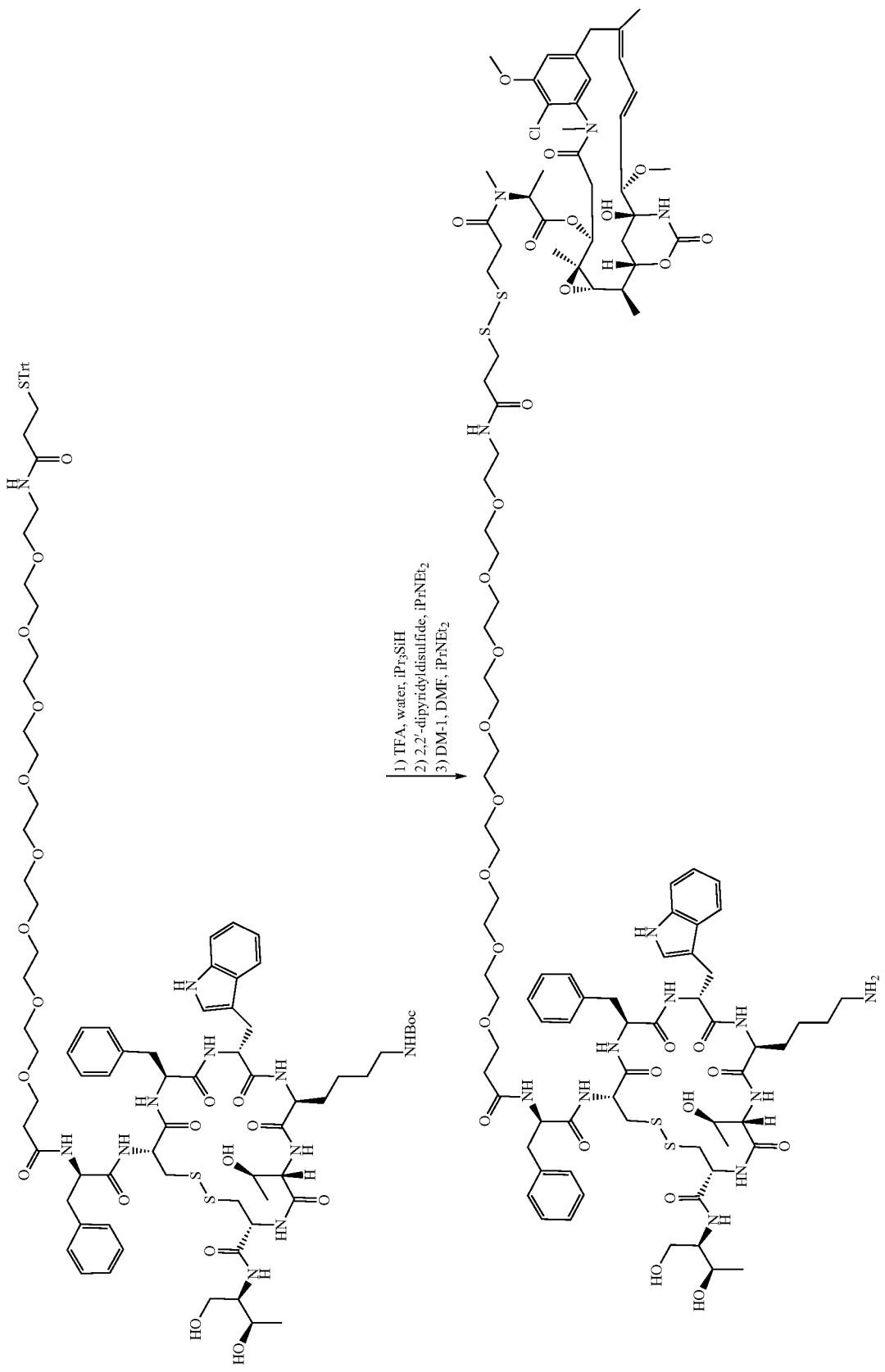

The starting material (21.2 mg, 0.0113 mmol) was dissolved in TFA (1 mL), water (25 μL), and triisopropylsilane (25 μL). The reaction was stirred at room temperature for 5 min, and all solvent was removed in vacuo. The remaining residue was dissolved in DMF (1 mL), and a solution of 2,2'-dipyridyldisulfide (15.0 mg, 0.0681 mmol) in DMF (1 mL) was added, followed by diisopropylethylamine (200 μL). The reaction was stirred at room temperature for 10 minutes, and purified by preparative HPLC. The intermediate 2-pyridyldisulfide was dissolved in DMF (1 mL), and a solution of DM-1 (6.0 mg, 0.0081 mmol) in DMF (1 mL) was added, followed by diisopropylethylamine (200 μL). The reaction was stirred at room temperature for 15 minutes, and the reaction mixture was purified by preparative HPLC to give the product (10.1 mg, 0.00445 mmol, 39% yield).

Example 7: Synthesis of Conjugate 7

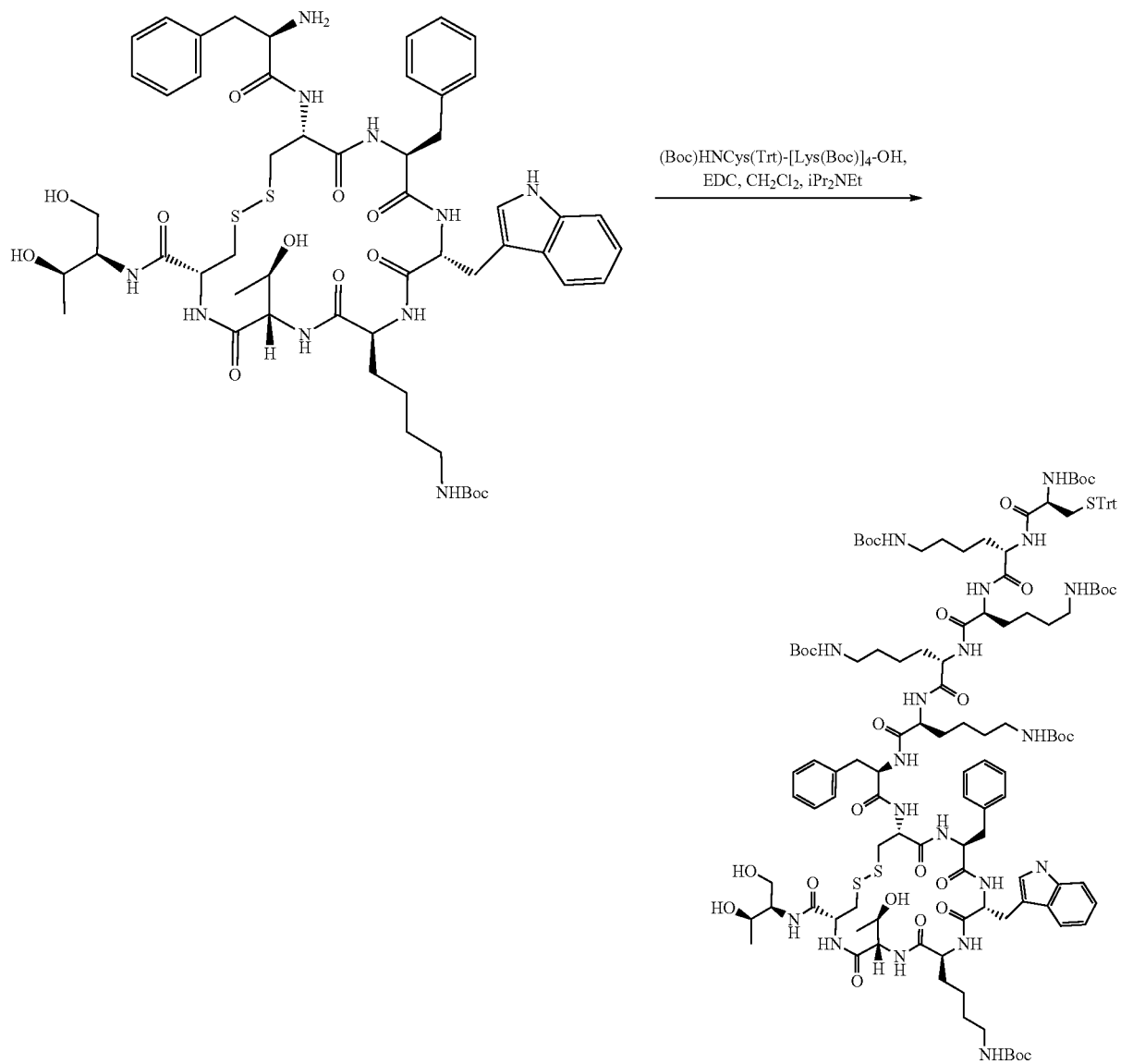

A mixture of Lys-Boc octreotide free base (50.0 mg, 0.0447 mmol), (Boc)HNCys(Trt)-[Lys(Boc)]₄—OH (80.0 mg, 0.0581 mmol), and EDC (19.1 mg, 0.100 mmol) in dichloromethane (3.0 mL) and diisopropylethylamine (0.20 mL) was stirred for 24 hours. The reaction was loaded onto a silica gel column, and eluting with 0% to 15% methanol in dichloromethane gave BocHN-Cys(Trt)-[Lys(Boc)]4-octreotide(Lys-Boc) (24.0 mg, 0.00968 mmol, 22% yield).

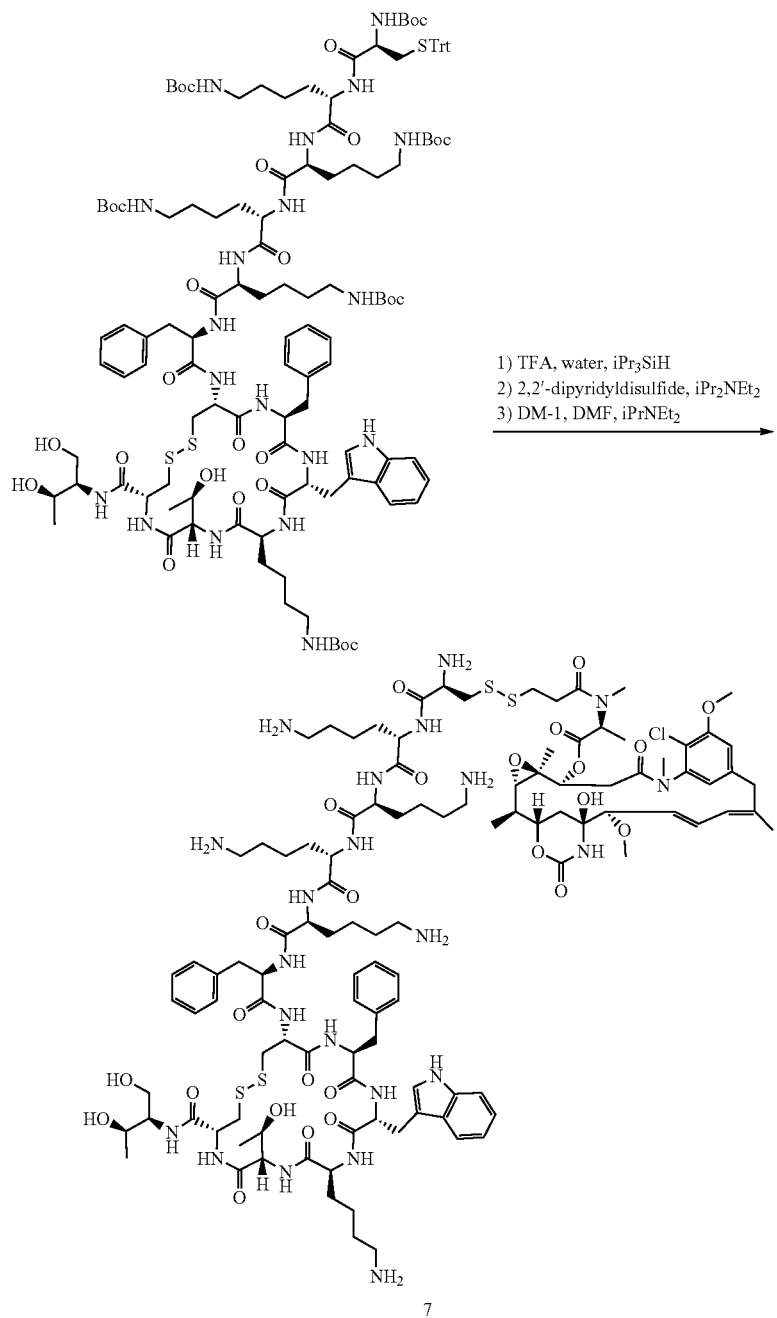

BocHN-Cys(Trt)-[Lys(Boc)]4-octreotide(Lys-Boc) (24.0 mg, 0.00968 mmol) was dissolved in water (25 μL), TFA (1 mL), and triisopropylsilane (25 μL). The reaction was stirred at room temperature for 5 minutes, and all solvent was removed in vacuo. The remaining residue was dissolved in DMF (1 mL), and a solution of 2,2'-dipyridyldisulfide (15.0 mg, 0.0681 mmol) in DMF (1 mL) was added, followed by diisopropylethylamine (100 μL). The reaction was stirred at room temperature for 5 minutes, and purified by preparative HPLC. The isolated pyridyl disulfide was dissolved in DMF (1 mL), and a solution of DM-1 (5.2 mg, 0.070 mmol) in DMF (1 mL) was added, followed by diisopropylethylamine (100 μL). The reaction was stirred at room temperature for 10 minutes, then purified by preparative HPLC to give the product (3.0 mg, 0.0013 mmol, 13% yield).

Example 8: Inhibition of Cell Proliferation by Conjugates

Conjugates were assessed in an in vitro assay evaluating inhibition of cell proliferation. NCI-H524 (ATCC) human lung cancer cells were plated in 96 well, V-bottomed plates (Costar) at a concentration of 5,000 cells/well and 24 hours later were treated with compound for 2 hours and further incubated 70 hours. Compound starting dose was 20 μM and three-fold serial dilutions were done for a total of ten points. After 2 hours of treatment, cells were spun down, the drug containing media was removed, and fresh complete medium was added and used to resuspend the cells, which were spun again. After removal of the wash media, the cells were resuspended in complete medium, then transferred into white walled, flat bottomed 96 well plates. Cells were further incubated for an additional 70 hours to measure inhibition of cell proliferation. Octreotide alone had no significant effect on cell proliferation. Proliferation was measured using CellTiter Glo reagent using the standard protocol (Promega) and a Glomax multi+detection system (Promega). Percent proliferation inhibition was calculated using the following formula: % inhibition=(control-treatment)/control*100. Control is defined as vehicle alone. $IC_{50}$ curves were generated using the nonlinear regression analysis (four parameter) with GraphPad Prism 6. Data for representative compounds (Conjugates 1-7) were shown in Table 6. $IC_{50}$ values for representative compounds with octreotide competition were also measured and were shown in Table 6.

TABLE 6

$IC_{50}$ of conjugates 1-7

| Conjugate | H524 $IC_{50}$ (nM) | H524 $IC_{50}$ + 100 μM octreotide (nM) |
|---|---|---|
| 1 | 110 | 146 |
| 2 | 2850 | 2940 |
| 3 | >20000 | >20000 |
| 4 | 229 | 853 |
| 5 | 433 | 826 |
| 6 | 234 | 629 |
| 7 | 955 | 1770 |

These data demonstrate that conjugates retain the ability to bind to somatostatin and internalize the receptor. In some instances, this also shows that the linker is cleaved to activate the cytotoxic payload effectively to kill the tumor cells.

Example 9: Ki of Conjugates for Somatostatin Receptor

Two conjugates were assessed in an in vitro assay evaluating binding to the somatostatin receptor 2 (SSTR2). A radioligand-receptor binding assay was conducted at Eurofins Panlabs (Taiwan) to determine the affinity of conjugates described herein to the SSTR2. The assay measures binding of radiolabeled ligand, [$^{125}$I] labeled somatostatin, to human SSTR2 using membrane preparations from SSTR2 expressing CHO-K1 cells. Membranes were incubated with radiolabeled somatostatin (0.03 nM) in the presence of conjugate/compound starting at a dose of 10 uM using 6× serial dilutions to obtain a 10-pt curve. After a four-hour incubation, membranes were filtered and washed 3× and counted to determine the remaining [$^{125}$I] somatostatin bound to the receptor. IC50 values were determined by a non-linear, least squares regression analysis using MathIQ™ (ID Business Solutions Ltd., UK). The Ki values were calculated using the equation of Cheng and Prusoff (Cheng and Prusoff, Biochem. Pharmacol. 22:3099-3108, 1973) using the observed IC50 of the tested conjugate/compound, the concentration of radioligand employed in the assay, and the historical values for the KD of the ligand obtained at Eurofins.

TABLE 7

Ki of conjugates 1-2

| Conjugate | SSTR2 Ki (nM) |
|---|---|
| 1 | 0.800 |
| 2 | 0.240 |
| 10 | 0.100 |
| 76 | 0.120 |
| 78 | 0.190 |

These data demonstrate that the high affinity of the peptide for the receptor is retained after addition of the linker and drug to the peptide.

Example 10: Internalization of Conjugates to Somatostatin Receptor

Two conjugates were assessed in an in vitro assay evaluating SSTR2. The steps outlined below provide the assay volumes and procedure for performing agonist assays using the PathHunter eXpress Activated GPCR Internalization cells and PathHunter Detection Reagents generally according to the manufacturer's recommendations. GraphPad Prism® was used to plot the agonist dose response.

TABLE 8

$EC_{50}$ of conjugates 1-2

| Conjugate | SSTR2 $EC_{50}$ (nM) |
|---|---|
| 1 | 4.4 |
| 2 | 35 |
| 76 | 3.0 |

These data demonstrate that the conjugates potently induce internalization of the receptor as a mechanism for the selective delivery of a conjugate to the cytoplasm of SSTR2 expressing cells.

Example 11: Nanoparticle Formulation of Conjugate 1

Nanoparticle formulation of conjugate 1. Octreotide-cabazitaxel conjugate 1 was successfully encapsulated in polymeric nanoparticles using a single oil in water emulsion method (refer to Table 9A and Table 9B below). In a typical water-emulsion method, the drug and a suitable polymer or block copolymer or a mixture of polymers/block copolymers, were dissolved in organic solvents such as dichloromethane (DCM), ethyl acetate (EtAc) or chloroform to form the oil phase. Co-solvents such as dimethyl formamide (DMF) or acetonitrile (ACN) or dimethyl sulfoxide (DMSO) or benzyl alcohol (BA) were sometimes used to control the size of the nanoparticles and/or to solubilize the drugs. A range of polymers including PLA97-b-PEG5, PLA35-b-PEG5 and PLA16-b-PEG5 copolymers were used in the formulations. Nanoparticle formulations were prepared by varying the lipophilicity of conjugate 1. The lipophilicity was varied by using hydrophobic ion-pairs of conjugate 1 with different counterions. Surfactants such as Tween® 80, sodium cholate, Solutol® HS or phospholipids were used in the aqueous phase to assist in the formation of the fine emulsion. The oil phase was slowly added to the continuously stirred aqueous phase containing an emulsifier (such as Tween® 80) at a typical 10%/90% v/v oil/water ratio and a coarse emulsion was prepared using a rotor-stator homogenizer or an ultrasound bath. The coarse emulsion was then processed through a high-pressure homogenizer (operated at 10,000 psi) for N=4 passes to form a nanoemulsion. The nanoemulsion was then quenched by a 10-fold dilution with cold (0-5° C.) water for injection quality water to remove the major portion of the ethyl acetate solvent resulting in hardening of the emulsion droplets and formation of a nanoparticle suspension. In some cases, volatile organic solvents such as dichloromethane can be removed by rotary evaporation. Tangential flow filtration (500 kDa MWCO, mPES membrane) was used to concentrate and wash the nanoparticle suspension with water for injection quality water (with or without surfactants/salts). A cryoprotectant serving also as tonicity agent (e.g., 10% sucrose) was added to the nanoparticle suspension and the formulation was sterile filtered through a 0.22 μm filter. The formulation was stored frozen at ≤−20° C. Particle size (Z-ave) and the polydispersity index (PDI) determined by dynamic light scattering of the nanoparticles were characterized by dynamic light scattering, as summarized in the table below. The actual drug load was determined using HPLC and UV-visible absorbance. This was accomplished by evaporating the water from a known volume of the nanoparticle solution and dissolving the solids in an appropriate solvent such as DMF. The drug concentration was normalized to the total solids recovered after evaporation. Encapsulation efficiency was calculated as the ratio between the actual and theoretical drug load.

Formulations Using Free Conjugate 1.

Conjugate 1 was observed to have a high solubility in aqueous media containing surfactants such as Tween® 80 and forms mixed micelles. In certain formulations, conjugate 1 was used without any changes to its native lipophilicity (free conjugate). Surprisingly, even with a high solubility of conjugate 1 in aqueous Tween® 80, the free conjugate exhibited a high degree of encapsulation in the nanoparticles. Without committing to any particular theory, the tendency of conjugate 1 to retain in the nanoparticle despite a high aqueous solubility in Tween®/water could be due to the high lipophilicity of cabazitaxel and its compatibility/miscibility with the polymeric matrix. The presence of two phenylalanine amino acids in the octreotide peptide may also assist in the interaction of the conjugate with the polymeric matrix.

Formulations Using Hydrophobic Ion Pairing (HIP) of Conjugate 1

HIP techniques were used to enhance the lipophilicity of conjugate 1. The conjugate has one positively charged moiety, on the lysine amino acid. A negatively charged dioctyl sodium sulfosuccinate (AOT) molecules was used for everyone molecule of the conjugate to form the HIP. The conjugate and the AOT were added to a methanol, dichloromethane and water mixture and allowed to shake for 1 hour. After further addition of dichloromethane and water to this mixture, the conjugate 1/AOT HIP was extracted from the dichloromethane phase and dried. Sometimes, DMF was used to solubilize the HIP complex. The results of the formulations are summarized in Table 9A and 9B.

TABLE 9A

Formulations of conjugate 1 nanoparticles using free drug conjugate (DC)

| | | | | Formulation # | | | | |
|---|---|---|---|---|---|---|---|---|
| | | | | | NP3 | | NP4 | NP6 |
| Process | Single emulsion | Single emulsion | Single emulsion | Single emulsion | Single emulsion | Single emulsion | Single emulsion | Single emulsion |
| Polymer | PLA97-mPEG5 | PLA16-mPEG5 | PLA16-mPEG5 | PLA97-mPEG5 | PLA16-mPEG5 | PLA16-mPEG5 | PLA35-mPEG5 |
| Polymer concentration, mg/mL | 100 | 100 | 100 | 100 | | 100 | 100 |
| Emulsion Volume, mL | 20 | 20 | 20 | 20 | 20 | 20 | 20 |
| Oil phase | 10% DMF/ 90% DCM | 10% DMF/ 90% DCM | 10% DMF/ 90% DCM | 10% DMF/ 90% EA | 10% DMF/ 90% EA | 10% DMF/ 90% EA | 20% DMF/ 80% EtOAc |
| Aqueous phase | cold 0.3% DiOctPC in water | cold 0.3% DiOctPC in water | cold water/EA | cold 0.2% Tween® 80 in water/EA | cold water/EA | cold 0.1% Tween® 80/EA | cold 0.1% DiOctPC in water/ EtOAc |
| Oil phase volume fraction, % | 10.00% | 10.00% | 10.00% | 10.00% | 10.00% | 10.00% | 10.00% |
| Wash* | ×10 cold water | ×10 cold water | ×20 cold water | Tween® 80 (0.5%) and ×30 cold water | Tween® 80 (0.2%) and ×25 cold water | Tween® 80 (0.2%) and ×25 cold water | Tween® 80 (0.2%) and ×25 cold water |
| Z.ave/PDI (quenched Emulsion) | 163.1/0.11 one peak | 69.3/0.159 one peak | 49.2/0.265 | 106.8/ 0.192 one peak | 95.6/0.564 | 44.95/ 0.191 | 69.4/0.190 |
| Z.ave/PDI (post TFF filtered) | 176(0.214) bump at small sizes | 78 (0.278) bump at small sizes | 50 (0.6) bimodal distribution with peaks at ~150 and 13 mn | 101.1 (0.194) one peak | 85.2/0.632 | 44.8/ 0.127 | 62.7/0.145 |

TABLE 9A-continued

Formulations of conjugate 1 nanoparticles using free drug conjugate (DC)

Formulation #

| | | | | NP3 | | NP4 | NP6 |
|---|---|---|---|---|---|---|---|
| TDL (wt %) | 9.27 | 9.18 | 9.26 | 9.13 | 9.31 | 5.93 | 4.87 |
| ADL (wt %) | 8.13 | 8.76 | 8.64 | 8.26 | 8.64 | 5.49 | 4.76 |
| EE = ADL/TDL, % | 87.7 | 95.4 | 93.4 | 96.85 | 92.73% | 92.49% | 102.32% |
| Potency, mg/mL | 0.52 | 0.54 | 0.49 | 0.45 | 0.835 | 0.228 | 0.52 |

TABLE 9B

Formulations of conjugate 1 nanoparticles using conjugate 1/AOT HIP

| Formulation # | | NP1 | NP2 | |
|---|---|---|---|---|
| Process | Single emulsion | Single emulsion | Single emulsion | Single emulsion |
| Polymer | PLA16-mPEG5 | PLA97-mPEG5 | PLA35-mPEG5 | PLA16-mPEG5 |
| Polymer concentration, mg/mL | 100 | 100 | 100 | 100 |
| Emulsion Volume, mL | 20 | 20 | 20 | 20 |
| Oil phase | 10% DMF/90% DCM | 20% DMF/80% EtOAc | 20% DMF/80% EtOAc | 10% DMF/90% EtOAc |
| Aqueous phase | cold water | cold 0.2% DiOctPC in water/EtOAc | cold 0.2% DiOctPC in water/EtOAc | cold 0.2% DiOctPC in water/EtOAc |
| Oil phase volume fraction, % | 10.00% | 10.00% | 10.00% | 10.00% |
| Wash* | Tween ® 80 (0.2%) and saline ×15 cold water | Tween ® 80 (0.2%) and saline ×25 cold water | Tween ® 80 (0.2%) and saline ×20 cold water | Tween ® 80 (0.2%) and saline ×20 cold water |
| Z.ave/PDI (quenched Emulsion) | 100/0.26 one major peak | 106/0.09 one peak | 102/0.05 one peak | 86.6/0.123 |
| Z.ave/PDI (post TFF filtered) | 90/0.28 one major peak | 91/0.1 one peak | 75/0.08 one peak | 54/0.184 |
| TDL (wt %) | 4.10 | 6.50 | 3.6 | 5.65 |
| ADL (wt %) | 4.89 | 6.73 | 3.62 | 5.7 |
| EE = ADL/TDL, % | 120.0 | 103.0 | 100 | 101 |
| Potency, mg/mL | 0.17 | 0.66 | 0.44 | 0.503 |

TDL: Theoretical Drug Loading
ADL: Actual Drug Loading
NA: not available
EE: encapsulation efficiency
*Washing was optimized for each nanoparticle formulation.

These data demonstrate that somatostatin receptor targeted conjugates can be efficiently and effectively encapsulated in nanoparticles.

Example 12: Nanoparticles Containing Conjugate 2

Conjugate 2 was successfully encapsulated in polymeric nanoparticles using a single oil in water emulsion method (refer to Table 6A and 6B below). In a typical water-emulsion method, the drug and a suitable polymer or block copolymer or a mixture of polymers/block copolymers, were dissolved in organic solvents such as dichloromethane (DCM), ethyl acetate (EtAc) or chloroform to form the oil phase. Co-solvents such as dimethyl formamide (DMF) or acetonitrile (ACN) or dimethyl sulfoxide (DMSO) or benzyl alcohol (BA) were sometimes used to control the size of the nanoparticles and/or to solubilize the drugs. A range of polymers including PLA97-b-PEG5, PLA74-b-PEG5, PLA35-b-PEG5 and PLA16-b-PEG5 copolymers were used in the formulations. Nanoparticle formulations were prepared by varying the lipophilicity of conjugate 2. The lipophilicity of conjugate 2 was varied by using hydrophobic ion-pairs of conjugate 2 with different counterions. Surfactants such as Tween® 80, sodium cholate, Solutol® HS or lipids were used in the aqueous phase to assist in the formation of the fine emulsion. The oil phase was slowly added to the continuously stirred aqueous phase containing an emulsifier (such as Tween® 80) at a typical 10/90% v/v oil/water ratio and a coarse emulsion was prepared using a rotor-stator homogenizer or an ultrasound bath. The coarse emulsion was then processed through a high-pressure homogenizer (operated at 10,000 psi) for N=4 passes to form a nanoemulsion. The nanoemulsion was then quenched by a 10-fold dilution with cold (0-5° C.) water for injection quality water to remove the major portion of the ethyl acetate solvent resulting in hardening of the emulsion droplets and formation of a nanoparticle suspension. In some cases, volatile organic solvents such as dichloromethane can be removed by rotary evaporation. Tangential flow filtration (500 kDa MWCO, mPES membrane) was used to concentrate and wash the nanoparticle suspension with water for injection quality water (with or without surfactants/salts). A lyoprotectant (e.g., 10% sucrose) was added to the nanoparticle suspension and the formulation was sterile filtered through a 0.22 μm filter. The formulation was stored frozen at ≤−20° C. Particle size (Z-avg.) and the polydispersity index (PDI) of the nanoparticles were characterized by dynamic light scattering, as summarized in the table below. The actual drug load was determined using HPLC and UV-Vis absorbance. This was accomplished by evaporating the water from a known volume of the nanoparticle solution and dissolving the solids in an appropriate solvent such as DMF. The drug concentration was normalized to the total solids recovered after evaporation. Encapsulation efficiency was calculated as the ratio between the actual and theoretical drug load.

In some formulations, conjugate 2 was used without any changes to its native lipophilicity (free conjugate). Surprisingly, even with a high solubility of 2 in aqueous Tween® 80, and the hydrophilic nature of octreotide, the free conjugate exhibited a high degree of encapsulation in the nanoparticles. The tendency of 2 to be retained in the nanoparticle was reduced compared to 1.

Formulations Using HIP of Conjugate 2

Hydrophobic ion-pairing (HIP) techniques were used to enhance the lipophilicity of conjugate 2. The conjugate has two basic moieties, on the lysine and on the doxorubicin. A negatively charged dioctyl sodium sulfosuccinate (AOT) molecule was used for every molecule of the conjugate to form the HIP. The conjugate and the AOT were added to a methanol, dichloromethane and water mixture and allowed to shake for 1 hour. After further addition of dichloromethane and water to this mixture, the conjugate 2/AOT HIP was extracted from the dichloromethane phase and dried. In some cases, DMF was used to solubilize the HIP complex. Specifications and data are shown in Table 10A and Table 10B.

Example of Preparing an HIP Complex of Conjugate 2 with AOT

Positive charges on conjugate 2=2; MW=1658.9 g/mol

Mass of conjugate 2=34.5 mg.

moles of conjugate 2=0.0208 mmoles

Moles of AOT required to cover the 2 positive charges=0.0416 mmoles.

Weight of AOT (mg) [MW=445 g/mol]=18.5 mg

Conjugate 2 and AOT were added to a solution of 1 mL of water and 2.1 mL of methanol. 1 mL of dichloromethane was added to this mixture. A clear red homogenous solution was obtained. This solution was shaken for at around 30 minutes. 1 mL water and 1 mL of dichloromethane were added to the solution and the mixture was shaken briefly. The two phases were allowed to separate. Sometimes in order to accelerate the separation of the two phases, the mixture may be centrifuged. The bottom phase consisted primarily of dichloromethane whereas the top phase (aqueous phase) was predominantly made of water and methanol. After the formation of the conjugate 2:AOT HIP complex, the lipophilicity introduced onto the compound increased its solubility in the dichloromethane phase. The HIP complex was then recovered from the bottom phase and the dichloromethane was evaporated. Sometimes additional dichloromethane was added to the remaining aqueous phase to extract the remaining conjugate 2:AOT HIP complex.

TABLE 10A

Formulations of conjugate 2 nanoparticles using free drug conjugate (DC)

| Formulation # | NP2 | NP5 |
|---|---|---|
| Process | Single emulsion | Single emulsion |
| Polymer | PLA16-mPEG5 | PLA35-mPEG5 |
| Polymer concentration, mg/mL | 80 | 160 |
| Emulsion Volume, mL | 20 | 20 |
| Oil phase | 20% BA/80% EA | 20% BA/80% EA |
| Aqueous phase | cold (ice) 0.15% Tween® 80/EA&BA | cold 0.1% Tween® 80 Water/EA |
| Oil phase volume fraction, % | 10% | 10% |
| Wash* | x25 with cold water diluted x10 RT water and concentrated 10 fold | x25 with cold water and concentrated |
| Z.ave/PDI (quenched Emulsion) | 46.3/0.065 | 92.7/0.20 |
| Z.ave/PDI (post TFF filtered) | 44.5/0.054 | 79.6/0.09 |
| TDL (wt %) | 5.88 | 3.03 |
| ADL (wt %) | 3.60 | 1.44 |
| EE = ADL/TDL, % | 61.2 | 47.6 |
| Potency, mg/mL | 0.170 | 0.30 |

TABLE 10B

Formulations of conjugate 2 nanoparticles using conjugate 2/AOP HIP

| | Formulation # | | | | | |
|---|---|---|---|---|---|---|
| | NP1 | NP3 | NP4 | NP6 | NP7 | NP8 |
| Process | Single emulsion | Single emulsion | Single emulsion | Single emulsion | Single emulsion | Single emulsion |
| Polymer | PLA97-mPEG5 | PLA35-mPEG5 | PLA16-mPEG5 | PLA74-mPEG5 | PLA35-mPEG5 | PLA97-mPEG5 |

TABLE 10B-continued

Formulations of conjugate 2 nanoparticles using conjugate 2/AOP HIP

| | Formulation # | | | | | |
|---|---|---|---|---|---|---|
| | NP1 | NP3 | NP4 | NP6 | NP7 | NP8 |
| Polymer concentration, mg/mL | 100 | 100 | 100 | 100 | 100 | 100 |
| Emulsion Volume, mL | 20 | 20 | 20 | 20 | 20 | 20 |
| Oil phase | 92% EA/ 8% DMF | 83% EA/ 17% DMF | 85% EA/ 15% DMF | 80% EA/ 20% DMF | 80% EA/ 20% DMF | 80% EA/ 20% DMF |
| Aqueous phase | cold (ice) 0.2% DiOctPC Water/EA | cold 0.1% Tween® 80 Water/EA | cold 0.1% Tween® 80 Water/EA | cold 0.2% Tween® 80 Water/EA | cold 0.1% Tween® 80 Water/EA | cold (ice) 0.2% DiOctPC Water/EA |
| Oil phase volume fraction, % | 7.50% | 10% | 10% | 10% | 10% | 10.00% |
| Wash* | ×25 with cold water, diluted ×10 RT water and concentrated | ×25 with 1XPBS diluted ×10 RT water and concentrated 10 fold | ×25 with 1XPBS diluted ×10 RT water and concentrated 10 fold | ×25 with 1XPBS diluted ×10 RT water and concentrated 10 fold | ×15 with saline, ×5 with water, warmed to 37 and diluted ×10 RT water and concentrated 10 fold | ×15 with cold saline, ×5 with cold water, warm to 37° C. for 3 min, diluted ×10 RT water and concentrated |
| Z.ave/PDI (quenched Emulsion) | 98.4/0.08 | 70.44/0.106 | 62.78/0.27 | 110.6/0.207 | 93.16/0.232 | 96.5/0.11 |
| Z.ave/PDI (post TFF filtered) | 88.3/0.05 | 66.55/0.073 | 65.65/0.258 | 100.7/0.127 | 80.86/0.153 | 96.1.3/0.10 |
| TDL (wt %) | 4.2 | 4.52 | 8.39 | 6.89 | 7.63 | 7.7 |
| ADL (wt %) | 3.7 | 4.07 | 6.85 | 4.69 | 7.39 | 6.4 |
| EE = ADL/TDL, % | 87 | 89.9 | 81.6 | 68.1 | 96.9 | 83 |
| Potency, mg/mL | 0.25 | 0.4 | 0.73 | 0.28 | 0.47 | 0.316 |

* Washing was optimized for each nanoparticle formulation.

These data further demonstrate that somatostatin receptor targeted conjugates can be efficiently and effectively encapsulated in nanoparticles.

Example 13: Pharmacokinetics of Nanoparticle Formulations of 1 and 2

Nanoparticles are typically formulated for in vivo delivery in 10% sucrose and free drug formulations varied, but are typically dosed in 10% Solutol®/10% sucrose, or physiological saline. In this example conjugate 1 without nanoparticle formulation was dosed as a solution in 20% propyleneglycol/80% aqueous sucrose (10%).

For rat pharmacokinetic studies using nanoparticles as described herein, a 0.1 mg/mL solution was dosed at 10 mL/kg such that a 1 mg/kg IV bolus dose was introduced by tail vein injection into rats. Following compound administration, blood was collected at 0.083 hours, 0.25 hours, 0.5 hours, 1 hour, 2 hours, 4 hours, 8 hours, and 24 hours post dose into lithium heparin coated vacuum tubes. Tubes were inverted for 5 minutes and then placed on wet ice until centrifuged for 5 minutes at 4° C. at 6000 rpm. Plasma was harvested, frozen at −80° C. and shipped to for bioanalysis on dry ice.

50 uL of rat plasma was precipitated with 300 uL of DMF and the resulting supernatant was measured for compound content by LC-MS/MS electrospray ionization in the positive mode.

Representative dose normalized rat pharmacokinetic curves for conjugate 1 and nanoparticle formulations of conjugate 1 are shown in FIG. 1. Table 11 shows the normalized area under the curve (AUC) calculations for conjugate 1 and the nanoparticles comprising conjugate 1 in FIG. 1.

TABLE 11

| AUC of conjugate 1 and nanoparticle formulations | | | | | |
|---|---|---|---|---|---|
| | 1 | NP1 | NP2 | NP4 | NP6 |
| AUC (0-inf) μmol/l*h | 18.3 | 42.5 | 154 | 127 | 256 |

Figure 2:
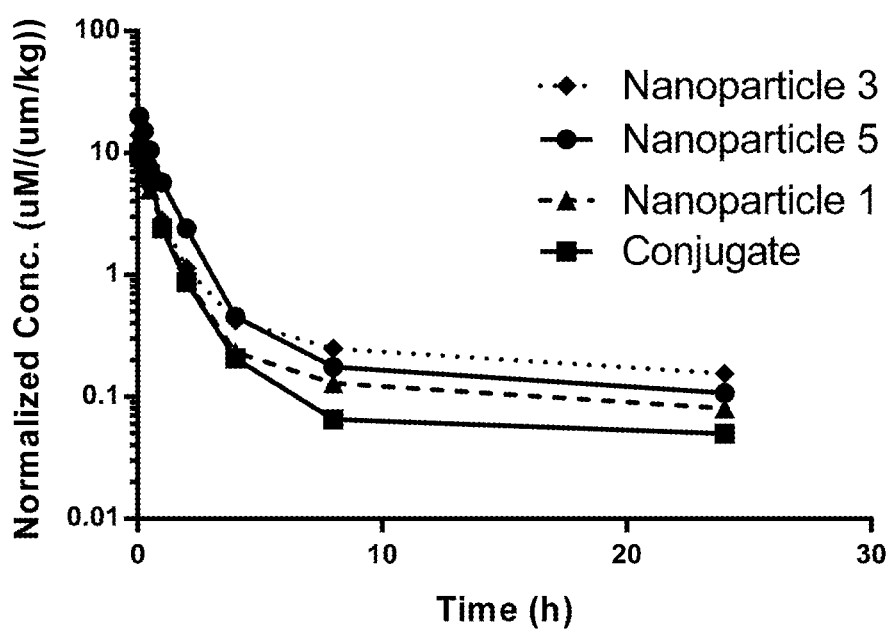
FIG. 2 is a graph of the blood plasma concentration (μM) of the octreotide-doxorubicin conjugate of Example 2 as a function of time (hours) after tail vein injection in rats. The formulations injected contained either the free octreotide-doxorubicin conjugate or octreotide-doxorubicinnano particles of Example 12.

Representative dose normalized rat pharmacokinetic curves for conjugate 2 and nanoparticle formulations of conjugate 2 are shown in FIG. 2. Table 12 shows the normalized area under the curve (AUC) calculations for conjugate 2 and the nanoparticles comprising conjugate 2 in FIG. 2.

TABLE 12

| AUC of conjugate 2 and nanoparticle formulations | | | | |
|---|---|---|---|---|
| | 2 | NP1 | NP3 | NP5 |
| AUC (0-inf) μmol/l*h | 14.3 | 16.0 | 21.8 | 29.5 |

These data demonstrate that nanoparticles increase the AUC of conjugates, thereby demonstrating that targeted nanoparticles can be synthesized using methods described herein having desirable properties indicative of improved use for drug delivery, for example, delivery of a chemotherapeutic agent to a tumor.

Example 14: Synthesis of DM1 Conjugates

Conjugates comprising DM1 were synthesized according to the following procedures:
Synthesis of Intermediates

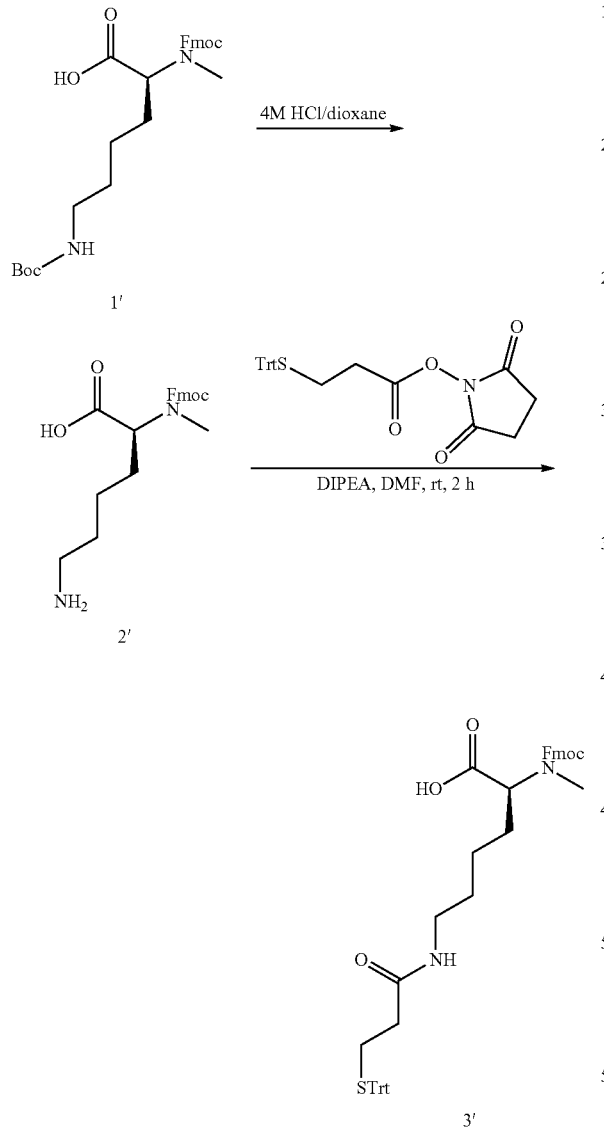

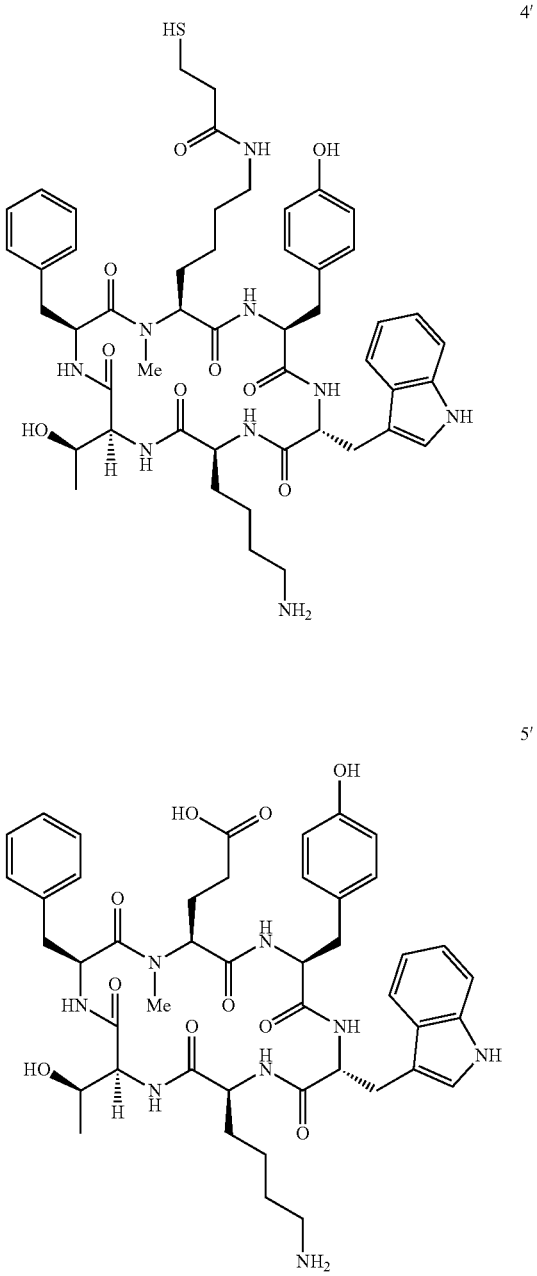

Nα-Me-Nα-Fmoc-Nε-Boc-lysine (640 mg, 1.31 mmol) was dissolved in dioxane (5 mL) and 4N HCl (5 mL). The reaction was stirred at room temperature until LCMS shows complete deprotection. The reaction mixture was purified by reverse phase chromatography to give Nα-Me-Nα-Fmoc-lysine (2', 500 mg, 1.31 mmol, 100% yield). This material was dissolved in DMF (5 mL) and diisopropylethylamine (0.50 mL), and trityl 3-mercaptopropionic acid NHS ester (875 mg, 1.98 mmol) was added. The reaction was stirred at room temperature, and purified by reverse phase chromatography to give Nα-Me-Nα-Fmoc-Nε-(STrt-propionate)-lysine (3', 600 mg, 0.843 mmol, 64% yield).

Fmoc-threonine(tBu)-OH was loaded onto 2-chlorotrityl resin (3.0 g resin, 1.5 mmol/g loading). Iterative deprotection with 4:1 DMF:piperidine, and coupling subsequently with Nα-Fmoc-Nε-Boc-lysine, Nα-Fmoc-N$^{in}$-Boc-D-tryptophan, Fmoc-tyrosine(tBu), Nα-Me-Nα-Fmoc-Nε-(3STrt-propionate)-lysine, and Fmoc-phenylalanine using standard SPPS conditions gave the linear peptide bound to the resin. Resin cleavage with 1% TFA in dichloromethane, followed by cyclization by dropwise addition of a solution of the linear peptide in 10 mL DMF to a flask with HATU (1.71 g, 4.5 mmol) and HOAt (0.6 M solution, 7.5 mL, 4.5 mmol) in DMF (45 mL) and diisopropylethylamine (3.0 mL). After stirring for 3 h at room temperature, all DMF was removed in vacuo, and the remaining material treated with 95:2.5:2.5 TFA:EDT:water for 30 min, the solvent removed in vacuo, and the remaining material purified by reverse phase chromatography to provide cyclo[Phe-Nα-Me-Nε-(3STrt-propionate)-Lys-Tyr-DTrp-Lys-Thr] (4', 427 mg, 0.447 mmol, 10% overall yield). LCMS M/Z: 956.5 [M+1].

Compound 5' was made in an analogous manner to compound 4'.

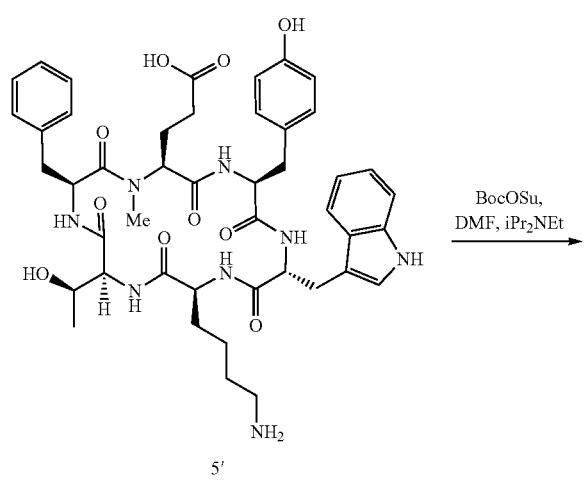

5'

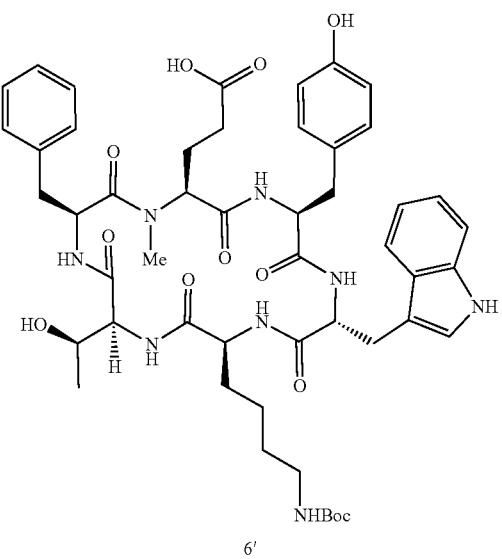

6'

To a solution of 5' trifluoroacetate salt (380 mg, 0.387 mmol) in DMF (5 mL) and diisopropylethylamine (0.50 mL) was added a solution of BocOSu (91.5 mg, 0.425 mmol) in DMF (2 mL). The reaction was stirred at room temperature for 4 h, then the reaction mixture loaded onto a 50 g C18 Isco column. Eluting with 5% to 75% acetonitrile in water with 0.1% AcOH yielded 6' (338 mg, 0.349 mmol, 90% yield).

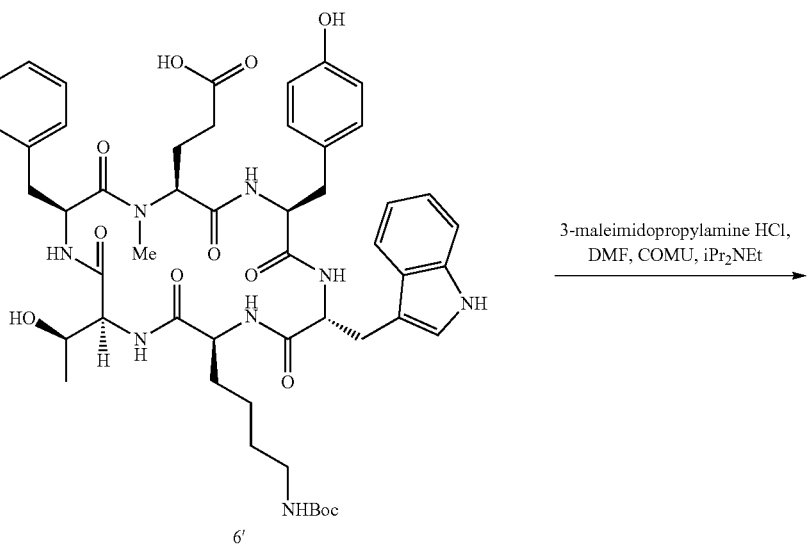

6'

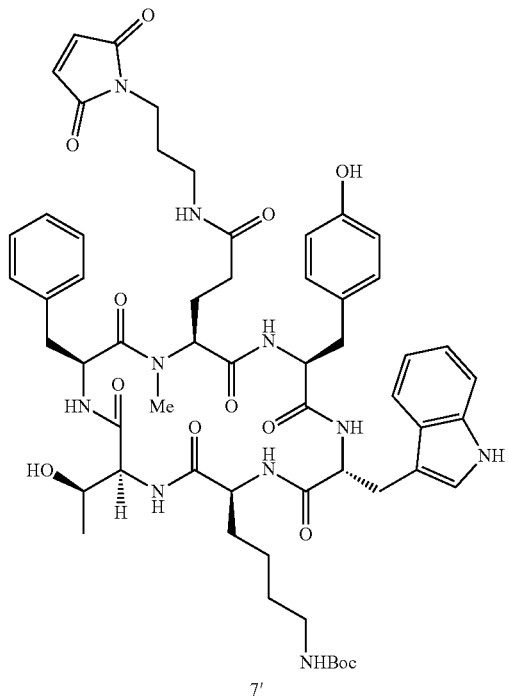

7'

A vial was charged with cyclo[Phe-NMeGlu-Tyr-DTrp-Lys(Boc)-Thr] (6', 41.8 mg, 0.0431 mmol), 3-maleimidopropylamine HCl (32.9 mg, 0.172 mmol) and COMU (73.7 mg, 0.172 mmol). DMF (1 mL) and diisopropylethylamine (0.10 mL) were added, and the reaction stirred at room temperature for 30 min. After 30 min, additional 3-maleimidopropylamine HCl (32.9 mg, 0.172 mmol) and diisopropylethylamine (0.10 mL) were added, and the reaction stirred for another 3 h. The reaction was acidified by addition of acetic acid (0.30 mL), water (1 mL) was added to solubilize any material that had come out of solution. The reaction mixture was purified by preparative HPLC (5% to 75% acetonitrile in water with 0.1% AcOH) to give 7' (25.7 mg, 0.0233 mmol, 54% yield).

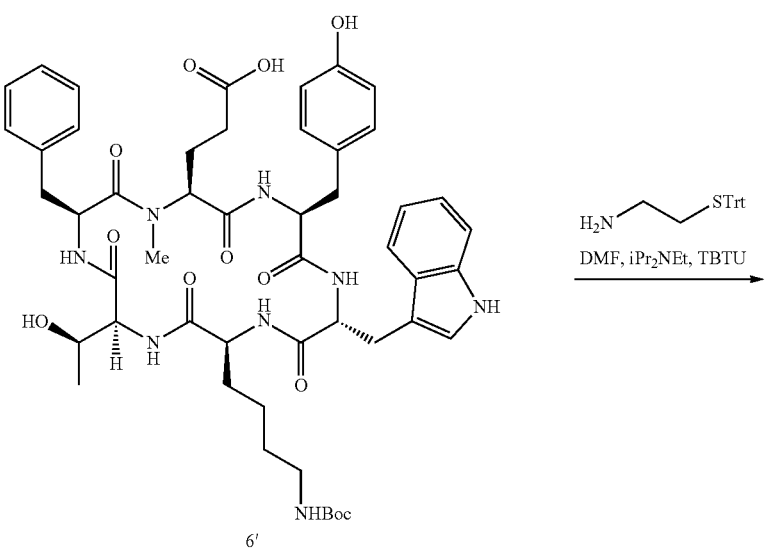

6'

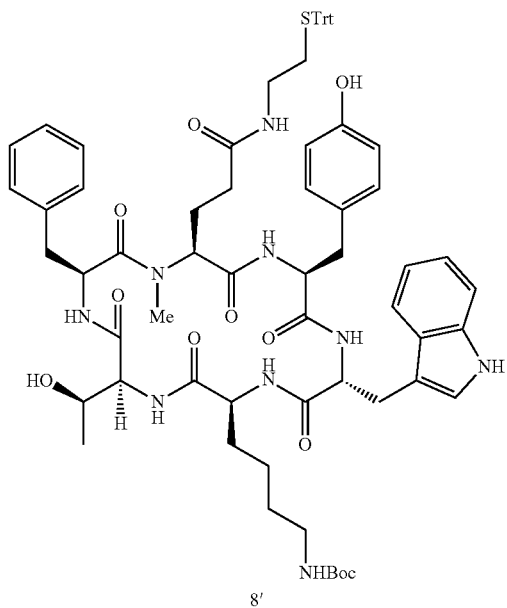

8'

A vial was charged with cyclo[Phe-NMeGlu-Tyr-DTrp-Lys(Boc)-Thr] (6', 39.0 mg, 0.0402 mmol), S-Trt cystamine (38.6 mg, 0.121 mmol) and TBTU (38.8 mg, 0.121 mmol). DMF (1.0 mL) and diisopropylethylamine (0.10 mL) were added, and the reaction stirred at room temperature for 2 h. The reaction mixture was purified by preparative. HPLC (5% to 95% acetonitrile in water with 0.1% AcOH) to give 8' (36.2 mg, 0.0285 mmol, 71% yield).

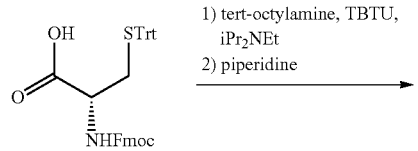

1) tert-octylamine, TBTU, iPr₂NEt
2) piperidine

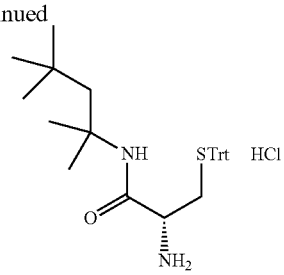

A vial was charged with Fmoc-STrt-cysteine (585 mg, 1.00 mmol) and TBTU (330 mg, 1.03 mmol). DMF (4 mL), tert-octylamine (0.176 mL, 1.10 mL) and diisopropylethylamine (0.30 mL) were added, and the reaction stirred at room temperature for 16 h. Piperidine (2 mL) was added, the reaction stirred at room temperature for 30 min, and the reaction mixture loaded onto a 50 g C18 Isco column, eluting with 15% to 85% acetonitrile in water with 0.1% AcOH. The purified product was dried-in vacuo, and the isolated product was redissolved in methanol (10 mL). 1N HCl (2 mL) was added, and all solvents removed in vacuo again to give S-trityl cysteine tert-octyl amide HCl salt (401 mg, 0.784 mmol, 78% yield).

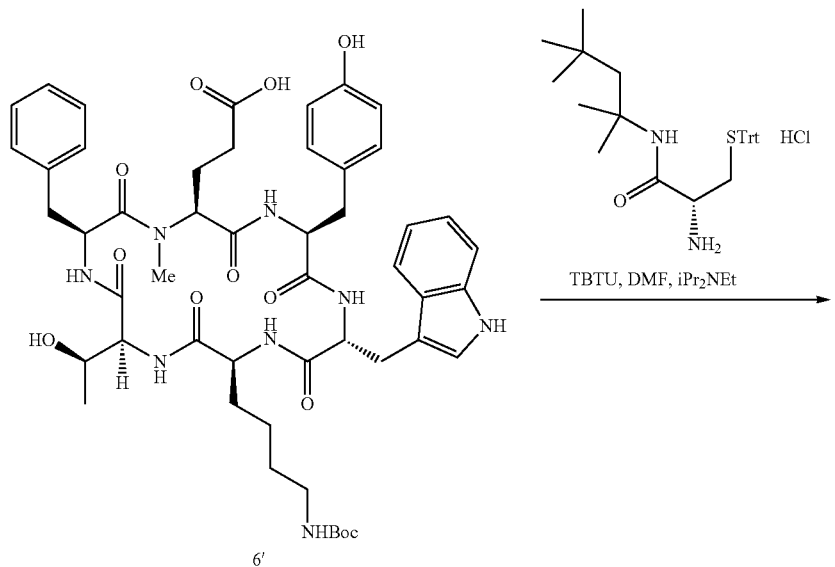
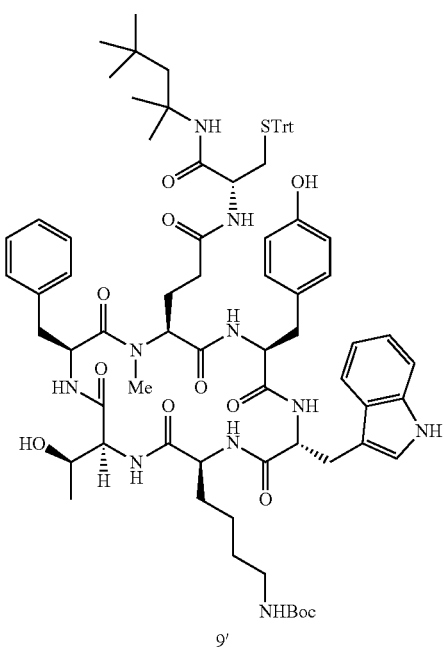
50
A vial was charged with cyclo[Phe-NMeGlu-Tyr-DTrp-Lys(Boc)-Thr] (6', 27.0 mg, 0.0279 mmol), S-trityl cysteine tert-octyl amide HCl (20.0 mg, 0.0391 mmol) and TBTU (11.0 mg, 0.0343 mmol). DMF (1 mL) and diisopropylethylamine (0.10 mL) were added, and the reaction stirred at room temperature for 1 h. The reaction mixture was purified by preparative HPLC (25% to 95% acetonitrile in water with 0.1% AcOH) to give 9' (24.2 mg, 0.0170 mmol, 61% yield).
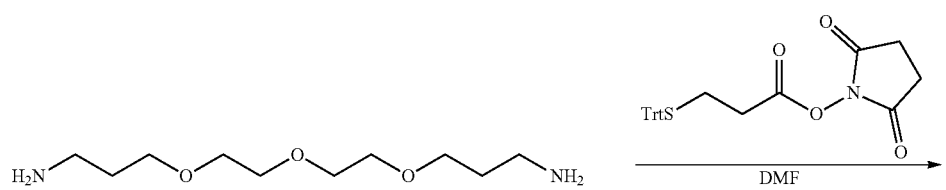

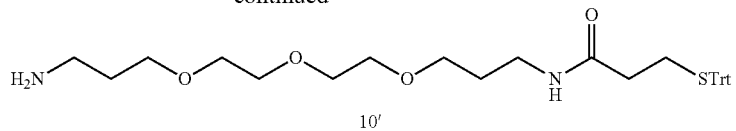

A flask was charged with trityl-3-mercaptopropionic acid NHS ester (1.02 g, 2.29 mmol), and this dissolved in DMF (10 mL). The reaction was cooled to 0° C., and 4,7,10-trioxa-1,13-tridecanediamine (3.00 mL, 13.7 mmol) was added all at once. The reaction was stirred at 0° C. for 10 min, then warmed to room temperature and stirred for 2 h.

The reaction mixture was loaded onto a 100 C18 Isco column, and eluting with 5% to 85% acetonitrile in water yielded 10' (552 mg, 1.00 mmol, 44% yield).

Compounds 11'-13' were made in an analogous manner to 10':

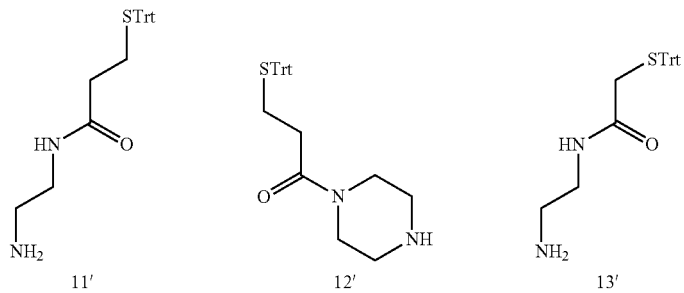

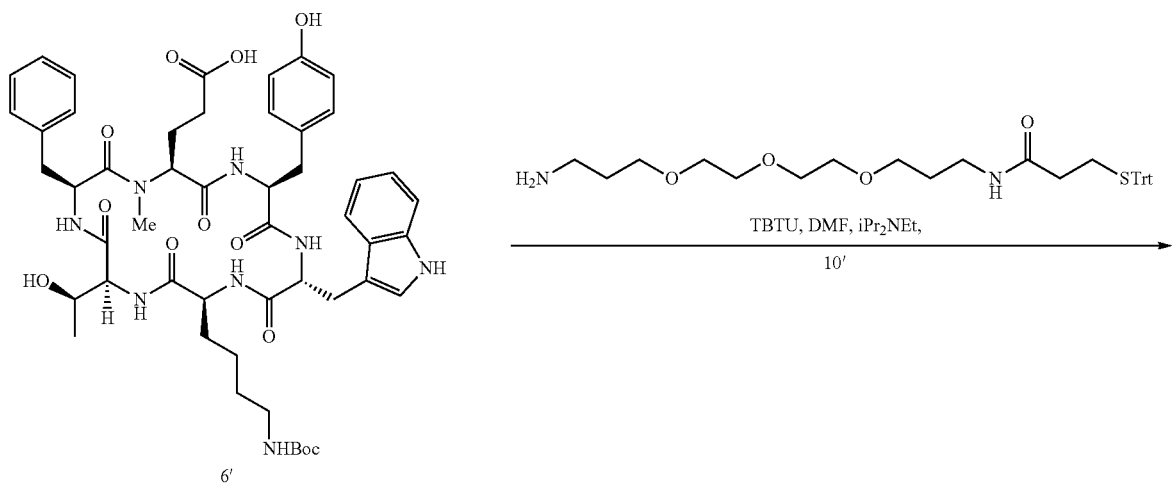

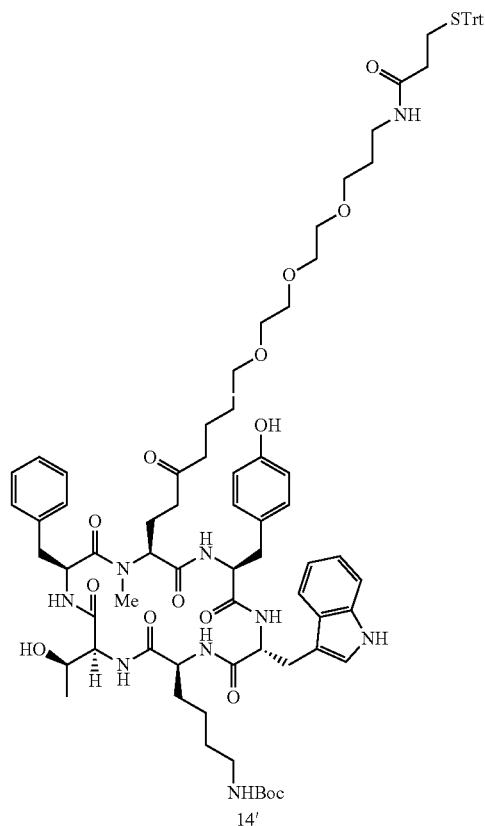
14'
A vial was charged with 6' (27.6 mg, 0.0285 mmol), 10' (31.4 mg, 0.0570 mmol) and TBTU (18.3 mg, 0.0570 mmol). DMF (1 mL) and diisopropylethylamine (0.10 mL) were added, and the reaction stirred at room temperature for 2 h. The reaction mixture was purified by prep HPLC (25% to 95% acetonitrile in water with 0.1% AcOH) to give 14' (29.6 mg, 0.0197 mmol, 69% yield).
Compounds 15'-17' were made in an analogous manner to 14':
-continued
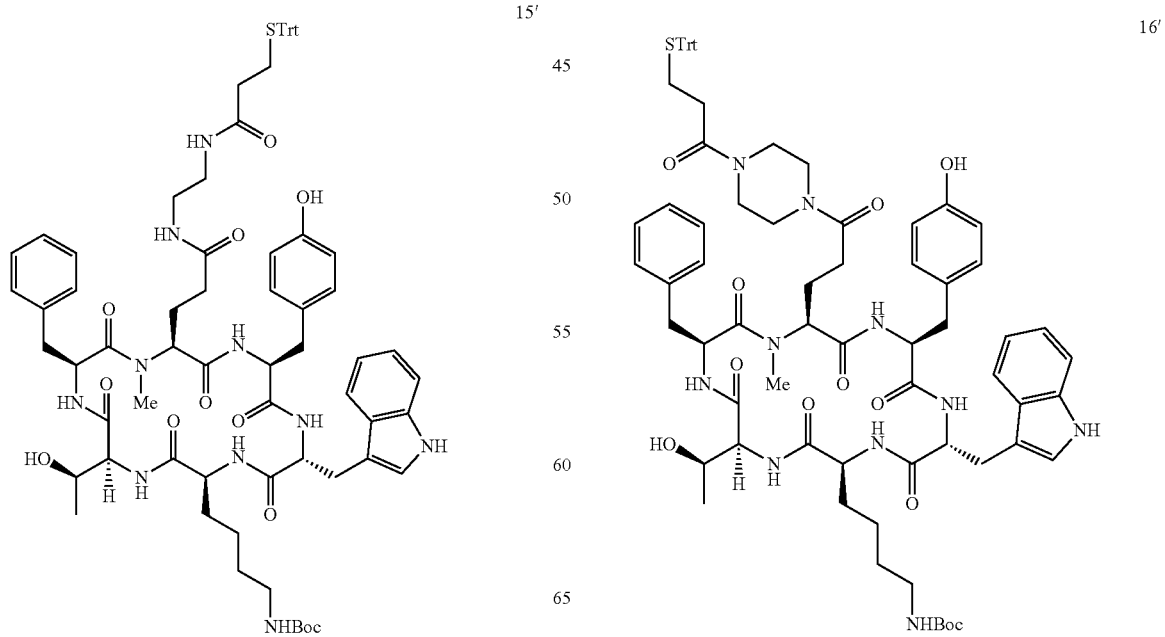

-continued

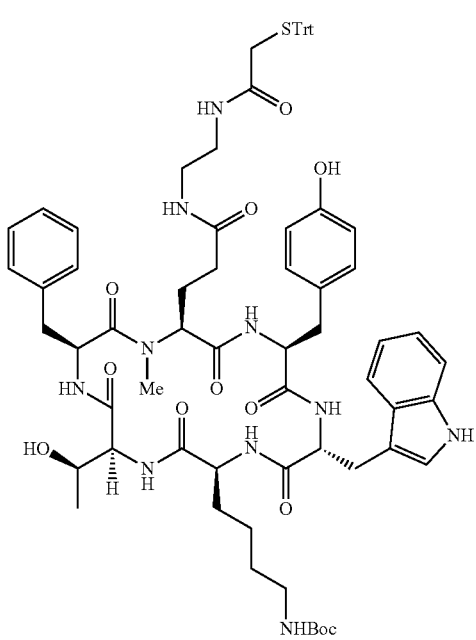

17'

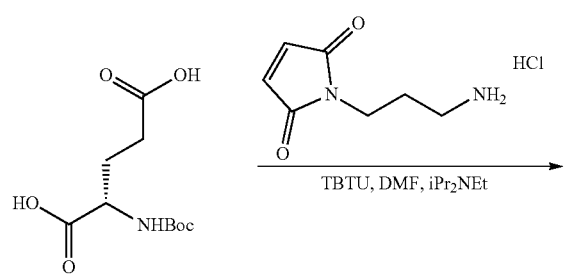

-continued

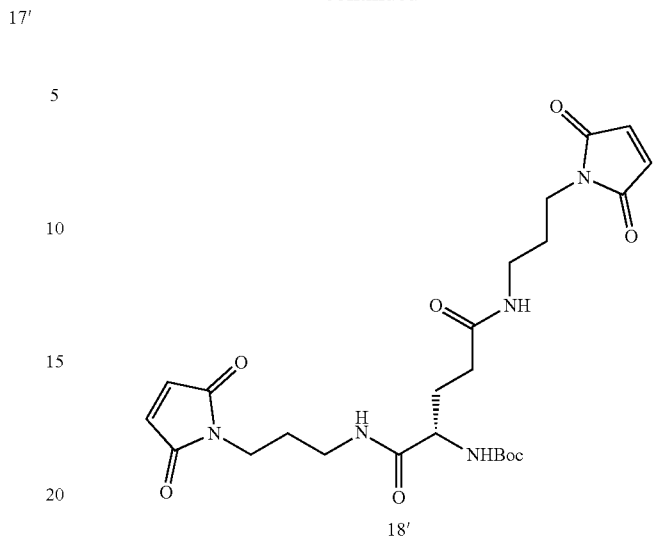

18'

A vial was charged with N-Boc-glutamic acid (125 mg, 0.506 mmol), 3-maleimidopropylamine HCl (200 mg, 1.05 mmol) and TBTU (330 mg, 1.03 mmol), DMF (5 mL) and diisopropylethylamine (0.30 mL) were added, the mixture sonicated for 10 min to give a smooth suspension, and the reaction stirred at room temperature for 18 h. The reaction was acidified with acetic acid (0.50 mL), and then diluted with water (2.0 mL). The reaction mixture was loaded onto a 30 g C18 Isco column, and eluting with 5% to 60% acetonitrile in water with 0.1% AcOH gave 18' (77.0 mg, 0.148 mmol, 29% yield). LCMS M/Z: 520.2 (M+1).

Compound 19' was made in an analogous manner:

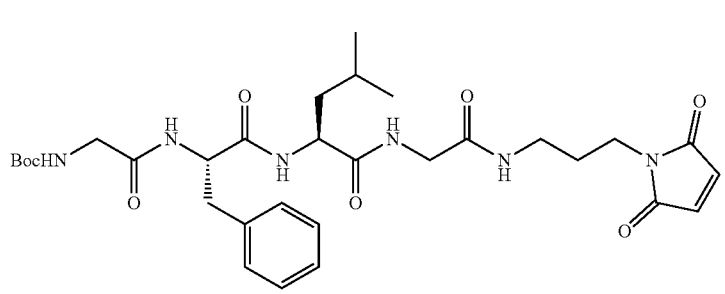

19'

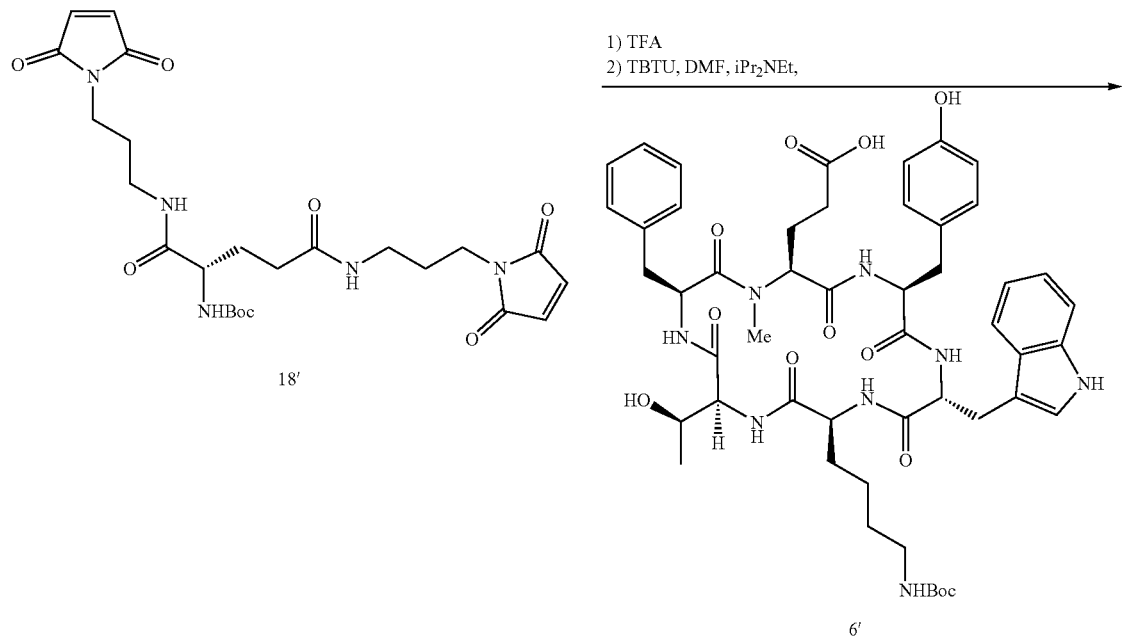

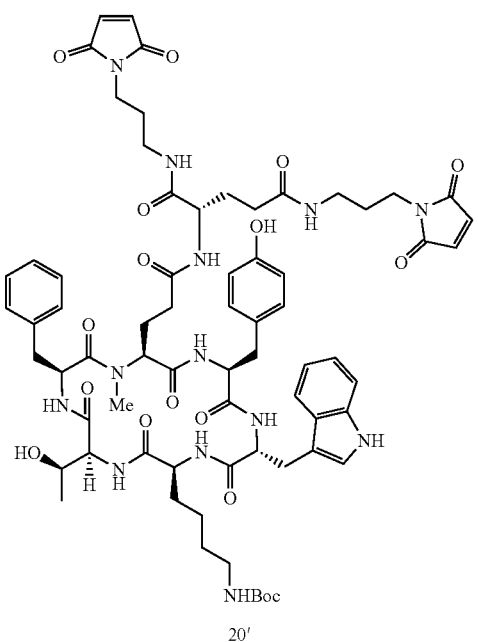

A vial was charged with 18' (12.0 mg, 0.0233 mmol), and TFA (1 mL) was added. The reaction stirred at room temperature for 5 min, then all TFA was removed in vacuo. In a second vial, cyclo[Phe-NMeGlu-Tyr-DTrp-Lys(Boc)-Thr] (6', 20.0 mg, 0.0206 mmol) and TBTU (9.0 mg, 0.0280 mmol) were dissolved in DMF (1 mL), and diisopropylethylamine (0.15 mL). This solution was stirred at room temperature for 5 min, then added to the vial with deprotected 18'. The reaction was stirred at room temperature for 2 h, and the reaction was acidified by adding AcOH (0.20 mL). The reaction was then purified by prep HPLC, eluting with 15% to 80% acetonitrile in water with 0.2% AcOH to give 20' (11.6 mg, 0.0085 mmol, 41% yield).

Compound 21' was made in an analogous manner to 20':
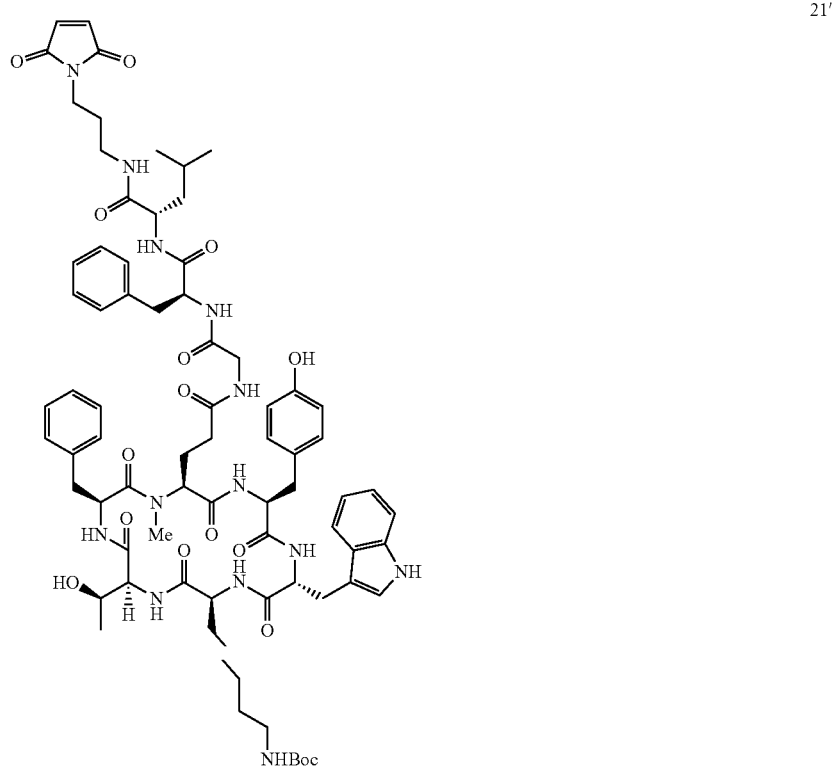
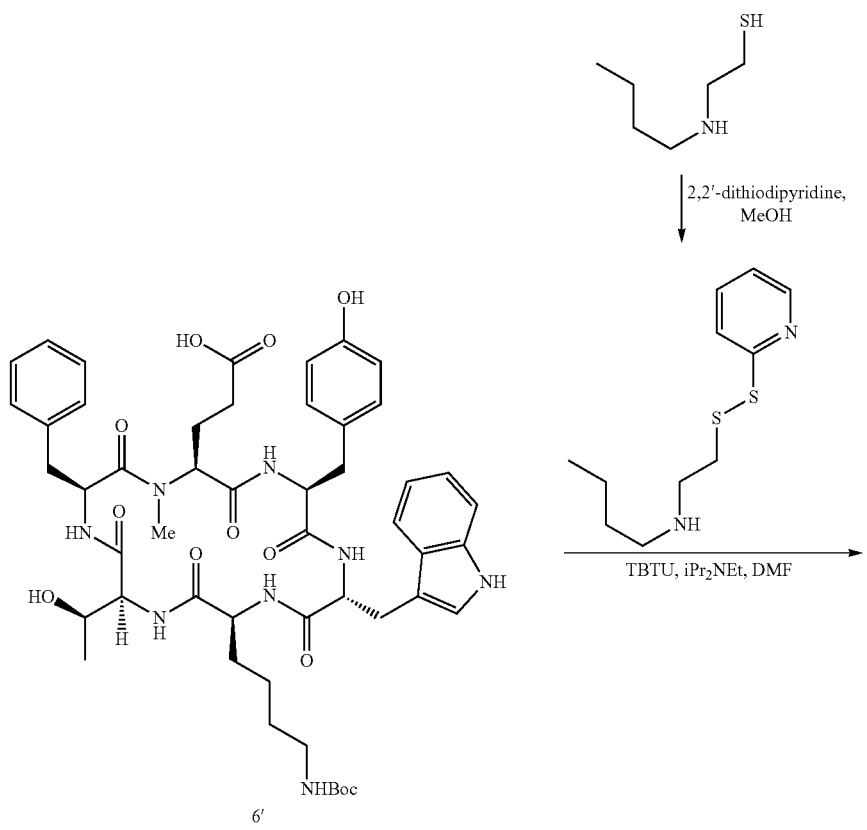

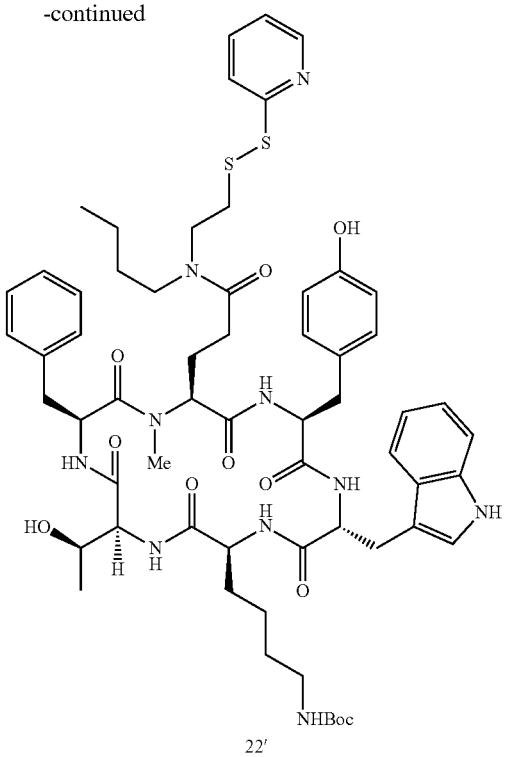

22'

A vial was charged with 2,2'-dithiodipyridine (110 mg, 0.500 mmol) and this dissolved in methanol (1 mL). A solution of 2-(butylamino)ethanethiol (37.0 μL, 0.250 mmol) in methanol (1 mL) was added dropwise, stirred for 5 min, and all methanol removed in vacuo. To the remaining residue was added a solution of cyclo[Phe-NMeGlu-Tyr-DTrp-Lys(Boc)-Thr] (6', 28.6 mg, 0.0295 mmol) and TBTU (14.2 mg, 0.0443 mmol) in DMF (2 mL) and diisopropylethylamine (0.10 mL). The reaction was stirred at room temperature for 1 h, and the reaction mixture was then loaded onto a 30 g C18 Isco column, eluting with 40% to 95% acetonitrile in water with 0.1% AcOH to give 22' (21.1 mg, 0.0177 mmol, 60% yield). LCMS M/Z: 547.4 [(M+2-Boc)/2].

Compound 23' was made in an analogous manner to 22':

23'

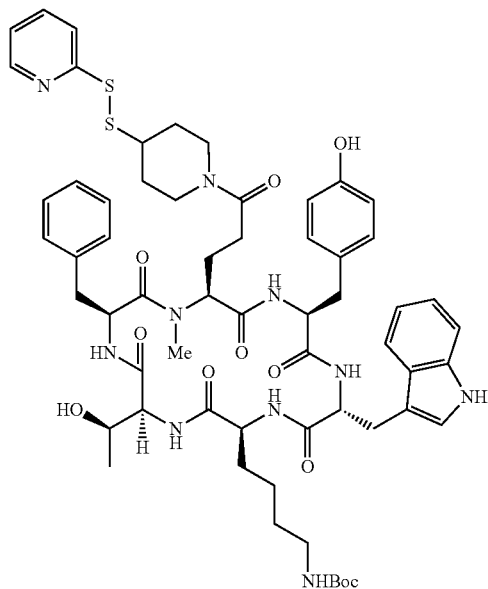

24'

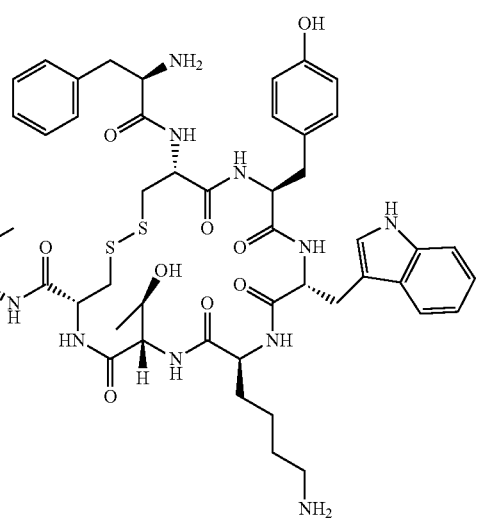

f-cyclo(CTwKTC)T-OH (24') was synthesized by loading Fmoc-threonine(tBu) onto 2-chlorotrityl resin, and by appending the subsequent amino acids by standard Fmoc chemistry, with Fmoc-S-trityl-cysteine, Fmoc-threonine (tBu), Nα-Fmoc-Nε-Boc-lysine, Nα-Fmoc-N$^{in}$-Boc-D-tryptophan, Fmoc-tyrosine(tBu), Fmoc-S-trityl-cysteine, and Fmoc-D-phenylalanine. Final deprotection was achieved by treating with 95:2.5:2.5 TFA:water:triisopropylsilane. The crude peptide was dried, weighed, dissolved in 1:1 acetonitrile:water, and treated with 2 equiv. iodine in methanol to give the cyclic disulfide. Purification on reverse phase gave the desired peptide.

Compounds 25'-28' were made in an analogous manner to 24':
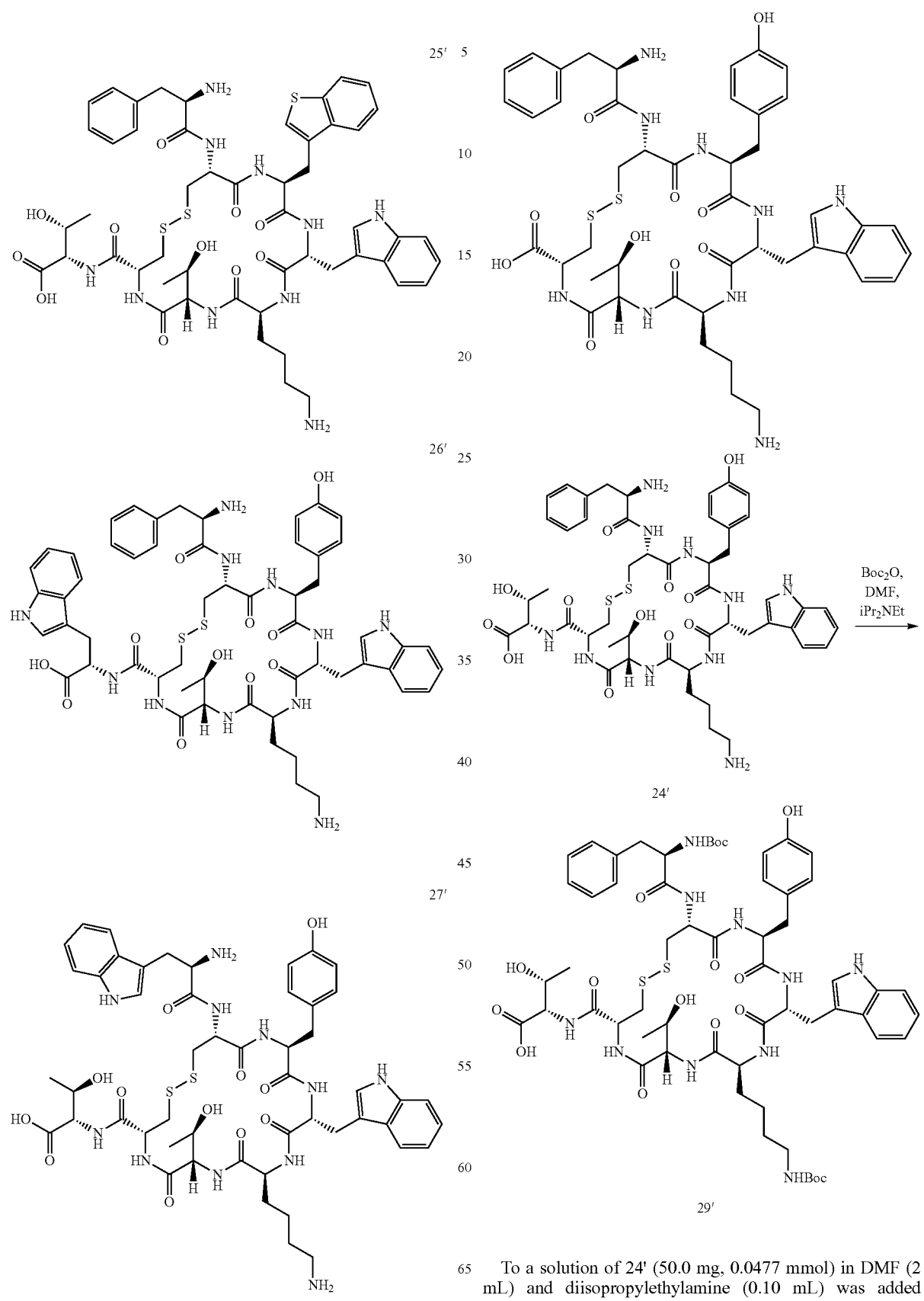
To a solution of 24' (50.0 mg, 0.0477 mmol) in DMF (2 mL) and diisopropylethylamine (0.10 mL) was added Boc₂O (52.0 mg, 0.238 mmol). The reaction was stirred at room temperature for 2 h, then the reaction mixture loaded onto a 30 g C18 Isco column, eluting with 30% to 95% acetonitrile in water with 0.1% AcOH to give 29' (42.0 mg, 0.0336 mmol, 70% yield).
Compounds 30'-34' were prepared in an analogous manner:
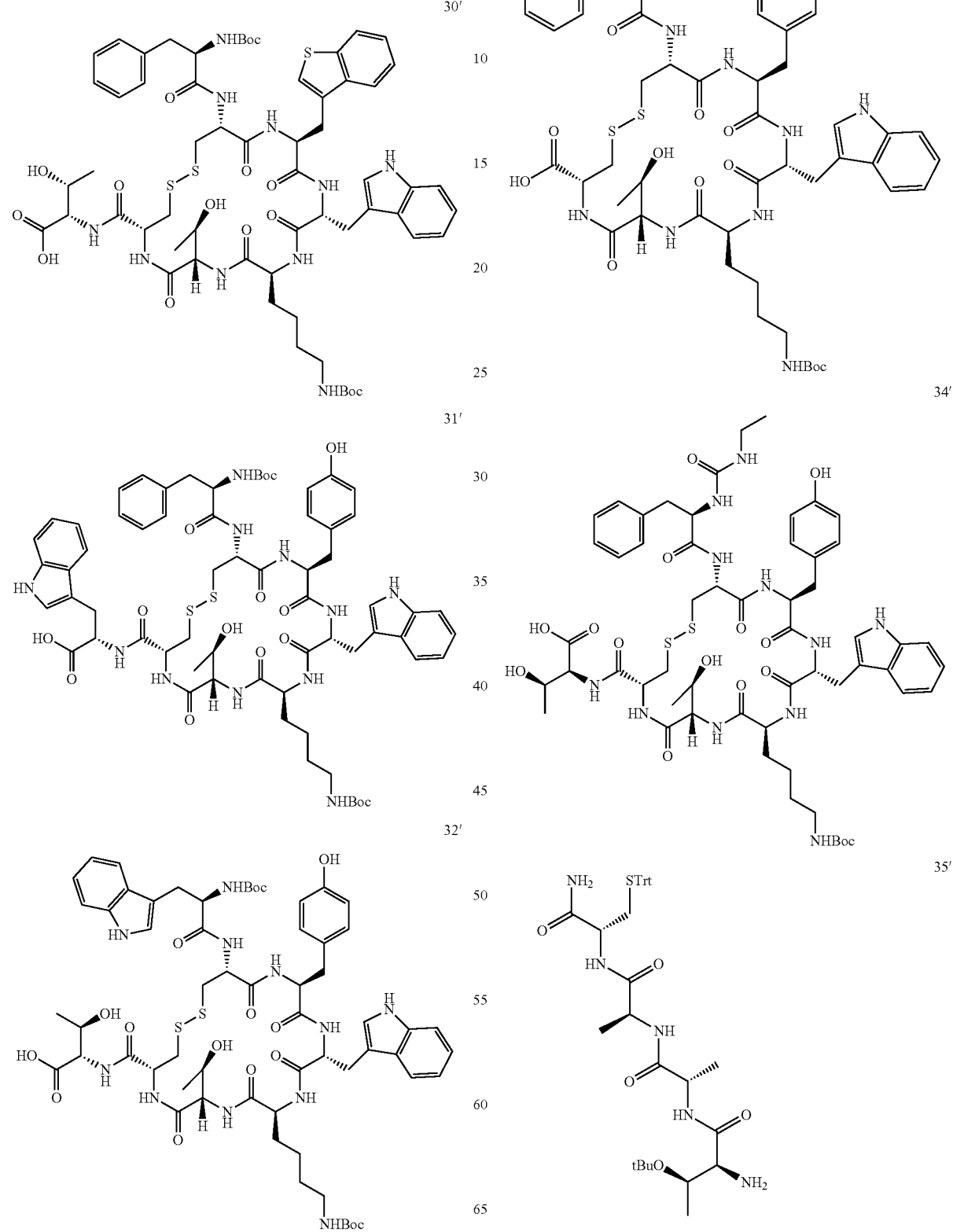

239

35' was synthesized by charging 1.49 g Sieber amide resin (0.67 mmol/g, 1.00 mmol) with FMoc-S-trityl-cysteine, and appending Fmoc-alanine, Fmoc-alanine, and Fmoc-threonine(tBu) through standard Fmoc chemistry. Cleavage of the resin with 95:3:2 dichloromethane:triisopropylsilane:TFA, followed by purification by preparative HPLC gave 35' (34.0 mg, 0.0514 mmol, 5.1% yield).

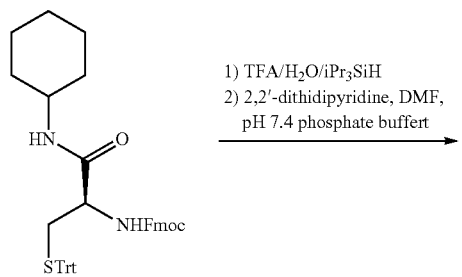

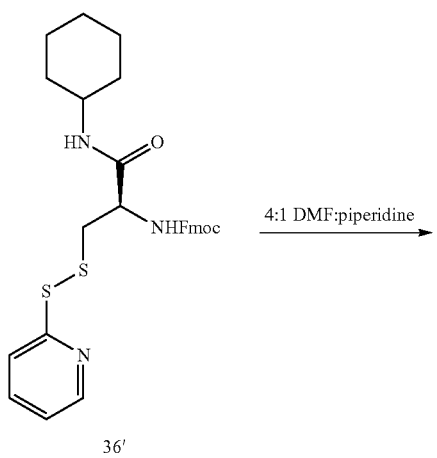

240

-continued

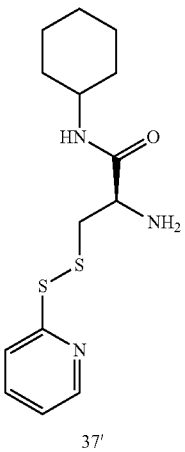

A flask was charged with Fmoc-S-trityl-cysteine cyclohexyl amide (514 mg, 0.771 mmol), and water (0.50 mL), TFA (10 mL) and triisopropylsilane (0.50 mL) were added. The reaction was stirred at room temperature for 10 min, until the yellow color had faded, and all solvents were removed in vacuo. The remaining residue was dissolved in DMF (2 mL) and a solution of 2,2'-dithiodipyridine (1.03 g, 4.68 mmol) in DMF (8 mL) was added. 100 mM pH 7.4 phosphate buffer (2.0 mL) was added dropwise, and the reaction was stirred at room temperature for 5 min. The reaction was then loaded onto a 50 g C18 Isco column, and eluting with 35% to 95% acetonitrile in water with 0.1% AcOH provided 36' (174 mg, 0.326 mmol, 42% yield).

A vial was charged with 36' (81.0 mg, 0.152 mmol), and this was dissolved in 4:1 DMF:piperidine (2 mL). The reaction was stirred at room temperature for 30 min, and all solvents were removed in vacuo. The remaining residue was redissolved in 4:1 DMF:piperidine (2 mL), stirred at room temperature for 30 min, and again all solvents removed in vacuo. The remaining residue was dissolved in 1:1 methanol:toluene (5 mL), and all solvents removed in vacuo, to ensure complete removal of any remaining piperidine. The crude amine 37' was then used directly in the next subsequent reaction.

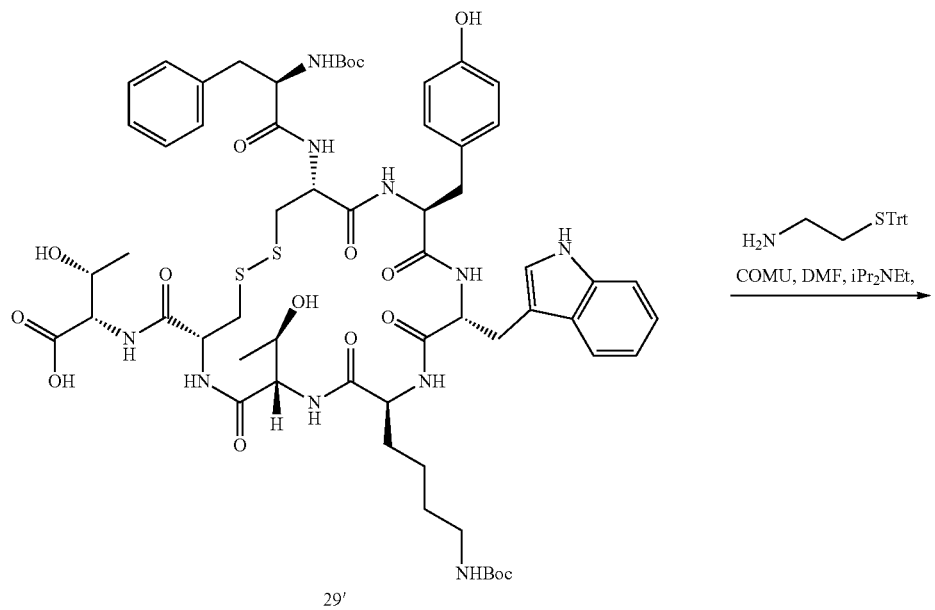

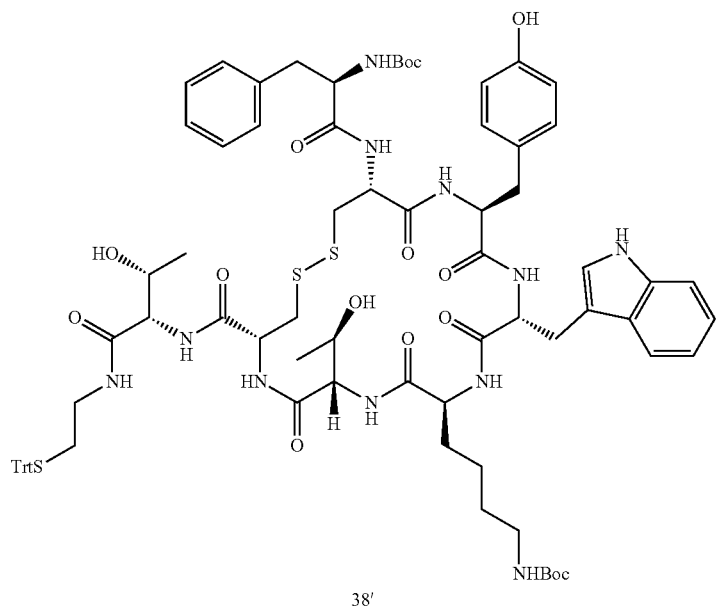
38'
A flask was charged with 29' (18.4 mg, 0.0147 mmol), S-Trt cystamine (25.0 mg, 0.0783 mmol) and COMU (30.0 mg, 0.0700 mmol). DMF (5 mL) and diisopropylethylamine (0.10 mL) were added, and the reaction stirred at room temperature for 24 h. The reaction mixture was purified by preparative HPLC, eluting with 5% to 95% acetonitrile in water with 0.2% AcOH, to give 38' (10.6 mg, 0.00684 mmol, 47% yield).
Compounds 39'-50' were made in an analogous manner to 38'.
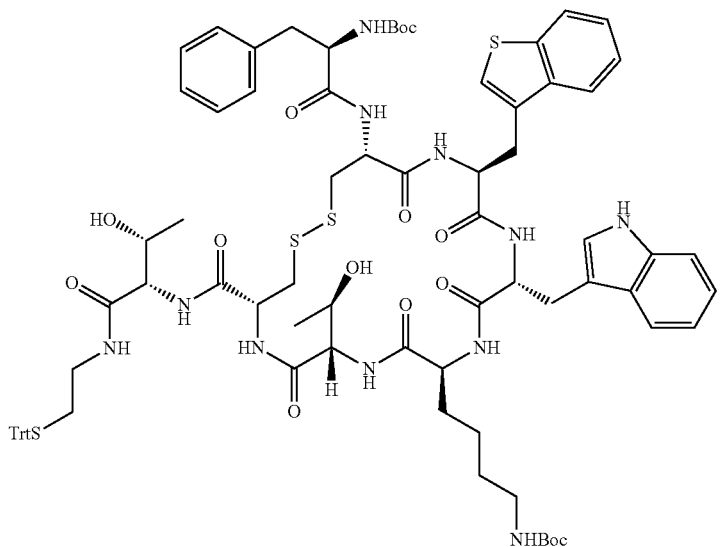
39'

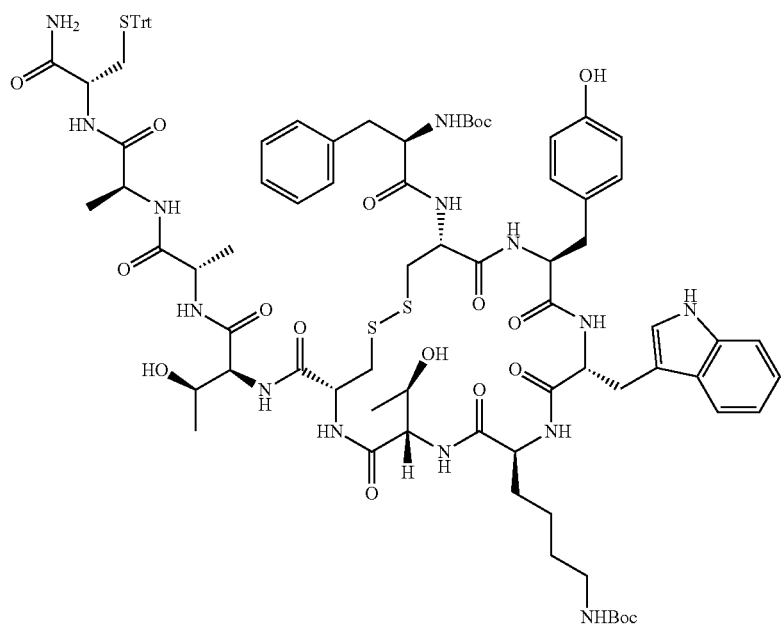
40'
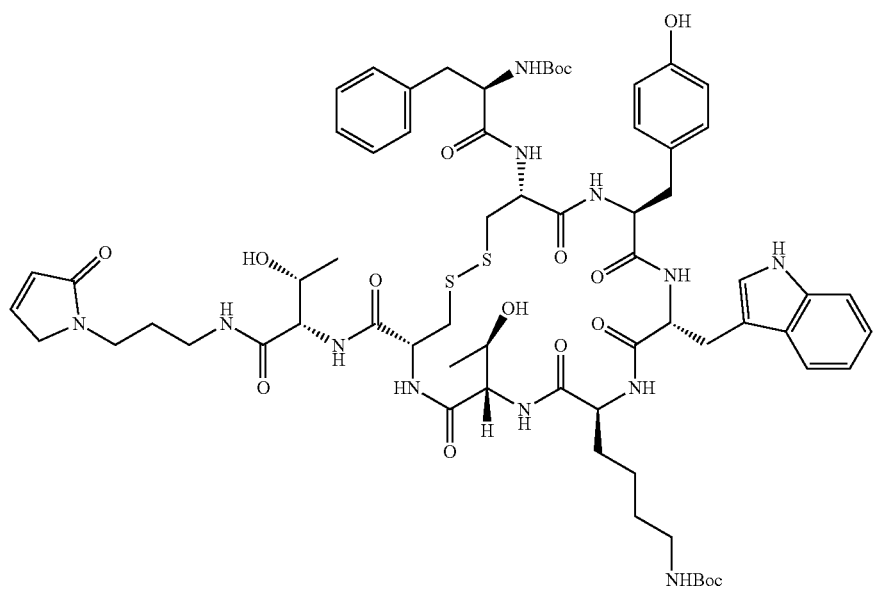
41'

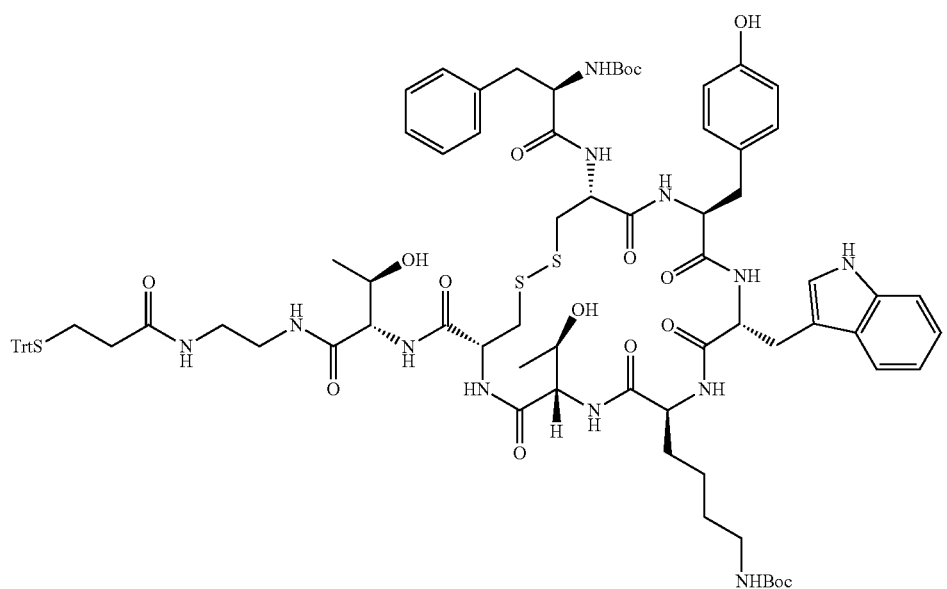
42'
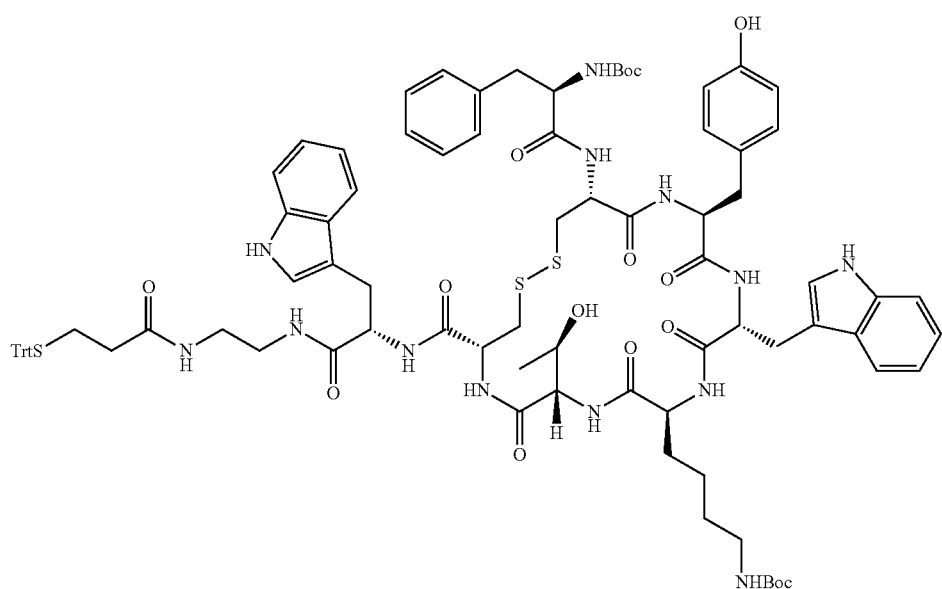
43'

-continued
44'
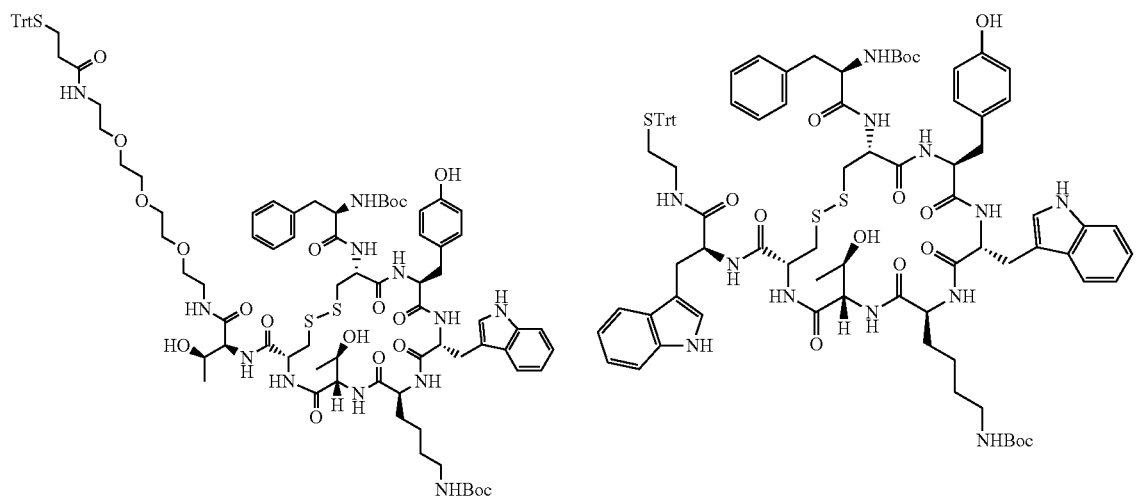
45'
46'
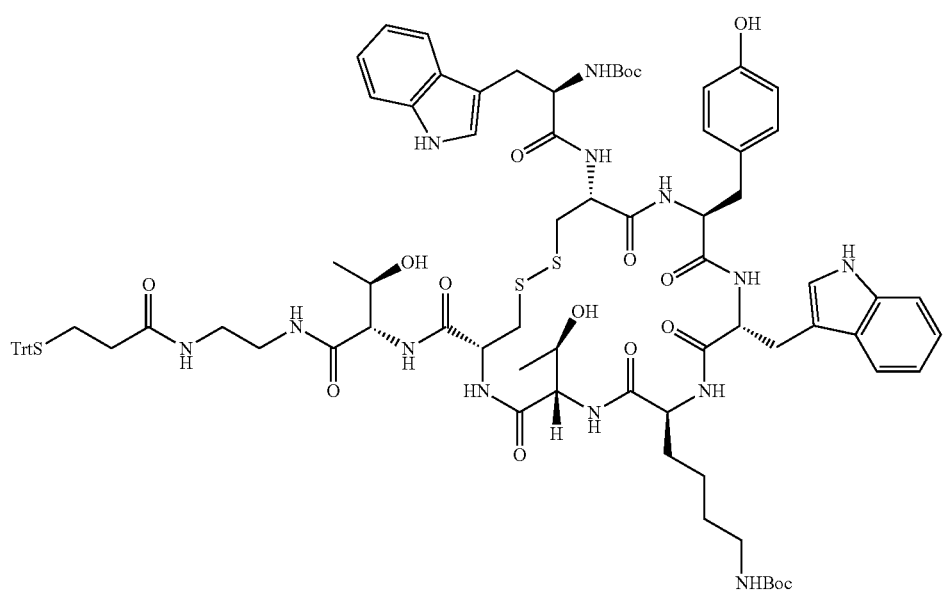
47'
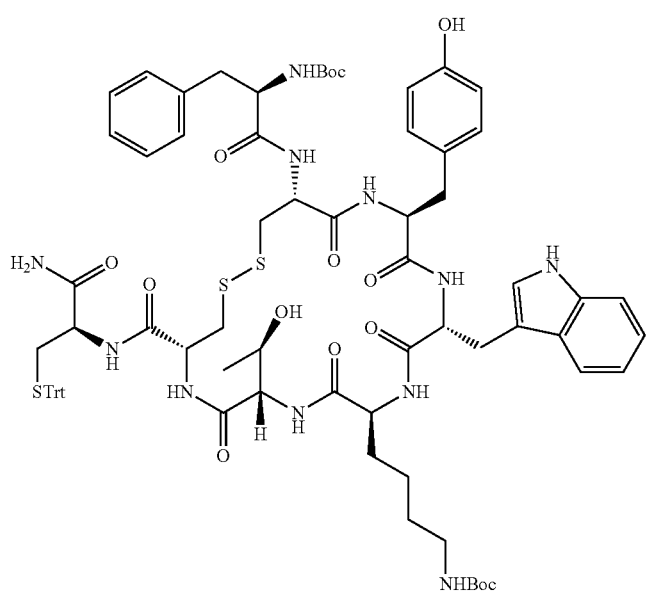

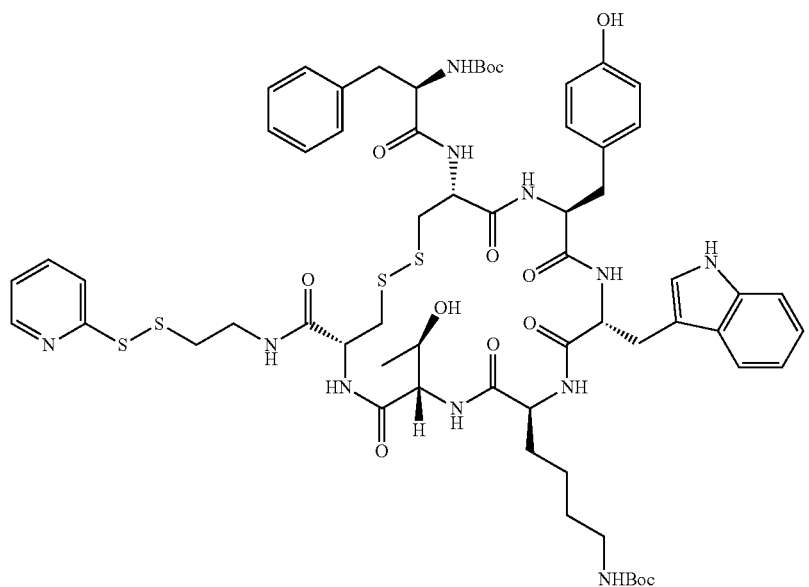
48'
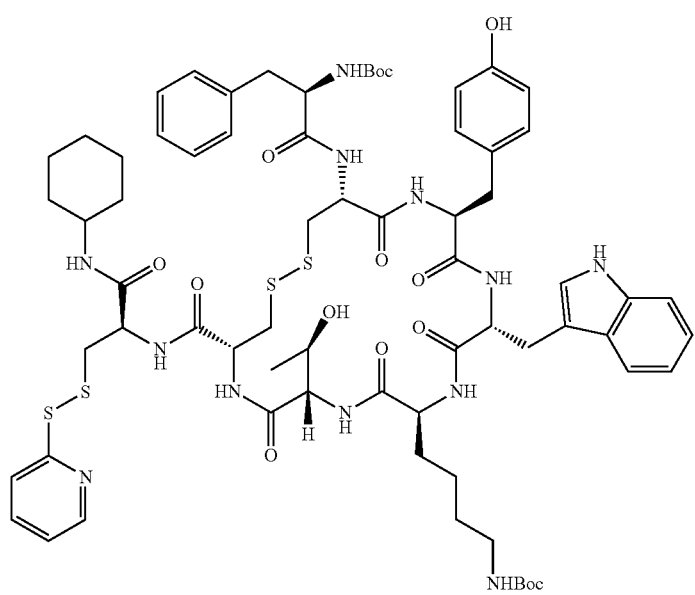
49'

-continued
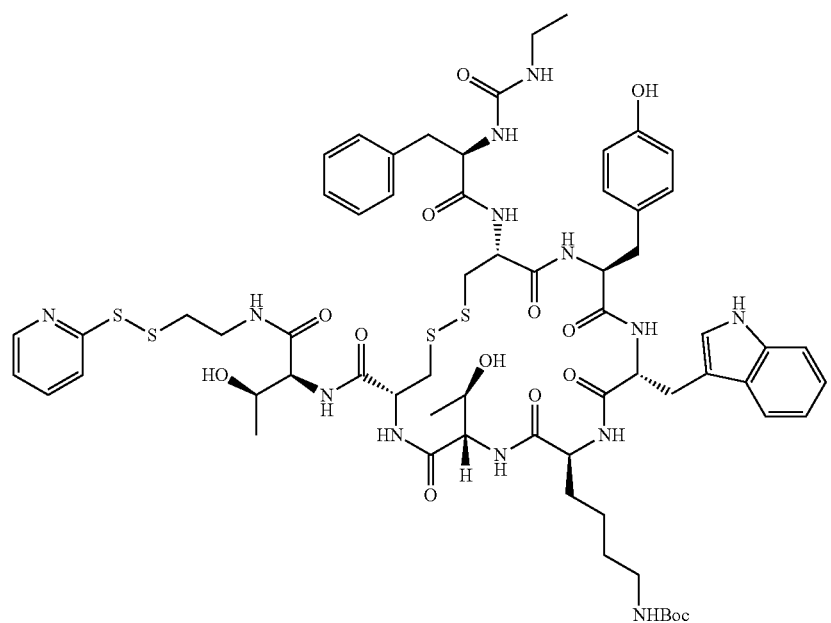
50'
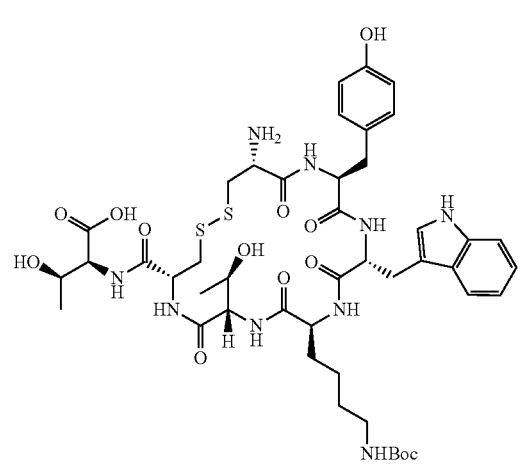
51'
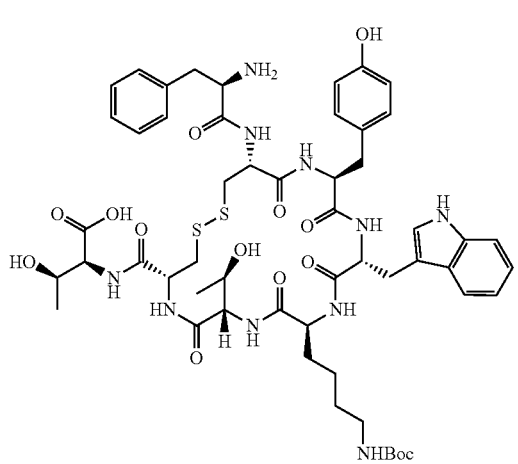
52'
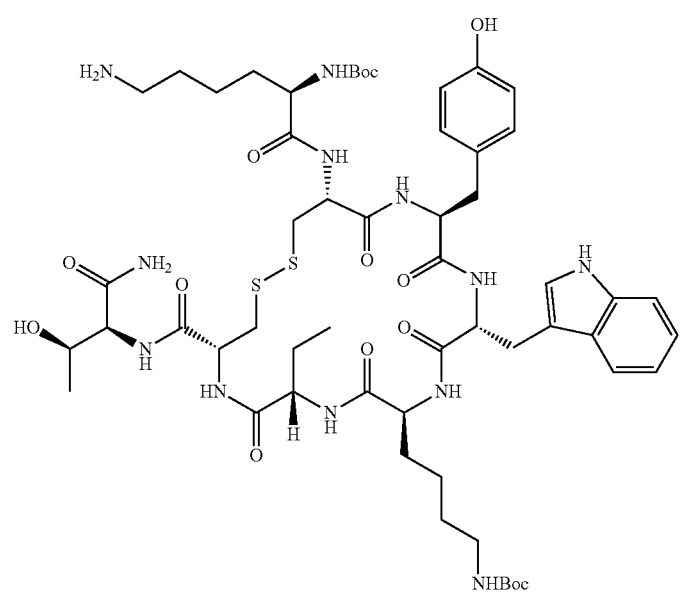
53' cyclo(CYwK(Boc)TC)T-OH (51') was synthesized by loading Fmoc-threonine(tBu) onto 2-chlorotrityl resin, and appending Fmoc-S-trityl-cysteine, Fmoc-threonine(tBu), Nα-Fmoc-Nε-Boc-lysine, Nα-Fmoc-N$^{in}$-Boc-D-tryptophan, Fmoc-tyrosine(tBu), and Fmoc-S-trityl-cysteine using standard Fmoc chemistry. Without cleaving the N-terminal Fmoc group, the peptide was cleaved from the resin with 95:2.5:2.5 TFA:water:triisopropylsilane, cyclized with iodine in 1:1 acetonitrile:water, treated with Boc$_2$O and diisopropylethylamine in DMF, and finally treated with 20% diethylamine in dichloromethane, and purified by reverse phase chromatography to provide 51'.

Compounds 52' and 53' were made in an analogous manner to 51'.

To a solution of octreotide acetate (545 mg, 0.505 mmol) in DMF (10 mL) was added diisopropylethylamine (0.50 mL). The solution was then cooled to −40° C., and a solution of BocOSu (119 mg, 0.553 mmol) in DMF (5 mL) was added dropwise. The reaction was stirred at −40° C. for 1 h, then gradually warmed up to room temperature over 1 h. Most of the DMF was removed in vacuo, and the remaining residue was loaded onto a 50 g C18 Isco column. Elution with 15% to 60% acetonitrile in water with 0.1% AcOH gave Lys-Boc octreotide acetate (54', 440 mg, 0.373 mmol, 74% yield) with >95% regioselectivity by $^1$H NMR.

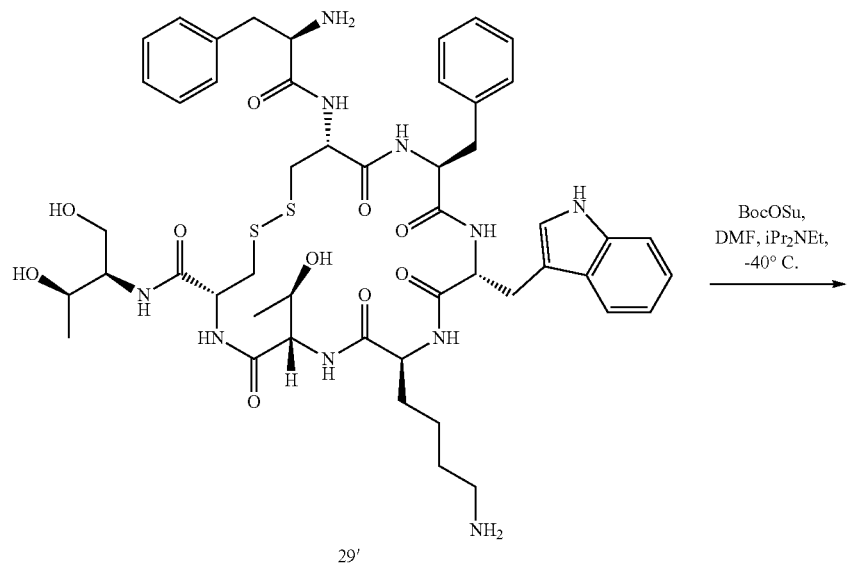

29'

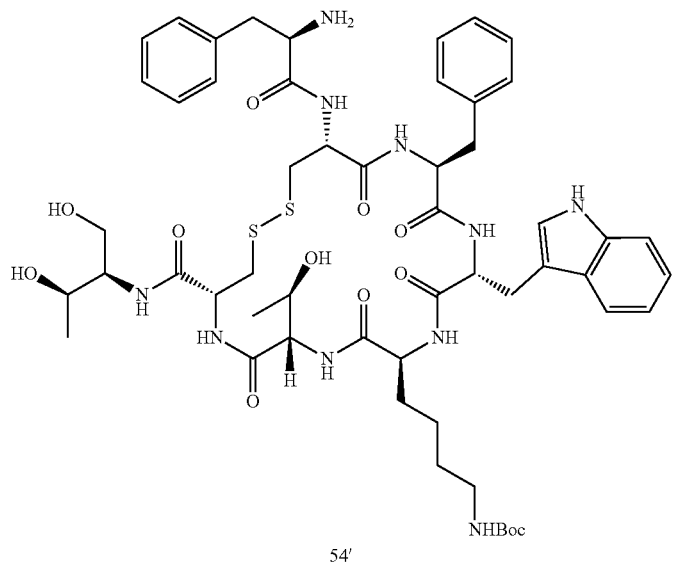

54'

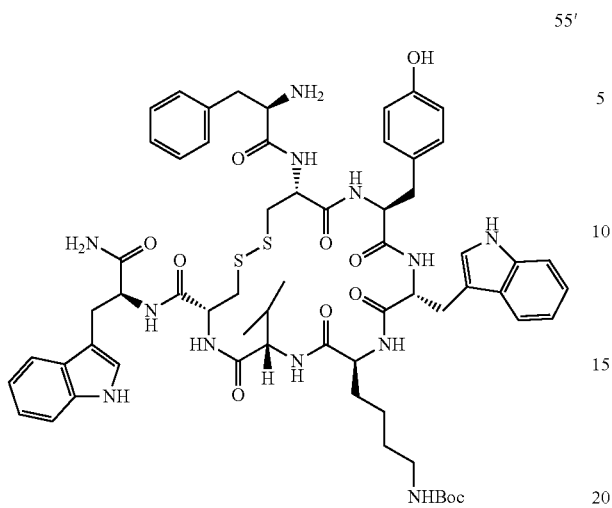

55'

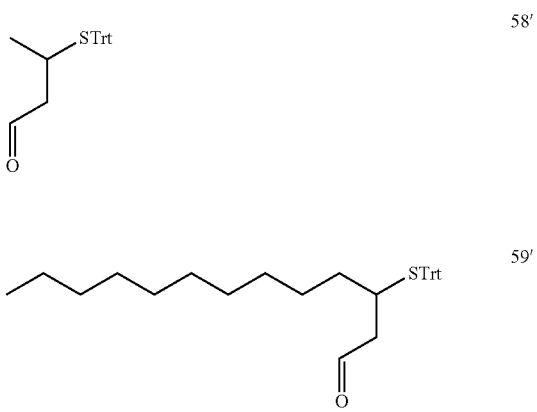

58'

59'

Compounds 58' and 59' were made in an analogous manner to compound 57'.

Compound 55', Lys-Boc vapreotide, was made in an analogous manner to 54'.

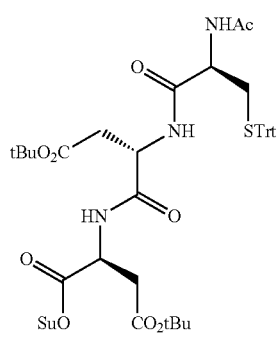

56'

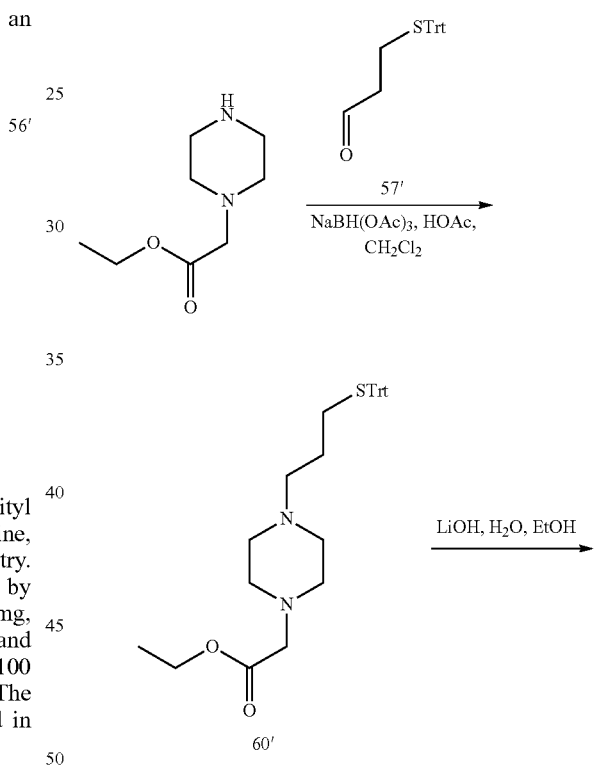

Fmoc-aspartic acid(tBu) was loaded onto 2-chlorotrityl resin, and Fmoc-aspartic acid(tBu), Fmoc-S-trityl-cysteine, and $Ac_2O$ were appended using standard Fmoc chemistry. The peptide was cleaved from the resin, and purified by reverse phase chromatography. The purified peptide (50 mg, 0.067 mmol) was dissolved in dichloromethane (3 mL), and DCC (20.6 mg, 0.100 mmol) and HOSu (11.5 mg, 0.100 mmol) were added, and the reaction stirred overnight. The resulting solution was filtered, the filtrate concentrated in vacuo, and the crude NHS ester used as is.

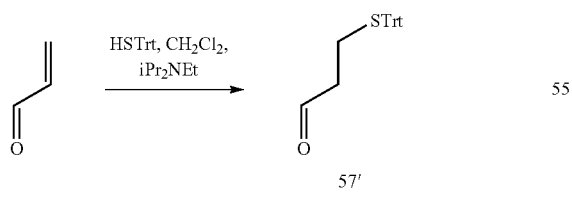

57'

A flask was charged with triphenylmethanethiol (1.23 g, 4.45 mmol) and dichloromethane (7 mL), diisopropylethylamine (1.0 mL) and acrolein (0.60 mL, 8.98 mmol) were added. The reaction was stirred at room temperature for 1 h, and all solvents were removed in vacuo to give trityl 3-mercaptopropionaldehyde (57', 1.48 g, 4.45 mmol) which was used crude in the next step.

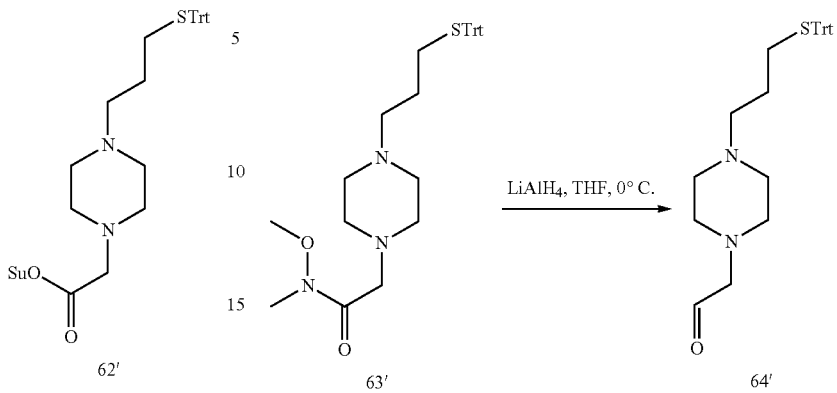

A flask was charged with ethyl 1-piperazinylacetate (1.03 g, 6.02 mmol) and trityl 3-mercaptopropionaldehyde (2.00 g, 6.02 mmol). The reagents were dissolved in dichloromethane (20 mL), acetic acid (0.10 mL) was added, and sodium triacetoxyborohydride (3.19 g, 15.0 mmol) was added. The reaction was stirred at room temperature for 2 h, then purified by silica gel chromatography to provide 60' (1.80 g, 3.69 mmol, 61% yield).

60' (640 mg, 1.31 mmol) was dissolved in 10:1 ethanol:water (10 mL), and lithium hydroxide (63.0 mg, 2.62 mmol) was added. The reaction was stirred at room temperature for 2 h, then acidified with 10% citric acid. The resulting solid was filtered, washed with water, and dried to provide 61' (400 mg, 0.870 mmol, 66% yield).

61' (76.3 mg, 0.167 mmol) was dissolved in dichloromethane (2 mL). DCC (51.5 mg, 0.250 mmol) and HOSu (28.8 mg, 0.250 mmol) were added, the reaction stirred overnight, then the reaction was filtered and the filtrate concentrated in vacuo. The resulting NHS ester was used crude in the next step.

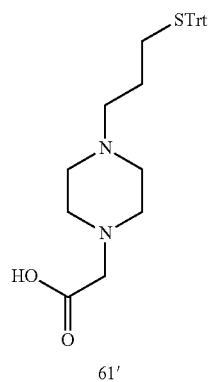

To a solution of 61' (450 mg, 0.978 mmol) in dichloromethane (15 mL) was added CDI (190 mg, 1.17 mmol) as a solid. The reaction was stirred at room temperature for 30 min, then N,O-dimethylhydroxylamine hydrochloride (114 mg, 1.17 mmol) was added as a solid. The reaction was stirred at room temperature for 4 h, the reaction washed with water (15 mL), and the organic layer dried and concentrated in vacuo to give 63' (200 mg, 0.398 mmol, 41% yield).

To a solution of 63' (50 mg, 0.099 mmol) in THF (5 mL), at 0° C., was added a solution of lithium aluminum hydride (0.13 mL, 1M in THF, 0.13 mmol). The reaction was stirred at 0° C. for 2 h, then quenched by 1 N HCl (5 mL) and extracted with ethyl acetate (10 mL). The organic layer was dried with MgSO$_4$, and the concentrated in vacuo to provide crude 64' (20 mg, 0.045 mmol, 45% yield), which was used crude in the next step.

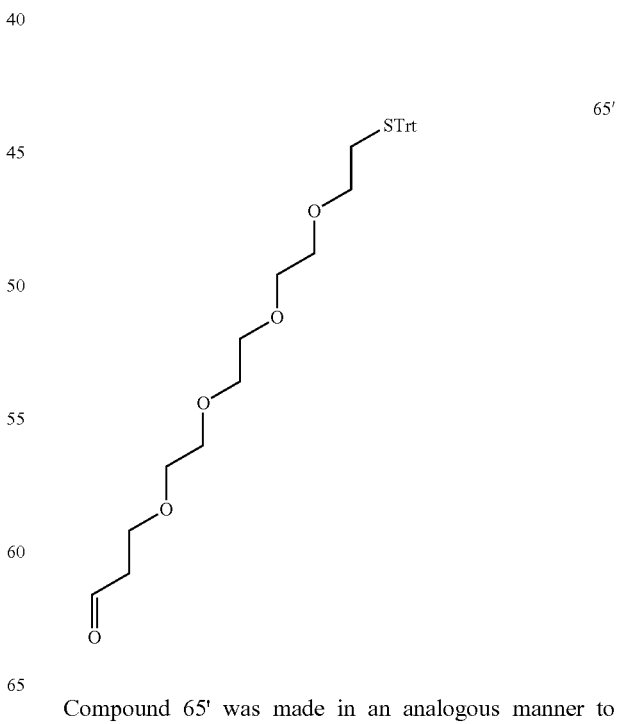

Compound 65' was made in an analogous manner to compound 64'.

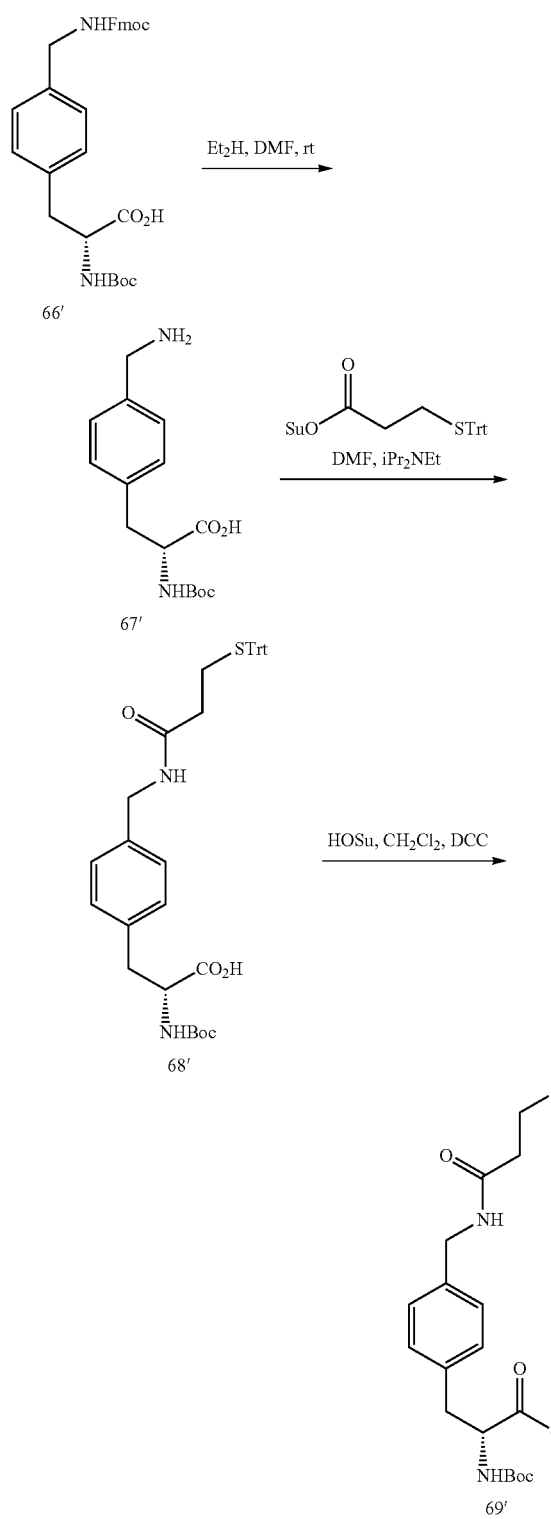

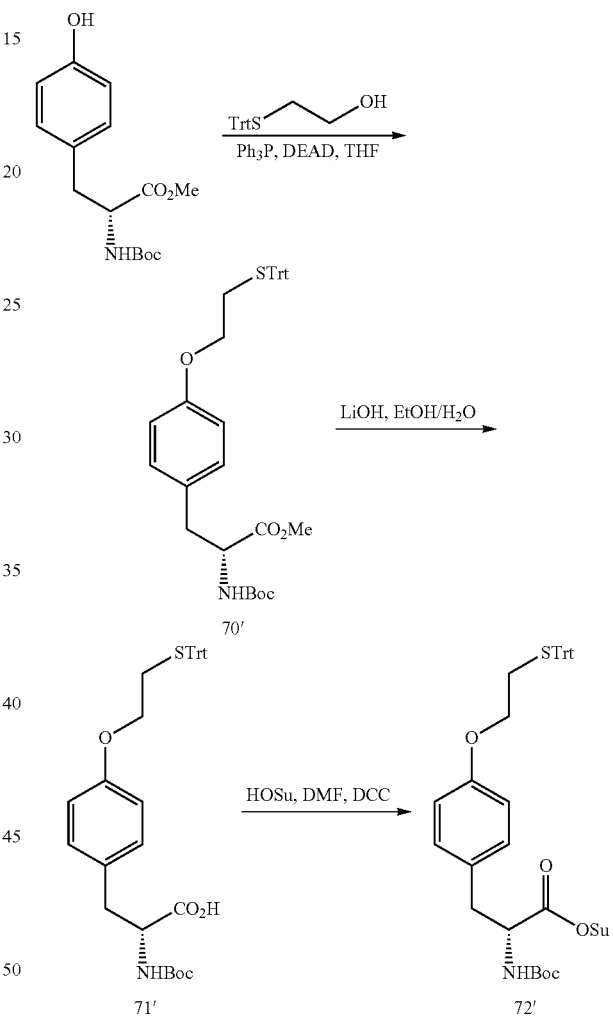

The crude 67' was dissolved in DMF (5 mL), and trityl 3-mercaptopropionic acid NHS ester (173 mg, 0.388 mmol) was added, followed by diisopropylethylamine (0.30 mL). The reaction was stirred at room temperature for 3 h, and the reaction was purified by preparative HPLC to provide 68' (140 mg, 0.224 mmol, 58% yield).

A vial was charged with 68' (40 mg, 0.064 mmol), DCC (14 mg, 0.064 mmol) and HOSu (7.4 mg, 0.064 mmol). Dichloromethane (2 mL) was added, the reaction stirred at room temperature for 16 h, and the reaction filtered, the filtrate collected and concentrated in vacuo, and the crude 69' used directly in the next step.

A flask was charged with N-Boc D-tyrosine methyl ester (1.00 g, 3.39 mmol), triphenylphosphine (977 mg, 3.73 mmol), and S-trityl-2-mercaptoethanol (1.08 g, 3.39 mmol). While under nitrogen, THF (20 mL) was added, followed by dropwise addition of diethylazodicarboxylate (0.64 mL, 4.1 mmol). The reaction was stirred at room temperature for 16 h, and the solvent removed in vacuo, and the remaining residue purified by preparative HPLC to provide 70' (880 mg, 1.48 mmol, 44% yield).

70' (880 mg, 1.48 mmol) was dissolved in ethanol (20 mL) and water (2 mL), and lithium hydroxide (72 mg, 3.0 mmol) was added. The reaction was stirred at room temperature for 3 h, and the reaction purified by preparative HPLC to provide 71' (820 mg, 1.41 mmol, 95% yield).

A flask was charged with 66' (200 mg, 0.388 mmol), and this was dissolved in 4:1 DMF:diethylamine (10 mL). The reaction was stirred at room temperature for 4 h, and the solvent removed in vacuo. The residue was dissolved in a few drops of dichloromethane, and diethyl ether (20 mL) was added to precipitate the product. The crude 67' was filtered, and taken directly on to the next step.

261

A vial was charged with 71' (58 mg, 0.10 mmol), DCC (21 mg, 0.10 mmol) and HOSu (11 mg, 0.10 mmol). Dichloromethane (2 mL) was added, the reaction stirred at room temperature for 16 h, then filtered. The filtrate was concentrated in vacuo, and the collected crude 72' was used directly in the next step.

262

To a solution of 52' (62.0 mg, 0.0539 mmol) in DMF (3 mL) was added trityl 3-mercaptopropionic acid NHS ester (90.0 mg, 0.202 mmol). Diisopropylethylamine (0.20 mL) was added, and the reaction stirred at room temperature for 24 h. The reaction mixture was then loaded onto a 30 g C18 Isco column, and eluting with 5% to 95% acetonitrile in

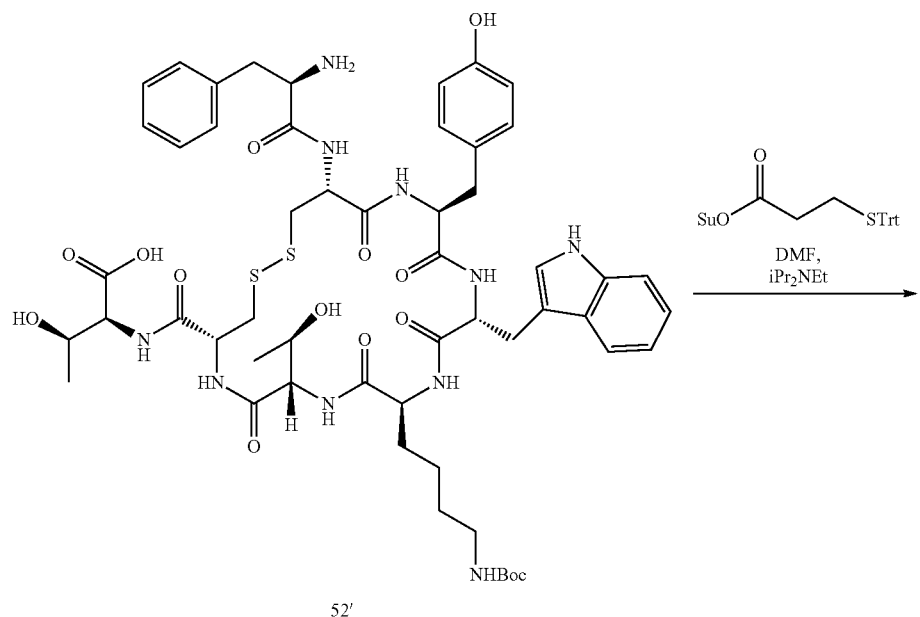

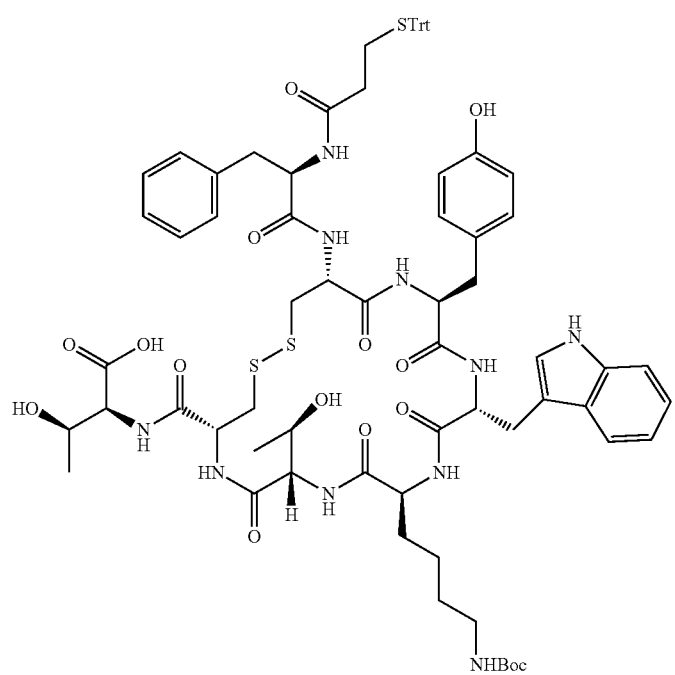

water with 0.1% AcOH provided 73' (43.1 mg, 0.0291 mmol, 54% yield).
Compounds 74'-85' were made in an analogous manner to 73'.
74'
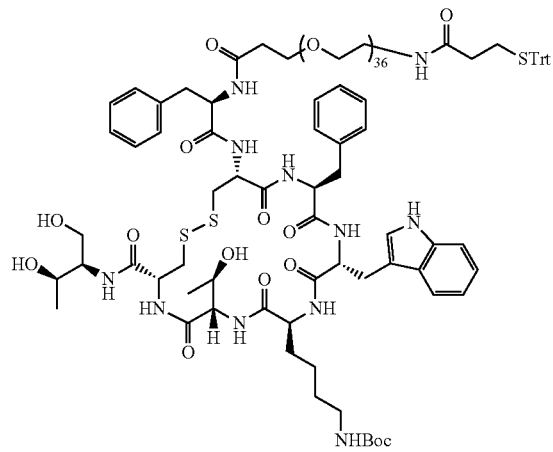
75'
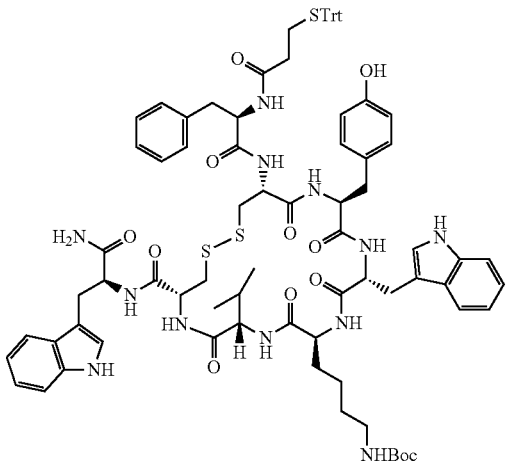
76'
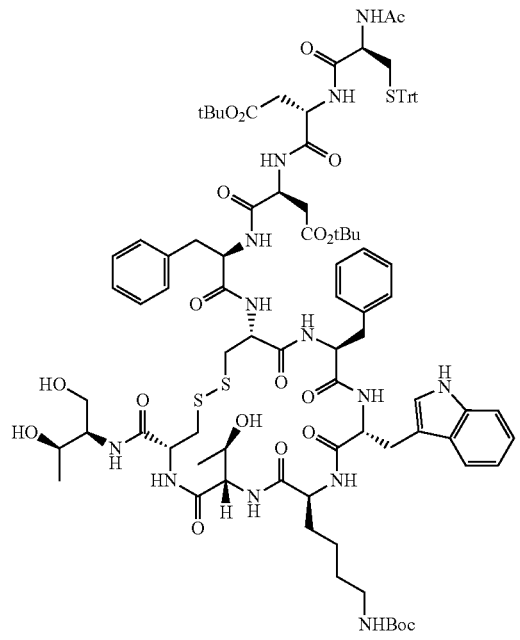
77'
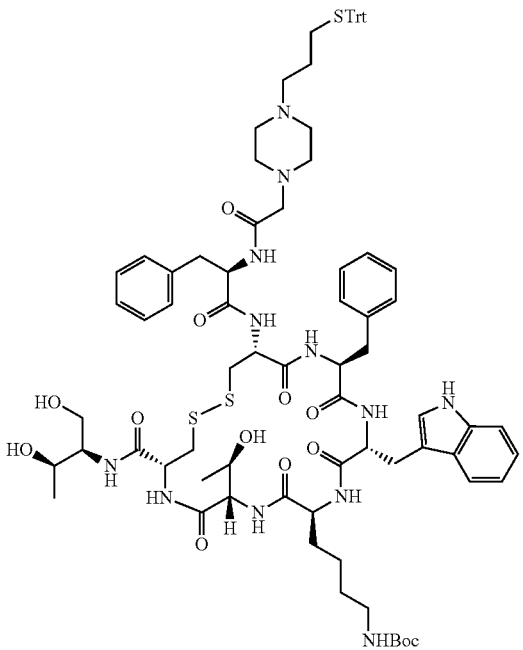

78'
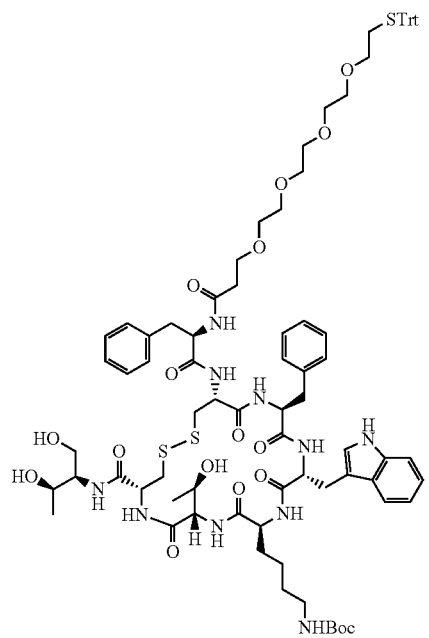
79'
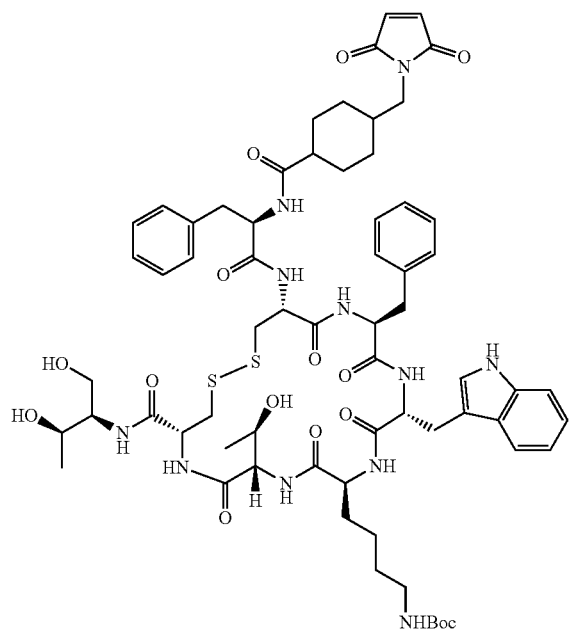
80'
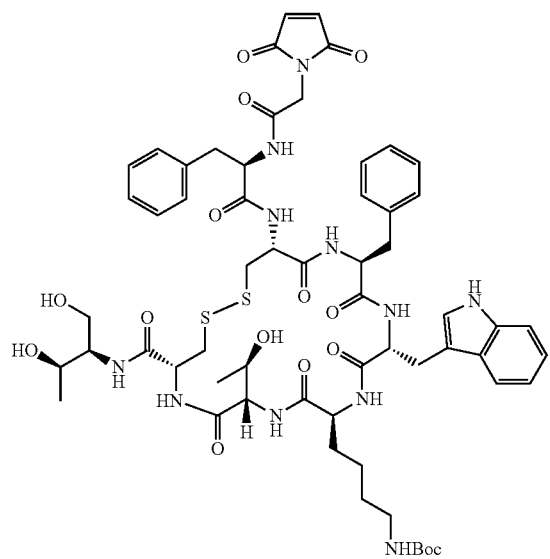
81'
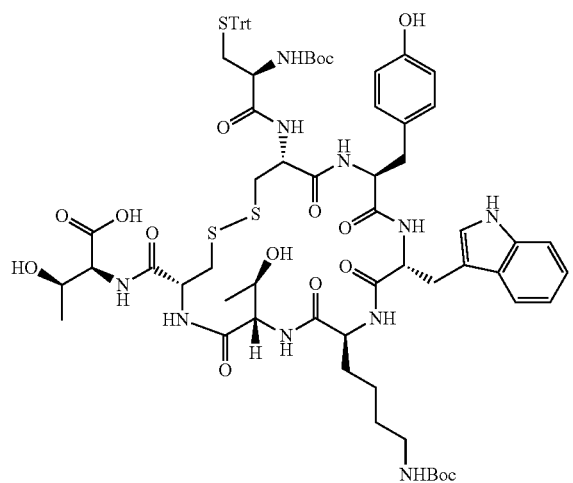

-continued
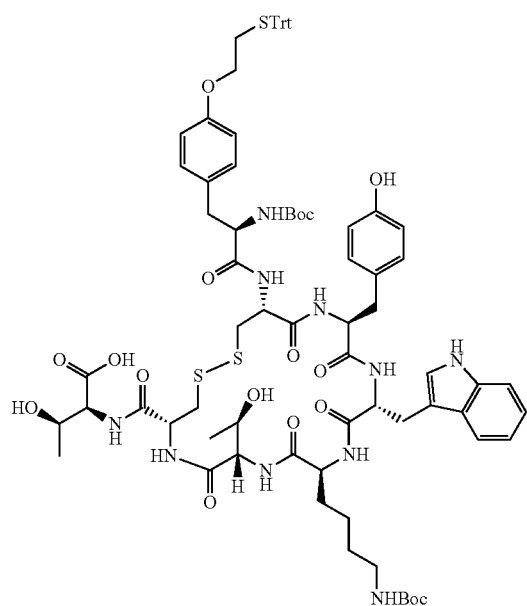
82'
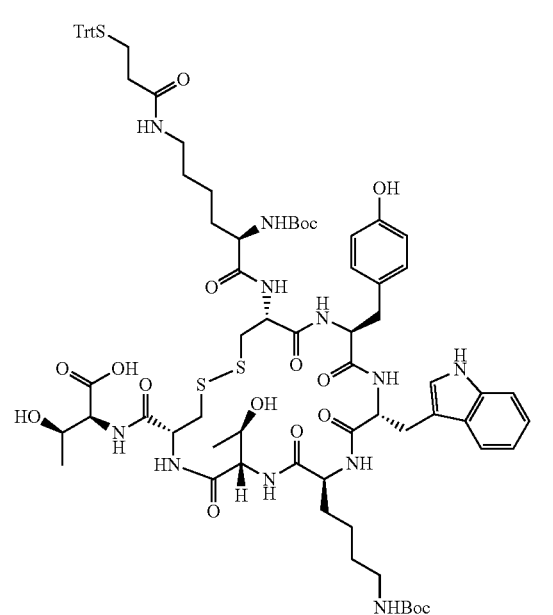
83'
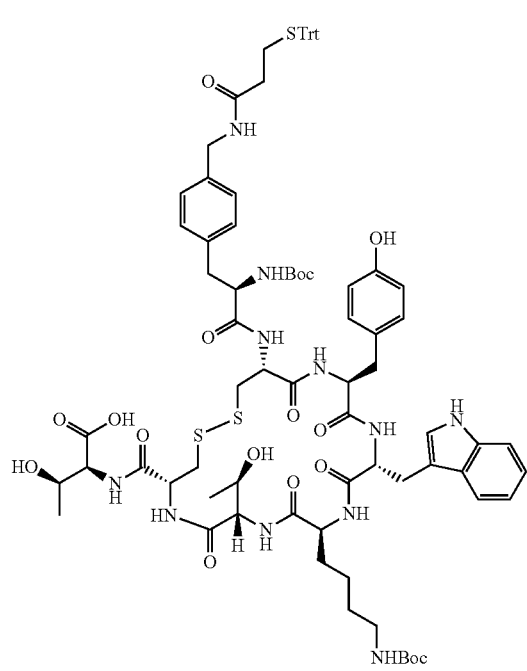
84'
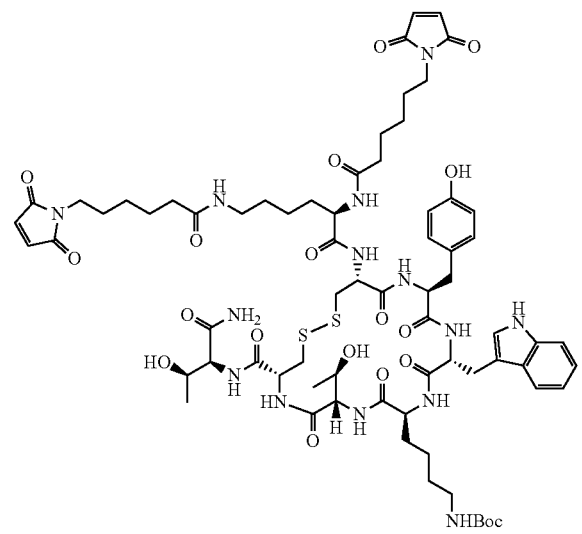
85'

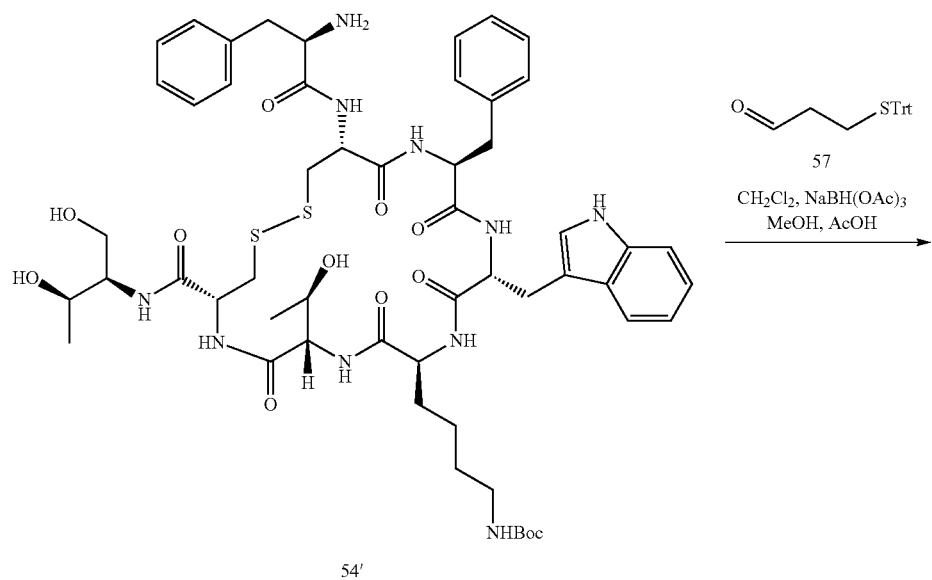

54'

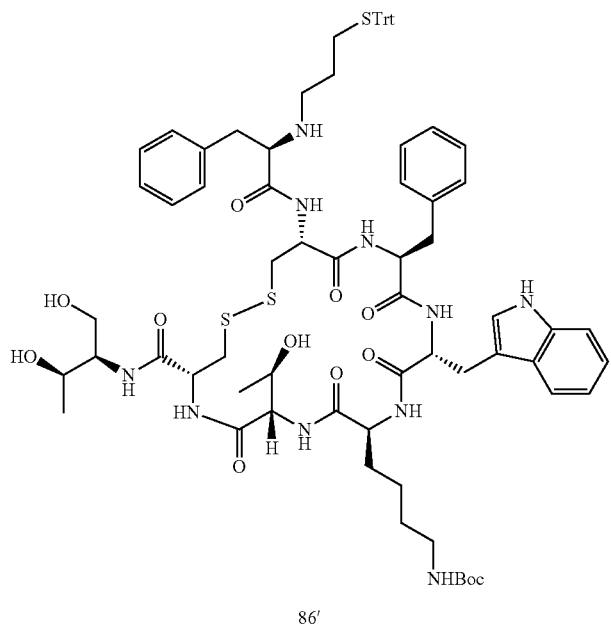

86'

54' (413 mg, 0.350 mmol) was dissolved in dichloromethane (10 mL), methanol (3 mL) and acetic acid (0.25 mL). 57' (180 mg, 0.541 mmol) was added, followed by sodium triacetoxyborohydride (115 mg, 0.541 mmol). The reaction was stirred at room temperature for 2 h, and all solvents were removed in vacuo. The remaining residue was dissolved in a minimal amount of DMF, and loaded onto a 50 g C18 Isco column. Eluting with 15% to 85% acetonitrile in water with 0.1% TFA provided 86' as the trifluoroacetate salt (389 mg, 0.251 mmol, 72% yield).

Compounds 87'-94' were made in an analogous manner to 86':
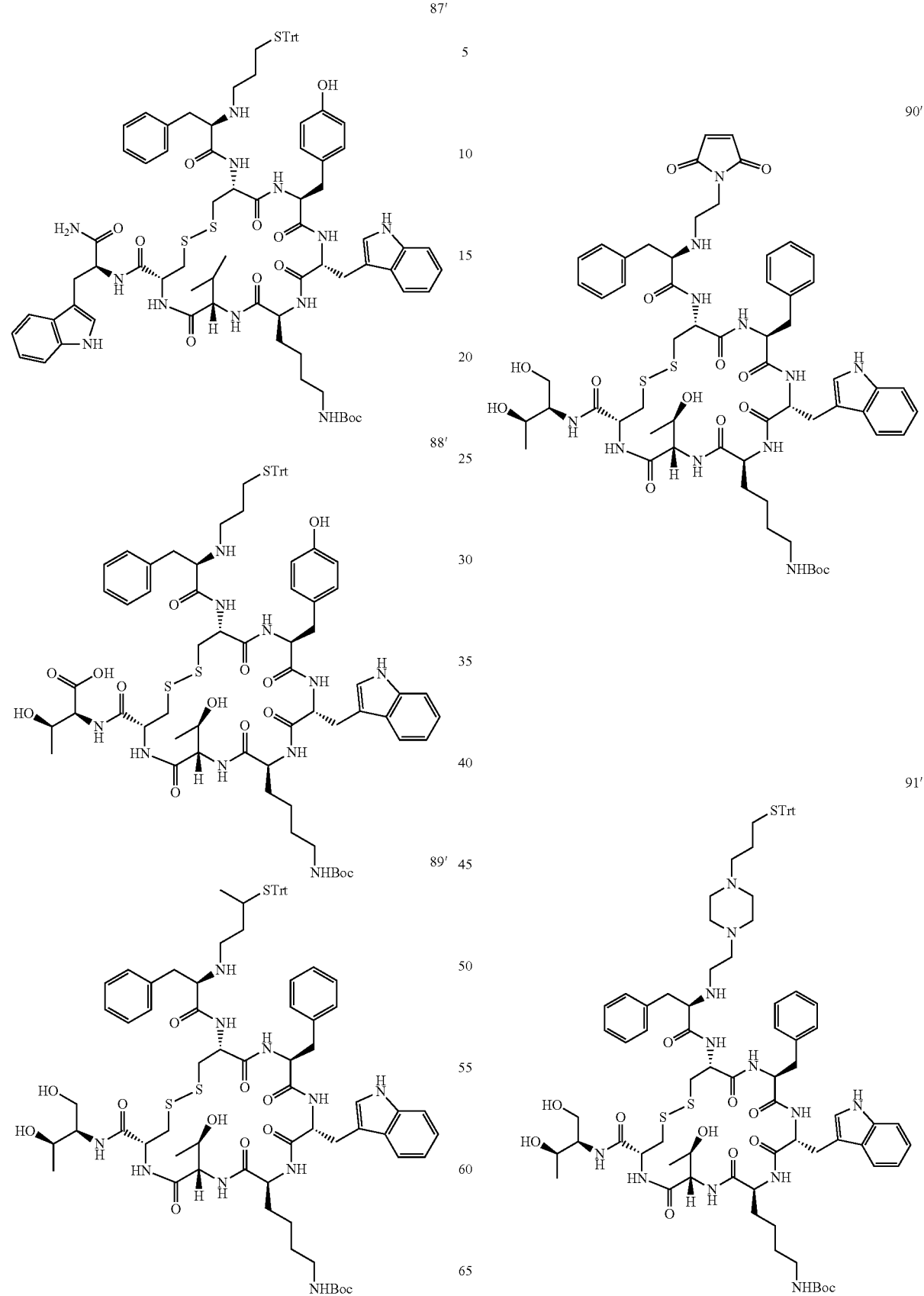

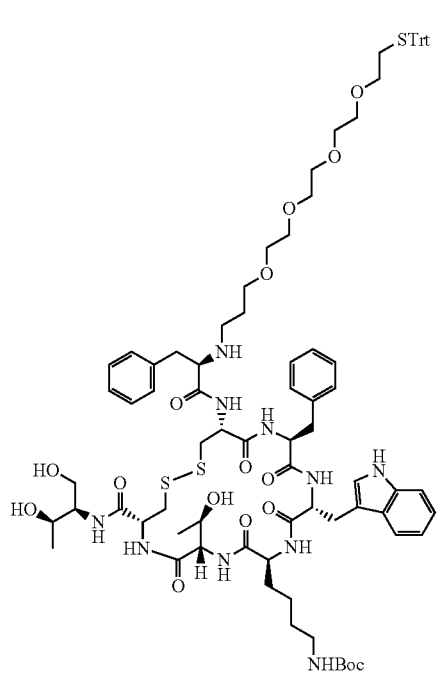

92'

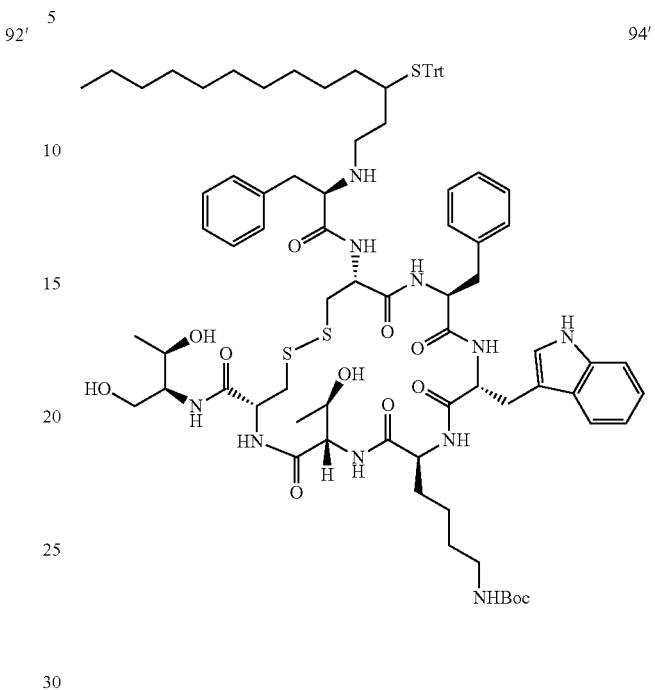

94'

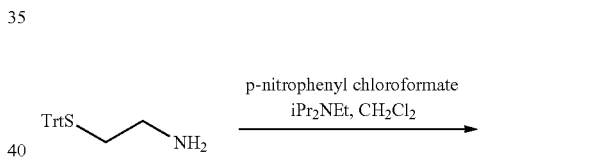

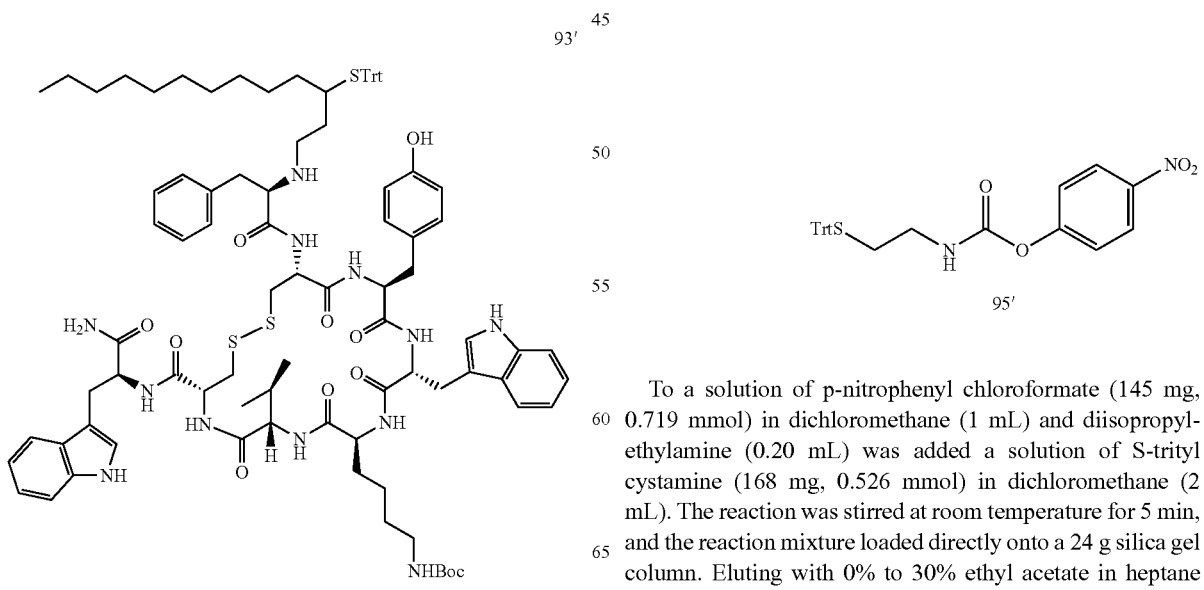

93'

95'

To a solution of p-nitrophenyl chloroformate (145 mg, 0.719 mmol) in dichloromethane (1 mL) and diisopropylethylamine (0.20 mL) was added a solution of S-trityl cystamine (168 mg, 0.526 mmol) in dichloromethane (2 mL). The reaction was stirred at room temperature for 5 min, and the reaction mixture loaded directly onto a 24 g silica gel column. Eluting with 0% to 30% ethyl acetate in heptane provided 95' (120 mg, 0.247 mmol, 47% yield).

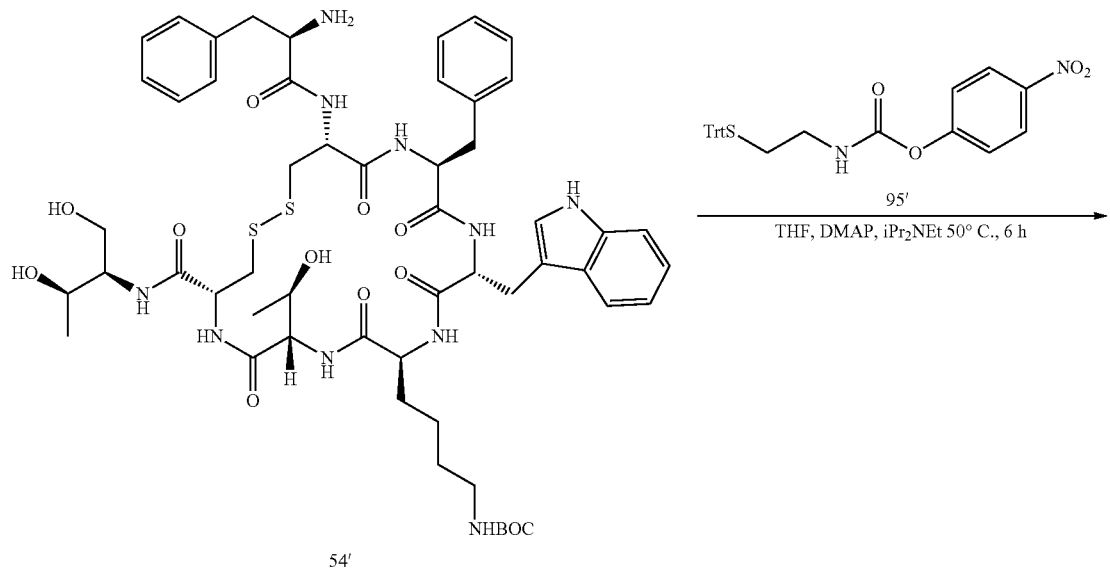
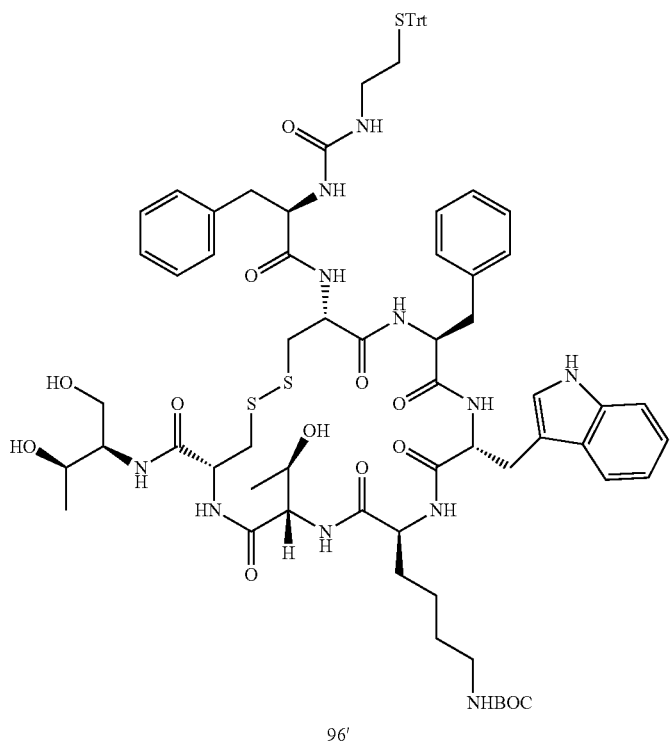
To a solution of 54' (162 mg, 0.137 mmol) in THF (3 mL) and diisopropylethylamine (0.50 mL) was added a solution of 95' (120 mg, 0.247 mmol) in THF (1 mL). DMAP (36.6 mg, 0.300 mmol) was added as a solid, and the reaction stirred at 50° C. for 6 h. All solvent was removed in vacuo, and the remaining material loaded onto a 30 g C18 Isco column, eluting with 15% to 95% acetonitrile in water with 0.1% AcOH to provide 96' (201 mg, 0.137 mmol, 100% yield).

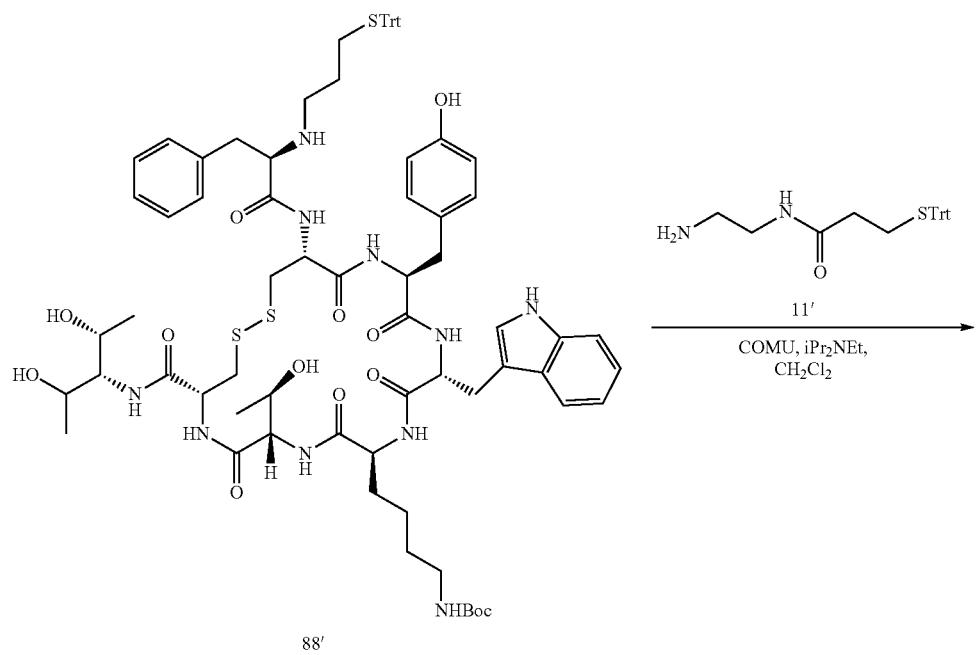
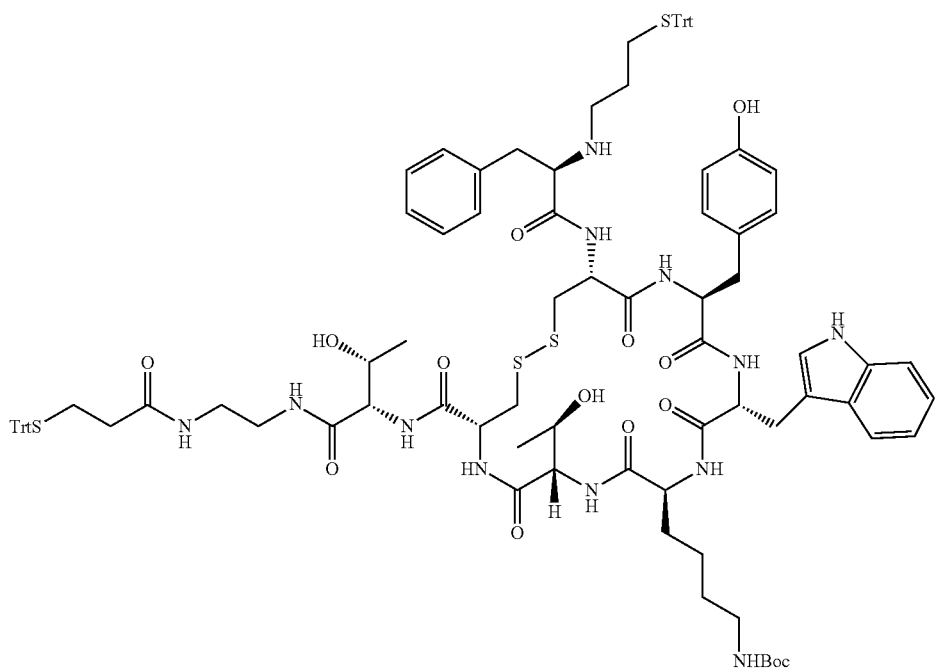
A vial was charged with 88' (30.0 mg, 0.0190 mmol), COMU (16.0 mg, 0.0.0374 mmol), and 11' (35.0 mg, 0.0896 mmol). Dichloromethane (2 mL) and diisopropylethylamine (0.20 mL) were added, and the reaction stirred at room temperature for 20 h. The solvent was removed in vacuo, and the remaining material loaded onto a 30 g C18 Isco column, and eluting with 40% to 95% acetonitrile in water with 0.1% AcOH provided 97' (16.6 mg, 0.00903 mmol, 47% yield).
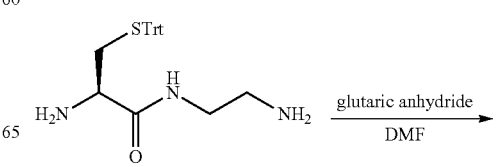

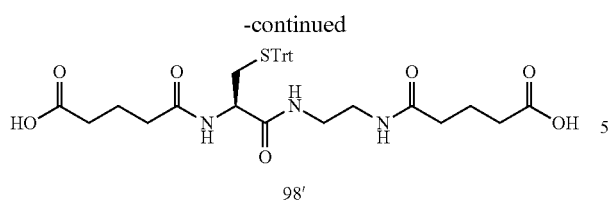
S-trityl-L-cysteine ethylenediamine amide (40.0 mg, 0.0986 mmol) and glutaric anhydride (45.0 mg, 0.395 mmol) were dissolved in DMF (2 mL). The reaction was stirred at room temperature for 16 h, and the reaction mixture purified by preparative HPLC to provide 98' (30.0 mg, 0.0473 mmol, 48% yield).
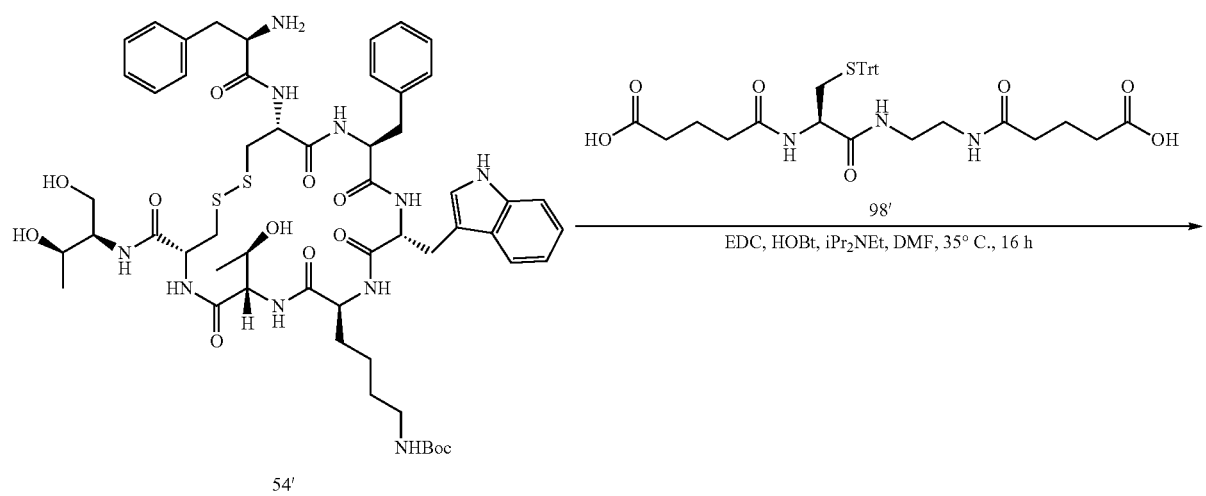
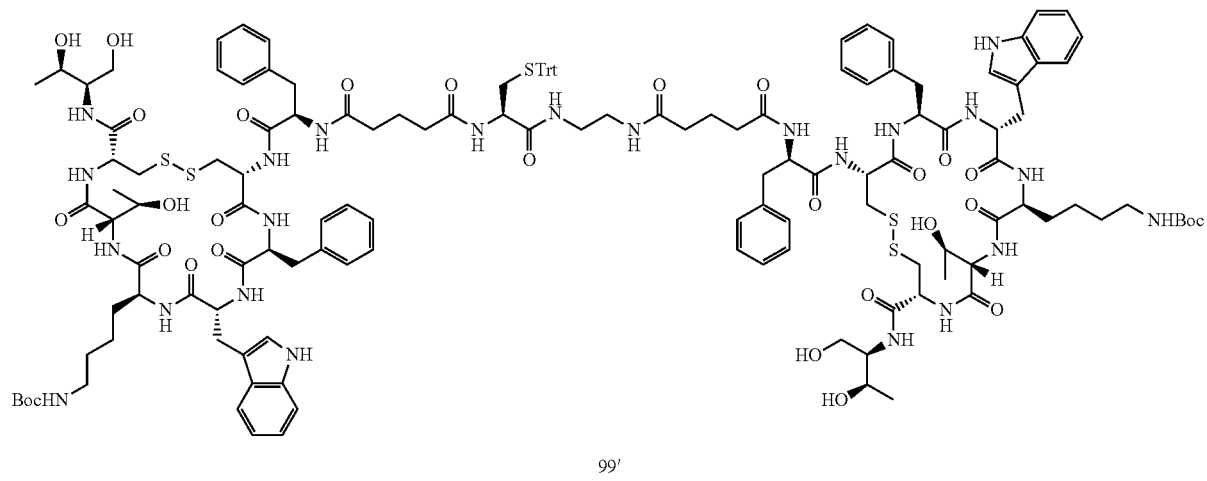

A vial was charged with 98' (8.0 mg, 0.0126 mmol), 54' (28.2 mg, 0.0252 mmol), EDC (5.8 mg, 0.030 mmol) and HOBt (4.1 mg, 0.30 mmol). DMF (2 mL) and diisopropylethylamine (9 μL, 0.05 mmol) were added, and the reaction stirred at 35° C. for 16 h. The reaction was then purified by preparative HPLC to give 99' (21.0 mg, 0.00740 mmol, 59% yield).
Synthesis of DM1 Conjugates
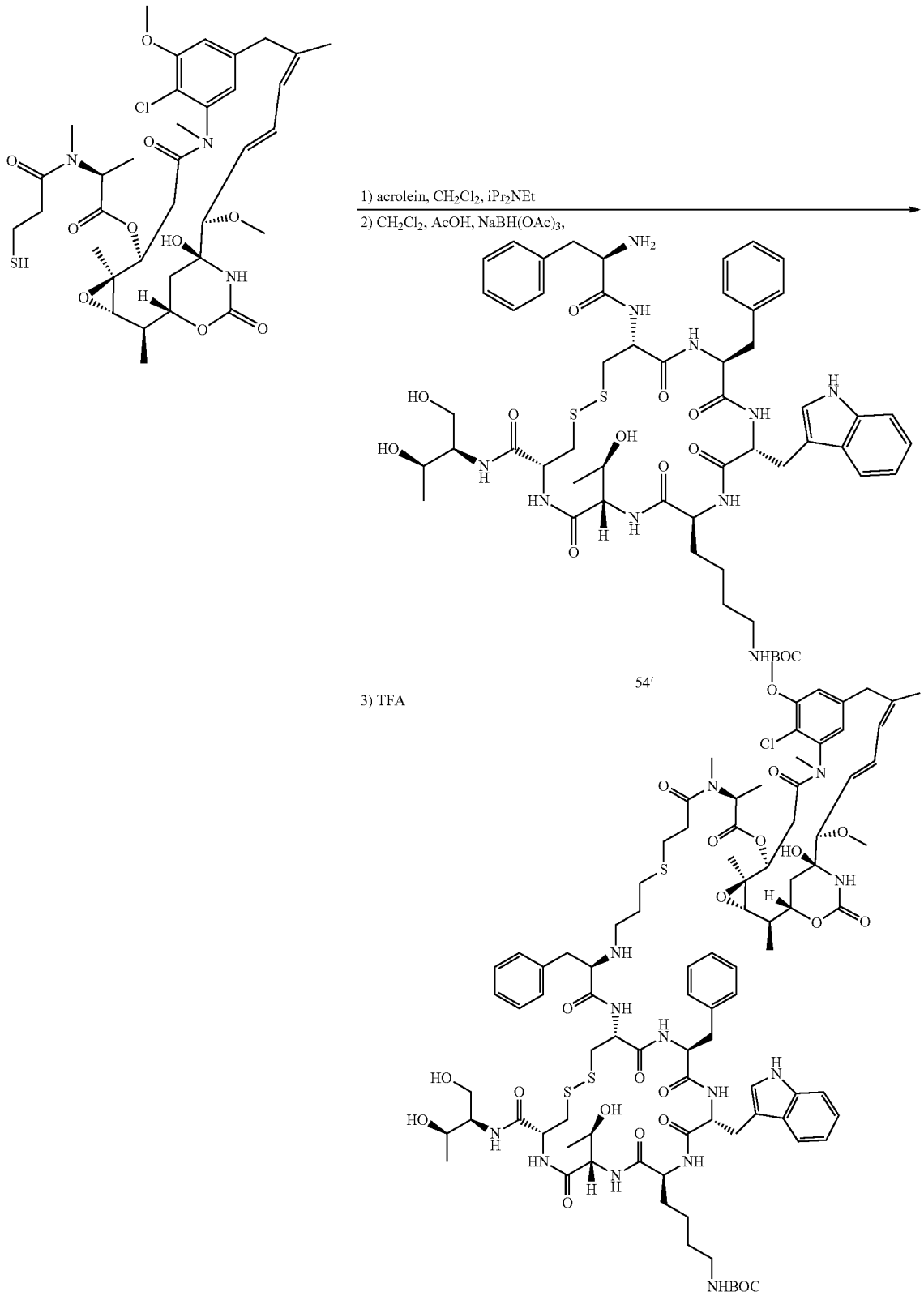

A flask was charged with DM-1 (41.8 mg, 0.0566 mmol), and dichloromethane (2 mL), diisopropylethylamine (0.10 mL) and acrolein (0.25 mL) were added. The reaction was stirred at room temperature for 5 min, and all solvents were removed in vacuo. The remaining residue was redissolved in dichloromethane (1 mL) and toluene (0.5 mL), and the solvents removed in vacuo again, to ensure complete removal of any remaining acrolein. To the remaining residue was added a solution of 54' (61.0 mg, 0.0517 mmol) in dichloromethane (2 mL) and acetic acid (0.05 mL). Sodium triacetoxyborohydride (11.5 mg, 0.0523 mmol) was added as a solid, and the reaction stirred at room temperature for 1 h. All solvent was removed in vacuo, and the remaining residue was dissolved in TFA (3 mL). The reaction was stirred at room temperature for 5 min, and most of the TFA was removed in vacuo. The remaining material was purified by preparative HPLC (5% to 55% acetonitrile in water with 0.2% AcOH) to provide Conjugate 100 as the acetate salt (7.6 mg, 0.0040 mmol, 7.6% yield). LCMS M/Z: 899.0 [(M+2)/2].

DMF, dropwise over 5 min. The reaction was stirred at room temperature for another 30 min, and the reaction mixture loaded onto a C18 Isco gold column. Eluting with 25% to 85% acetonitrile in water provided DM1-SSPy (287 mg, 0.339 mmol, 60% yield). LCMS M/Z: 847.3 [M+1].

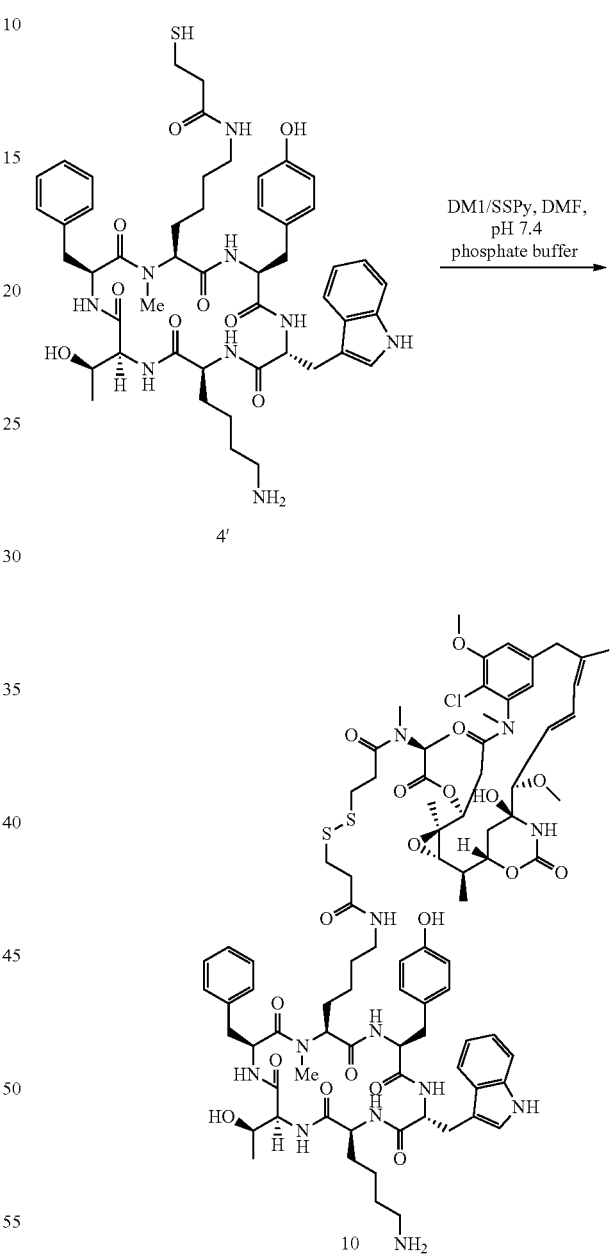

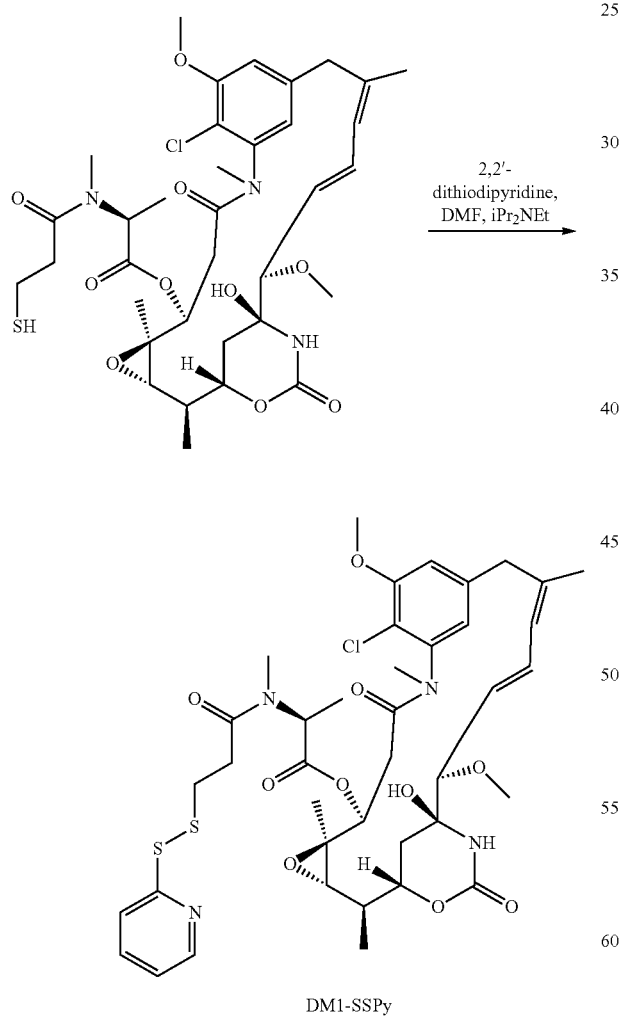

To a solution of 2,2'-dithiodipyridine (1.24 g, 5.65 mmol) in DMF (8 mL) and diisopropylethylamine (1 mL) was added a solution of DM-1 (417 mg, 0.565 mmol) in 2 mL A vial was charged with 4' (20.0 mg, 0.0209 mmol), and a solution of DM-1/SSPy (17.7 mg, 0.0209 mmol) in DMF (2 mL) was added. 100 mM pH 7.4 phosphate buffer (1.0 mL) was added dropwise while stirring rapidly, and the reaction stirred for another 5 min at room temperature. The reaction mixture was purified by preparative HPLC (5% to 65% acetonitrile in water with 0.2% AcOH) to provide Conjugate 10 (22.1 mg, 0.0126 mmol, 60% yield) as the acetate salt. LCMS M/Z: 837.5 [(M+2-H$_2$O)/2].

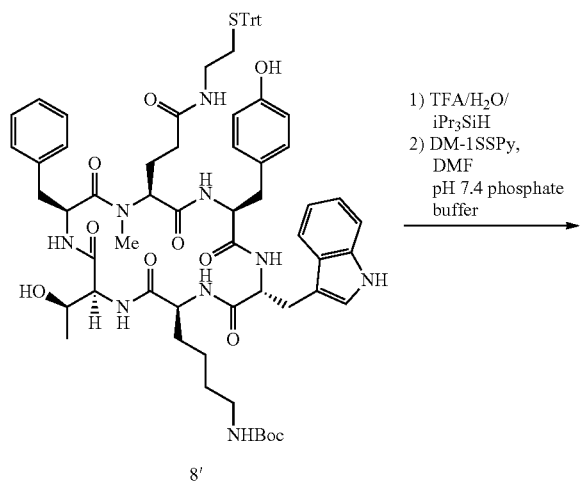

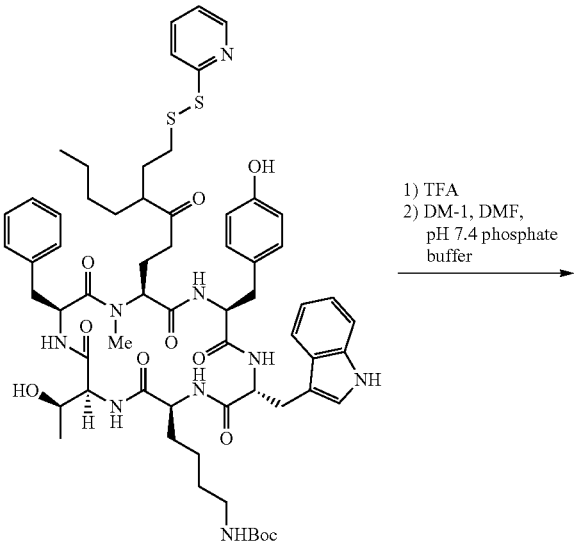

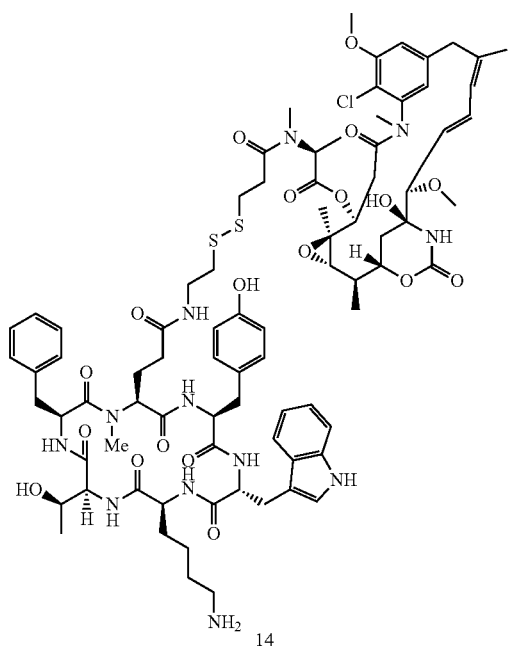

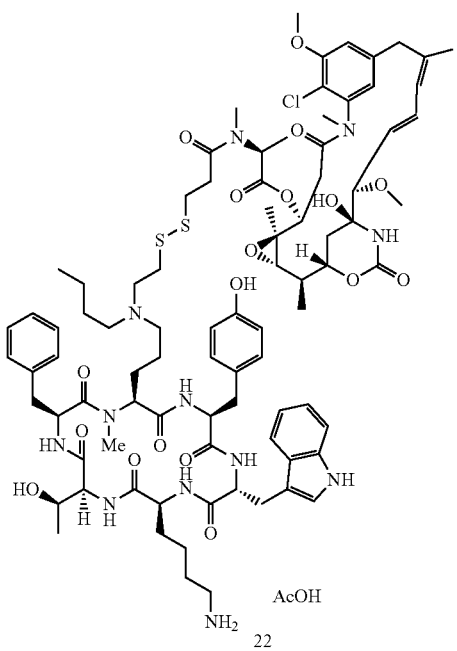

DM-1 conjugation method A: A vial was charged with 8' (20.2 mg, 0.0159 mmol), and water (0.025 mL), TFA (1 mL) and triisopropylsilane (0.025 mL) were added. The reaction was stirred at room temperature for 5 min, and all solvents were removed in vacuo. To the remaining residue was added a solution of DM-1/SSPy (13.5 mg, 0.0159 mmol) in DMF (3 mL) was added. While stirring, 100 mM pH 7.4 phosphate buffer (1 mL) was added dropwise, and the reaction stirred for an additional 5 min at room temperature. The reaction was then acidified with acetic acid (0.25 mL). The reaction mixture was then purified by preparative HPLC (5% to 70% acetonitrile in water with 0.2% AcOH) to provide Conjugate 14 (9.3 mg, 0.0054 mmol, 34% yield) as the acetate salt. LCMS M/Z: 832.3 [(M+2)/2].

DM-1 conjugation method B: A vial was charged with 22' (21.2 mg, 0.0177 mmol) and TFA (1 mL) was added. The reaction stirred at room temperature for 5 min, and all solvent was removed in vacuo. To the remaining residue was added a solution of DM-1 (13.1 mg, 0.0177 mmol) in DMF (2 mL). While stirring, 100 mM pH 7.4 phosphate buffer (1 mL) was added dropwise, and the reaction then stirred at room temperature for another 5 min. The reaction was acidified by adding acetic acid (0.25 mL), and the reaction mixture purified by preparative HPLC (5% to 75% acetonitrile in water with 0.2% AcOH) to yield Conjugate 22 (20.2 mg, 0.0114 mmol, 64% yield) as the acetate salt. LCMS M/Z: 860.5 [(M+2)/2].

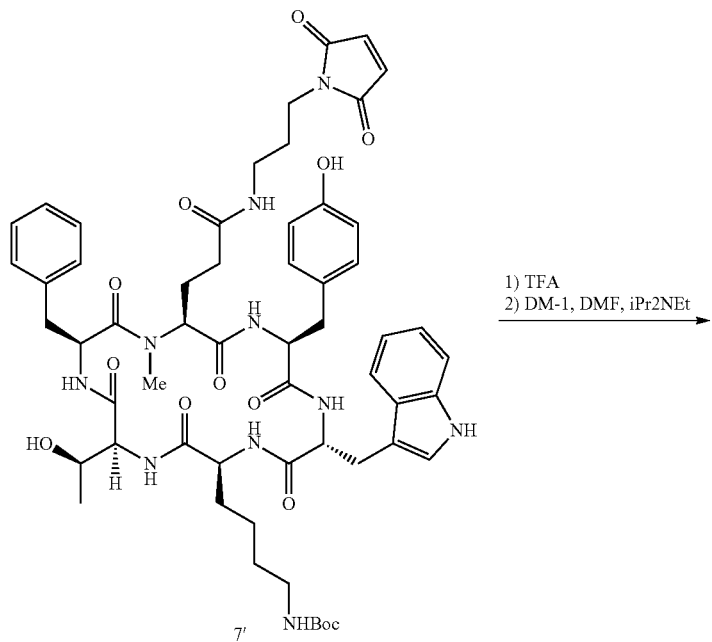

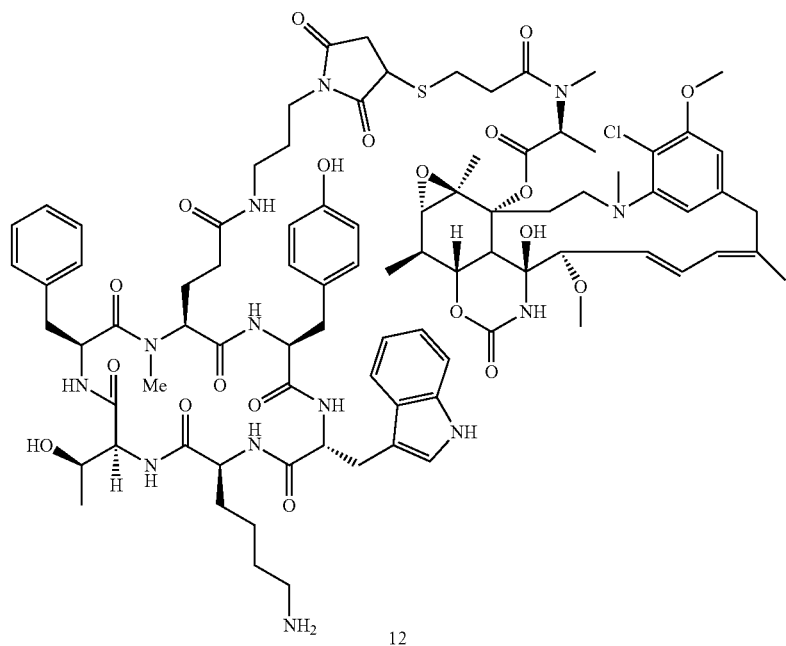

DM-1 conjugation method C: A vial was charged with 7 (25.7 mg, 0.0233 mmol), and TFA (1 mL) was added. The reaction was stirred at room temperature for 5 min, and all solvent was removed in vacuo. To the remaining residue was added a solution of DM-1 (17.2 mg, 0.0233 mmol) in DMF (4 mL), followed by diisopropylethylamine (0.25 mL). The reaction was stirred at room temperature for 10 min, and was then acidified by adding acetic acid (0.40 mL). The reaction mixture was then purified by preparative HPLC (5% to 70% acetonitrile in water with 0.2% AcOH) to provide Conjugate 12 (25.6 mg, 0.0142 mmol, 61% yield) as the acetate salt. LCMS M/Z: 872.0 [(M+2)/2].

2-Chloro-2-trityl resin ⟶

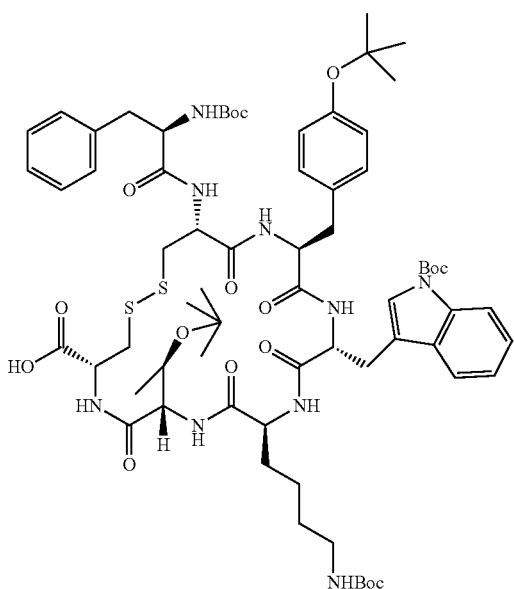

57A

Synthesis of 57A. Fmoc-Cysteine(Trt)-OH was loaded onto 2-chlorotrityl resin (25.0 g resin, 100-200, 1 meq/g loading). Iterative deprotection with 4:1. DMF:piperidine, and coupling subsequently with Fmoc-Threonine(tBu)-OH, Nα-Fmoc-Nε-Boc-lysine, Nα-Fmoc-N$^{in}$-Boc-D-tryptophan, Fmoc-tyrosine(tBu), Fmoc-Cysteine(Trt)-OH, and Boc-D-phenylalanine using standard SPPS conditions (Nature Prot. 2012, 432) gave the linear peptide bound to the resin. 8 g of resin (0.338 mmol/g) was stirred with DMF (80 mL) containing iodine (3 equiv.) for 3 h at rt, then filtered and washed with DMF (2×40 mL). The resin was resubmitted with iodine (3 equiv.) in DMF (80 mL) for 3 h. Resin was washed with DMF (2×40 mL), then DCM (2×40 mL) and resin was dried in vacuo at rt.

Resin (8 g, 0.338 mmol/g) was swelled in DCM (80 mL) and hexafluoroisopropanol (30 mL) was added at rt over ~1 min. The resulting mixture was stirred for 30 min at rt, then filtered and washed with DCM (2×40 mL). The filtrate was concentrated in vacuo at 20-25 C. The resin was resubmitted to cleavage conditions with DCM (80 mL) and hexafluoroisopropanol (30 mL), stirred for 30 min, then filtered and washed with DCM (2×40 mL). The filtrate was evaporated under reduced pressure at 20-25° C. Crude residue was dissolved in MTBE (minimum amount), then added dropwise to n-heptane stirred at rt to produce a precipitate. The solid was filtered and dried at rt to yield 57A (2.95 g, 2.17 mmol, 80% yield). LCMS M/Z: 1361 [M+1].

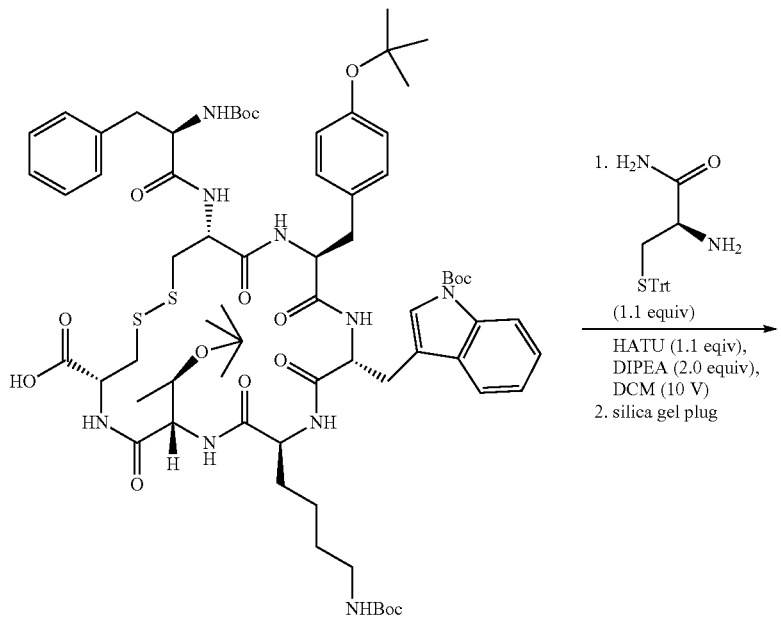

57A

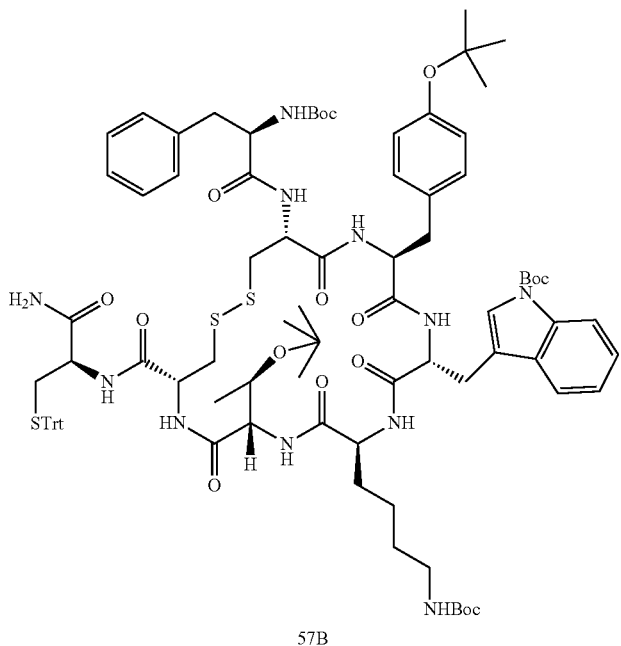

57B 100 mL RBF was charged with 57A (2.73 g, 2.01 mmol) and (2R)-2-amino-3-tritylsulfanyl-propanamide (728.60 mg, 2.01 mmol). Dichloromethane (27.00 mL) was added followed by diisopropylethylamine (519.54 mg, 4.02 mmol) and HATU (840.69 mg, 2.21 mmol). After 1.5 h, conversion was complete by HPLC/MS. 27 g silica gel (10 weighs) was charged in a fritted glass funnel. 40:60 TBME/DCM was used to wet silica. The DCM solution was added on top of the silica gel, then eluted with 40:60 TBME/DCM (250 mL), followed by 2% isopropanol in 40:60 TBME/DCM (250 mL). The filtrate was evaporated. The desired product 57B was obtained. (3.16 g, 92% yield). LCMS M/Z: 1705 [M+1].

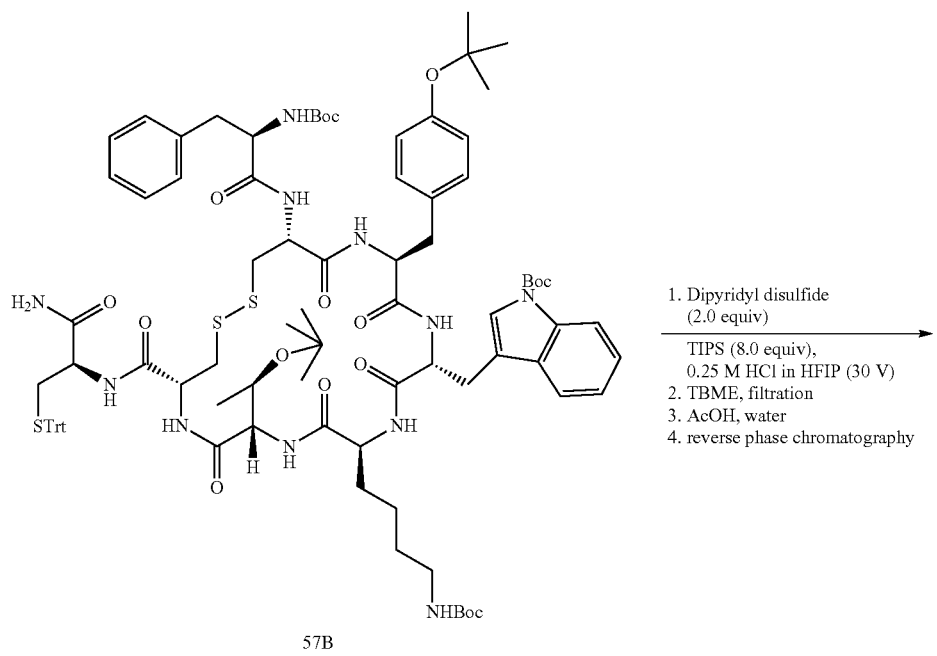

57B

1. Dipyridyl disulfide (2.0 equiv)
TIPS (8.0 equiv), 0.25 M HCl in HFIP (30 V)
2. TBME, filtration
3. AcOH, water
4. reverse phase chromatography -continued

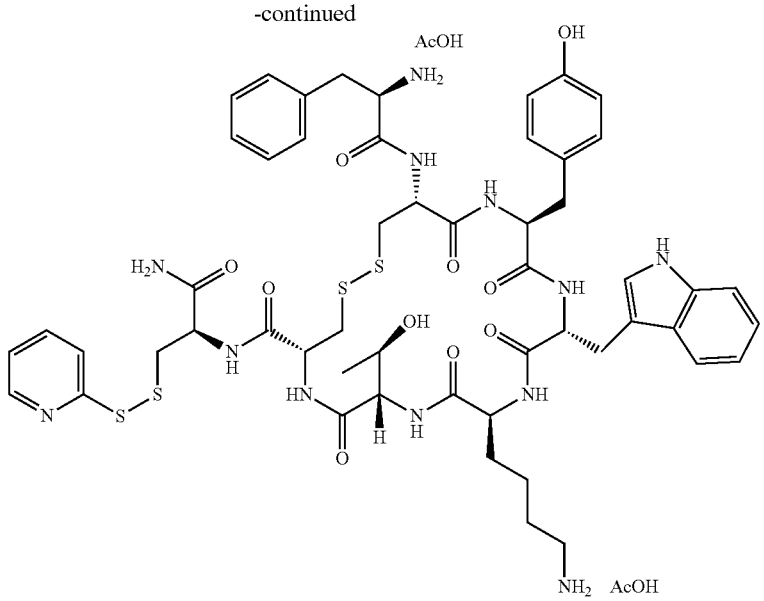

57C

Deprotection method A. 57B (500.00 mg, 293.23 umol) was charged in a 50 mL RBF, 2,2'-dithiodipyridine (129.85 mg, 589.39 umol) and triisopropylsilane (386.81 mg, 2.44 mmol) were added, followed by hexafluoroisopropanol (8 mL), then by 8 mL of 0.5 M HCl in hexafluoroisopropanol (8 mL). After 2 h, HPLC/MS showed complete conversion. Solution was added slowly to TBME (30 mL) and the precipitate formed was filtered, then washed with TBME (30 mL). The solid was dissolved in 1 M AcOH (8 mL) and the solution was stirred at RT for 2 h. HPLC/MS showed complete conversion to desired product. The crude mixture was directly injected on a 100 g C18 Isco gold column. Column was flushed with 360 mL (3 volumes) 100 mM ammonium acetate, then re-equilibrated with 5% acetonitrile in water with 0.1% AcOH (2 volumes) and eluted using gradient of 5% to 30% acetonitrile in water with 0.1% AcOH for 24 mins. Pure fractions were lyophilized to give 57C as the acetate salt. LCMS M/Z: 1160 [M+1].

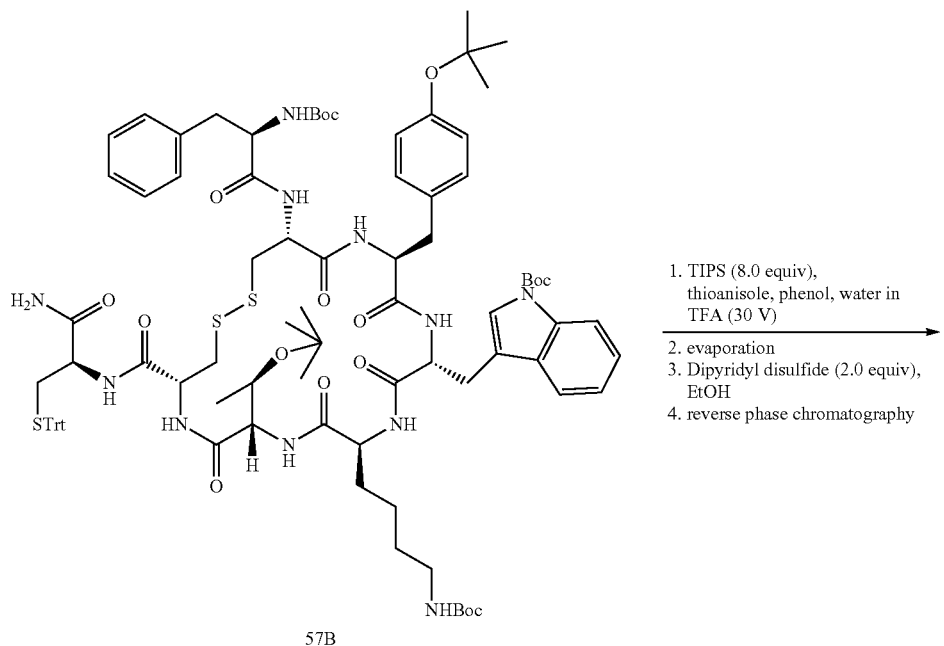

57B

1. TIPS (8.0 equiv), thioanisole, phenol, water in TFA (30 V)
2. evaporation
3. Dipyridyl disulfide (2.0 equiv), EtOH
4. reverse phase chromatography

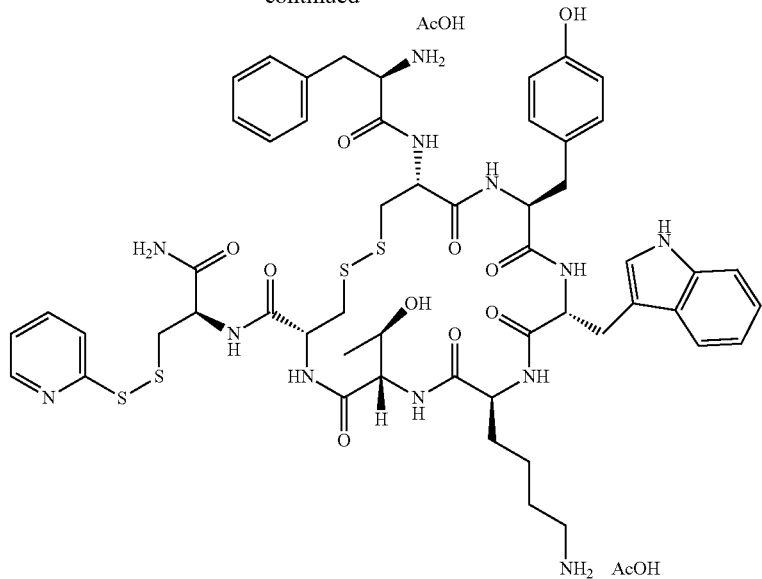

57C

Deprotection method B. Flask was charged with 57C (502 mg, 0.294 mmol). In a separate vial was charged TFA (8.8 mL), triisopropylsilane (0.20 mL), water (0.50 mL), and thioanisole (0.50 mL). This vial was shaken until the mixture turned homogeneous, then the deprotection cocktail was added to the solid 57C. The flask was stirred until everything went into solution, then stirred at room temperature for another 30 min. HPLC/MS shows complete deprotection. TFA was removed in vacuo, until volume of reaction mixture ca. 1 mL. Ethanol (30 mL) was added to the reaction, solution was cooled to 0° C., then a solution of 2,2'-dithiodipyridine (130 mg) in 10 mL ethanol was added. Solution was stirred at 0° C. for 1 h, then stirred at room temperature for 2 h. HPLC/MS showed complete conversion to SSPy product. Pyridine (5 mL) was added, solution was stirred at room temperature for 5 min, then all solvents were removed in vacuo. Residue was dissolved in 2 mL DMF and 8 mL 1% AcOH in water, loaded onto a 100 g C18 Isco gold column. Column was flushed with 360 mL (3 volumes) 100 mM ammonium acetate, then re-equilibrated with 5% acetonitrile in water with 0.1% AcOH (2 volumes) and eluted using gradient of 5% to 30% acetonitrile in water with 0.1% AcOH for 24 mins. Pure fractions were lyophilized to give 57C as the acetate salt. 241 mg isolated (61.5% yield). LCMS M/Z: 1160 [M+1].

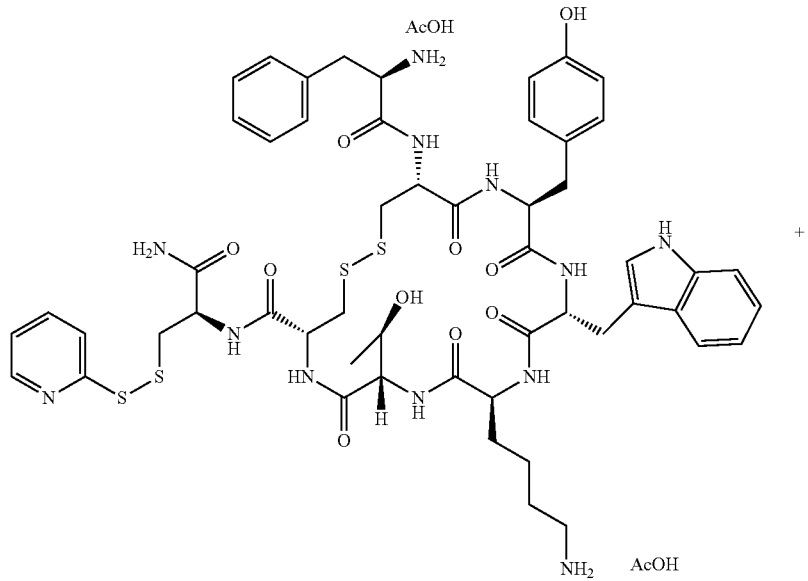

57C

-continued

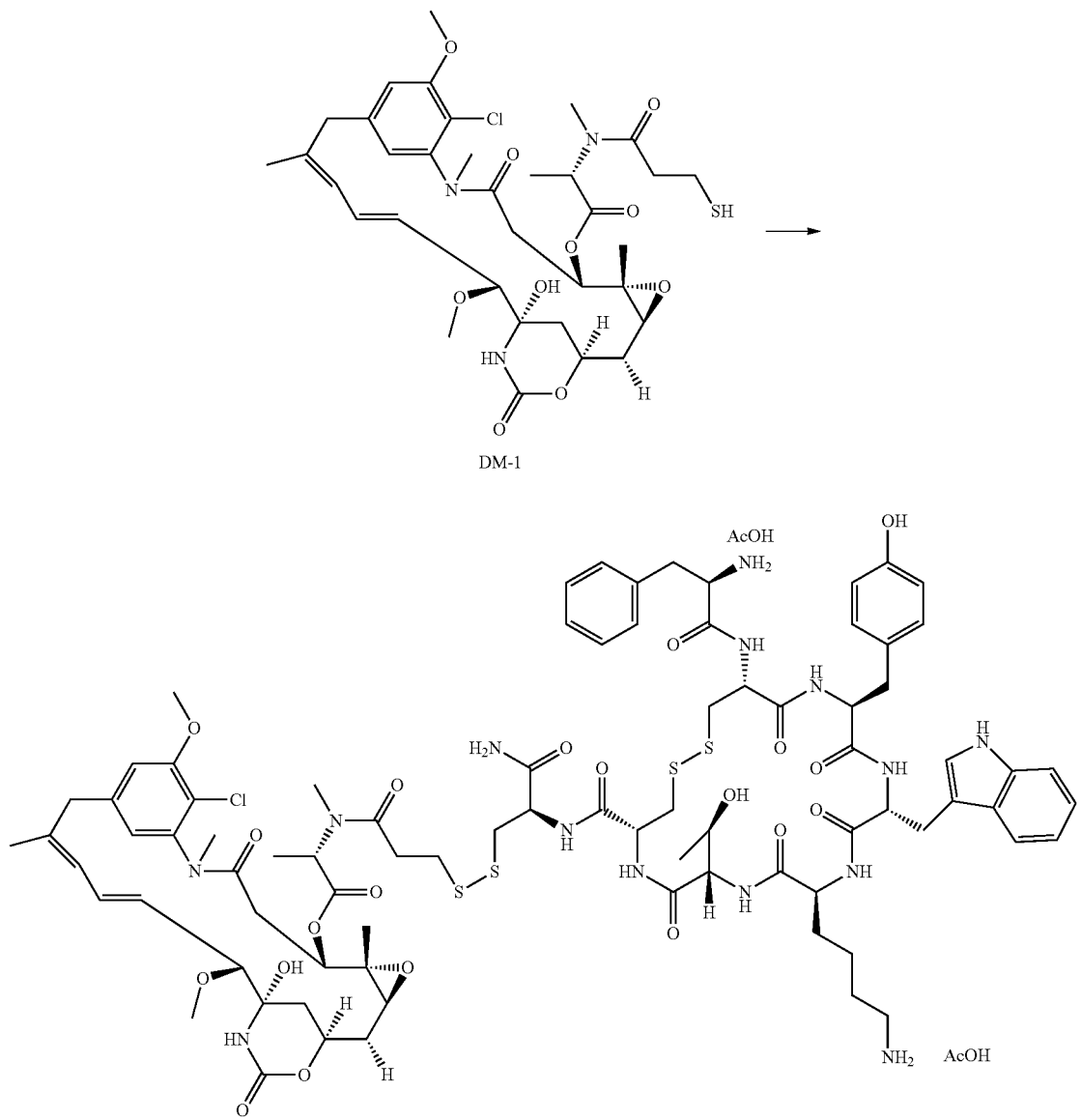

A 100 mL RBF was charged with 57C bis-acetate salt (210 mg, 0.164 mmol) and this was dissolved in THF (4 mL) and 0.2M AcOH (3.6 mL) and 0.2M NaOAc (0.4 mL). 57C was checked by LCMS by taking an aliquot of 2 uL and dissolving in 50 uL methanol, and running on the method below. To the reaction mixture was added a solution of DM-1 (124 mg, 0.167 mmol) in THF (4 mL). The reaction was stirred at room temperature for 1 h. A 2 uL aliquot was removed, diluted with 50 uL methanol, and checked by LCMS. Area of BT-891:area of BT-976 is >10:1 at 280 nm, and the reaction is judged complete. All solvents were removed in vacuo, with bath temperature at 35° C., and at 10 mbar for 45 min to remove all water. The remaining residue was dissolved in 1 mL DMF, and this was diluted with 3 mL aqueous 1% acetic acid. This solution was loaded onto a 50 g RediSep Rf Gold C18 column (20-40 micron particle size). Another 1 mL DMF and 3 mL 1% acetic acid was added to the reaction flask, and this was also loaded onto the C18 column. Column eluted with 40 mL/min gradient, 17 min run. 2 min @ 5% acetonitrile in water with 0.1% AcOH, then 15 min gradient from 5% to 40% acetonitrile in water with 0.1% AcOH. Product elutes as a single peak around 35% acetonitrile. Eluted fractions collected, most of the solvent removed in vacuo until total volume was 5 mL. This solution was transferred to an amber vial, and 5 mL of a 1:1 mix of acetonitrile:water was used to rinse the flask, and transferred to the amber vial. 2 uL aliquot was diluted with 50 uL methanol, checked by LCMS method below. The resulting solution was frozen by placing in a dry ice/acetone bath, and dried in a benchtop freeze drier at 200 millitorr for 3 d. Isolated 57 as the bis-acetate salt (262 mg, 0.137 mmol, 84% yield). LCMS M/Z: 893.4 [(M+2)/2].

TABLE 13

Synthesis of DM1 conjugates

| Compound | DM-1 conjugation method | Final conjugate | LCMS M/Z |
|---|---|---|---|
| 9' | A | 16 | 910.2 [(M + 2)/2] |
| 14' | A | 18 | 948.0 [(M + 2)/2] |
| 15' | A | 24 | 868.0 [(M + 2)/2] |
| 16' | A | 26 | 880.9 [(M + 2)/2] |
| 17' | A | 30 | 860.8 [(M + 2)/2] |
| 20' | C | 20 | 916.0 [(M + 3)/3] |
| 21' | C | 32 | 1030.4 [(M + 2)/2] |
| 23' | B | 28 | 852.5 [(M + 2)/2] |
| 38' | A | 35 | 924.3 [(M + 2)/2] |
| 39' | A | 37 | 942.3 [(M + 2)/2] |
| 40' | A | 39 | 1015.0 [(M + 2)/2] |
| 41' | C | 41 | 962.0 [(M + 2)/2] |
| 42' | A | 43 | 958.0 [(M + 2)/2] |
| 43' | A | 45 | 1001.0 [(M + 2)/2] |
| 44' | A | 47 | 1024.0 [(M + 2)/2] |
| 45' | A | 49 | 965.0 [(M + 2)/2] |
| 46' | A | 51 | 977.5 [(M + 2)/2] |
| 47' | A | 57 | 893.4 [(M + 2)/2] |
| 48' | B | 59 | 871.9 [(M + 2)/2] |
| 49' | B | 63 | 934.5 [(M + 2)/2] |
| 50' | B | 65 | 957.8 [(M + 2)/2] |
| 73' | A | 74 | 937.0 [(M + 2)/2] |
| 74' | A | 68 | n.d. |
| 75' | A | 70 | 978.0 [(M + 2)/2] |
| 76' | A | 72 | 1065.5 [(M + 2)/2] |
| 77' | A | 86 | 977.9 [(M + 2)/2] |
| 78' | A | 98 | 1001.5 [(M + 2 − H$_2$O)/2] |
| 79' | C | 104 | 979.5 [(M + 2 − H$_2$O)/2] |
| 80' | C | 108 | 938.5 [(M + 2 − H$_2$O)/2] |
| 81' | A | 119 | 871.1 [(M + 2)/2] |
| 82' | A | 111 | 930.9 [(M + 2)/2] |
| 83' | A | 113 | 927.4 [(M + 2)/2] |
| 84' | A | 115 | 951.5 [(M + 2)/2] |
| 85' | C | 117 | n.d. |
| 86' | A | 76 | 915.0 [(M + 2)/2] |
| 87' | A | 78 | 971.9 [(M + 2)/2] |
| 88' | A | 80 | 930.0 [(M + 2)/2] |
| 89' | A | 82 | 921.9 [(M + 2)/2] |
| 90' | C | 90 | 940.5 [(M + 2)/2] |
| 91' | A | 94 | 971.0 [(M + 2)/2] |
| 92' | A | 96 | 1003.0 [(M + 2)/2] |
| 93' | A | 102 | 1041.6 [(M + 2)/2] |
| 94' | A | 106 | 985.0 [(M + 2)/2] |
| 96' | A | 84 | 965.0 [(M + 2)/2] |
| 97' | A | 88 | n.d. |
| 99' | A | 92 | 1044.1 [(M + 3)/3] |

Example 15: Nanoparticle Formulation of Drug Conjugate

Nanoparticle formulation of a typical conjugate X, which may be any conjugate of the present invention. Conjugate X was successfully encapsulated in polymeric nanoparticles using a single oil in water emulsion method (refer to Table 14 below). In a typical water-emulsion method, the drug conjugate and a suitable polymer or block copolymer or a mixture of polymers/block copolymers, were dissolved in organic solvents such as dichloromethane (DCM), ethyl acetate (EtAc) or chloroform to form the oil phase. Co-solvents such as dimethyl formamide (DMF) or acetonitrile (ACN) or dimethyl sulfoxide (DMSO) or benzyl alcohol (BA) were sometimes used to control the size of the nanoparticles and/or to solubilize the drug conjugates. A range of polymers including PLA97-b-PEG5, PLA35-b-PEG5 and PLA16-b-PEG5 copolymers were used in the formulations. Surfactants such as Tween® 80, sodium cholate, Solutol® HS or phospholipids were used in the aqueous phase to assist in the formation of a fine emulsion. The oil phase was slowly added to the continuously stirred aqueous phase containing an emulsifier (such as Tween 80) at a typical 10%/90% v/v oil/water ratio and a coarse emulsion was prepared using a rotor-stator homogenizer or an ultrasound bath. The coarse emulsion was then processed through a high-pressure homogenizer (operated at 10,000 psi) for N=4 passes to form a nanoemulsion. The nanoemulsion was subsequently quenched by a 10-fold dilution with cold (0-5° C.) water for injection quality water to remove the major portion of the ethyl acetate solvent in the nanoemulsion droplet, resulting in hardening of the emulsion droplets and formation of a nanoparticle suspension. In some cases, volatile organic solvents such as dichloromethane can be removed by rotary evaporation. Tangential flow filtration (500 kDa MWCO, mPES membrane) was used to concentrate and wash the nanoparticle suspension with water for injection quality water (with or without surfactants/salts). The free drug conjugate was removed from the nanosuspension using a variety of techniques. A cryoprotectant serving also as tonicity agent (e.g., 10% sucrose) was added to the nanoparticle suspension and the formulation was sterile filtered through a 0.22 μm filter. The formulation was stored frozen at ≤−20° C. Particle size (Z-ave) and the polydispersity index (PDI) determined by dynamic light scattering of the nanoparticles were characterized by dynamic light scattering, as summarized in the table below. The actual drug load was determined using HPLC and UV-visible absorbance. This was accomplished by evaporating the water from a known volume of the nanoparticle solution and dissolving the solids in an appropriate solvent such as DMF. The drug concentration was normalized to the total solids recovered after evaporation. Encapsulation efficiency was calculated as the ratio between the actual and theoretical drug load.

Formulations Using Hydrophobic Ion-Pairing (HIP) of Conjugate X

In some instances, HIP techniques were used to enhance the lipophilicity of conjugate X. The conjugate X has one or more positively charged moieties. A negatively charged counter-ion such as dioctyl sodium sulfosuccinate (AOT) molecules was used for everyone molecule of the conjugate to form the HIP. The conjugate X and the AOT were added to a methanol, dichloromethane and water mixture and allowed to shake for 1 hour. After further addition of dichloromethane and water to this mixture, the X/AOT HIP was extracted from the dichloromethane phase and dried. In some embodiments, DMF was used to solubilize the HIP complex. The results of the formulations are summarized in Table 14 below.

TABLE 14

Formulations of conjugates 76, 10 and 78

| | Drug Conjugate | | |
|---|---|---|---|
| | 76<br>NP3-Efficacy | 10<br>NP6-Efficacy | 78<br>NP05-Efficacy |
| Process | Single emulsion | Single emulsion | Single emulsion |
| Polymer | PLA35-mPEG5 | PLA35-mPEG5/PLA50-Me (50%/50%) | PLA35-mPEG5/PLA50-Me (50%/50%) |
| Polymer concentration, mg/mL | 100 | 100 | 100 |
| Emulsion Volume, mL | 100 | 200 | 200 |
| Oil phase | 87.5% EA/12.5% DMF/ | 43.05% EA/13.9% DMF/43.05% DCM | 42.5% EA/15% DMF/42.5% DCM |
| Drug | 76:AOT | 10 | 78 |
| Aqueous phase | 0.1% Tween 80/Water | 0.05% DiOctPC/Water | 0.05% DiOctPC/Water |
| Oil phase volume fraction, % | 10.00% | 10.00% | 10.00% |
| Wash | Wash 12X with Saline; 5X cold water; Quench 7X in 30oC water, wash 5X in ice cold water; | Wash 4X with cold water; Quench 7X in 30oC water, wash 21X in ice cold water; drug extraction | Wash 6X with cold water; Quench 10X in 30oC water, wash 25X in ice cold water; drug extraction |
| Z.ave/PDI (quenched Emulsion) | 72.7/0.057 | 129.00 | 137.50 |
| Z.ave/PDI (post TFF filtered) | 67.16/0.04 | 115.7/0.095 | 119.1/0.044 |
| TDL (wt %) | 6.09 | 3.91 | 4.93 |
| ADL (wt %) | 4.70 | 0.48 | 1.04 |
| EE = ADL/TDL, % | 0.772 | 0.122 | 0.211 |
| Potency, mg/mL | 1.214 | 0.2763 | 0.363 |

TDL: Theoretical Drug Loading
ADL: Actual Drug Loading
NA: not available
EE: encapsulation efficiency These data demonstrate that conditions can be invented for the efficient encapsulation of conjugate X in nanoparticles.

Example 16: $IC_{50}$ in H524 Cells

Conjugates of the present invention were assessed in an in vitro assay evaluating inhibition of cell proliferation. NCI-H524 (ATCC) human lung cancer cells were plated in 96 well, V-bottomed plates (Costar) at a concentration of 5,000 cells/well. 24 hours later, cells were treated with either conjugate for. 2 hours and further incubated 70 hours, or for octreotide competition experiments, treated with 100 μM octreotide for 30 min, and then treated with conjugate for 2 hours, and further incubated for 70 hours. Conjugate starting dose was 20 μM and three fold serial dilutions were done for a total of ten points. After 2 hours of treatment, cells were spun down, the drug containing media was removed, and fresh complete medium was added and used to resuspend the cells, which were spun again. After removal of the wash media, the cells were resuspended in complete medium, then transferred into white walled, flat bottomed 96 well plates. Cells were further incubated for an additional 70 hours to measure inhibition of cell proliferation. Proliferation was measured using CellTiter Glo reagent using the standard protocol (Promega) and a Glomax multi+detection system (Promega). Percent proliferation inhibition was calculated using the following formula: % inhibition=(control-treatment)/control*100. Control is defined as vehicle alone. IC50 curves were generated using the nonlinear regression analysis (four parameter) with GraphPad Prism 6. $IC_{50}$ values for the conjugates comprising DM1 were shown in Table 15 below. These data demonstrate that conjugates retain the ability to bind to somatostatin and internalize the receptor. In some instances, this also shows that the linker is cleaved to activate the cytotoxic payload effectively to kill the tumor cells.

Example 17: Activity Dependence on the Receptor

Figure 3:
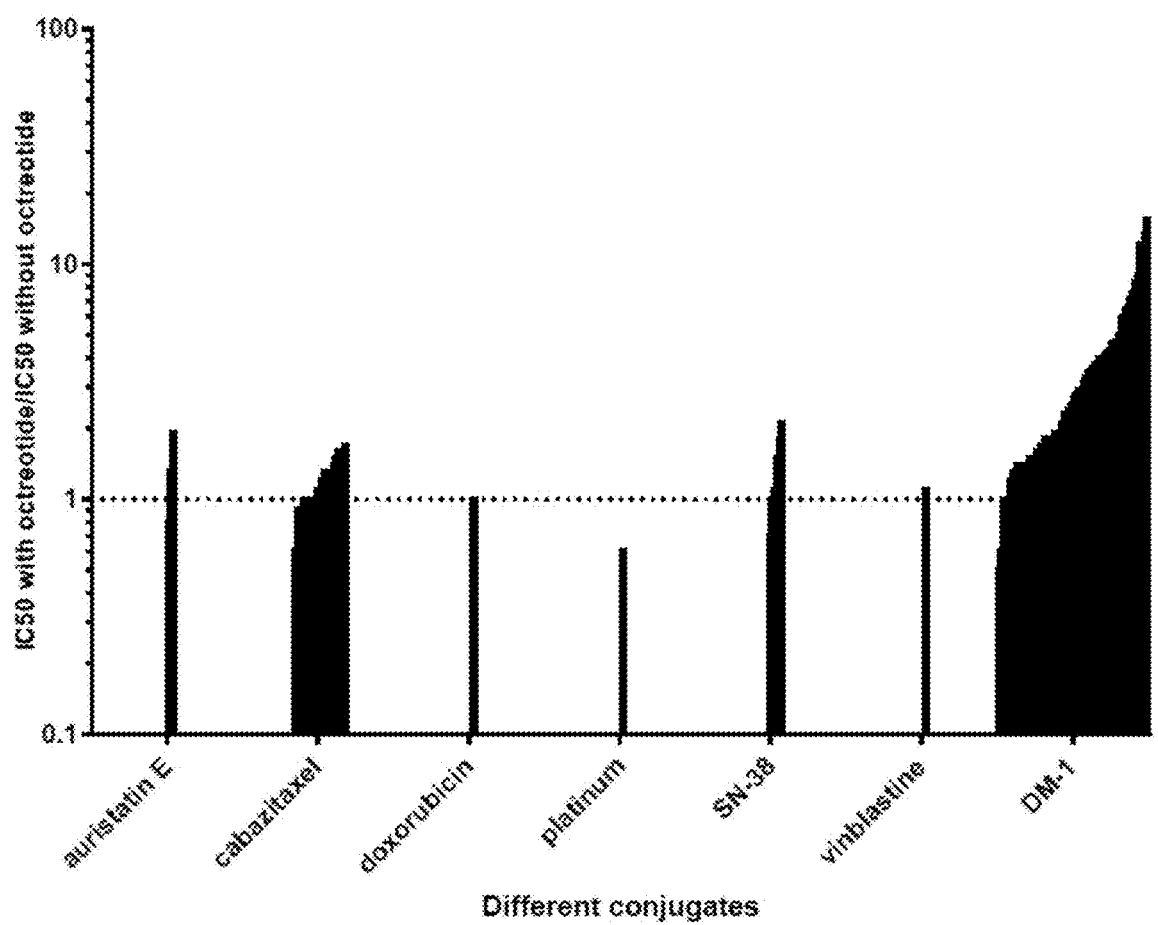
FIG. 3 is a graph of various conjugates represented as bars and showing on the Y-axis their activity in an H524 proliferation assay with and without competition by octreotide. The Y-axis shows the ratio of the IC$_{50}$ with octreotide added to the IC$_{50}$ without octreotide added. This assay demonstrates the extent to which the activity of the conjugates depends on the somatostatin receptors. Only DM1 conjugates show a ratio significantly greater than 1. This illustrates the surprising finding that only DM1 conjugates show activity that is dependent on the receptor.

Conjugates of the present invention were tested for their activity dependence on the somatostatin receptor. Active agent Z in the conjugate was selected from auristatin, carbazitaxel, DM1, doxorubicin, platinum, SN-38 and vinblastine. Active agent Z is connected to octreotide with various linkers. Proliferation $IC_{50}$, values of the conjugates were measured. Proliferation $IC_{50}$ values of the conjugates without octreotide competition were also measured. The ratios of $IC_{50}$ with octreotide competition and $IC_{50}$ without octreotide competition were shown in FIG. 3. The ratio of $IC_{50}$ with octreotide competition and $IC_{50}$ without octreotide competition is an indicator of whether activity is at least partially dependent on bind to the somatostatin receptor. Conjugates comprising DM1 showed a ration of more than 1, indicating lower $IC_{50}$, i.e., better efficacy, without octreotide competition than with octreotide competition. Therefore, the activity of conjugates comprising DM1 is dependent on the binding to the somatostatin receptor.

$IC_{50}$ values for the conjugates comprising DM1 with octreotide competition were shown in Table 15 below. The results in Table 15 showed $IC_{50}$ values for all the conjugates comprising DM1 increased with octreotide competition, which means the efficacy of the conjugates comprising DM1 decreased with octreotide competition. DM1 alone did not show such a change in $IC_{50}$ values with octreotide competition. Therefore, the efficacy of conjugates comprising DM1 at least partially depends on the binding of the conjugates to the somatostatin receptor.

Example 18: H69 Tumor DM-1 Levels

To examine the ability of conjugates of the present invention to accumulate in tumors, a murine cancer model was used. All mice were treated in accordance with the OLAW Public Health Service Policy on Human Care and Use of Laboratory Animals and the ILAR Guide for the Care and Use of Laboratory Animals. All in vivo studies were conducted following the protocols approved by the Blend Therapeutics Institutional Animal Care and Use Committee. Animals were inoculated with 2.5×10^6 NCI-H69 SCLC (small cell lung cancer) cells in 1:1 RPMI 1640 (Invitrogen, Carlsbad, Calif.)/Matrigel® (BD Biosciences, San Jose, Calif.) via subcutaneous injection to the right flank. Tumors were allowed to reach an approximate volume of ~500 mm3. Animals were then randomized into treatment groups of 3 animals per time point and were dosed at 1 mg/kg (10% propylene glycol in water for injection for free conjugates, or 10% sucrose for nanoparticles), or 0.4 mg/kg for DM-1 (10% propylene glycol in water for injection). The 24 hour time point was used as a benchmark across conjugates.

Tumor DM-1 levels were determined by liquid chromatography mass spectrometry (LC/MS-MS). Four volumes of 5 mM 6-maleimidohexanoic acid to 1 part tumor v/w was added and homogenized for about 10-15 seconds with a handheld homogenizer. 10 μL of 500 mM Tris(2-carboxyethyl)phosphine was added to 100 uL of tumor homogenate, mixed well and incubated at room temperature for about 5-15 min. 200-300 uL of acetonitrile was used to precipitate proteins in tumor homogenate, samples were centrifuged for 5 min, and supernatant was injected onto LC/MS-MS system for DM-1 analysis. H69 tumor DM-1 levels were shown in Table 15.

TABLE 15

H524 cell assay and in vivo tumor uptake results for DM1 conjugates

| Conjugate | H524 $IC_{50}$ (nM) | H524 $IC_{50}$ + 100 uM octreotide (nM) | H69 tumor DM-1 levels (nM) |
|---|---|---|---|
| 4 | 367 | 853 | n.d. |
| 6 | 234 | 629 | n.d. |
| 7 | 955 | 1770 | n.d. |
| 68 | 821 | 1340 | n.d. |
| 70 | 317 | 417 | n.d. |
| 72 | n.d. | n.d. | n.d. |
| 74 | 549 | 562 | n.d. |
| 76 | 120 | 768 | 62.2 |
| 76 NP7 | n.d. | n.d. | 221 |
| 10 | 156 | 625 | 72.1 |
| 10 NP6 | n.d. | n.d. | 883 |
| 35 | 253 | 1000 | 23.2 |
| 78 | 124 | 365 | 36.2 |
| 78 NP5 | n.d. | n.d. | 223 |
| 80 | 152 | 157 | 91.2 |
| 82 | 148 | 867 | n.d. |
| 84 | 76 | 312 | n.d. |
| 37 | 44 | 166 | n.d. |
| 111 | 123 | 742 | 82.6 |
| 86 | 386 | 553 | n.d. |
| 113 | 1080 | 4920 | n.d. |
| 115 | 327 | 1495 | 37.1 |
| 39 | 2642 | 3578 | 11.8 |
| 88 | 80 | 180 | n.d. |
| 41 | 86 | 1343 | n.d. |
| 90 | 84 | 1021 | n.d. |
| 92 | 367 | 471 | n.d. |
| 94 | 285 | 1017 | n.d. |
| 96 | 206 | 397 | n.d. |
| 98 | 690 | 1121 | n.d. |
| 100 | 303 | 1055 | n.d. |
| 117 | 6 | 54 | n.d. |
| 102 | 335 | 579 | n.d. |
| 43 | 1165 | 2046 | n.d. |
| 45 | 345 | 481 | n.d. |
| 47 | 2129 | 1267 | n.d. |
| 49 | 69 | 243 | n.d. |
| 51 | 124 | 238 | n.d. |
| 12 | 1685 | 2345 | n.d. |
| 104 | 279 | 705 | n.d. |
| 14 | 298 | 877 | 70.1 |
| 106 | 400 | 666 | n.d. |
| 16 | 223 | 398 | 96.4 |
| 53 | 42 | 175 | n.d. |
| 18 | 1480 | 2160 | 86.3 |
| 20 | 241 | 427 | n.d. |
| 108 | 96 | 1280 | n.d. |
| 22 | 332 | 741 | 145 |
| 24 | 149 | 982 | n.d. |
| 26 | 787 | 1161 | n.d. |
| 55 | 47 | 395 | 95.3 |
| 28 | 669 | 1000 | n.d. |
| 57 | 136 | 1654 | 243 |
| 59 | 24 | 170 | n.d. |
| 30 | 470 | 2017 | n.d. |
| 32 | 310 | 733 | n.d. |
| 61 | 89 | 274 | n.d. |
| 63 | 44 | 168 | n.d. |
| 65 | 30 | 229 | n.d. |
| 119 | 2656 | >5000 | n.d. |
| DM-1 | 90 | 90 | 31.6 |

Example 19: Effect of Conjugate 10 and Conjugate 10 NP6 Compounds on Tumor Growth and Pharmacokinetics Studies Applicants assessed the activity of a conjugate and a nanoparticle formulation of the conjugate in vivo. In these experiments, the ability of compounds to affect the growth of human NCI-H69 SCLC was tested. For the in vivo study, 8 week old female NCR nude mice were inoculated subcutaneously into the right flank with 2 million cells in 1:1 RPMI 1640 (Invitrogen, Carlsbad, Calif.)/Matrigel® (BD Biosciences, San Jose, Calif.). Tumor measurements were taken twice weekly, using vernier calipers. Tumor volume was calculated using the formula: V=0.5×width×width×length.

When tumors approached a volume of 200 mm³, mice were randomized into four groups of ten animals. Mice were treated with vehicle control (10% propylene glycol in water for injection), Conjugate 10 at 2 mg/kg (10% propylene glycol in water for injection), Conjugate 10 NP6 nanoparticle at 2 mg/kg (10% Sucrose), or DM1 at 0.8 mg/kg (10% propylene glycol in water for injection). Mice were dosed once weekly for two doses. Final tumor volumes were analyzed using with a one-way analysis of variance and Tukey multiple comparison test. Tumor volumes were tracked over a course of up to 100 days as shown in FIG. 4.

Figure 4:
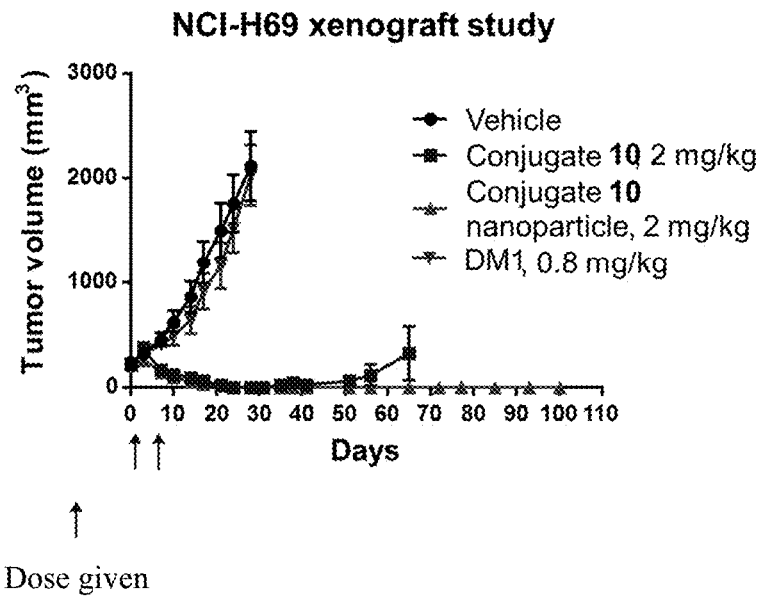
FIG. 4 shows the tumor volume change over a period of up to 100 days after treatment with Conjugate 10, Conjugate 10 NP6 and DM1 in a NCI-H69 model.
Figure 5:
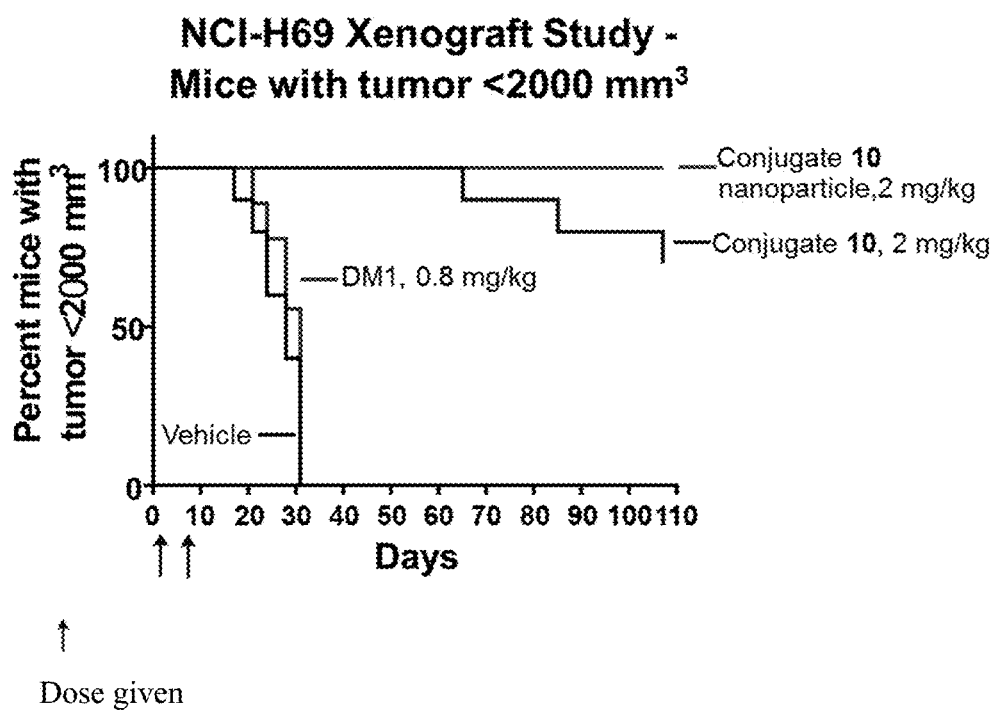
FIG. 5 is a graph of percent of mice with tumor <2000 mm$^3$ over a period of up to 100 days after treatment with Conjugate 10, Conjugate 10 NP6 and DM1 in a NCI-H69 model.

As shown in FIG. 4, the tumor volume increased rapidly for vehicle and DM1 controls. Conjugate 10 alone initially provided tumor regression, but tumors regrew over the course of the study. Conjugate 10 NP6 provided complete cures, i.e., 9 out of 9 mice were tumor-free at 100 days post dosing after only two doses on days 1 and 8. A Kaplan-Merier tumor volume curve of percentage of mice with tumor size less than 2000 mm$^3$ in FIG. 5 shows that out to 100 days no animals have come off of the study in the Conjugate 10 NP6 group, but in the Conjugate 10 alone group three animals had to be removed from the study due to large tumor size.

Figure 6:
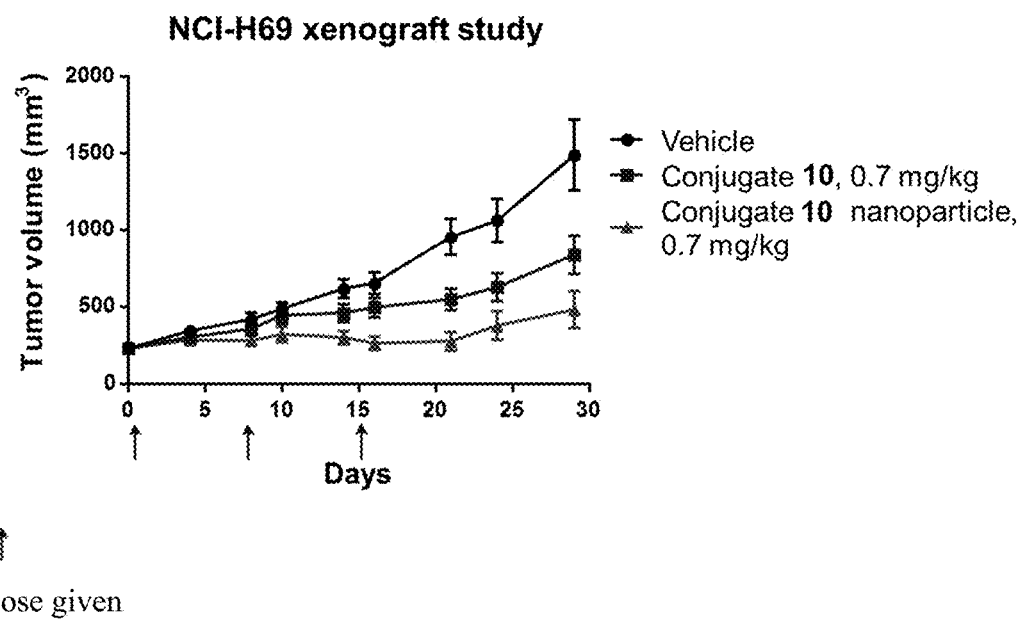
FIG. 6 demonstrates tumor volume change over a period of 30 days with multidoses of conjugate 10 and conjugate 10 NP6.

Tumor volume study was repeated with three doses for vehicle, Conjugate 10 (0.7 mg/kg each), and Conjugate 10 NP6 (0.7 mg/kg each). Tumor volumes were tracked for 30 days. The results were shown in FIG. 6. Conjugate 10 NP6 again showed significantly superior efficacy to free Conjugate 10.

Figure 7:
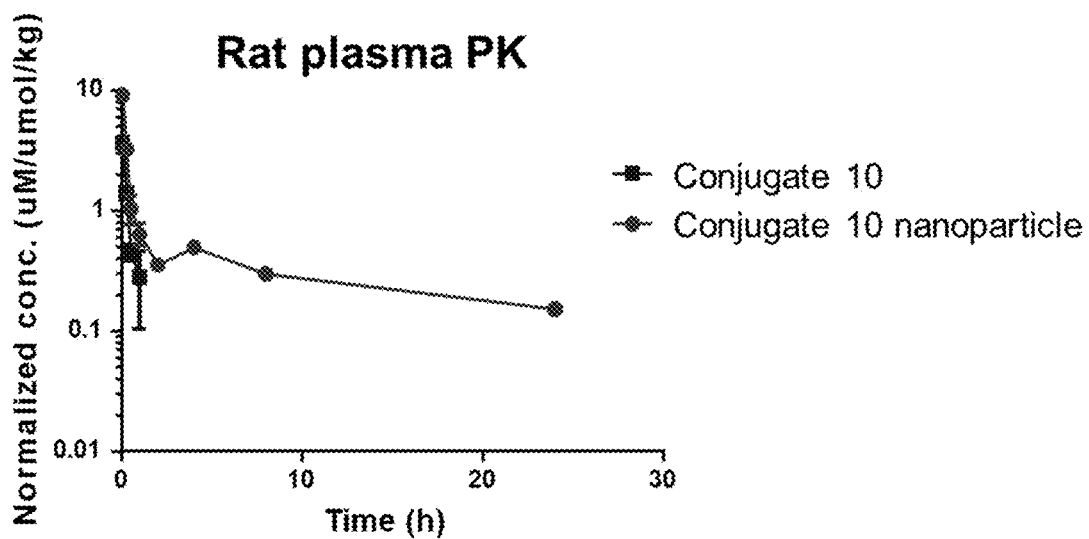
FIG. 7 shows rat plasma pK of conjugate 10 and conjugate 10 NP6.

Pharmacokinetics studies in rat plasma were also carried out. Rat plasma pK of Conjugate 10 and Conjugate 10 NP6 was shown in FIG. 7. AUC values were show in Table 16. Incorporating Conjugate 10 in a nanoparticle increases AUC for Conjugate 10 by around 10 fold.

TABLE 16

AUC for Conjugate 10 and Conjugate 10 NP6

| | Conjugate 10 | Conjugate 10 NP6 |
|---|---|---|
| AUC 0-inf (nmol/L*h) | 377 | 3650 |
| Cl (mL/kg/min) | 13.0 | 1.35 |

Figure 8:
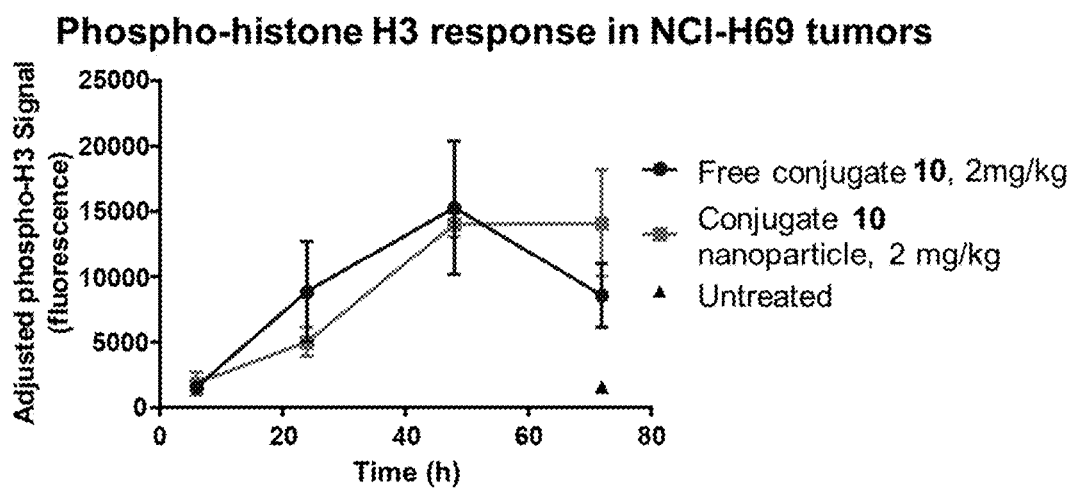
FIG. 8 shows phospho-histone H3 response in NCI-H69 tumors after treatment with conjugate 10 and conjugate 10 NP6.

Phospho-histone H3 response in NCI-H69 tumors was shown in FIG. 8. Increase in phospho-histone H3 was observed in tumors after treatment with Conjugate 10 and Conjugate 10 NP6. At around 50 hour, phospho-histone H3 response for free Conjugate 10 started to decrease, while phospho-histone H3 response for Conjugate 10 NP6 remained high. Pharmacokinetics study suggested a delayed and lengthened response for Conjugate 10 NP6.

Therefore, conjugates incorporated in nanoparticles are much more effective than the conjugates alone and DM1 alone.

The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

We claim:

1. A method of treating lung cancer in a subject in need thereof comprising administering a therapeutically effective amount of a conjugate to the subject, wherein the conjugate comprises an active agent coupled to a somatostatin receptor (SSTR) targeting moiety by a linker, wherein the active agent is mertansine (DM1) and wherein the SSTR targeting moiety is a peptide, and wherein the conjugate has a formula of

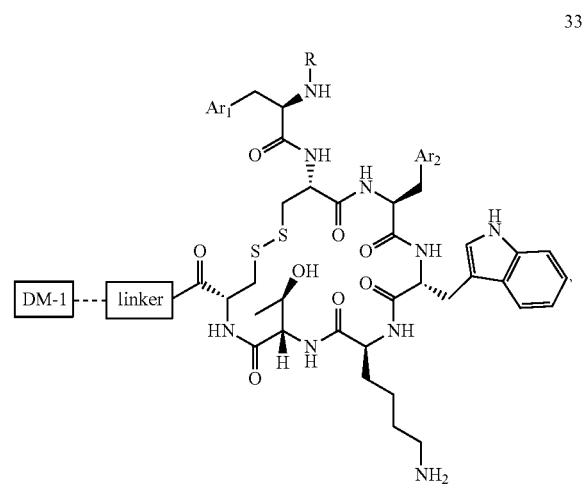

wherein
R is selected from the group consisting of H, alkyl, aryl, and amide groups; and
$Ar_1$ and $Ar_2$ are independently selected from the group consisting of heterocyclyl, aryl, and heteroaryl groups.

2. The method of claim 1, wherein the molecular weight of the conjugate is less than about 50,000 Da, less than about 40,000 Da, less than about 30,000 Da, less than about 20,000 Da, less than about 15,000 Da, less than about 10,000 Da, less than about 8,000 Da, less than about 5,000 Da, or less than about 3,000 Da.

3. The method of claim 1, wherein the linker is selected from the group consisting of an ester bond, disulfide, amide, acylhydrazone, ether, carbamate, carbonate, and urea.

4. The method of claim 1, wherein the conjugate is selected from the group consisting of Compound 57, Compound 35, Compound 37, Compound 39, Compound 41, Compound 43, Compound 45, Compound 47, Compound 49, Compound 51, Compound 55, Compound 59, Compound 61, Compound 63, and Compound 65.

5. A method of inhibiting the rate of growth of a tumor, the size of a tumor or the volume of a tumor, the method comprising contacting the tumor with an effective amount of a conjugate comprising an active agent coupled to a somatostatin receptor (SSTR) targeting moiety by a linker, wherein the active agent is mertansine (DM1) and wherein the SSTR targeting moiety is a peptide, wherein the tumor is lung cancer, and wherein the conjugate has a formula of

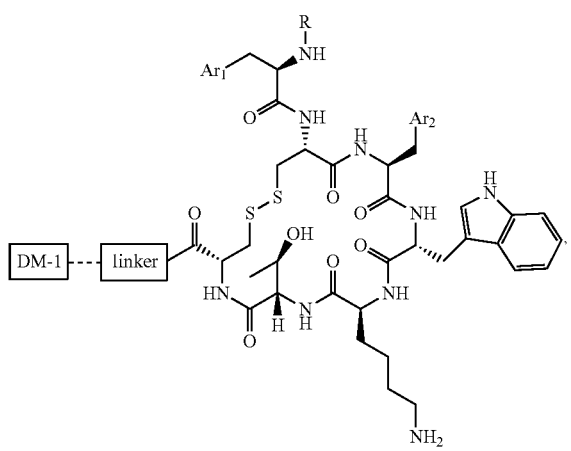

wherein
R is selected from the group consisting of H, alkyl, aryl, and amide groups; and
$Ar_1$ and $Ar_2$ are independently selected from the group consisting of heterocyclyl, aryl, and heteroaryl groups.

6. A method of delivering DM1 to a tumor in a subject, the method comprising administering a conjugate to the subject in need thereof, wherein the conjugate comprises an active agent coupled to a somatostatin receptor (SSTR) targeting moiety by a linker, wherein the active agent is mertansine (DM1) and wherein the SSTR targeting moiety is a peptide, wherein the tumor is lung cancer, and wherein the conjugate has a formula of

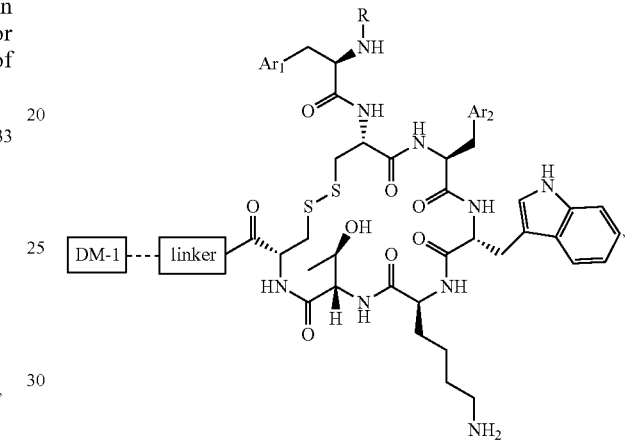

wherein
R is selected from the group consisting of H, alkyl, aryl, and amide groups; and
$Ar_1$ and $Ar_2$ are independently selected from the group consisting of heterocyclyl, aryl, and heteroaryl groups.

* * * * *